US012754192B2

(12) United States Patent
Rioux et al.

(10) Patent No.: US 12,754,192 B2
(45) Date of Patent: Oct. 6, 2026

(54) METABOLIC BIOMARKERS OF INFLAMMATORY BOWEL DISEASE

(71) Applicant: INSTITUT DE CARDIOLOGIE DE MONTREAL, Montreal (CA)

(72) Inventors: John D. Rioux, Westmount (CA); Christine Des Rosiers, Rigaud (CA); Anik Forest, Sainte-Lucie des Laurentides (CA); Gabrielle Boucher, Laval (CA); Romain Ferru-Clément, Poitiers (FR)

(73) Assignee: INSTITUT DE CARDIOLOGIE DE MONTREAL, Montreal (CA)

( * ) Notice: Subject to any disclaimer, the term of this patent is extended or adjusted under 35 U.S.C. 154(b) by 532 days.

(21) Appl. No.: 18/140,188

(22) Filed: Apr. 27, 2023

(65) Prior Publication Data

US 2023/0349933 A1 Nov. 2, 2023

Related U.S. Application Data

(60) Provisional application No. 63/335,844, filed on Apr. 28, 2022.

(51) Int. Cl.
*G01N 33/92* (2006.01)

(52) U.S. Cl.
CPC ......... *G01N 33/92* (2013.01); *G01N 2405/04* (2013.01); *G01N 2405/08* (2013.01); *G01N 2800/065* (2013.01); *G01N 2800/52* (2013.01)

(58) Field of Classification Search
None
See application file for complete search history.

(56) References Cited

PUBLICATIONS

Soler et al., J. Pharm. Exp. Ther. 330: 864-875 (2009).*
Tefas et al., Bosn. J. Basic Med. Sci. 20(2): 262-270 (2020).*
Ferru-Clément et al., "Serum Lipidomic Screen Identifies Key Metabolites, Pathways, and Disease Classifiers in Crohn's Disease," Inflammatory Bowel Diseases. 29(7):1024-1037. Jan. 2023.

* cited by examiner

*Primary Examiner* — Erin M. Bowers
(74) *Attorney, Agent, or Firm* — Clark & Elbing LLP

(57) ABSTRACT

Disclosed are various lipid biomarkers of inflammatory bowel disease, including biomarkers for inflammatory bowel diseases including Crohn's disease and Ulcerative colitis. Also disclosed are various biomarkers of disease location and/or disease behavior in inflammatory bowel disease. The present disclosure also provides methods of using the biomarkers, including methods for diagnosis of inflammatory bowel disease, methods of determining pre-disposition to inflammatory bowel disease, methods of monitoring progression/regression of inflammatory bowel disease, and methods of assessing efficacy of compositions for treating inflammatory bowel disease.

14 Claims, 18 Drawing Sheets
(15 of 18 Drawing Sheet(s) Filed in Color)

METABOLIC BIOMARKERS OF INFLAMMATORY BOWEL DISEASE

FIELD OF THE INVENTION

The invention relates to metabolic biomarkers for inflammatory bowel diseases and methods of their detection and use in the treatment of Crohn's disease or ulcerative colitis.

BACKGROUND

Inflammatory bowel disease (IBD), including Crohn's disease (CD) and ulcerative colitis (UC) are becoming major public health concerns, due to their dramatic expansion worldwide (Ng et al. Lancet 2017; 390:2769-2778), lack of cure and challenges in disease management. These diseases exhibit, however, heterogeneity in terms of disease onset, behavior, location, progression and response to therapy. Currently, there is an unmet need to identify biomarkers that would capture both host and environmental contributions to and thereby improve diagnosis, patient stratification, as well as treatment monitoring.

SUMMARY OF THE INVENTION

In general, the invention provides lipid biomarkers for inflammatory bowel disease and methods of their use. The biomarkers may be used, for example, to generate quantitative data in a subject, treat inflammatory bowel disease and/or assign treatment regimens to a subject.

In an aspect, the invention provides a method for generating quantitative data for a subject, including determining a level of a biomarker in a blood sample from the subject, wherein the biomarker is selected from 1) a phosphatidylcholine ether, 2) a phosphatidylethanolamine ether, 3) a phospholipid, 4) a sphingomyelin, 5) a cholesterol ester, 6) a very long-chain dicarboxylic acid (VLCDCA), 7) sitosterol sulfate, 8) cholesta-4,6-dien-3-one, 9) a triglyceride, 10) a diglyceride, and 11) a ceramide, or a combination thereof, and wherein the subject is suffering from an inflammatory bowel disease or is suspected of suffering from an inflammatory bowel disease.

In another aspect, the invention provides a method of assigning a treatment regimen to a subject diagnosed with an inflammatory bowel disease, the method including determining a level in a blood sample of at least one biomarker relative to a control, wherein the biomarker is selected from 1) a phosphatidylcholine ether, 2) a phosphatidylethanolamine ether, 3) a phospholipid, 4) a sphingomyelin, 5) a cholesterol ester, 6) a very long-chain dicarboxylic acid (VLCDCA), 7) sitosterol sulfate, 8) cholesta-4,6-dien-3-one, 9) a triglyceride, 10) a diglyceride, and 11) a ceramide, or a combination thereof, and wherein the treatment regimen is assigned to the subject based on the determination of the level of the biomarker.

In some embodiments of the foregoing aspects, the phosphatidylethanolamine ether is PE(O-16:0/20:4), PE(O-18:0/20:4), PE(O-16:0/22:6), or PE(O-18:0/22:6), the phosphatidylcholine ether is PC(O-20:0/22:6) or PC(O-18:0/22:6), the phospholipid is PC(18:1_22:5), PC(18:2_20:5), PC(19:0_18:2), PE(18:1_20:4)-1, PE(18:1_20:4)-2, PE(16:0_18:1), or PE(18:0_22:5), the sphingomyelin is SM(d18:1/21:0), SM(d17:1/24:1), SM(d18:2/16:0), SM(d18:2/23:0), SM(d18:2/24:0), SM(d17:1/24:1), SM(d18:1/25:1)-2, SM(d18:1/25:1)-1, SM(d18:1/24:0), SM(d19:1/24:0), SM(d18:1/21:0), or SM(d16:1/22:0), the cholesterol ester is CE(14:1) or CE(14:0), the ceramide is Cer(d16:1/23:0), the triglyceride is TG(16:0_18:1_20:4), TG(18:1_18:2_22:5), TG(16:0_18:1_22:5), TG(18:1_18:2_20:4), TG(56:4), TG(18:1_18:2_22:4), or TG(18:2_16_0_20:4), the diglyceride is DG(16:0_18:2), and/or the very long-chain dicarboxylic acid is 28:1(OH) or 28:4.

In some embodiments, the determination of the level of the biomarker includes performing an in vitro assay. In some embodiments, the in vitro assay includes spectrometry. In some embodiments, the spectrometry is mass spectrometry (MS) or liquid chromatography-mass spectrometry (LC-MS). In some embodiments, the MS or LC-MS includes multiple reaction monitoring, selected reaction monitoring or full scan monitoring.

In some embodiments, the blood sample is serum or plasma.

In some embodiments, the inflammatory bowel disease is Crohn's disease. In some embodiments, the inflammatory bowel disease is Ulcerative Colitis. In some embodiments, the inflammatory bowel disease is indeterminate colitis.

In some embodiments, a decrease in the level of PE(O-16:0/20:4), a decrease in the level of VLCDCA 28:1 (OH), an increase in the level of sitosterol sulfate, or an increase in the level of cholesta-4,6-dien-3-one relative to the control is indicative of the subject suffering from stricturing or penetrating (62/63) Crohn's Disease.

In some embodiments, a decrease in the level of CE(14:1), an increase in the level of sitosterol sulfate, or an increase in the level of cholesta-4,6-dien-3-one relative to the control is indicative of the subject suffering from ileal disease.

In some embodiments, a level of the phosphatidylethanolamine ether, the sphingomyelin, the cholesterol ester, or the very long-chain dicarboxylic acid lower relative to the control is indicative of the subject suffering from Crohn's Disease.

In some embodiments, the subject is assigned a treatment regimen including the administration of a biologic drug. In some embodiments, the biologic drug is a molecularly targeted therapy. In some embodiments, the biologic drug is an antibody. In some embodiments, the biologic drug binds α4137 integrin. In some embodiments, the biologic drug is vedolizumab.

In another aspect, the invention provides a method of treating an inflammatory bowel disease in a subject, the method including:

a) determining a level in a blood sample of at least one biomarker selected from 1) a phosphatidylcholine ether, 2) a phosphatidylethanolamine ether, 3) a phospholipid, 4) a sphingomyelin, 5) a cholesterol ester, 6) a very long-chain dicarboxylic acid (VLCDCA), 7) sitosterol sulfate, 8) cholesta-4,6-dien-3-one, 9) a triglyceride, 10) a diglyceride, and 11) a ceramide, or a combination thereof, relative to a control;
b) based on the determining of step (a), assigning a treatment regimen to the subject, and
c) administering to the subject a therapeutically effective amount of a therapeutic agent.

In some embodiments, the phosphatidylethanolamine ether is PE(O-16:0/20:4), PE(O-18:0/20:4), PE(O-16:0/22:6), or PE(O-18:0/22:6), the phosphatidylcholine ether is PC(O-20:0/22:6) or PC(O-18:0/22:6), the phospholipid is PC(18:1_22:5), PC(18:2_20:5), PC(19:0_18:2), PE(18:1_20:4)-1, PE(18:1_20:4)-2, PE(16:0_18:1), or PE(18:0_22:5), the sphingomyelin is SM(d18:1/21:0), SM(d17:1/24:1), SM(d18:2/16:0), SM(d18:2/23:0), SM(d18:2/24:0), SM(d17:1/24:1), SM(d18:1/25:1)-2, SM(d18:1/25:1)-1, SM(d18:1/24:0), SM(d19:1/24:0), SM(d18:1/21:0), or SM(d16:1/22:0), the cholesterol ester is CE(14:1) or CE(14:

0), the ceramide is Cer(d16:1/23:0), the triglyceride is TG(16:0_18:1_20:4), TG(18:1_18:2_22:5), TG(16:0_18:1_22:5), TG(18:1_18:2_20:4), TG(56:4), TG(18:1_18:2_22:4), or TG(18:2_16_0_20:4), the diglyceride is DG(16:0_18:2), and/or the very long-chain dicarboxylic acid is 28:1(OH) or 28:4.

In some embodiments, the inflammatory bowel disease is Crohn's disease. In some embodiments, the inflammatory bowel disease is Ulcerative Colitis. In some embodiments, the inflammatory bowel disease is indeterminate colitis.

In some embodiments, the therapeutic agent is a biologic drug. In some embodiments, the biologic drug is a molecularly targeted therapy. In some embodiments, the biologic drug is an antibody. In some embodiments, the biologic drug binds $\alpha 4\beta 7$ integrin. In some embodiments, the biologic drug is vedolizumab.

In some embodiments of any of the foregoing aspects, the subject is a human.

Abbreviations

AUC is area under the curve; $C_{4,6}D_3O$ is cholesta-4,6-dien-3-one; CD is Crohn's Disease; CE is cholesterol ester; FA is fatty acid; HPLC is high-performance liquid chromatography; IBD is inflammatory bowel diseases; LC is liquid chromatography; MS is mass spectrometry; NIDDK is National Institute of Diabetes and Digestive and Kidney Diseases; IBDGC is NIDDK IBD Genetics Consortium; OCFA is odd-chain fatty acid; PC is phosphatidylcholine; PCO- is PC ether; PE is phosphatidylethanolamine; PEO- is PE ether; QTOF is quadrupole time-of-flight; ROC is receiver operating characteristic; RT is retention time; Sit is sitosterol; SitS is sitosterol sulfate; SM is sphingomyelin; SP is sphingolipid; UC is ulcerative colitis; VLCDCA is very long-chain dicarboxylic acid; VLCFA is very long-chain fatty acid.

Definitions

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

As used herein, a "biologic drug" or "biologic" refers to a product that is produced from living organisms or contains components of living organisms. Biologic drugs include a wide variety of products derived from human, animal, or microorganisms by using biotechnology.

The term "ileal disease," as used herein, refers to a subtype of Crohn's disease in which inflammation occurs in the ileum, the last division of the small intestine extending between the jejunum and large intestine.

The term "inflammatory bowel disease," as used herein, refers to any disease that is characterized by chronic inflammation of the digestive tract. Exemplary inflammatory bowel diseases include Crohn's disease and ulcerative colitis. The Montreal Disease Classification of inflammatory bowel disease is used herein to define the subtypes of Crohn's disease and ulcerative colitis. This system of classification is described, for example, in Satsangi et al. Gut 2006; 55:749-753. These classifications include Crohn's disease location (L), including ileal (L1), colorectal (L2) and ileocolonic (L3) subtypes; Crohn's disease behavior (B), including non-stricturing and non-penetrating (B1, also referred as inflammatory), stricturing (B2), and penetrating (B3) subtypes; and ulcerative colitis disease extent (E), including ulcerative proctitis (E1), left sided UC (E2) and extensive UC (E3).

The term "subject," as used herein, refers to a human suffering from or at risk for an inflammatory bowel disease. The inflammatory bowel disease may be, for example, Crohn's disease or ulcerative colitis. A subject may be diagnosed as having an inflammatory bowel disease or may be one experiencing one or more symptoms of an inflammatory bowel disease. Non-limiting examples of symptoms of an inflammatory bowel disease include fever, nausea, diarrhea, fatigue, abdominal pain, blood in stool, reduced appetite, mouth sores, and unexpected weight loss.

"Treatment" and "treating," as used herein, refer to the medical management of a subject with the intent to improve, ameliorate, stabilize, prevent, or cure a disease, disorder, or condition. This term includes active treatment (treatment directed to improve the disease, disorder, or condition); palliative treatment (treatment designed for the relief of symptoms of the disease, disorder, or condition); and supportive treatment (treatment employed to supplement another therapy). "Treatment" and "treating," as used herein, also refers to disease modification, meaning, that the expression of the disease is modified towards a less severe expression of the symptoms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 10A lipid identifications are shown for the four CD-associated lipids reaching our thresholds (p-value<1E-4 and $|log_2(FC)|>0.3$) in IBDGC-2. The 20 CD-associated lipid features with a p-value<0.05 in IBDGC-2 are circled in bold.

DETAILED DESCRIPTION

Figure 1:
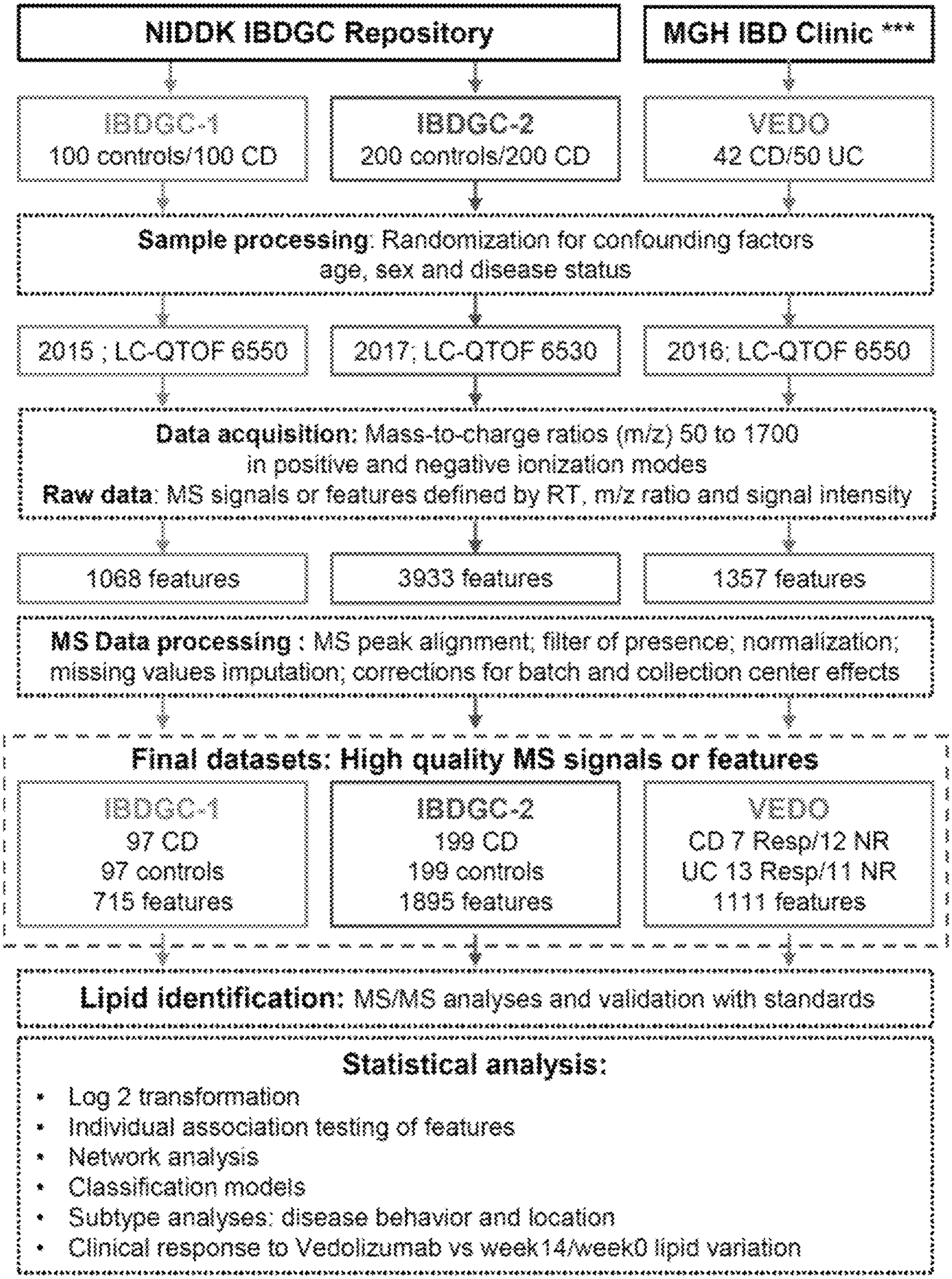
FIG. 1 depicts the design and analytical aspects for an untargeted lipidomic screen.

In general, the invention provides metabolic biomarkers for inflammatory bowel disease and their use in treating the inflammatory bowel disease. Circulating lipids play crucial roles in many biological mechanisms relevant to IBD pathophysiology (Chiurchiu et al. Front Immunol 2018; 9:38) and originate from host metabolic processes occurring in specific tissues/cells or from the incorporation/modification of dietary or gut microbiota metabolites. Lipids represent 75% of all circulating metabolites (Quehenberger et al. N Engl J Med 2011365:1812-23). The application of mass spectrometry (MS)-based lipidomics to large number of blood samples from clinical cohorts remains, however, challenging (Burla B et al. J Lipid Res 2018; 59:2001-2017; Gallagher K et al. J Crohns Colitis 202115:813-826). Notably the ability to adequately resolve and identify the multiple lipid isomers is still limiting biological data interpretation. For example, specifically in IBD, identification of lipid subclasses with their acyl side chains is likely crucial because specific groups of fatty acids (FAs) could possibly discriminate between host vs microbiome metabolism (odd-chain FAs; OCFAs) (Jenkins B et al. Molecules 2015; 20:2425-44), determine intestinal barrier integrity (very-long chain FAs; VLCFA)(Kim Y R, et al. J Cell Mol Med 2017; 21:3565-3578; Oertel et al. Cell Mol Life Sci 2017; 74:3039-3055) or distinguish between reservoirs of pro- and anti-inflammatory precursors, namely omega-6 vs. omega-3 polyunsaturated fatty acids (PUFAs)(Alhouayek M et al. Biochim Biophys Acta Mol Cell Biol Lipids 20211866: 158854), whose synthesis requires desaturase encoding enzymes (FADS1 and FADS2) which are known IBD risk genes (Jostins et al. Nature 2012; 491:119-24; de Lange K M et al. Nat Genet 2017; 49:256-261).

A validated LC-MS-based lipidomic workflow which is optimized for wide coverage of polar and non-polar lipids as well as resolution of their isomers was applied. It enables measurement of >1,500 high-quality MS signals, from 100 μL of plasma or serum with a single instrument, of which 509 structurally unique lipid species covering 25 lipid sub-classes, including their acyl side chains, have been annotated to date by MS/MS analyses. Median inter- and intra-assay coefficients of variations (or relative standard deviation (RSD)) for the resulting annotated lipids meet criteria of the Food and Drug Administration (i.e. >85% with RSD<20%), thereby enabling robust semi-quantification. First, this workflow was applied to 300 CD and 300 control subjects, matched for sex, age and ethnicity, collected by the National Institute of Diabetes and Digestive and Kidney Disease (NIDDK) IBD Genetics Consortium (IBDGC), in two independent phases. Second, it was tested if quantitative variations in circulating lipids were associated with response to therapy by analyzing serum samples from an independent cohort of 92 CD and UC patients commencing Vedolizumab, an anti-α4β7 integrin blocker antibody that is approved for moderate to severe IBD in patients who are refractory to conventional and/or anti-TNF therapy. The analyses identified candidate circulating lipid biomarkers that are strong CD disease classifiers, as well as being differently associated with location and/or behavior and response to therapy, thereby supporting their potential for capturing patient heterogeneity and improving disease management.

Inflammatory Bowel Disease

Inflammatory bowel disease (IBD) refers to a group of conditions characterized by inflammation of the large and/or small intestine. The most common subtypes of IBD are Crohn's disease (CD) and ulcerative colitis (UC). Other non-limiting forms of IBD include indeterminate colitis, collagenous colitis, lymphocytic colitis, ischemic colitis, diversion colitis, Behcet's syndrome, infective colitis.

Crohn's Disease

Crohn's disease is a disease characterized by chronic inflammation of the gastrointestinal tract, often the ileum and the cecum. It can also be confined to the small intestine, colon, anorectal region. It may further involve the duodenum, stomach, esophagus, or oral cavity. As a result of varying anatomic localization of the disease, the symptoms may differ among subjects. The most common symptoms are abdominal pain, diarrhea, and fever. It is also commonly associated with intestinal obstruction or fistula. It may lead to complications including inflammation of the eye, joints, and skin, liver disease, kidney stones, and amyloidosis.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

There are three categories of disease presentation in Crohn's disease: (B1) inflammatory, (B2) stricturing, and (B3) penetrating. Stricturing disease causes narrowing of the bowel which may lead to bowel obstruction or changes in the caliber of the feces. Penetrating disease creates abnormal passageways (fistulae) between the bowel and other structures such as the skin. Inflammatory disease (also known as non-stricturing, non-penetrating disease) causes inflammation without causing strictures or fistulae.

Subjects with CD can be classified as having complicated CD, which is a clinical subtype characterized by stricturing or penetrating phenotypes. In certain other instances, subjects with CD can be classified as having a form of CD characterized by one or more of the following complications: fibrostenosis, internal perforating disease, and the need for small bowel surgery. Subjects with CD can be also classified as having an aggressive form of fibrostenotic disease requiring small bowel surgery. Criteria relating to these subtypes have been described, for example, in Gasche et al., *Inflamm. Bowel Dis.,* 6:8-15 (2000); Abreu et al., *Gastroenterology,* 123:679-688 (2002); Vasiliauskas et al., *Gut,* 47:487-496 (2000); Vasiliauskas et al., *Gastroenterology,* 110:1810-1819 (1996); and Greenstein et al., *Gut,* 29:588-592 (1988).

One skilled in the art understands that overlap can exist between clinical subtypes of CD and that a subject having CD can have more than one clinical subtype of CD. For example, a subject having CD can have the fibrostenotic subtype of CD and can also meet clinical criteria for a clinical subtype characterized by the need for small bowel surgery or the internal perforating disease subtype. Similarly, the metabolic biomarkers described herein can be associated with more than one clinical subtype of CD.

Ulcerative Colitis

Ulcerative colitis (UC) is a disease of the large intestine characterized by chronic diarrhea with cramping, abdominal pain, rectal bleeding, loose discharges of blood, pus, and mucus. UC may present widely different clinical manifestations. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC usually extends from the most distal part of the rectum for a variable distance proximally. Left-sided colitis describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC.

In certain instances, with respect to UC, the variability of symptoms reflect differences in the extent of disease (i.e., the amount of the colon and rectum that are inflamed) and the intensity of inflammation. Disease starts at the rectum and moves "up" the colon to involve more of the organ. UC can be categorized by the amount of colon involved. Typically, patients with inflammation confined to the rectum and a short segment of the colon adjacent to the rectum have milder symptoms and a better prognosis than patients with more widespread inflammation of the colon.

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

The different clinical subtypes of ulcerative colitis are classified according to the location and the extent of inflammation. As non-limiting examples, subjects with UC can be classified as having ulcerative proctitis, proctosigmoiditis, left-sided colitis, pancolitis, fulminant colitis, and combinations thereof. Criteria relating to these subtypes have been described, for example, in Kornbluth et al., *Am. J. Gastroenterol.,* 99: 1371-85 (2004).

Ulcerative proctitis is a clinical subtype of UC defined by inflammation that is limited to the rectum. Proctosigmoiditis is a clinical subtype of UC which affects the rectum and the sigmoid colon. Left-sided colitis is a clinical subtype of UC which affects the entire left side of the colon, from the rectum to the place where the colon bends near the spleen and begins to run across the upper abdomen (the splenic flexure). Pancolitis is a clinical subtype of UC which affects the entire colon. Fulminant colitis is a rare, but severe form of pancolitis. Patients with fulminant colitis are extremely ill with dehydration, severe abdominal pain, protracted diarrhea with bleeding, and even shock.

In some embodiments, classification of the clinical subtype of UC is important in planning an effective course of treatment. While ulcerative proctitis, proctosigmoiditis, and left-sided colitis can be treated with local agents introduced through the anus, including steroid-based or other enemas and foams, pancolitis must be treated with oral medication so that active ingredients can reach all of the affected portions of the colon.

One skilled in the art understands that overlap can exist between clinical subtypes of UC and that a subject having UC can have more than one clinical subtype of UC. Similarly, the metabolic biomarkers described herein can be associated with more than one clinical subtype of UC.

Indeterminate Colitis

Indeterminate colitis (IC) is a clinical subtype of IBD that includes features of CD and UC. The overlap of symptoms can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC.

Treatment of Inflammatory Bowel Disease

Inflammatory bowel disease is currently not curable. However, there are a number of treatments for IBD. The goal of such treatments is multifold, and includes improvement of the subject's clinical condition, reducing side effects, improving quality of life, reducing drug poisoning, nutritional support, and reducing the need for hospital admission or surgery. Diagnosis and treatment of IBD is discussed in Seyedian et al., *J. Med. Life.,* 12:113-122 (2019), the disclosure of which is incorporated herein by reference. Typically, treatment occurs in stages, with drugs with fewer expected side effects being prescribed first and advancing to other drugs if the initial therapy does not provide relief. The biomarkers disclosed herein may be used in determining a treatment regimen that includes any of the drugs described herein.

Anti-Inflammatory Drugs

The first line treatment for IBD is often anti-inflammatory drugs of the aminosalicylate family. Non-limiting examples of these drugs include balsalazide, mesalamine, olsalazine, and sulfasalazine, the structure of which are shown below.

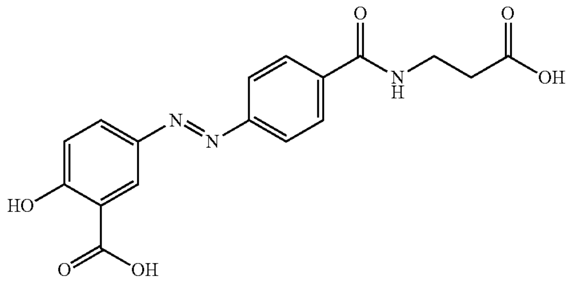

balsalazide

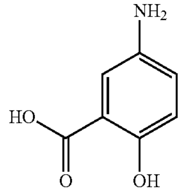

mesalamine

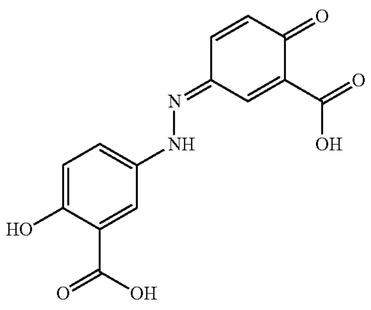

olsalazine

-continued

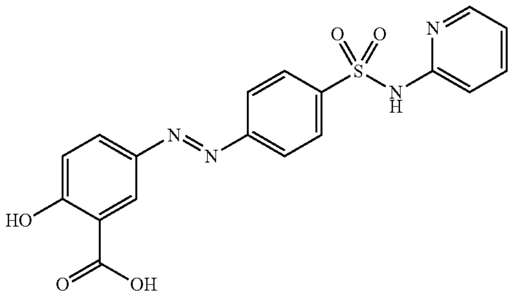

sulfasalazine

Other examples of anti-inflammatory drugs used to treat IBD are corticosteroids. Non-limiting examples of corticosteroids include budenoside, hydrocortisone, methylprednisolone, and prednisone, the structure of which are shown below.

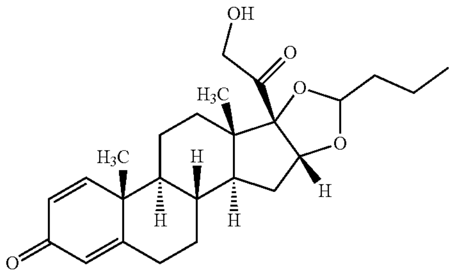

budenoside

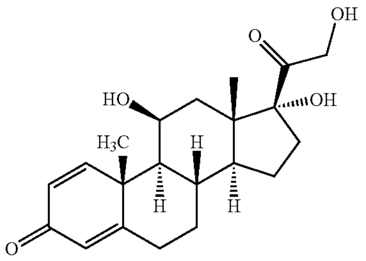

hydrocortisone

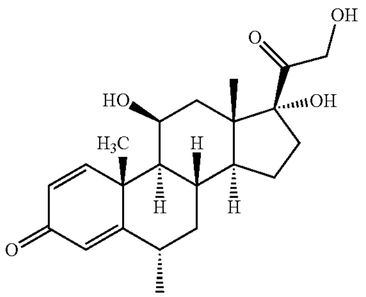

methylprednisolone

-continued

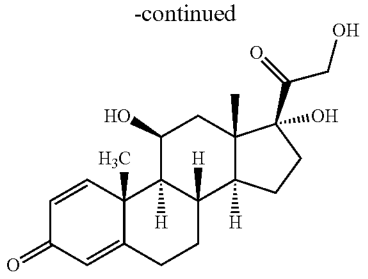

methylprednisolone

Immunosuppressive Drugs

Immunosuppressive drugs are also used to treat IBD when the above anti-inflammatory drugs are unsuccessful. Immunomodulators include, but are not limited to, 6-mercaptopurine, azathioprine, cyclosporine, and methotrexate.

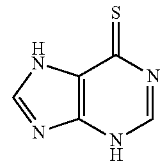

6-mercaptopurine

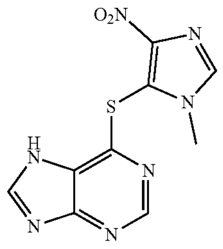

azathioprine

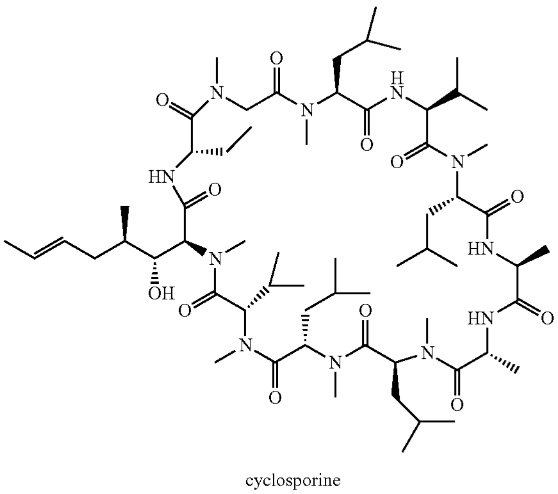

cyclosporine

-continued

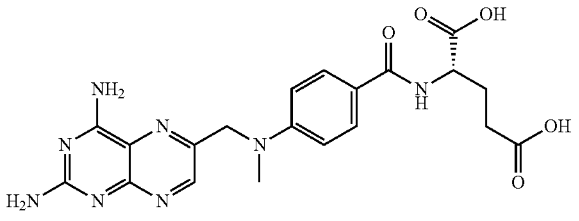

methotrexate

Antibiotics

Antibiotic medications may also be used in addition to other medications or when there is concern for infection, such as in perianal Crohn's disease. Commonly used antibiotics to treat IBD include ciprofloxacin and metronidazole.

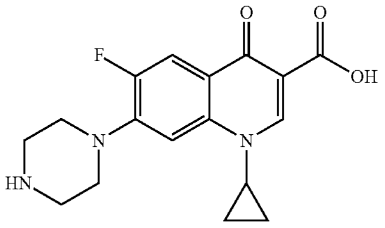

ciprofloxacin

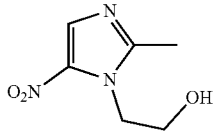

metronidazole

Biologics

Biologic therapies can also be used to treat IBD. Anti-TNF (tumor necrosis factor) agents, such as infliximab, adalimumab, and certolizumab, are a class of biologics used to treat IBD. Alternatively, biologic therapies may be anti-integrin agents, such as natalizumab and vedolizumab. Specifically, vedolizumab binds α4β7 integrin. As a further alternative, anti-IL-12 and IL-23 antibodies, such as ustekinumab, may be used to treat IBD.

Integrins play a role in leukocyte trafficking and extravasation from the vascular compartment into target tissues. They are heterodimers having an a and a β subunit. Anti-integrin therapies modulate inflammation by binding to integrins that contribute to leukocyte trafficking, thereby preventing leukocyte migration into GI mucosa and the development of inflammation within these tissues. Natalizumab targets the α4 subunit, and therefore blocks both α4β1 and α4β7 integrin. Vedolizumab blocks α4β7 without binding to α4β1. By only binding α4β7, the ability of α4β1 to bind its ligand, vascular cell adhesion protein 1 (VCAM-1) is preserved, permitting continued immune surveillance within the CNS and theoretically eliminating the risk of progressive multifocal leukoencephalopathy associated with natalizumab treatment.

The use of biologic drugs in the context treatment of IBD is known as molecularly targeted therapy (MTT). Molecularly targeted therapies used an agent (or combination of agents) that acts with a high degree of specificity on a well-defined target or biologic pathway.

Lipid Biomarkers

The methods disclosed herein may include the detection in serum of one or more lipid biomarkers of inflammatory bowel disease. These lipid biomarkers may include, but are not limited to, the classes of lipids described below.

Sphingolipids

The lipid biomarker used in the methods described herein may be a sphingolipid. Sphingolipids are structural molecules of cell membranes that play a role in maintaining barrier function and fluidity. They also regulate various biological processes (e.g., growth, proliferation, migration, invasion and/or metastasis) by controlling signaling functions within the cell signal transduction network.

In some embodiments, the sphingolipid is a sphingomyelin (SM). The sphingomyelin may be SM(d18:1/21:0), SM(d17:1/24:1), SM(d18:2/16:0), SM(d18:2/23:0), SM(d18:2/24:0), SM(d17:1/24:1), SM(d18:1/25:1)-2, SM(d18:1/25:1)-1, SM(d18:1/24:0), SM(d19:1/24:0), SM(d18:1/21:0), or SM(d16:1/22:0).

SM(d18:1/21:0) is described in the Human Metabolome Database (identification number HMDB0240611). It is a type of sphingolipid found in animal cell membranes, especially in the membranous myelin sheath which surrounds some nerve cell axons. It usually contains phosphorylcholine and ceramide. SM(d18:1/21:0) has a sphingosine backbone and a heneicosanoic acid chain. In humans, sphingomyelin is the only membrane phospholipid not derived from glycerol. Like all sphingolipids, SM has a ceramide core (sphingosine bonded to a fatty acid via an amide linkage). In addition, it contains one polar head group, which is either phosphocholine or phosphoethanolamine. The plasma membrane of cells is highly enriched in sphingomyelin and is considered largely to be found in the exoplasmic leaflet of the cell membrane. However, there is some evidence that there may also be a sphingomyelin pool in the inner leaflet of the membrane. Moreover, neutral sphingomyelinase-2, an enzyme that breaks down sphingomyelin into ceramide, has been found to localize exclusively to the inner leaflet further suggesting that there may be sphingomyelin present there. Sphingomyelin can accumulate in a rare hereditary disease called Niemann-Pick Disease, types A and B. Niemann-Pick disease is a genetically-inherited disease caused by a deficiency in the enzyme sphingomyelinase, which causes the accumulation of sphingomyelin in spleen, liver, lungs, bone marrow, and the brain, causing irreversible neurological damage. SMs play a role in signal transduction. Sphingomyelins are synthesized by the transfer of phosphorylcholine from phosphatidylcholine to a ceramide in a reaction catalyzed by sphingomyelin synthase. The structure of SM(d18:1/21:0) is below.

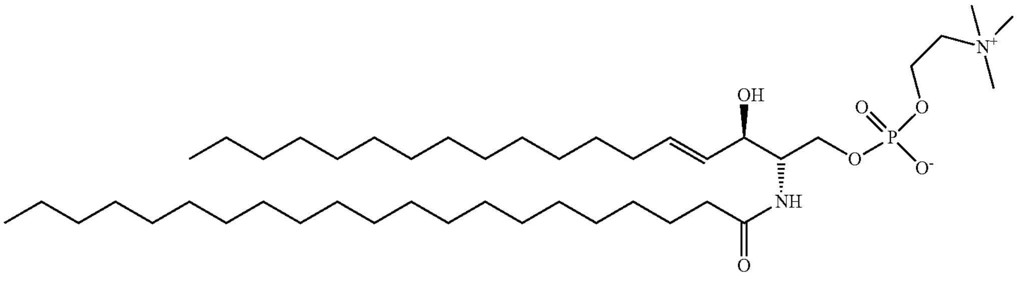

Alternatively, the sphingolipid may be a ceramide. Ceramides are structurally similar to sphingomyelins but lack the phosphatidylcholine group. An exemplary ceramide used herein is Cer(d16:1/23:0), the structure of which is shown below.

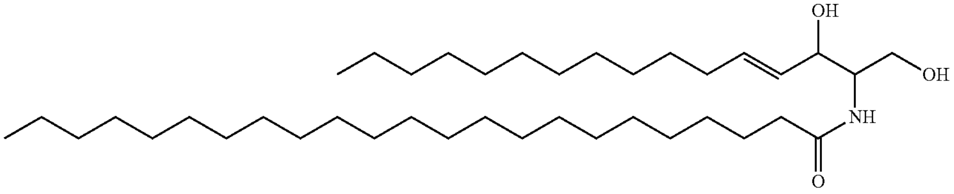 [SMILES: CCCCCCCCCCC/C=C/C(O)C(CO)NC(=O)CCCCCCCCCCCCCCCCCCCCCC]

Phosphatidylcholines

The lipid biomarker used in the methods described herein may be a phosphatidylcholine. Phosphatidylcholines are a class of phospholipids that incorporate choline as a head group. They are glycerophosphocholines in which the two free —OH are attached to one fatty acid each through an ester linkage. They are a component of biological membranes.

The phosphatidylcholine may be a phosphatidylcholine ether. For example, the lipid biomarker may be the phosphatidylcholine ether PC(19:0_18:2), PC(18:2_20:5), PC(O-20:0/22:6), PC(19:0_18:2), or PC(O-18:0/22:6), PC(18:1_22:5). The structure of PC(19:0_18:2) is shown below.

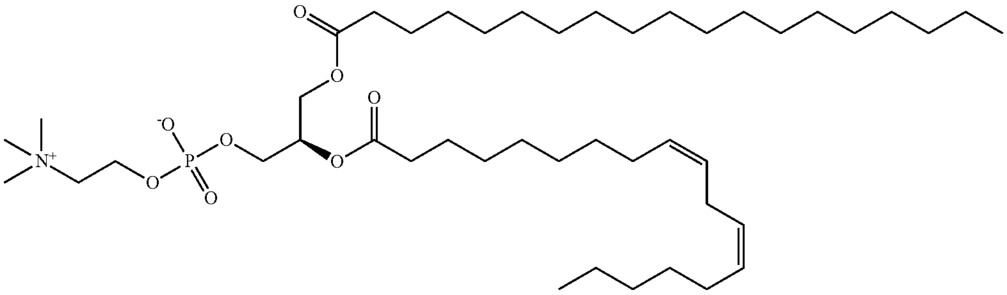

Phosphatidylethanolamines

The lipid biomarker used in the methods described herein may be a phosphatidylethanolamine. Phosphatidylethanolamines are glycerophospholipids in which a phosphorylethanolamine moiety occupies a glycerol substitution site. They are found in biological membranes.

The phosphatidylethanolamine may be a phosphatidylethanolamine ether such as PE(O-16:0/20:4), PE(O-18:0/20:4), PE(O-16:0/22:6), PE(18:1_20:4)-1, PE(18:1_20:4)-2, PE(16:0_18:1), PE(18:0_22:5), or PE(O-18:0/22:6). The structure of PE(O-16:0/20:4) is shown below.

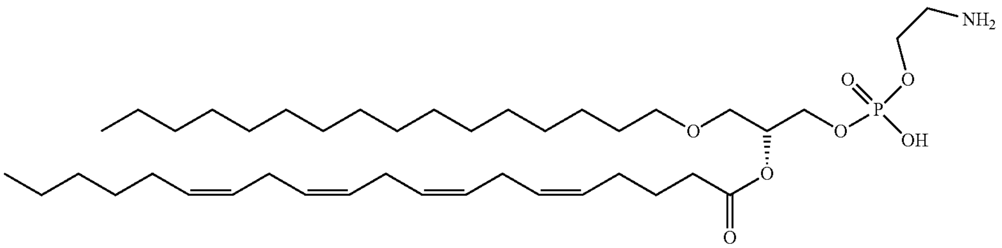

Carboxylic Acids

The lipid biomarker used in the methods described herein may be a carboxylic acid. For example, it may be a fatty acid, such as caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, and arachidonic acid. The carboxylic acid may also be a dicarboxylic acid. In preferred embodiments, the dicarboxylic acid is a very long-chain dicarboxylic acid. For example, the dicarboxylic acid may be a VLCDCA 28:1 (OH) or 28:4.

Sterols

The biomarker used in the methods described herein may be a sterol. For example, the sterol may be cholesterol or an analog thereof. In preferred embodiments, the cholesterol analog is cholesta-4,6-dien-3-one. The biomarker could be an ester of cholesterol, where the alcohol in cholesterol forms an ester with a fatty acid. For example, the cholesterol ester can be CE(14:1) or CE(14:0). The sterol may also be sitosterol or an analog thereof. In preferred embodiments, the sterol is sitosterol sulfate (SitS).

Glycerides

The biomarker used in the methods described herein may be a triglycerides. Triglycerides, also referred to as triacylglycerols, are esters derived from glycerol and three fatty acids. Triglycerides are the major dietary fat, and they are hydrolyzed in the guy by lipases to fatty acids and monoglycerides. Endogenous triglycerides are, to a large extent, synthesized in the liver and adipose tissue.

Exemplary triglycerides used herein include TG(16:0_18:1_20:4), TG(18:1_18:2_22:5), TG(16:0_18:1_22:5), TG(18:1_18:2_20:4), TG(56:4), TG(18:1_18:2_22:4), and TG(18:2_16_0_20:4). The structure of TG(16:0_18:1_20:4) is shown below.

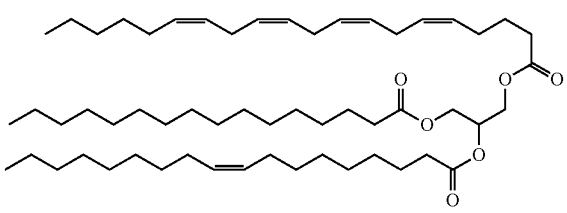 [SMILES: CCCCC/C=C\C/C=C\C/C=C\C/C=C\CCCC(=O)OCC(COC(=O)CCCCCCCCCCCCCCC)OC(=O)CCCCCCC/C=C\CCCCCCCC]

Alternatively, the biomarker may be a diglyceride, also referred to as a diacylglycerol. Diglycerides contain a glycerol with two fatty acids attached through ester linkages. Diglycerides may be 1,2-aiacylglycerols or 1,3-diacylglycerols. Diacylglycerols may be intermediates in lipid biosynthetic pathways and may act as signaling lipids. An exemplary diglyceride used herein is DG(16:0_18:2), the structure of which is shown below.

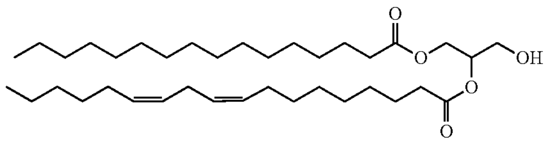 [SMILES: CCCCC/C=C\C/C=C\CCCCCCCC(=O)OC(CO)COC(=O)CCCCCCCCCCCCCCC]

The following examples are meant to illustrate the invention. They are not meant to limit the invention in any way.

EXAMPLES

Example 1. General Methods and Study Design

IBD Subtypes

CD and UC subtypes were defined according to the Montreal classification as follows: (i) CD disease location (L), including ileal (L1), colorectal (L2) and ileocolonic (L3) subtypes, (ii) CD disease behavior (B), including non-stricturing and non-penetrating (B1, also referred as inflammatory), stricturing (B2) and penetrating (B3) subtypes, with B2 and B3 being severe forms of CD frequently resulting in the requirement for surgery, and (iii) UC disease extent (E), including ulcerative proctitis (E1), left sided UC (E2) and extensive UC (E3).

Materials

LC-MS grade methanol, acetonitrile, isopropanol, ethyl acetate and high-performance liquid chromatography (HPLC) grade methyl tert-butyl ether (MTBE) were purchased from J.T. Baker (USA), HPLC grade hexane from Laboratoire Mat (Quebec, QC, Canada) and HPLC grade chloroform and formic acid from Fisher Scientific (Ottawa, ON, Canada). Ultra-pure water was produced using a Milli-Q system (Millipore, Billerica, MA, USA). Ammonium formate was obtained from Sigma-Aldrich (St. Louis, MO, USA). Lipid standards: LPC(13:0), PC(19:0/19:0), PC(14:0/14:0), PS(12:0/12:0), PG(15:0/15:0) and PE(17:0/17:0) were purchased from Avanti Polar Lipids Inc, (Alabaster, USA).

Human Serum Samples and Study Design.

First, serum samples from non-fasting CD patients and healthy donors matched for sex, age and ethnicity, collected by the six Genetic Research Centers of the IBDGC between 2004 and 2011, were selected from the IBDGC repository and processed in two separate phases, referred to as IBDGC-1 and IBDGC-2. For the discovery phase (IBDGC-1), 100 CD patients with a more complicated disease behavior (stricturing or penetrating according to the Montreal classification) were selected, whereas 200 CD patients with a more representative proportion of disease behavior and location subtypes were selected for the second phase (IBDGC-2), as described in Boucher et al., Inflamm Bowel Dis 2021. Second, serum samples from 92 IBD patients commencing Vedolizumab (42 CD and 50 UC) were obtained from the Massachusetts General Hospital, from a previously described multicenter cohort. Two samples per patient were collected at weeks 0 and 14 (i.e., immediately prior to commencing therapy and at first assessment visit). Clinical response and remission were defined as described in Shelton et al., Inflamm Bowel Dis 2015; 21:2879-85 and considered together to assess the lipidome rearrangements associated with response to Vedolizumab. A study flow diagram is shown in FIG. 1. Three sets of serum samples were obtained as frozen aliquots (−80° C.) which had not been previously thawed, and analyzed on different LC-MS instruments in a year and a half-interval as three independent studies, hereafter referred as IBDGC-1, IBDGC-2 and VEDO.

Untargeted Lipidomic Screen Using LC-QTOF

All samples were analyzed using a previously validated untargeted LC-MS-based lipidomic workflow (Forest A et al. J Proteome Res 2018; 17:3657-3670). Following recommended guidelines, stratified randomization of samples was achieved according to potential confounding factors, namely age, sex, disease status, as well as treatment whenever applicable, in order to minimize batch-dependent bias. MS data were acquired in positive and negative modes. MS quality controls (QCs) were performed by (i) injecting "in-house" plasma pool QC sample at the beginning, the end and every 20 runs, (ii) injecting blanks every 20 runs and (iii) monitoring six internal standards spiked in samples for signal intensity, mass mass-to-charge ratios (m/z) and retention time (RT) accuracies.

Raw MS data were processed as previously described (Forest A et al. J Proteome Res 2018; 17:3657-3670) using Mass Hunter Qualitative Analysis (Agilent, Santa Clara, USA) for peak picking and using an in-house bioinformatic script encoded in both Perl and R languages for (i) MS peak alignment; (ii) filter of presence (features retained must be present in 80% of samples from at least one group and have coefficient of variation<80% in healthy donors samples); (iii) normalization of signal intensities using cyclic loess algorithm; (iv) imputation of missing values using k-Nearest Neighbor (KNN) on scaled data; (v) batch and collection center effect correction using Combat. The resulting final datasets listed high-quality MS signals, thereafter referred to as features, defined by their m/z, RT and signal intensity.

All features associated with stricturing or penetrating (B2/B3) CD vs control with p-value<0.05 in IBDGC-1 or 2 were analyzed by MS/MS for annotation to lipid species as previously described (Forest A et al. J Proteome Res 2018; 17:3657-3670). Cholesta-4,6-dien-3-one ($C_{4,6}D_3O$) and cholesterol sulfate IDs were validated using analytical standards purchased from BOC Sciences (Shirley, NY, USA) and Sigma-Aldrich (St. Louis, MO, USA), respectively. Sitosterol sulfate (SitS) ID was validated using a standard kindly provided by Pr Hubert Schaller. All lipid IDs are mentioned herein as annotated lipid molecular species, irrespective of validation with an analytical standard. Features without ID assumption were classified as unidentified and mentioned using their feature ID, defined as ionization mode:mass@RT.

Statistical Analysis

MS data retained in the final IBDGC-1 and 2 datasets were analyzed independently, following untargeted data mining approaches. (i) Individual testing identified features associated with B2/B3 vs control. Results were compared between the IBDGC phases to assess replicability. (ii) The larger IBDGC-2 dataset was selected for network analysis of correlations existing between B2/B3-associated features. (iii) Individual testing was used to test the association of lipid features with CD subtypes. (iv) Classification models validated the potential of circulating lipids to discriminate between CD and control phenotypes. Similarly, the final VEDO dataset was analyzed using individual testing to identify changes in lipid features associated with response to Vedolizumab.

After $\log_2$-transformation of the signal intensity values, independent testing was done for each individual feature using regression analysis corrected for sex. For annotated features detected in both IBDGC datasets, the evidence of association with B2/B3 vs control was compared and then pooled using Z-score statistics. Association with disease behavior was performed as B2/B3 vs inflammatory (B1), conditional on sex and age. Analyses of disease location was performed conditional on sex and age and considered ileocolonic (L3) as intermediate between colorectal (L2) and ileal (L1). Multiple testing was accounted for by evaluating false discovery rate, using q-values (R package qvalue).

For the IBDGC datasets, threshold for selecting associated features using individual testing was p-value<1E-4. For the pilot VEDO study, p-value<0.05 threshold was used.

Positive correlation (r>0.4) between B2/B3-associated features (p-value<1E-4 and $|\log_2(FC)|>0.3$) was projected onto a 2-dimensional display using Fruchterman-Reingold layout algorithm (R package igraph) (Csardi G, Nepusz T. InterJournal 2006; Complex Systems: 1695). A starting point was given to the algorithm as the first two principal component analysis coordinates.

A classification model was built from the IBDGC-2 dataset using 135 features associated with B2/B3 vs control with p-value<0.05 and $|\log_2(FC)|>0.3$, based on the Bayesian Information Criterion. Annotated lipid molecular species were prioritized to be included in the model. Evaluation of the model performances were represented using receiver operating characteristic (ROC) curves and summarized with area under the curve (AUC). Confidence intervals (95% CI) were computed using bootstrap (R package pROC) (Robin X et al. BMC Bioinformatics 201112:77). Given these performances are expected to be overestimated when the model is built (trained) and validated within the same samples, five-fold cross validation, as well as an alternate model built in IBDGC-2 and tested independently in IBDGC-1, were used to evaluate a lower-bound for AUC.

Example 2. An Untargeted Lipidomic Screen Identifies Circulating Lipid Features Associated with Stricturing or Penetrating CD Serum samples from a total of 300 CD patients and 300 healthy donors matched for sex, age and ethnicity were analyzed in two independent phases. The demographic and clinical information for these subjects is presented in Table 1.

TABLE 1

| | IBDGC-1 | | IBDGC-2 | |
|---|---|---|---|---|
| | Control (n = 97) | CD (n = 97) | Control (n = 199) | CD (n = 199) |
| **Age at recruitment** | | | | |
| Range | 19-70 | 19-70 | 16-76 | 16-87 |
| Median | 39 | 39 | 35 | 37 |
| Quartiles: Q1-Q3 | 28-50 | 27-50 | 26-50 | 28-46 |
| **Ethnicity** | | | | |
| White non-Jewish [n (%)] | 84 (86.6) | 83 (85.6) | 156 (78.4) | 156 (78.4) |
| Jewish [n (%)] | 8 (8.2) | 9 (9.3) | 43 (21.6) | 43 (21.6) |
| Black/African-American [n (%)] | 5 (5.2) | 5 (5.1) | 0 (0) | 0 (0) |
| Female gender [n (%)] | 50 (51.5) | 52 (53.6) | 111 (55.8) | 111 (55.8) |
| **Surgery history** | | | | |
| Yes [n (%)] | — | 86 (88.7) | — | 96 (48.2) |
| No [n (%)] | — | 10 (10.3) | — | 103 (51.8) |
| Missing [n (%)] | — | 1 (1) | — | 0 (0) |
| **Tobacco use** | | | | |
| Smoker [n (%)] | 9 (9.3) | 21 (21.7) | 21 (10.5) | 47 (23.6) |
| Ex-smoker [n (%)] | 13 (13.4) | 8 (8.2) | 30 (15.1) | 20 (10.1) |
| Non-smoker [n (%)] | 74 (76.3) | 67 (69.1) | 145 (72.9) | 129 (64.8) |
| Missing In (%)] | 1 (1) | 1 (1) | 3 (1.5) | 3 (1.5) |
| **Montreal Classification Disease behaviors (B)** | | | | |
| Inflammatory (B1) [n (%)] | — | 0 (0) | — | 106 (53.3) |
| Stricturing (B2) [n (%)] | — | 51 (52.6) | — | 52 (26.1) |
| Penetrating (B3) [n (%)] | — | 46 (47.4) | — | 41 (20.6) |
| **Disease locations (L)** | | | | |
| Ileal (L1) [n (%)] | — | 30 (31) | — | 53 (26.6) |
| Colorectal (L2) [n (%)] | — | 8 (8.2) | — | 47 (23.6) |
| Ileocolonic (L3) [n (%)] | — | 58 (59.8) | — | 99 (49.8) |
| Missing [n (%)] | — | 1 (1) | — | 0 (0) |

Figure 2A:
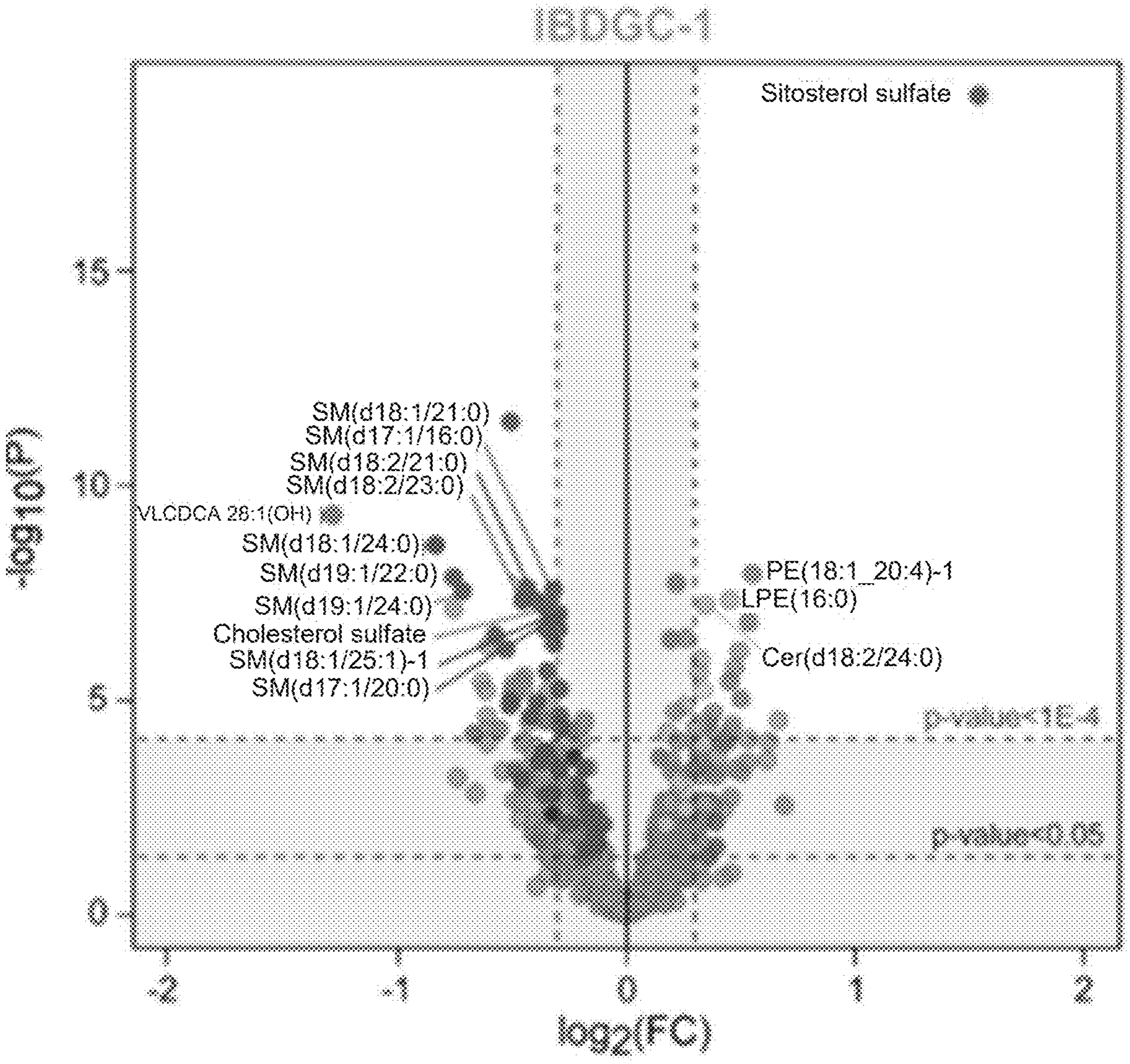
FIG. 2A and FIG. 2B are volcano plots that show all 715 and 1894 lipid features retained in the final dataset following analysis of serum samples of CD patients and control subjects in IBDGC-1 (A) and IBDGC-2 (B), respectively. X-axes show fold-change (FC) ($\log_2$) in MS signal intensity values and y-axes show association p-values ($-\log_{10}$) for B2/B3 vs control. All 321 and 784 features associated with p-value<0.05 in IBDGC-1 and 2, respectively, were analyzed by MS/MS. Lipid identification is shown for the 15 most significant B2/B3-associated features annotated by MS/MS in each dataset.

In the first phase (IBDGC-1), we conducted an untargeted LC-MS-based lipidomic profiling of 100 CD patients with stricturing or penetrating disease behavior (B2/B3) and 100 control samples. Raw data consisted of 1068 MS signals that were processed for peak alignment, filters of presence normalization of signal intensities, imputation of missing values as well as corrections for batch and collection center effects (see FIG. 1). The final dataset included 715 lipid features defined by their m/z, RT and signal intensity. Next, $log_2$-transformed signal intensity values were used to performed statistical analyses of each individual feature to test quantitative differences in circulating levels between CD patients and healthy controls, using regression analysis corrected for sex. Many features were quantitatively different between CD and controls (FIG. 2A). Applying modest thresholds for significance (p-value<0.05; corresponding to false discovery rate with q-value<0.03) 321 features were found that were nominally significantly different between CD and control individuals (Table 2C). Given this large number, the analysis was focused on those of larger effect sizes ($|log_2(FC)|>0.3$) and highest significance (p-value<1E-4, corresponding to a q-value<2E-4). With these more stringent thresholds, 72 features were found to be significantly associated with CD.

Given the untargeted nature of this lipidomic screen, the next step was to determine the identity of these lipid features. This was performed by MS/MS analyses that resulted in the annotation of 46 of these features (46/72, 64%), corresponding to 37 structurally unique lipid molecular species once duplicate ions had been removed (Tables 2A and 2B). Interestingly, these can be grouped into four distinct lipid categories and 12 sub-classes (Table 2C). Among these lipid sub-classes, sphingomyelins (SMs; decreased in CD vs control) are known to modulate inflammatory processes and the intestinal epithelium barrier function. Tables 2A and 2B list the 72 B2/B3-associated lipid features with p-value<1E-4 and |log 2(FC)|>0.3 in IBDGC-1. ID and characteristics of features (m/z, RT, ionization mode, detected adducts and MS/MS fragments considered for annotation) as well as lipid ID and category are shown. Association with B2/B3 vs control (p- and q-values), as well as effect size (log 2(FC)) and standard error (SE) are shown for each feature. Bold lipid IDs correspond to the 15 most significant structurally unique B2/B3-associated lipids, that are also replaced in FIG. 2A. Bold feature IDs correspond to features used for inter-study alignment in Tables 4A and 4B. Table 2C shows the number of B2/B3-associated features annotated by lipid sub-classes (ND are non-determined). Very long-chain dicarboxylic acid (VLCDCA), free fatty acid (FFA), acylcarnitine (AC), lysophosphatidylcholine (LPC), PLC ether (LPCO-), lysophosphatidylethanolamine (LPE), phosphatidylcholine (PC), PC ether (PCO-), phosphatidylethanolamine (PE), PE ether (PEO-), phosphatidylinositol (PI), sphingomyelin (SM), ceramide (Cer), glucosylceramide (Ulcer), cholesterol derivative (Chol der), sterol sulfate (ST sulf), cholesterol ester (CE), diglyceride (DG) and triglyceride (TG) species are shown with various colors as in (A) and (B). ST: sterol, FA: fatty acyl, SP; sphingolipid, GP; glycerophospholipid, GL; glycerolipid.

TABLE 2A

| Feature No. | Feature ID | m/z | RT | Ionization | Adduct | MS/MS Pos fragment S | MS/MS Neg fragment S |
|---|---|---|---|---|---|---|---|
| 1 | Neg:494.3417@14.96 | 493.3339 | 14.96 | Neg | [M − H]− | | 96.96 |
| 2 | Neg:818.6492@32.55 | 817.6414 | 32.55 | Neg | [M + HCOO]− | 184,074, 264,263 | 168.041 |
| 3 | Neg:468.38@13.91 | 469.3878 | 13.91 | Neg | [M − H]− | | 449,360, 431,344, 405,375, 387,366 |
| 4 | Pos:814.6920@36.91 | 815.6998 | 36.91 | Pos | [M + H]+ | 184,074, 264,268 | 168.038 |
| 5 | Neg:765.5287@25.64 | 764.5209 | 25.64 | Neg | [M − H]− | 625,521, 339,292 | 303,229, 281,248 |
| 6 | Pos:800.6763@35.67 | 801.6841 | 35.67 | Pos | [M + H]+ | 184.072 | 168.034 |
| 7 | Pos:798.6613@33.29 | 799.6691 | 33.29 | Pos | [M + H]+ | 184,075, 262,257 | 168.039 |
| 8 | Pos:688.5517@20.11 | 689.5595 | 20.11 | Pos | [M + H]+ | 184,075, 250,253 | 168.042 |
| 9 | Pos:828.7077@37.82 | 829.7155 | 37.82 | Pos | [M + H]+ | 184,075, 278,277 | |
| 10 | Pos:770.6288@28.94 | 771.6366 | 28.94 | Pos | [M + H]+ | 184,073, 262,250 | 168.042 |
| 11 | Neg:453.2843@10.01 | 452.2765 | 10.01 | Neg | [M − H]− | | 255.233 |
| 12 | Neg:844.6649@33.41 | 843.6571 | 33.41 | Neg | [M + HCOO]− | 184,075, 262,257 | 168.039 |
| 13 | Pos:669.6028@37.78 | 670.6106 | 37.78 | Pos | [M + Na]+ | 262.252 | 44.999 |
| 14 | Neg:846.6810@36.20 | 845.6732 | 36.2 | Neg | [M + HCOO]− | 184,075, 264,276 | 168.041 |
| 15 | Neg:466.3104@13.66 | 465.3026 | 13.66 | Neg | [M − H]− | | 96.96 |
| 16 | Neg:614.5578@36.06 | 613.5500 | 36.06 | Neg | | | |
| 17 | Pos:800.6778@36.12 | 801.6856 | 36.12 | Pos | [M + H]+ | 184,075, 264,276 | 168.041 |
| 18 | Pos:744.6136@28.04 | 745.6214 | 28.04 | Pos | [M + H]+ | 184,072, 250,248 | 168.043 |
| 19 | Pos:739.5145@24.89 | 740.5223 | 24.89 | Pos | [M + H]+ | 599,505, 313,275 | 303,231, 255,228 |
| 20 | Pos:784.6457@30.44 | 785.6535 | 30.44 | Pos | [M + H]+ | 184,075, 264,269 | 168.041 |
| 21 | Pos:812.6763@34.03 | 813.6841 | 34.03 | Pos | [M + H]+ | 184,074, 264,262 | 168.039 |
| 22 | Neg:734.5556@20.19 | 733.5478 | 20.19 | Neg | [M + HCOO]− | 184,075, 250,253 | 168.042 |
| 23 | Neg:642.5891@38.30 | 641.5813 | 38.3 | Neg | | | |
| 24 | Neg:874.7123@37.89 | 873.7045 | 37.89 | Neg | [M + HCOO]− | 184,075, 278,277 | 168.043 |
| 25 | Pos:1529.9602@10.03 | 1530.9680 | 10.03 | Pos | | | |
| 26 | Neg:706.6032@37.85 | 705.5954 | 37.85 | Neg | [M + CH2COO]− | | |
| 27 | Neg:1565.1576@27.57 | 1564.14988 | 27.57 | Neg | [2M + HCOO]− | | 804,5715, 281,244, 255,231 |
| 28 | Neg:830.6492@30.56 | 829.6414 | 30.56 | Neg | [M + HCOO]− | 184,075, 264,270 | 168.041 |
| 29 | Neg:481.3155@11.90 | 480.3077 | 11.9 | Neg | [M − H]− | | 283.236 |
| 30 | Pos:364.3061@14.08 | 365.3139 | 14.08 | Pos | | | |
| 31 | Pos:267.2926@14.08 | 268.3004 | 14.08 | Pos | | | |
| 32 | Neg:739.5132@25.00 | 738.5054 | 25 | Neg | [M − H]− | | 303,231, 255,229 |
| 33 | Neg:712.5688@40.39 | 711.5610 | 40.39 | Neg | | | |
| 34 | Pos:239.2613@12.32 | 240.2691 | 12.32 | Pos | | | |
| 35 | Neg:388.3292@14.11 | 387.3214 | 14.11 | Neg | | | |
| 36 | Pos:310.2981@14.08 | 311.3059 | 14.08 | Pos | | | |
| 37 | Pos:336.2749@12.32 | 337.2827 | 12.32 | Pos | | | |
| 38 | Neg:888.5700@25.29 | 887.5622 | 25.29 | Neg | [M − H]− | | 283,259, 305,249, 241,006 |
| 39 | Neg:843.6778@36.68 | 842.6700 | 36.68 | Neg | [M + HCOO]− | 264,272, 618,623 | 634.609 |
| 40 | Pos:575.5631@40.37 | 576.5709 | 40.37 | Pos | | | |
| 41 | Neg:386.3134@12.70 | 385.3056 | 12.7 | Neg | | | |

TABLE 2A-continued

| Feature No. | Feature ID | m/z | RT | Ionization | Adduct | MS/MS Pos fragment S | MS/MS Neg fragment S |
|---|---|---|---|---|---|---|---|
| 42 | Neg:360.2980@12.33 | 359.2902 | 12.33 | Neg | | | |
| 43 | Neg:717.5288@28.34 | 716.5210 | 28.34 | Neg | [M − H]− | 577.521 | 281,248, 255,228 |
| 44 | Pos:826.6920@35.72 | 827.6998 | 35.72 | Pos | [M + H]+ | 184,075, 278,282 | 168.046 |
| 45 | Pos:702.5668@21.45 | 703.5746 | 21.45 | Pos | [M + H]+ | 184,074, 264,262 | 168.036 |
| 46 | Pos:282.2670@12.32 | 283.2748 | 12.32 | Pos | | | |
| 47 | Pos:819.5766@24.89 | 820.5844 | 24.89 | Pos | [M + H]+ | 184.074 | 327,235, 279,226 |
| 48 | Neg:846.6801@35.76 | 845.6723 | 35.76 | Neg | [M + HCOO]− | 184,074, 278,277 | 168.039 |
| 49 | Neg:855.5970@27.18 | 854.5892 | 27.18 | Neg | [M + HCOO]− | | 255,229, 331,261 |
| 50 | Neg:817.5810@26.21 | 816.5732 | 26.21 | Neg | [M + HCOO]− | | 279,230, 269,244 |
| 51 | Neg:709.6562@40.69 | 708.5484 | 40.69 | Neg | [M + HCOO]− | 278.284 | |
| 52 | Pos:1415.1489@51.21 | 1416.1567 | 51.21 | Pos | | | |
| 53 | Pos:826.6918@36.63 | 827.6996 | 36.63 | Pos | | 184,073, 264,266 | 168.041 |
| 54 | Pos:2322.6950@27.48 | 2323.7028 | 27.48 | Pos | | | |
| 55 | Pos:1541.1375@27.46 | 1542.1453 | 27.46 | Pos | | | |
| 56 | Pos:791.5824@25.56 | 792.5902 | 25.56 | Pos | [M + H]+ | | 327,231, 283,235 |
| 57 | Neg:722.6342@40.68 | 721.6264 | 40.68 | Neg | | | |
| 58 | Neg:710.6135@37.85 | 709.6057 | 37.85 | Neg | unknown | | |
| 59 | Neg:801.5499@22.78 | 800.5421 | 22.78 | Neg | [M + HCOO]− | | |
| 60 | Neg:539.3207@7.95 | 538.3129 | 7.95 | Neg | [M + HCOO]− | 184.072 | 253.217 |
| 61 | Neg:693.6253@37.85 | 692.6175 | 37.85 | Neg | [M + HCOO]− | 264,267, 82,063 | |
| 62 | Pos:603.5946@43.22 | 604.6024 | 43.22 | Pos | | | |
| 63 | Neg:710.5535@38.69 | 709.5457 | 38.69 | Neg | | | |
| 64 | Pos:368.3438@51.20 | 369.3516 | 51.2 | Pos | [M + H− H2O]+ | | |
| 65 | Pos:833.5925@25.26 | 834.6003 | 25.26 | Pos | | | |
| 66 | Neg:446.339@13.94 | 445.3312 | 13.94 | Neg | [M − H]− | | 427,322, 401,337, 383,31, 205,157 |
| 67 | Neg:801.5499@22.30 | 800.5421 | 22.3 | Neg | | | |
| 68 | Neg:370.2497@11.05 | 369.2419 | 11.05 | Neg | | | |
| 69 | Neg:777.5502@23.74 | 776.5424 | 23.71 | Neg | | | |
| 70 | Pos:631.6258@47.16 | 632.6336 | 47.16 | Pos | | | |
| 71 | Pos:715.5145@25.33 | 716.5223 | 25.33 | Pos | [M + H]+ | 575.502 | 279,229, 255,229 |
| 72 | Neg:151.0092@11.81 | 150.0014 | 11.81 | Neg | | | |

TABLE 2B

| Feature No. | Lipid category | Lipid ID | B2/B3 vs control log$_2$(FC) | SE | p-value | q-value |
|---|---|---|---|---|---|---|
| 1 | ST | Sitosterol sulfate* | 1.54 | 0.15 | 8.25E−20 | 1.50E−17 |
| 2 | SP | SM(d18:1/21:0) | −0.51 | 0.07 | 3.39E−12 | 3.20E−10 |
| 3 | FA | VLCDCA 28:1(OH) | −1.29 | 0.20 | 4.88E−10 | 3.10E−08 |
| 4 | SP | SM(d18:1/24:0) | −0.84 | 0.13 | 2.45E−09 | 1.10E−07 |
| 5 | GP | PE(18:1_20:4)-1 | 0.55 | 0.09 | 1.16E−08 | 4.30E−07 |
| 6 | SP | SM(d19:1/22:0) | −0.76 | 0.13 | 1.38E−08 | 4.30E−07 |
| 7 | SP | SM(d18:2/23:0) | −0.44 | 0.08 | 2.44E−08 | 5.40E−07 |
| 8 | SP | SM(d17:1/16:0) | −0.32 | 0.06 | 2.71E−08 | 5.40E−07 |
| 9 | SP | SM(d19:1/24:0) | −0.72 | 0.12 | 2.89E−08 | 5.40E−07 |
| 10 | SP | SM(d18:2/21:0) | −0.40 | 0.07 | 4.59E−08 | 6.90E−07 |
| 11 | GP | LPE(16:0) | 0.45 | 0.08 | 4.66E−08 | 6.90E−07 |
| 12 | SP | SM(d18:2/23:0) | −0.46 | 0.08 | 4.81E−08 | 6.90E−07 |
| 13 | SP | Cer(d18:2/24:0) | 0.34 | 0.06 | 6.03E−08 | 7.60E−07 |
| 14 | SP | SM(d18:1/25:1)-1§ | −0.35 | 0.06 | 6.04E−08 | 7.60E−07 |
| 15 | ST | Cholesterol sulfate* | −0.35 | 0.06 | 7.38E−08 | 8.50E−07 |
| 16 | | | −0.76 | 0.14 | 7.66E−08 | 8.50E−07 |
| 17 | SP | SM(d18:1/25:1)-1§ | −0.34 | 0.06 | 8.26E−08 | 8.60E−07 |

TABLE 2B-continued

| Feature No. | Lipid category | Lipid ID | B2/B3 vs control log$_2$(FC) | SE | p-value | q-value |
|---|---|---|---|---|---|---|
| 18 | SP | SM(d17:1/20:0) | −0.33 | 0.06 | 9.74E−08 | 9.20E−07 |
| 19 | GP | PE(16:0_20:4) | 0.53 | 0.10 | 1.53E−07 | 1.40E−06 |
| 20 | SP | SM(d18:1/22:1) | −0.35 | 0.07 | 2.25E−07 | 1.80E−06 |
| 21 | SP | SM(d18:1/24:1) | −0.58 | 0.11 | 3.01E−07 | 2.30E−06 |
| 22 | SP | SM(d17:1/16:0) | −0.32 | 0.06 | 4.80E−07 | 3.30E−06 |
| 23 | | | −0.61 | 0.12 | 5.44E−07 | 3.60E−06 |
| 24 | SP | SM(d19:1/24:0) | −0.53 | 0.10 | 6.40E−07 | 4.10E−06 |
| 25 | | | 0.49 | 0.10 | 7.14E−07 | 4.50E−06 |
| 26 | SP | Cer(d18:1/24:1) | 0.32 | 0.06 | 1.10E−06 | 6.70E−06 |
| 27 | GP | PC(16:0_18:1) | 0.47 | 0.10 | 1.74E−06 | 1.00E−05 |
| 28 | SP | SM(d18:1/22:1) | −0.35 | 0.07 | 2.11E−06 | 1.20E−05 |
| 29 | GP | LPE(18:0) | 0.32 | 0.07 | 2.16E−06 | 1.20E−05 |
| 30 | | | −0.45 | 0.09 | 2.71E−06 | 1.50E−05 |
| 31 | | | −0.46 | 0.10 | 3.54E−06 | 1.80E−05 |
| 32 | GP | PE(16:0_20:4) | 0.45 | 0.09 | 3.60E−06 | 1.80E−05 |
| 33 | | | −0.63 | 0.13 | 3.71E−06 | 1.80E−05 |
| 34 | | | −0.50 | 0.10 | 4.13E−06 | 1.90E−05 |
| 35 | | | −0.46 | 0.10 | 4.14E−06 | 1.90E−05 |
| 36 | | | −0.45 | 0.10 | 5.44E−06 | 2.40E−05 |
| 37 | | | −0.50 | 0.11 | 5.65E−06 | 2.40E−05 |
| 38 | GP | PI(18:0_20:3) | 0.33 | 0.07 | 5.69E−06 | 2.40E−05 |
| 39 | SP | GlcCer(d18:1/23:0) | −0.35 | 0.07 | 6.00E−06 | 2.40E−05 |
| 40 | | | −0.62 | 0.13 | 6.01E−06 | 2.40E−05 |
| 41 | | | −0.49 | 0.11 | 6.03E−06 | 2.40E−05 |
| 42 | | | −0.50 | 0.11 | 7.85E−06 | 3.10E−05 |
| 43 | GP | PE(16:0_18:1) | 0.50 | 0.11 | 9.47E−06 | 3.60E−05 |
| 44 | SP | SM(d19:1/24:1) | −0.51 | 0.11 | 1.00E−05 | 3.80E−05 |
| 45 | SP | SM(d18:1/16:0) | −0.39 | 0.09 | 1.13E−05 | 4.20E−05 |
| 46 | | | −0.36 | 0.08 | 1.21E−05 | 4.30E−05 |
| 47 | GP | PC(17:0_22:6) | −0.50 | 0.11 | 1.22E−05 | 4.30E−05 |
| 48 | SP | SM(d19:1/22:0) | −0.51 | 0.11 | 1.38E−05 | 4.70E−05 |
| 49 | GP | PC(16:0_22:4) | 0.38 | 0.09 | 1.94E−05 | 6.40E−05 |
| 50 | GP | PC(17:0_18:2) | −0.40 | 0.09 | 2.02E−05 | 6.50E−05 |
| 51 | SP | Cer(d19:1/24:0) | −0.40 | 0.09 | 2.20E−05 | 7.00E−05 |
| 52 | | | −0.61 | 0.14 | 2.46E−05 | 7.50E−05 |
| 53 | SP | SM(d18:1/25:1)-2 | −0.42 | 0.10 | 2.49E−05 | 7.50E−05 |
| 54 | | | 0.66 | 0.16 | 3.10E−05 | 9.10E−05 |
| 55 | | | −0.35 | 0.08 | 3.26E−05 | 9.30E−05 |
| 56 | GP | PC(O-16:0/22:6) | 0.36 | 0.08 | 3.26E−05 | 9.30E−05 |
| 57 | | | −0.43 | 0.10 | 3.53E−05 | 9.90E−05 |
| 58 | SP | Cer(d18:1/24:1) | 0.32 | 0.07 | 3.67E−05 | 1.00E−04 |
| 59 | GP | PC(16:0_18:3) | 0.46 | 0.11 | 3.86E−05 | 1.00E−04 |
| 60 | GP | LPC(16:1) | 0.35 | 0.08 | 4.01E−05 | 1.10E−04 |
| 61 | SP | Cer(d18:1/24:1) | 0.30 | 0.07 | 4.52E−05 | 1.20E−04 |
| 62 | | | −0.56 | 0.13 | 4.86E−05 | 1.20E−04 |
| 63 | | | −0.61 | 0.15 | 4.87E−05 | 1.20E−04 |
| 64 | ST | CE(22:6)§§ | −0.57 | 0.14 | 5.40E−05 | 1.30E−04 |
| 65 | FA | | 0.45 | 0.11 | 5.45E−05 | 1.30E−04 |
| 66 | | VLCDCA 28:4 | −0.67 | 0.16 | 6.27E−05 | 1.50E−04 |
| 67 | | | 0.39 | 0.10 | 7.95E−05 | 1.80E−04 |
| 68 | | | 0.53 | 0.13 | 8.41E−05 | 1.90E−04 |
| 69 | | | 0.43 | 0.11 | 9.29E−05 | 2.00E−04 |
| 70 | | | −0.45 | 0.11 | 9.39E−05 | 2.00E−04 |
| 71 | GP | PE(16:0_18:2) | 0.44 | 0.11 | 9.57E−05 | 2.00E−04 |
| 72 | | | 0.62 | 0.16 | 9.61E−05 | 2.00E−04 |

*Confirmed with an anaytical standard

§Identified by MS/MS as SM(d18:1/23:0). but with the same RT as SM(d18:1/25:1)

§§Identified by MS/MS as cholesterol. but with the same RT as CE(22:6)

TABLE 2C

| | | Lipid sub-class | | | | | | | | | | |
|---|---|---|---|---|---|---|---|---|---|---|---|---|
| | | VLCDCA | FFA | AC | LPC | LPCO- | LPE | PC | PCO- | PE | PEO- | PI |
| # features | IBDGC-1 - $p < 0.05$ | 2 | 1 | 3 | 23 | 3 | 11 | 40 | 9 | 10 | 1 | 6 |
| | IBDGC-2 - $p < 0.05$ | 3 | 1 | 3 | 11 | 5 | 9 | 51 | 18 | 14 | 9 | 3 |

TABLE 2C-continued

| | | | | | | | | | |
|---|---|---|---|---|---|---|---|---|---|
| | IBDGCC-1 - p < 1E−4 & $\lvert log_2(FC) \rvert$ > 0.3 | 2 | 1 | 2 | 4 | 1 | 5 | | 1 |
| | IBDGCC-2 - p < 1E−4 & $\lvert log_2(FC) \rvert$ > 0.3 | 3 | | | 3 | 2 | 4 | 5 | |

| | | Lipid sub-class | | | | | | | | | |
|---|---|---|---|---|---|---|---|---|---|---|---|
| | | SM | Cer | Glc-Cer | Chol der | ST sulf | CE | DG | TG | NG | Total |
| # features | IBDGC-1 - p < 0.05 | 47 | 11 | 3 | | 2 | 11 | 3 | 3 | 132 | 321 |
| | IBDGC-2 - p < 0.05 | 60 | 24 | 7 | 1 | 2 | 36 | 5 | 20 | 502 | 784 |
| | IBDGCC-1 - p < 1E−4 & $\lvert log_2(FC) \rvert$ > 0.3 | 20 | 5 | 1 | | 2 | 1 | | | 27 | 72 |
| | IBDGCC-2 - p < 1E−4 & $\lvert log_2(FC) \rvert$ > 0.3 | 14 | 1 | | 1 | 1 | 2 | 1 | 8 | 28 | 73 |

Figure 2B:
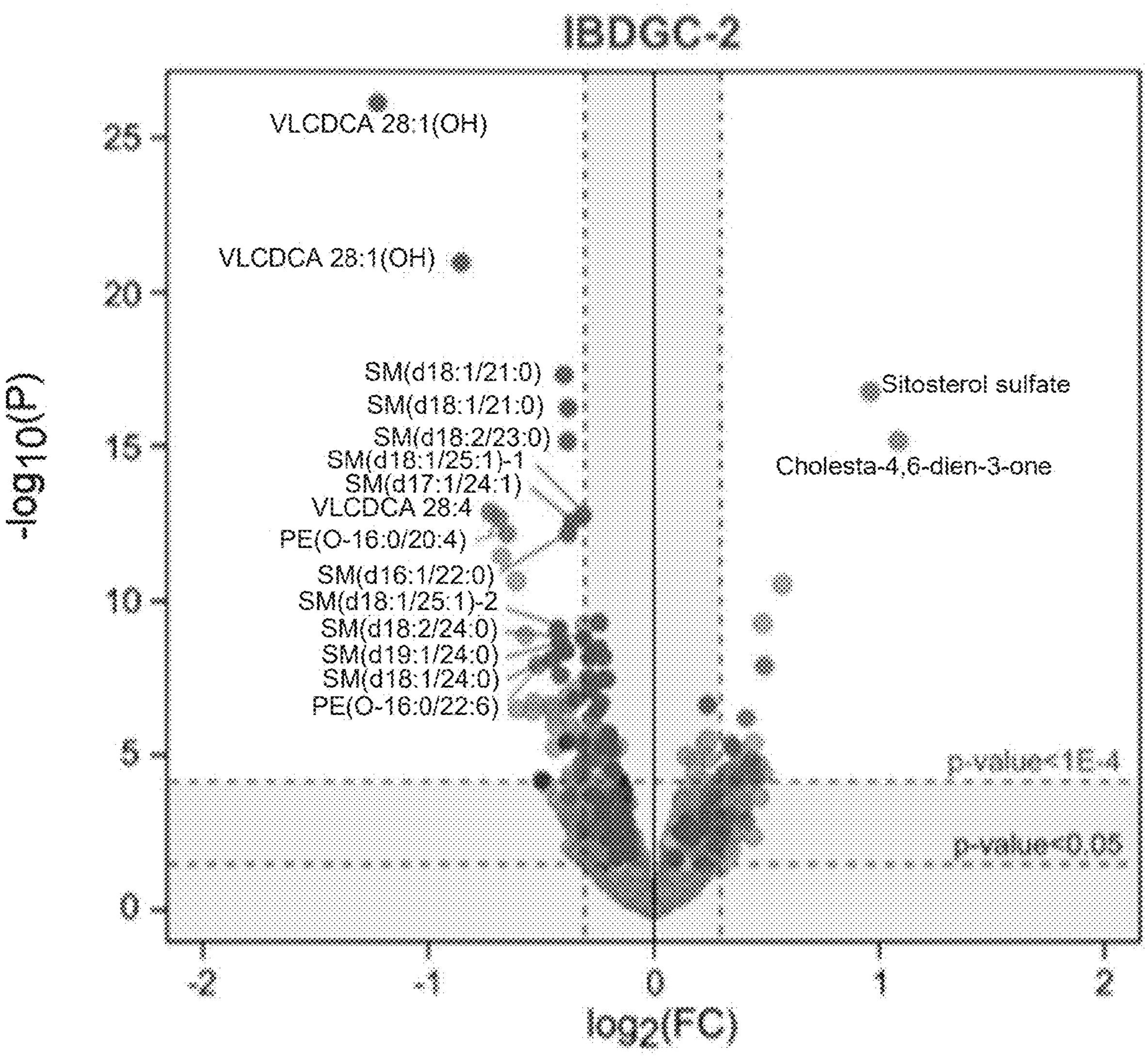

Given these very positive results, this lipidomic profiling was extended to a larger set of samples consisting of 200 CD patients and 200 matched controls (IBDGC-2), that didn't overlap with IBDGC-1. IBDGC-2 had roughly equivalent numbers of cases in the inflammatory (B1) and stricturing (B2) or penetrating (B3) behavior categories (Table 1). Processed MS data retained 1894 features in the final IBDGC-2 dataset. The larger number of detected features, in comparison to IBDGC-1, is attributed to the difference in sensitivity performances between the LC-QTOF instruments used for the two phases. To be comparable to IBDGC-1, the initial analysis of IBDGC-2 focused on CD patients with either B2 or B3 phenotype. Using the same criteria as above (p-value<1E-4, corresponding to q-value<5E-4, and $\lvert log_2(FC) \rvert$>0.3), 73 features were significantly associated with B2/B3 vs control (FIG. 2B). MS/MS analyses of these revealed the identity of 45 (45/73, 62%) (Tables 3A and 3B), corresponding to 38 structurally unique lipid molecular species. Globally, the B2/B3 lipidomic profile observed in IBDGC-2 was remarkably similar to that in IBDGC-1 in terms of lipid categories and sub-classes. The table lists the 73 B2/B3-associated lipid features with p-value<1E-4 and |log 2(FC)|>0.3 in IBDGC-2. ID and characteristics of features (m/z, RT, ionization mode, detected adducts and MS/MS fragments considered for annotation) as well as lipid ID, category and correlation cluster are shown. Association with B2/B3 vs control (p- and q-values), as well as effect size (log 2(FC)) and standard error (SE) are shown for each feature. Bold lipid IDs correspond to the 15 most significant structurally unique B2/B3-associated lipids, that are also replaced in FIG. 2B. Bold feature IDs correspond to the features used for inter-study alignment in Tables 4A and 4B. Feature IDs in with an asterisk are the components of the classification model. FA: fatty acyl, SP: sphingolipid, ST; sterol, GP: glycerophospholipid, GL; glycerolipid.

TABLE 3A

| | | Feature characteristics | | | | | |
|---|---|---|---|---|---|---|---|
| Feature No. | Feature ID | m/z | RT | Ionization | Adduct | MS/MS Pos fragments | MS/MS Neg fragments |
| 73* | **Neg: 468.3817@12.87** | 467.3739 | 12.9 | Neg | [M − H]− | | 449, 360, 431, 344, 405, 375, 387, 366 |
| 74 | Pos: 468.3809@12.93 | 469.3887 | 12.9 | Pos | [M + H]+ | | |
| 75* | **Pos: 772.6469@30.80** | 773.6547 | 30.8 | Pos | [M + H]+ | 184,074, 264, 263 | 168.041 |
| 76* | **Neg: 494.3450@13.93** | 493.3372 | 13.9 | Neg | [M − H]− | | 96.959 |
| 77 | Neg: 818.6498@30.55 | 817.642 | 30.6 | Neg | [M + HCOO]− | 184,074, 264, 263 | 168.041 |
| 78 | **Pos: 382.3253@18.09** | 383.3331 | 18.1 | Pos | [M + H]+ | 95,085, 81,070 | |
| 79 | **Pos: 798.6629@31.63** | 799.6707 | 31.6 | Pos | [M + H]+ | 184,075, 262, 257 | 168.039 |
| 80 | **Neg: 446.3394@13.11** | 445.3316 | 13.1 | Neg | [M − H]− | | 427, 322, 401, 337, 383, 31, 205, 157 |
| 81 | **Pos: 800.6783@34.78** | 801.6861 | 34.8 | Pos | [M + H]+ | 184,075, 264, 276 | 168.041 |
| 82* | **Neg: 725.5345@25.50** | 724.5267 | 25.5 | Neg | [M − H]− | 585.523 | 303.223 |

TABLE 3A-continued

| Feature No. | Feature ID | Feature characteristics m/z | RT | Ionization | Adduct | MS/MS Pos fragments | MS/MS Neg fragments |
|---|---|---|---|---|---|---|---|
| 83 | Neg: 844.6655@31.39 | 843.6577 | 31.4 | Neg | [M + HCOO]− | 184,075, 262, 257 | 168.039 |
| 84 | **Pos: 758.6315@28.70** | 759.6393 | 28.7 | Pos | [M + H]+ | 184,075, 236, 237 | 168.041 |
| 85 | Pos: 725.5367@25.70 | 726.5445 | 25.7 | Pos | [M + H]+ | 585.523 | 303.223 |
| 86* | Pos: 552.4389@14.25 | 553.4467 | 14.3 | Pos | | | |
| 87 | Pos: 534.4276@14.26 | 535.4354 | 14.3 | Pos | | | |
| 88 | Pos: 412.2979@9.95 | 413.3057 | 9.95 | Pos | | | |
| 89* | Pos: 771.5425@19.10 | 772.5503 | 19.1 | Pos | | | |
| 90* | Pos: 368.3443@12.77 | 369.3521 | 12.8 | Pos | | | |
| 91 | Neg: 872.6961@35.25 | 871.6883 | 35.3 | Neg | [M + HCOO]− | 184,075, 264, 272 | 168.039 |
| 92 | Pos: 749.5364@24.89 | 750.5442 | 24.9 | Pos | | | |
| 93 | Pos: 1215.0900@52.85 | 1216.098 | 52.9 | Pos | | | |
| 94 | **Pos: 812.6785@33.81** | 813.6863 | 33.8 | Pos | [M + H]+ | 184,075, 262, 254 | 168.041 |
| 95 | **Pos: 828.7092@36.62** | 829.717 | 36.6 | Pos | [M + H]+ | 184,075, 278, 277 | |
| 96 | **Neg: 860.6963@35.57** | 859.6885 | 35.6 | Neg | [M + HCOO]− | 184,073, 264, 270 | 168.043 |
| 97 | **Neg: 749.5352@24.71** | 748.5274 | 24.7 | Neg | [M − H]− | 609.528 | 327, 2262, 438, 29 |
| 98 | **Pos: 700.5516@19.06** | 701.5594 | 19.1 | Pos | [M + H]+ | 184,075, 262, 246 | |
| 99 | **Pos: 753.5687@29.69** | 754.5765 | 29.7 | Pos | [M + H]+ | 613.539 | 303, 2349, 466, 31 |
| 100 | **Pos: 921.7813@49.56** | 922.7891 | 49.6 | Pos | [M + NH4]+ | 601, 53, 623, 52, 625, 53 | |
| 101 | **Pos: 633.6055@30.86** | 634.6133 | 30.9 | Pos | [M + H]+ | 262.256 | |
| 102 | Neg: 845.6132@28.88 | 844.6054 | 28.9 | Neg | [M + HCOO]− | 184.075 | 279.234 |
| 103 | Pos: 607.5886@30.05 | 608.5964 | 30.1 | Pos | [M + H]+ | 250.253 | |
| 104 | Neg: 874.7116@36.49 | 873.7038 | 36.5 | Neg | [M + HCOO]− | 184,075, 278, 277 | |
| 105 | Pos: 265.2768@11.82 | 266.2846 | 11.8 | Pos | | | |
| 106 | Pos: 308.2831@11.82 | 309.2909 | 11.8 | Pos | | | |
| 107 | **Pos: 777.5696@28.78** | 778.5774 | 28.8 | Pos | [M + H]+ | 637.556 | 327, 2348, 466, 31 |
| 108 | Neg: 642.5898@36.90 | 641.582 | 36.9 | Neg | | | |
| 109 | Pos: 267.2929@13.16 | 268.3007 | 13.2 | Pos | | | |
| 110 | Pos: 362.2902@11.83 | 363.298 | 11.8 | Pos | | | |
| 111 | Neg: 670.6212@39.00 | 669.6134 | 39 | Neg | | | |
| 112 | Pos: 310.2988@13.17 | 311.3066 | 13.2 | Pos | | | |
| 113 | **Pos: 928.7515@54.39** | 929.7593 | 54.4 | Pos | [M + Na]+ | 341, 3 (18:0), 339, 295 (18:1) | 647, 502, 625, 518 |
| 114* | Neg: 873.6871@35.86 | 872.6793 | 35.9 | Neg | | | |
| 115 | Neg: 386.3151@11.79 | 385.3073 | 11.8 | Neg | | | |
| 116 | Pos: 853.5630@19.62 | 854.5708 | 19.6 | Pos | | | |
| 117 | **Pos: 613.5800@52.89** | 614.5878 | 52.9 | Pos | [M + NH4]+ | 369.354 | |
| 118 | **Pos: 607.5179@28.48** | 608.5257 | 28.5 | Pos | [M + NH4]+ | 311, 253, 337, 275 | |
| 119 | **Pos: 826.6932@35.39** | 827.701 | 35.4 | Pos | [M + H]+ | 184,075, 264, 273 | 168.037 |
| 120 | Pos: 885.7788@51.00 | 886.7866 | 51 | Pos | [M − C3H6 + NH4]+ | | |
| 121 | Pos: 296.2815@12.27 | 297.2893 | 12.3 | Pos | | | |
| 122 | **Pos: 927.8238@51.00** | 928.8316 | 51 | Pos | [M + NH4]+ | | |
| 123 | Pos: 414.3497@20.82 | 415.3575 | 20.8 | Pos | | | |
| 124 | **Pos: 949.8111@53.74** | 950.8189 | 53.7 | Pos | | | |
| 125 | **Pos: 819.6146@27.95** | 820.6224 | 28 | Pos | [M + H]+ | 184.075 | 327.232 |
| 126 | Pos: 919.7688@45.95 | 920.7766 | 46 | Pos | | | |
| 127 | **Pos: 833.5946@25.01** | 834.6024 | 25 | Pos | [M + H]+ | 184.075 | 329, 244, 281, 242 |
| 128 | Pos: 336.2748@11.48 | 337.2826 | 11.5 | Pos | | | |
| 129 | **Pos: 895.7651@49.23** | 896.7729 | 49.2 | Pos | [M + NH4]+ | 575, 505, 599, 505, 623, 605 | |

TABLE 3A-continued

| Feature No. | Feature ID | m/z | RT | Ionization | Adduct | MS/MS Pos fragments | MS/MS Neg fragments |
|---|---|---|---|---|---|---|---|
| | | Feature characteristics | | | | | |
| 130 | Pos: 936.7921@49.24 | 937.7999 | 49.2 | Pos | | | |
| 131 | Pos: 684.5469@43.77 | 685.5547 | 43.8 | Pos | | | |
| 132 | **Neg: 793.5603@27.53** | 792.5525 | 27.5 | Neg | [M − H]− | 653.553 | 329, 2450, 283, 2572 |
| 133 | **Neg: 765.5314@24.31** | 764.5236 | 24.3 | Neg | [M − H]− | 625.522 | 303, 227, 281, 24 |
| 134 | Neg: 254.2259@11.45 | 253.2181 | 11.5 | Neg | | | |
| 135 | Neg: 360.2995@11.43 | 359.2917 | 11.4 | Neg | | | |
| 136 | **Pos: 847.6474@31.97** | 848.6552 | 32 | Pos | [M + H]+ | 184.076 | 327.229 |
| 137 | Pos: 717.5316@26.75 | 718.5394 | 26.8 | Pos | | | |
| 138 | **Pos: 947.7953@51.13** | 948.8031 | 51.1 | Pos | [M + NH4]+ | 601, 52, 649, 52, 651, 51 | |
| 139 | Pos: 239.2616@11.48 | 240.2694 | 11.5 | Pos | | | |
| 140 | **Pos: 897.7805@53.99** | 898.7883 | 54 | Pos | [M + NH4]+ | 577, 52, 599, 50, 625, 51 | |
| 141* | **Pos: 611.5657@47.54** | 612.5735 | 47.5 | Pos | [M + NH4]+ | 369.357 | |
| 142 | **Pos: 803.5477@18.76** | 804.5555 | 18.8 | Pos | [M + H]+ | 184.074 | |
| 143 | **Neg: 717.5297@26.55** | 716.5219 | 26.6 | Neg | [M − H]− | 577.521 | 281, 239, 255, 22 |
| 144 | **Neg: 765.5307@23.93** | 764.5229 | 23.9 | Neg | [M − H]− | 625, 522, 339, 295 | 303, 227, 281, 24 |
| 145 | Pos: 564.5340@11.48 | 565.5418 | 11.5 | Pos | | | |

TABLE 3B

| Feature No. | Lipid category | Cluster | Lipid ID | B2/B3 vs control log$_2$(FC) | SE | p-value | q-value |
|---|---|---|---|---|---|---|---|
| 73 | FA | B | **VLCDCA 28:1(OH)** | −1.23 | 0.10 | 7.69E−27 | 4.50E−24 |
| 74 | FA | B | VLCDCA 28:1(OH) | −0.86 | 0.08 | 1.11E−21 | 3.30E−19 |
| 75 | SP | C | **SM(d18:1/21:0)** | −0.40 | 0.04 | 5.12E−18 | 1.00E−15 |
| 76 | ST | D | **Sitosterol sulfate*** | 0.96 | 0.11 | 1.79E−17 | 2.60E−15 |
| 77 | SP | C | SM(d18:1/21:0) | −0.38 | 0.04 | 6.03E−17 | 7.10E−15 |
| 78 | ST | D | **Cholesta-4,6-dien-3-one*** | 1.09 | 0.13 | 6.87E−16 | 5.90E−14 |
| 79 | SP | C | **SM(d18:2/23:0)** | −0.38 | 0.04 | 6.96E−16 | 5.90E−14 |
| 80 | FA | B | **VLCDCA 28:4** | −0.73 | 0.09 | 1.38E−13 | 1.00E−11 |
| 81 | SP | C | **SM(d18:1/25:1)-1§** | −0.32 | 0.04 | 1.71E−13 | 1.10E−11 |
| 82 | GP | A | **PE(O-16:0/20:4)** | −0.69 | 0.09 | 2.13E−13 | 1.30E−11 |
| 83 | SP | C | **SM(d17:1/24:1)** | −0.36 | 0.05 | 2.86E−13 | 1.50E−11 |
| 84 | SP | C | **SM(d16:1/22:0)** | −0.38 | 0.05 | 6.83E−13 | 3.10E−11 |
| 85 | GP | A | PE(O-16:0/20:4) | −0.65 | 0.09 | 6.85E−13 | 3.10E−11 |
| 86 | | B | | −0.68 | 0.09 | 3.98E−12 | 1.70E−10 |
| 87 | | B | | −0.61 | 0.09 | 2.23E−11 | 8.70E−10 |
| 88 | | D | | 0.57 | 0.08 | 2.95E−11 | 1.10E−09 |
| 89 | | | | 0.48 | 0.08 | 5.49E−10 | 1.80E−08 |
| 90 | | | | −0.31 | 0.05 | 6.23E−10 | 1.90E−08 |
| 91 | SP | C | **SM(d18:1/25:1)-2** | −0.42 | 0.07 | 7.98E−10 | 2.30E−08 |
| 92 | | A | | −0.43 | 0.07 | 1.13E−09 | 3.20E−08 |
| 93 | | E | | −0.57 | 0.09 | 1.32E−09 | 3.50E−08 |
| 94 | SP | C | **SM(d18:2/24:0)** | −0.31 | 0.05 | 1.75E−09 | 4.50E−08 |
| 95 | SP | C | **SM(d19:1/24:0)** | −0.41 | 0.07 | 2.43E−09 | 6.00E−08 |
| 96 | SP | C | **SM(d18:1/24:0)** | −0.39 | 0.06 | 4.07E−09 | 9.20E−08 |
| 97 | GF | A | **PE(O-16:0/22:6)** | −0.41 | 0.07 | 4.60E−09 | 1.00E−07 |
| 98 | SP | C | SM(d18:2/16:0) | −0.45 | 0.08 | 7.83E−09 | 1.50E−07 |
| 99 | GP | A | PE(O-18:0/20:4) | −0.52 | 0.09 | 1.17E−08 | 2.20E−07 |
| 100 | GL | D | TG(18:1_18:2_20:4) | 0.49 | 0.08 | 1.27E−08 | 2.30E−07 |
| 101 | SP | C | SM(d17:1/24:1)§§ | −0.41 | 0.07 | 2.49E−08 | 4.30E−07 |
| 102 | GP | C | PC(19:0_18:2) | −0.34 | 0.06 | 6.87E−08 | 1.00E−06 |
| 103 | SP | C | Cer(d16:1/23:0) | −0.39 | 0.07 | 1.25E−07 | 1.80E−06 |
| 104 | SP | C | SM(d19:1/24:0) | −0.35 | 0.06 | 1.50E−07 | 2.10E−06 |
| 105 | | A | | −0.53 | 0.10 | 1.95E−07 | 2.60E−06 |
| 106 | | A | | −0.46 | 0.09 | 2.40E−07 | 3.10E−06 |
| 107 | GP | A | PE(O-18:0/22:6) | −0.38 | 0.07 | 2.57E−07 | 3.20E−06 |
| 108 | | A | | −0.60 | 0.12 | 3.30E−07 | 4.00E−06 |
| 109 | | A | | −0.45 | 0.09 | 3.44E−07 | 4.10E−06 |
| 110 | | A | | −0.45 | 0.09 | 3.53E−07 | 4.10E−06 |
| 111 | | A | | −0.53 | 0.10 | 3.93E−07 | 4.50E−06 |

TABLE 3B-continued

| Feature No. | Lipid category | Cluster | Lipid ID | B2/B3 vs control log$_2$(FC) | SE | p-value | q-value |
|---|---|---|---|---|---|---|---|
| 112 | | A | | −0.44 | 0.09 | 6.21E−07 | 6.90E−06 |
| 113 | GL | D | TG(16:0_18:1_22:5) | 0.41 | 0.08 | 6.52E−07 | 7.10E−06 |
| 114 | | | | −0.37 | 0.07 | 1.20E−06 | 1.30E−05 |
| 115 | | A | | −0.44 | 0.09 | 1.23E−06 | 1.30E−05 |
| 116 | | A | | −0.32 | 0.07 | 2.38E−06 | 2.30E−05 |
| 117 | ST | E | CE(14:0) | −0.39 | 0.08 | 4.01E−06 | 3.70E−05 |
| 118 | GL | D | DG(16:0_18:2) | 0.44 | 0.09 | 4.19E−06 | 3.70E−05 |
| 119 | SP | C | SM(d18:1/25:1)-2 | −0.32 | 0.07 | 4.46E−06 | 3.90E−05 |
| 120 | GL | D | TG(56:4) | 0.34 | 0.07 | 4.56E−06 | 3.90E−05 |
| 121 | | A | | −0.44 | 0.10 | 5.96E−06 | 4.70E−05 |
| 122 | GL | D | TG(56:4) | 0.35 | 0.08 | 6.40E−06 | 5.00E−05 |
| 123 | | | | 0.39 | 0.09 | 7.80E−06 | 5.90E−05 |
| 124 | GL | D | TG(18:1_18:2_22:4) | 0.44 | 0.10 | 1.60E−05 | 1.10E−04 |
| 125 | GP | A | PC(O-18:0/22:6) | −0.32 | 0.07 | 1.79E−05 | 1.20E−04 |
| 126 | | D | | 0.38 | 0.09 | 1.81E−05 | 1.20E−04 |
| 127 | GP | D | PC(18:1_22:5) | 0.47 | 0.11 | 1.99E−05 | 1.30E−04 |
| 128 | | A | | −0.32 | 0.07 | 2.33E−05 | 1.50E−04 |
| 129 | GL | D | TG(18:2_16:0_20:4) | 0.42 | 0.10 | 2.53E−05 | 1.60E−04 |
| 130 | | D | | 0.44 | 0.10 | 2.55E−05 | 1.60E−04 |
| 131 | | | | 0.38 | 0.09 | 2.84E−05 | 1.70E−04 |
| 132 | GP | D | PE(18:0_22:5) | 0.34 | 0.08 | 3.22E−05 | 1.90E−04 |
| 133 | GP | D | PE(18:1_20:4)-2 | 0.32 | 0.08 | 3.93E−05 | 2.30E−04 |
| 134 | | | | 0.49 | 0.12 | 4.27E−05 | 2.50E−04 |
| 135 | | A | | −0.37 | 0.09 | 4.37E−05 | 2.50E−04 |
| 136 | GP | A | PC(O-20:0/22:6) | −0.32 | 0.08 | 4.73E−05 | 2.70E−04 |
| 137 | | D | | 0.39 | 0.09 | 4.74E−05 | 2.70E−04 |
| 138 | GL | D | TG(18:1_18:2_22:5) | 0.45 | 0.11 | 5.67E−05 | 3.20E−04 |
| 139 | | A | | −0.33 | 0.08 | 6.37E−05 | 3.50E−04 |
| 140 | GL | D | TG(16:0_18:1_20:4) | 0.37 | 0.09 | 6.75E−05 | 3.60E−04 |
| 141 | ST | E | CE(14:1) | −0.50 | 0.12 | 6.97E−05 | 3.70E−04 |
| 142 | GP | A | PC(18:2_20:5) | −0.37 | 0.09 | 6.98E−05 | 3.70E−04 |
| 143 | GP | D | PE(16:0_18:1) | 0.38 | 0.09 | 7.06E−05 | 3.70E−04 |
| 144 | GP | D | PE(18:1_20:4)-1 | 0.32 | 0.08 | 8.67E−05 | 4.30E−04 |
| 145 | | A | | −0.47 | 0.12 | 9.46E−05 | 4.60E−04 |

Replicability of results between the two IBDGC studies was also assessed by a manual inter-study alignment based on feature characteristics (i.e. MS/MS spectra and RT matching to avoid misinterpretation related to potential isomers), primarily focusing on annotated unique lipid molecular species associated with B2/B3 vs control with p-value<1E-4 and $|\log_2(FC)|>0.3$ in either dataset and detected in both datasets (Tables 4A and 4B). High replicability was found between findings obtained through independent analyses of the two IBDGC studies using two LC-QTOF instruments in a year and a half-interval (Tables 4A and 4B). Nearly 90% (28 of 32) of these were associated with B2/B3 with p-value<0.05 in both datasets. It should be noted, however, given the greater sensitivity performance in IBDGC-2, we not only identified more ether lipids of both phosphatidylcholine (i.e. PCO-) and phosphatidylethanolamine (i.e. PEO-) that were lower in CD patients, but we also identified two additional lipids that were associated to CD, but that were not detectable in the first phase. These were: (i) $C_{4,6}D_3O$ (higher in CD patients) and (ii) cholesterol ester (CE 14:1); lower).

Figure 9A:
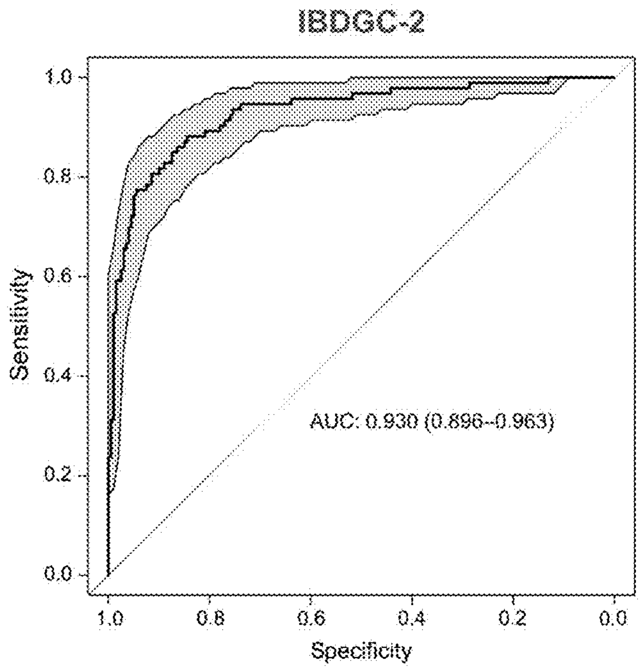
FIG. 9A and FIG. 9B are ROC curves presenting the performances of the alternate classification model built from the IBDGC-2 dataset consisting of 16 B2/B3-associated lipids with p-value<1E-4 and $|log_2(FC)|>0.3$, and also detected in IBDGC-1, for discriminating B2/B3 vs control. This alternate model is built with five components listed in (Table 7). X- and y-axes correspond to the specificity and sensitivity of the model. The 95% CI is shown in grey and performances are expressed as AUC. ROC curves show performance for B2/B3 vs control classification in IBDGC-2 (FIG. 9A) and IBDGC-1 (FIG. 9B). In these conditions, IBDGC-1 constitutes an independent set of samples for model validation.

Tables 4A and 4B lists 27 and 36 annotated lipid molecular species associated with B2/B3 vs control with p-value<1E-4 and |log 2(FC)|>0.3 in IBDGC-1 and 2, respectively, that were included in the inter-study alignment. Feature IDs and adducts are shown, as well as the corresponding lipid IDs. Association for B2/B3 vs control (p- and q-values) as well as effect size (log 2(FC)) are shown for each feature, in both datasets. Symbols Ø indicate that the feature was not detected in the dataset. Bold feature IDs correspond to features associated with p-value<0.05 in the other dataset. Grey feature IDs correspond to features with p-value>1E-4 and/or |log 2(FC)|<0.3 in the corresponding dataset. Bold lipid IDs correspond to 16 B2/B3-associated features in IBDGC-2, also detected in IBDGC-1, and used to build the alternate classification model (FIG. 9).

For inter-study alignment, Neg features were considered for ceramides. Whereas the Cer(d16:1/23:0)-corresponding feature, namely Pos:607.5886@30.05, was associated with B2/B3 vs control in IBDGC-2 (Tables 3A and 3B), the corresponding Neg feature was not detected in either of the two datasets. For similar reasons PC(19:0_18:2) is missing in the list, and 36 instead of 38 B2/B3-associated lipids were included in the list for IBDGC-2. Similarly, 27 instead of 37 B2/B3-associated lipids were included in the list for IBDGC-1. Accordingly, 96% (26/27) of the B2/B3-associated lipids with p-value<1E-4 and |log 2(FC)|>0.3 in IBDGC-1 were also detected in IBDGC-2, and 89% (24/27) were also associated with p-value<0.05 in IBDGC-2. Conversely, of the 36 B2/B3-associated lipids with p-value<1E-4 and |log 2(FC)|>0.3 in IBDGC-2, 21 could not be detected in IBDGC-1, with 93% (14/15) of the remaining being associated with p-value<0.05 in IBDGC-1.

For the 31 B2/B3-associated lipids with p-value<1E-4 and |log 2(FC)|>0.3 in at least one dataset and detected in both datasets, association (p-value) was calculated for the combined datasets (combined-IBDGC). Crossed-out boxes are for features not detected in one or the other dataset. Symbols * indicate 19 unique lipid molecular species associated with B2/B3 vs control with p-value<1E-4 in both datasets.

TABLE 4A

| | IBDGC-1 | | | | |
|---|---|---|---|---|---|
| Lipid ID | Feature ID | Adduct | $log_2$(FC) | p-value | q-value |
| Sitosterol sulfate* | Neg:494.3417@14.96 | | 1.54 | 8.25E−20 | 1.55E−17 |
| VLCDCA 28:1(OH)* | Neg:468.38@13.91 | H− | −1.29 | 4.88E−10 | 3.05E−08 |
| SM(d18:2/23:0)* | Pos:798.6613@33.29 | H+ | −0.44 | 2.44E−08 | 5.42E−07 |
| SM(d18:1/25:1)-1* | Pos:800.6778@36.12 | H+ | −0.34 | 8.26E−08 | 8.60E−07 |
| SM(d18:1/24:0)* | Pos:814.6920@36.91 | H+ | −0.84 | 2.45E−09 | 1.15E−07 |
| SM(d18:1/21:0) | Pos:772.6455@62.43 | H+ | −0.36 | 1.69E−03 | 1.98E−03 |
| SM(d19:1/24:0)* | Pos:828.7077@37.82 | H+ | −0.72 | 2.89E−08 | 5.42E−07 |
| VLCDCA 28:4* | Neg:446.339@13.94 | H− | −0.67 | 6.27E−05 | 1.47E−04 |
| SM(d17:1/16:0)* | Pos:688.5517@20.11 | H+ | −0.32 | 2.71E−08 | 5.42E−07 |
| PE(O-16:0/20:4) | Neg:725.5345@27.36 | H− | −0.49 | 4.41E−04 | 6.72E−04 |
| Cholesterol sulfate* | Neg:466.3104@13.66 | H− | −0.35 | 7.38E−08 | 8.45E−07 |
| SM(d18:1/22:1)* | Pos:784.6457@30.44 | H+ | −0.35 | 2.25E−07 | 1.83E−06 |
| SM(d18:1/19:0)* | Pos:744.6136@28.04 | | −0.33 | 9.74E−08 | 9.22E−07 |
| PE(18:1_20:4)-1* | Neg:765.5287@25.64 | H− | 0.55 | 1.16E−08 | 4.32E−07 |
| SM(d18:2/24:0) | Pos:812.6777@36.36 | H+ | −0.29 | 4.26E−04 | 6.65E−04 |
| LPE(16:0)* | Neg:453.2843@10.01 | H− | 0.45 | 4.66E−08 | 6.94E−07 |
| SM(d19:1/22:0) | Pos:800.6763@35.67 | H+ | −0.76 | 1.38E−08 | 4.32E−07 |
| GlcCer(d18:1/23:0)* | Neg:843.6778@36.68 | FA-H | −0.35 | 6.00E−06 | 2.41E−05 |
| SM(d18:1/25:1)-2* | Pos:826.6918@36.63 | H+ | −0.42 | 2.49E−05 | 7.54E−05 |
| Cer(d18:1/24:1)* | Neg:693.6253@37.85 | FA-H | 0.30 | 4.52E−05 | 1.17E−04 |
| SM(d18:1/24:1) | Pos:812.6763@34.03 | H+ | −0.58 | 3.01E−07 | 2.35E−06 |
| SM(d18:2/21:0) | Pos:770.6288@28.94 | H+ | −0.40 | 4.59E−08 | 6.94E−07 |
| PE(16:0_20:4) | Neg:739.5132@25.00 | H− | 0.45 | 3.60E−06 | 1.82E−05 |
| PC(O-16:0/22:6)* | Pos:791.5824@25.56 | H+ | −0.35 | 3.26E−05 | 9.27E−05 |
| PE(16:0_18:1)* | Neg:717.5288@28.34 | H− | 0.50 | 9.47E−06 | 3.63E−05 |
| Cer(d19:1/24:0)* | Neg:709.6562@40.69 | FA-H | −0.40 | 2.20E−05 | 7.00E−05 |
| PE(O-16:0/22:6) | Neg:749.5352@26.51 | H− | −0.27 | 2.16E−02 | 1.47E−02 |
| TG(18:1_18:2_20:4) | Pos:926.7334@53.40 | Na+ | 0.26 | 1.24E−01 | 5.64E−02 |
| SM(d19:1/24:1) | Pos:826.6920@35.72 | H+ | −0.51 | 1.00E−05 | 3.77E−05 |
| LPE(18:0) | Neg:481.3155@11.90 | H− | 0.32 | 2.16E−06 | 1.19E−05 |
| PI(18:0_20:3) | Neg:888.5700@25.29 | H− | 0.33 | 5.69E−06 | 2.41E−05 |
| SM(d18:1/16:0) | Pos:702.5668@21.45 | H+ | −0.39 | 1.13E−05 | 4.17E−05 |
| Cholesta-4,6-dien-3-one | Ø | | | | |
| SM(d16:1/22:0) | Ø | | | | |
| SM(d18:2/16:0) | Ø | | | | |
| PE(O-18:0/20:4) | Ø | | | | |
| SM(d17:1/24:1) | Ø | | | | |
| PE(O-18:0/22:6) | Ø | | | | |
| TG(16:0_18:1_22:5) | Ø | | | | |
| DG(16:0_18:2) | Ø | | | | |
| TG(56:4) | Ø | | | | |
| TG(18:1_18:2_22:4) | Ø | | | | |
| PC(O-18:0/22:6) | Ø | | | | |
| PC(18:1_22:5) | Ø | | | | |
| TG(18:2_16:0_20:4) | Ø | | | | |
| PE(18:0_22:5) | Ø | | | | |
| PE(18:1_20:4)-2 | Ø | | | | |
| PC(O-20:0/22:6) | Ø | | | | |
| TG(18:1_18:2_22:5) | Ø | | | | |
| TG(16:0_18:1_20:4) | Ø | | | | |
| CE(14:1) | Ø | | | | |
| CE(14:0) | Ø | | | | |
| PC(18:2_20:5) | Ø | | | | |

TABLE 4B

| | IBDGC-2 | | | | | Combined- |
|---|---|---|---|---|---|---|
| Lipid ID | Feature ID | Adduct | $log_2$(FC) | p-value | q-value | IBDGC p-value |
| **Sitosterol sulfate*** | **Neg: 494.3450@13.93** | | 0.96 | 1.79E−17 | 2.63E−15 | 1.28E−35 |
| **VLCDCA 28:1(OH)*** | **Neg: 468.3817@12.87** | H− | −1.23 | 7.69E−27 | 4.53E−24 | 4.28E−33 |
| **SM(d18:2/23:0)*** | **Pos: 798.6629@31.63** | H+ | −0.38 | 6.96E−16 | 5.85E−14 | 4.85E−22 |
| **SM(d18:1/25:1)-1*** | **Pos: 800.6783@34.78** | H+ | −0.32 | 1.71E−13 | 1.12E−11 | 2.21E−19 |
| **SM(d18:1/24:0)*** | **Neg: 860.6963@35.57** | FA − H | −0.39 | 4.07E−09 | 9.23E−08 | 5.46E−17 |
| **SM(d18:1/21:0)** | **Pos: 772.6469@30.80** | H+ | −0.40 | 5.12E−18 | 1.01E−15 | 7.60E−17 |
| **SM(d19:1/24:0)*** | **Pos: 828.7092@36.62** | H+ | −0.41 | 2.43E−09 | 5.95E−08 | 3.89E−16 |
| **VLCDCA 28:4*** | **Neg: 446.3394@13.11** | H− | −0.73 | 1.38E−13 | 1.02E−11 | 7.53E−16 |
| SM(d17:1/16:0)* | Pos:688.5532@18.89 | H+ | −0.23 | 6.58E−09 | 1.34E−07 | 9.52E−16 |
| **PE(O-16:0/20:4)** | **Neg: 725.5345@25.50** | H− | −0.69 | 2.13E−13 | 1.26E−11 | 1.65E−14 |
| Cholesterol sulfate* | Neg:466.3133@12.72 | H− | −0.28 | 6.88E−07 | 7.37E−06 | 2.55E−13 |
| SM(d18:1/22:1)* | Pos:784.6473@28.86 | H+ | −0.20 | 2.10E−06 | 2.10E−05 | 2.29E−12 |

TABLE 4B-continued

| | IBDGC-2 | | | | | Combined- |
|---|---|---|---|---|---|---|
| Lipid ID | Feature ID | Adduct | $\log_2$(FC) | p-value | q-value | IBDGC p-value |
| SM(d18:1/19:0)* | Pos:744.6146@26.54 | H+ | −0.18 | 6.76E−06 | 5.17E−05 | 3.58E−12 |
| **PE(18:1_20:4)-1*** | **Neg: 765.5307@23.93** | H− | 0.32 | 8.67E−05 | 4.26E−04 | 9.75E−12 |
| **SM(d18:2/24:0)** | **Pos: 812.6785@33.81** | H+ | −0.31 | 1.75E−09 | 4.49E−08 | 1.50E−11 |
| LPE(16:0)* | Neg:453.2858@9.43 | H− | 0.24 | 8.37E−05 | 4.14E−04 | 3.03E−11 |
| SM(d19:1/22:0) | Pos:800.6780@34.20 | H+ | −0.27 | 2.00E−04 | 8.13E−04 | 3.08E−11 |
| GlcCer(d18:1/23:0)* | Neg:843.6766@35.29 | FA − H | −0.23 | 5.19E−06 | 4.19E−05 | 1.34E−10 |
| **SM(d18:1/25:1)-2*** | **Pos: 826.6932@35.39** | H+ | −0.32 | 4.46E−06 | 3.87E−05 | 4.81E−10 |
| Cer(d18:1/24:1)* | Neg:693.6257@36.52 | | 0.24 | 3.36E−06 | 3.14E−05 | 6.79E−10 |
| SM(d18:1/24:1) | Pos:612.6777@32.37 | H+ | −0.21 | 4.48E−04 | 1.41E−03 | 1.03E−09 |
| SM(d18:2/21:0) | Pos:770.6287@27.41 | H+ | −0.13 | 2.47E−03 | 4.39E−03 | 1.90E−09 |
| PE(16:0_20:4) | Neg:739.5144@23.31 | H− | 0.31 | 1.20E−04 | 5.36E−04 | 2.03E−09 |
| **PC(O-16:0/22:6)*** | Neg:837.5865@23.92 | FA − H | −0.28 | 1.62E−05 | 1.09E−04 | 2.15E−09 |
| **PE(16:0_18:1)*** | **Neg: 717.5297@26.55** | H− | 0.38 | 7.06E−05 | 3.68E−04 | 2.82E−09 |
| Cer(d19:1/24:0)* | Neg:709.6577@39.12 | FA − H | −0.28 | 7.94E−05 | 4.03E−04 | 7.01E−09 |
| **PE(O-16:0/22:6)** | **Neg: 749.5352@24.71** | H− | −0.41 | 4.60E−09 | 1.00E−07 | 7.98E−09 |
| **TG(18:1_18:2_20:4)** | Pos: 921.7813@49.56 | NH4+ | 0.49 | 1.27E−08 | 2.27E−07 | 3.19E−07 |
| SM(d19:1/24:1) | Pos:826.6931@34.29 | H+ | −0.20 | 5.26E−03 | 7.24E−03 | 3.47E−07 |
| LPE(18:0) | Neg:509.3480@11.00 | H− | −0.09 | 1.92E−01 | 9.61E−02 | 1.92E−05 |
| PI(18:0_20:3) | Neg:888.5696@23.70 | H− | 0.07 | 3.35E−01 | 1.41E−01 | 1.00E−04 |
| SM(d18:1/16:0) | Ø | | | | | |
| Cholesta-4,6-dien-3-one | Pos: 382.3253@18.09 | H+ | 1.09 | 6.87E−16 | 5.85E−14 | |
| SM(d16:1/22:0) | Pos: 758.6315@28.70 | H+ | −0.38 | 6.83E−13 | 3.10E−11 | |
| SM(d18:2/16:0) | Pos: 700.5516@19.06 | H+ | −0.45 | 7.83E−09 | 1.49E−07 | |
| PE(O-18:0/20:4) | Pos: 753.5687@29.69 | H+ | −0.52 | 1.17E−08 | 2.15E−07 | |
| SM(d17:1/24:1) | Pos: 633.6055@30.86 | H+ | −0.41 | 2.49E−08 | 4.31E−07 | |
| PE(O-18:0/22:6) | Pos: 777.5696@28.78 | H+ | −0.38 | 2.57E−07 | 3.22E−06 | |
| TG(16:0_18:1_22:5) | Pos: 928.7515@54.39 | Na+ | 0.41 | 6.52E−07 | 7.11E−06 | |
| DG(16:0_18:2) | Pos: 607.5179@28.48 | NH4+ | 0.44 | 4.19E−06 | 3.74E−05 | |
| TG(56:4) | Pos: 927.8238@51.00 | NH4+ | 0.35 | 6.40E−06 | 4.96E−05 | |
| TG(18:1_18:2_22:4) | Pos: 949.8111@53.74 | NH4+ | 0.44 | 1.60E−05 | 1.08E−04 | |
| PC(O-18:0/22:6) | Pos: 819.6146@27.95 | H+ | −0.32 | 1.79E−05 | 1.17E−04 | |
| PC(18:1_22:5) | Pos: 833.5946@25.01 | H+ | 0.47 | 1.99E−05 | 1.27E−04 | |
| TG(18:2_16:0_20:4) | Pos: 895.7651@49.23 | NH4+ | 0.42 | 2.53E−05 | 1.58E−04 | |
| PE(18:0_22:5) | Neg: 793.5603@27.53 | H− | 0.34 | 3.22E−05 | 1.94E−04 | |
| PE(18:1_20:4)-2 | Neg: 765.5314@24.31 | H− | 0.32 | 3.93E−05 | 2.29E−04 | |
| PC(O-20:0/22:6) | Pos: 847.6474@31.97 | H+ | −0.32 | 4.73E−05 | 2.66E−04 | |
| TG(18:1_18:2_22:5) | Pos: 947.7953@51.13 | NH4+ | 0.45 | 5.67E−05 | 3.15E−04 | |
| TG(16:0_18:1_20:4) | Pos: 897.7805@53.99 | NH4+ | 0.37 | 6.75E−05 | 3.63E−04 | |
| CE(14:1) | Pos: 611.5657@47.54 | NH4+ | −0.50 | 6.97E−05 | 3.67E−04 | |
| CE(14:0) | Pos: 613.5800@52.89 | NH4+ | −0.39 | 4.01E−06 | 3.70E−05 | |
| PC(18:2_20:5) | Pos: 803.5477@18.76 | H+ | −0.37 | 6.98E−05 | 3.67E−04 | |

Figure 3:
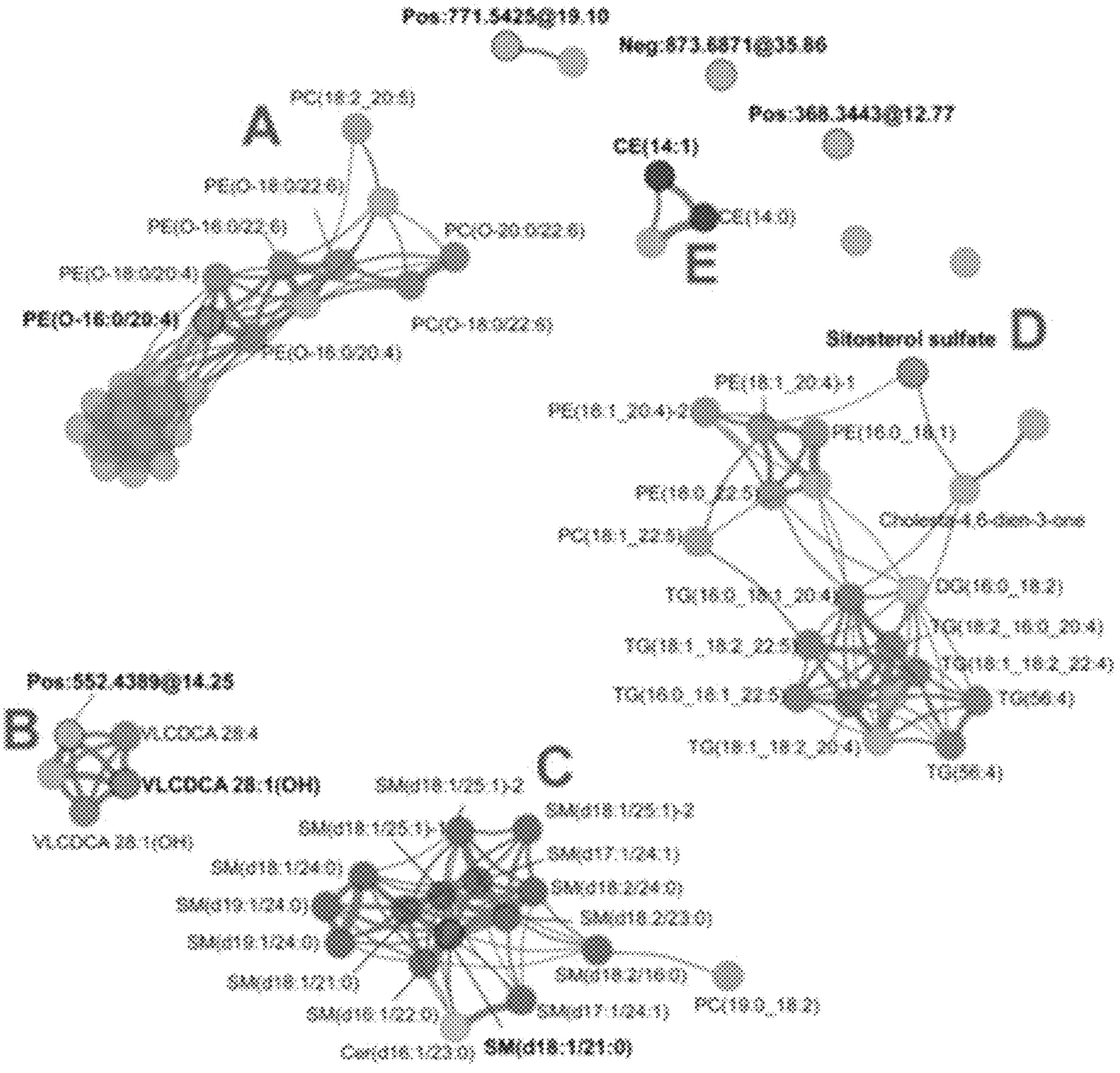
FIG. 3 shows a graphical representation of the correlations existing between the 73 B2/B3-associated features with p-value<1E-4 and $|\log_2(FC)|>0.3$ in IBDGC-2. It has been carried out using Fruchterman-Reingold algorithm and a positive correlation threshold r>0.4. Bond thickness corresponds to the strength of correlation between features. Circled features with bold ID are the nine components of the classification model.
Figure 4A:
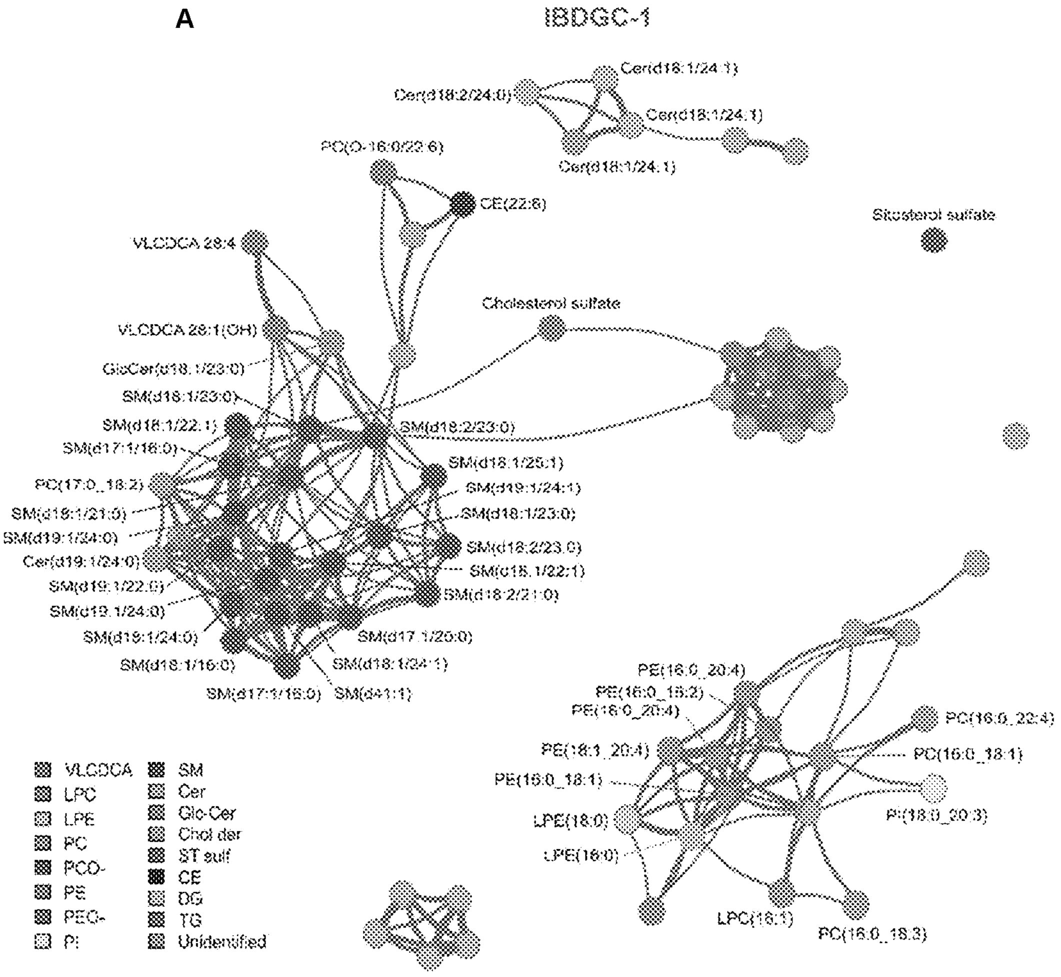
FIG. 4A and FIG. 4B show graphical representation of the correlations existing between the 72 and 73 B2/B3-associated features with p-value<1E-4 and $|\log_2(FC)|>0.3$ in IBDGC-1 (FIG. 4A) and IBDGC-2 (FIG. 4B), respectively. They have been carried out using Fruchterman-Reingold algorithm and positive correlation threshold r>0.5 and 0.4 for IBDGC-1 and 2, respectively. Bond thickness corresponds to the strength of the correlations between features. The correlations in IBDGC-1 were less precisely defined due to the smaller number of samples and features detected. Even though associated lipid molecular species differ in some extent between IBDGC-1 and 2, the representations are very similar with clustering of lipids from a same sub-class and/or entities from different sub-classes sharing similar structural characteristics with regard to their fatty acyl moieties.
Figure 4B:
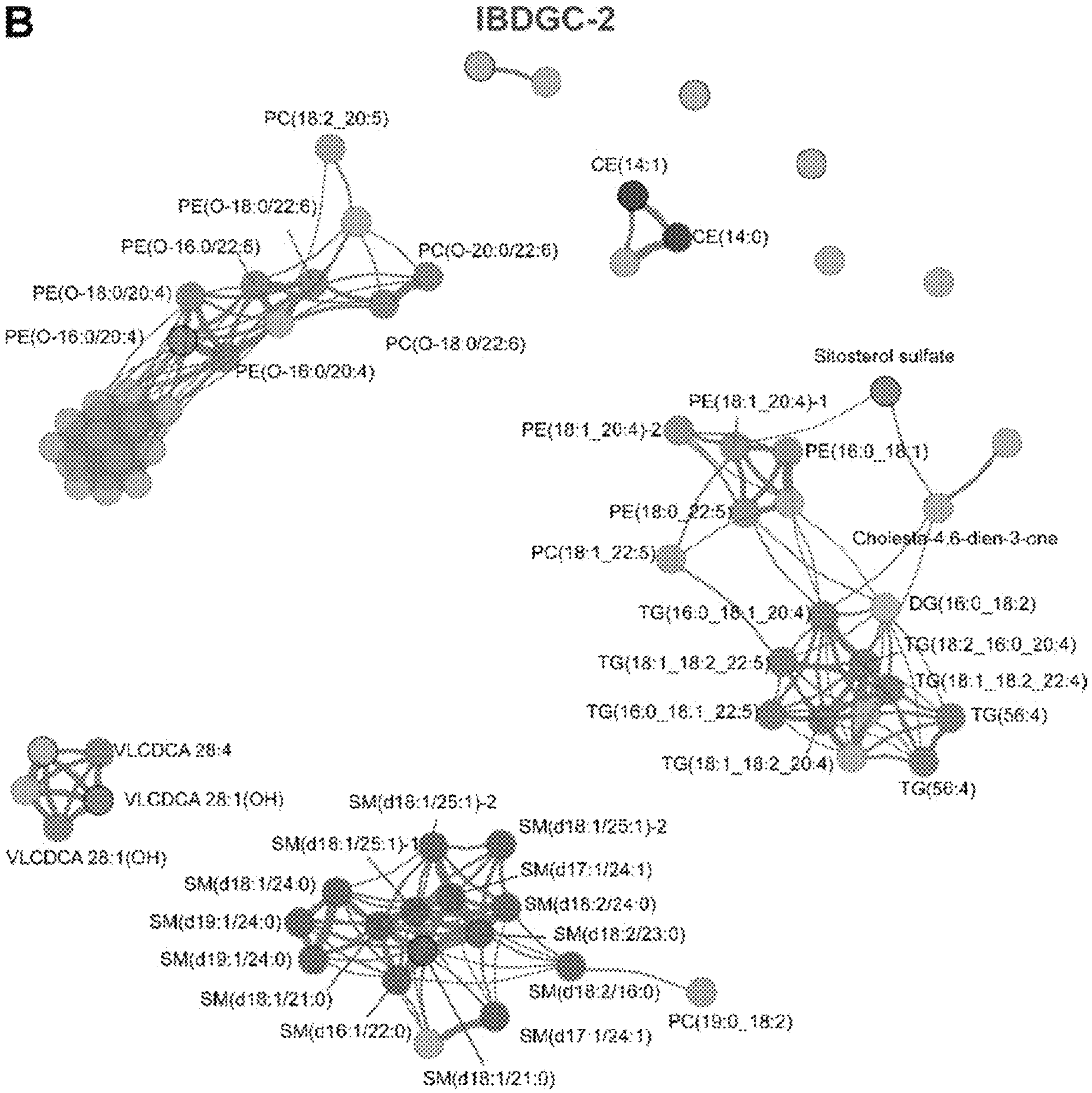

Example 3. Correlation Structure Identifies Lipid Sub-Classes, Shared Structures and Specific Entities Perturbed in CD Since high dimensional lipidomic data is expected to have a correlation structure, this was assessed in the 73 B2/B3-associated features from IBDGC-2. Six correlation clusters and four individual features were found (FIG. 3), with clusters primarily encompassing lipids of a same (sub-)class and/or entities from different sub-classes but sharing similar structural characteristics with regard to their fatty acyl moieties. For instance, PEO- and PCO-containing omega-3 or omega-6 PUFAs were found in cluster A, while several SMs and a phosphatidylcholine (PC) containing (VLCFAs; ≥22 carbons) or OCFAs were in cluster C. Clustering, however, could be independent of lipid (sub-)classes as seen for the sterol species SitS and $C_{4,6}D_3O$ vs. CE(14:1) that were found in two distinct correlation clusters, namely D and E, respectively. A similar clustering was observed with the 72 B2/B3-associated lipids in IBDGC-1, albeit, as expected for this smaller dataset, correlations were less precisely defined (FIG. 4). Interestingly, lipids in cluster D were elevated in patient sera as compared to controls, whereas those in all other clusters were lower. Altogether, the finding of a small number of clusters of correlated features suggests that a limited number of lipids support non-redundant biological information, most likely reflecting different CD pathogenic mechanisms.

>70 structurally unique lipids were identified with strong association to CD (p-value<1E-4 and q-value<5E-4) and effect size (|$\log_2$(FC)|>0.3) in both datasets described herein, of which over 60% were annotated at the molecular species level by MS/MS. Changes encompass four lipid categories and 12 sub-classes including the lipid species VLCDCA 28:1(OH), SitS and $C_{4,6}D_3O$. Most associated lipid features fell into five major correlation clusters that included lipids predominantly of similar (sub-)classes and/or sharing similar acyl side chains. A few other lipid features were, however, independent of these major clusters. This suggests that a relatively smaller number of biological pathways are involved in, and/or impacted by, disease mechanisms than the number of associated lipid features.

Given the relatively strong effect sizes observed for the associated lipid metabolites, a model could be built with only nine lipid features that had very high-performance characteristics with the ROC curve having an AUC of 0.97. Of note, the nine lipid features were from six different correlation clusters plus 2 individual features, highlighting the non-redundant information provided by these different clusters of lipids and likely distinct biological pathways. The identity of five of these classifiers has been determined, namely PE(O-16:0/20:4), VLCDCA 28:1 (OH), SM(d18:1/21:0), SitS and CE(14:1). Cross validation of this model demonstrated that this classifier was robust, and alternate models with as few as five lipid features were also of high quality (ROC curves with AUC ranging from 0.84 to 0.9). The strong performance characteristics suggest that a small set of circulating lipids are candidate biomarkers to assist disease classification in CD.

Figure 11:
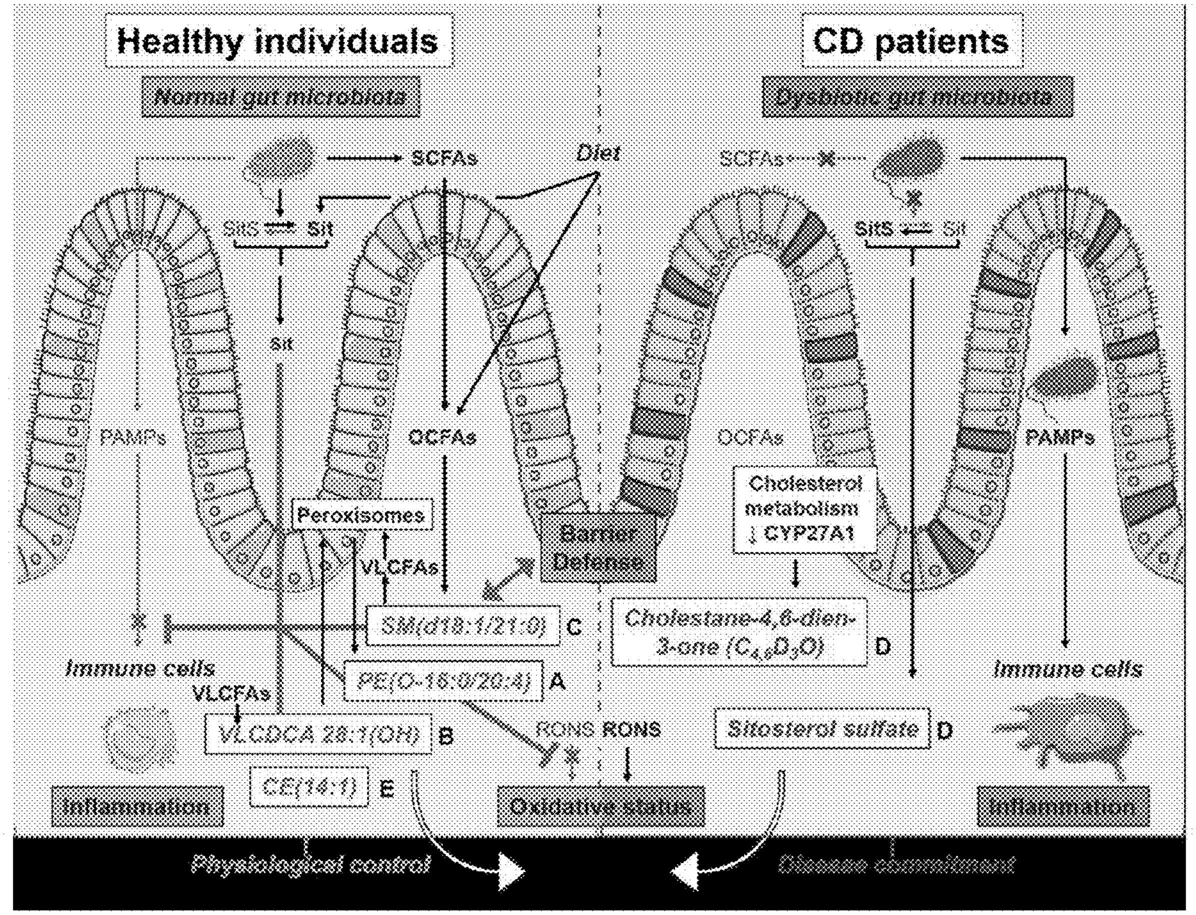
FIG. 11 illustrates the proposed mechanisms underlying the observed changes (lower in green; left panel; higher in red; right panel) in serum levels of candidate biomarker lipids and their correlated clusters (letters on the left of the lipid names) in CD patients. This figure was created from Servier Medical Art (SMART) images by Servier (smart-.servier.com), licensed under a Creative Commons Attribution 3.0 Unported License (CC BY 3.0).

Given that a majority of the lipid entities detected have been identified, the markers selected could be analyzed by the classifier models and the lipids present in their correlation clusters, with the objective of identifying structural commonalities within each cluster to inform about the important biological properties of each. Changes in serum levels of identified lipid classifiers or their correlated counterparts as well as their potential impact on the (patho) physiology of IBD are illustrated in FIG. 11. These changes are proposed to reflect alterations in the respective metabolism of these lipid classifers and in several CD pathogenic processes as follows.

Cluster A

Cluster A includes PE(O-16:0/20:4) and five other correlated phospholipids identified by MS/MS analyses. Correlated lipids include the ether phospholipids PE(O-18:0/20:4), PE(O-16:0/22:6), PE(O-18:0/22:6), PC(O-20:0/22:6), and PC(O-18:0/22:6), and the phospholipid PC(18:2_20:5). PE(O-16:0/20:4) was selected by the predictive models, was lower in the serum of patients with CD as compared to controls, and was significantly associated with the B2/B3 phenotype, but not disease location. Ether lipids are known to be unusually abundant in neutrophil membranes where they are essential for cell viability. Additional lipids within this cluster share a structural feature with ether lipids; they have a PUFA moiety in sn-2 position, predominantly the omega-6 arachidonic acid (AA; C20:4) or omega-3 docosahaexanoic acid (C22:6; DHA), which are susceptible to oxidative stress and likely contribute to their biological role via their well-known metabolism to pro/anti-inflammatory as well as pro-resolving mediators. Given these ether lipids are plasmanyls, which are intermediates in plasmalogen synthesis, these findings suggest also a host dysmetabolism in CD of ether lipids in peroxisomes, which are specialized cellular organelle recently shown to function as hubs that coordinate responses to stress, metabolism and immune signaling to maintain enteric health and the functionality of the gut-microbe interface. Hence, the lower circulating levels in ether lipids containing PUFAs may reflect an enhanced oxidative stress and/or dysregulated peroxisomal lipid metabolism and likely compromise inflammation resolution in CD.

Cluster B

Cluster B includes VLCDCA 28:1(OH) and four correlated lipid features, with one of the latter also being classified as very-long-chain dicarboxylic acids (VLCDCA). A correlated lipid includes VLCDCA 28:4. VLCDCA 28:1 (OH) was lower in the serum of patients with CD, associated with the B2/B3 phenotypes, but not disease location. Of particular relevance, it has been reported that VLCDCAs have anti-proliferative and anti-inflammatory properties in vitro. While originally named Gastrointestinal Tract Acids, VLCDCAs are known to be reduced in patients with colorectal cancer. Given that IBD patients are at risk for colitis-associated cancer, likely due to mechanisms associated with chronic inflammation and repeated events of inflammatory relapse, one may consider that VLCDCAs belong to the endogenous chemopreventive/anti-inflammatory genius. If so, VLCDCAs would fall into the sphere of the bioactive lipids, where they would join their structurally and functionally related cousins, namely the specialized pro-resolution mediators (SPMs), which are hydroxylated ω-3 or ω-6 PUFA metabolites actively produced to trigger the resolution phase of inflammation via signaling through G Protein-Coupled Receptor-dependent signaling. Disclosed herein is the finding that of VLCDCA 28:1(OH) and its non-hydroxylated and polyunsaturated relative VLCDCA 28:4, exhibit lower circulating levels in serum in CD. This may reflect a dysregulation of the metabolism of VLCDCAs in CD patients, which may result from (i) reduced VLCFA metabolism via cytochrome P450 of the CYP4 family (CYP4F) of enzymes in liver, which was associated with IBD, and/or (ii) their enhanced catabolism in peroxisomes. Irrespective of the mechanism, this is, however, likely impacting inflammatory processes possibly via SPM-like effects which have not been explored to date in IBD.

Cluster C

Cluster C contains SM(d18:1/21:0) and 11 correlated lipids that were lower in the sera of CD patients as compared to controls. Correlated lipids include SM(d17:1/24:1), SM(d18:2/16:0), SM(d18:2/23:0), SM(d18:2/24:0), SM(d17:1/24:1), SM(d18:1/25:1)-2, SM(d18:1/25:1)-1, SM(d18:1/24:0), SM(d19:1/24:0), SM(d18:1/21:0), SM(d16:1/22:0), Cer(d16:1/23:0), and PC(19:0_18:2). Examination of the structural features of these lipids found that they bear OCFA and/or VLCFA moieties. It is likely that OCFA levels reflect gut microbiota-mediated synthesis of its short-chain FA precursor, namely propionic acid, and/or branched-chain amino acid by the host. Given a dysbiosis-related reduction of short-chain FA-producing bacterial species has been described in CD and reduced levels of branched-chain amino acids were also reported, the lower levels of circulating biomarkers bearing OCFAs and correlated with SM(d18:1/21:0), which is strongly associated with disease behavior but independent of location, are particularly consistent. Since incorporation of VLCFAs into sphingolipid species, which involves intestinal ceramide synthase 2 activity, has also been connected to intestinal defense in mice, lower serum SMs bearing OCFA/VLCFA likely reflect dysbiosis and/or a defective synthesis and may impact on intestinal epithelial barrier function.

Cluster D

Cluster D includes SitS and 15 other MS/MS-identified lipids, including $C_{4,6}D_3O$, which were all found to be elevated in the serum of patients with CD vs. control individuals, and associated with disease behavior and location. Additional lipids in this cluster include PE(18:1_20:4)-1, PE(18:1_20:4)-2, PE(16:0_18:1), PE(18:0_22:5), PC(18:1_22:5), TG(16:0_18:1_20:4), TG(18:1_18:2_22:5), TG(16:0_18:1_22:5), TG(18:1_18:2_20:4), TG(56:4), TG(18:1_18:2_22:4), TG(18:2_16_0_20:4), TG(56:4), and DG(16:0_18:2). The SitS precursor, sitosterol, is a dietary phytosterol with known anti-proliferative and anti-inflammatory properties. By analogy with bile acids, dysbiosis may favor elevated levels of its putative inactive 3-OH sulfated form (i.e. SitS). Given non-cholesterol sterols are absorbed in the small intestine but their transfer into the lymph fluid is far less efficient, the elevated levels of SitS, which are more pronounced in B2/B3 and L1 presentation, may therefore reflect dysbiosis and/or intestinal epithelial barrier dysfunction. As for $C_{4,6}D_3O$, little is known about this specific oxysterol, except for its reported accumulation in patients with cerebrotendinous xanthomatosis, of which more than 50% suffer from chronic diarrhea. This disease is attributed to mutations in the mitochondrial enzyme sterol 27-hydroxylase, a cytochrome P450 oxidase encoded in humans by the CYP27A1 gene, involved in cholesterol metabolism. Several oxysterols play important roles in CD pathophysiology, acting through immune cells receptors such as GPR183 and liver X receptors (LXR), which are IBD risk genes identified by GWAS. While the specific role of $C_{4,6}D_3O$ in CD remains to be clarified, its higher serum levels concur with the lower CYP27A1 mRNA levels recently documented in colon biopsies of CD patients and also add to our knowledge about the dysregulated metabolism of cholesterol and bile acids in CD.

Cluster E

Cluster E includes the cholesterol ester CE(14:1) and two other correlated lipids. An additional lipid in this cluster includes CE(14:0). CE(14:1) was found to be lower in the serum of patients with CD when compared to controls and was also found to be associated with the ileal disease location. As with SitS, CE(14:1) belongs to the sterol lipid class but is likely to represent distinct biological information given that they are in different clusters. CE(14:1) may result from the acylation of cholesterol by acyl-CoA cholesterol acyltransferase activity in the intestine or liver, as well as lecithin-cholesterol acyltransferase activity in high density lipoproteins HDL. While it could be expected that CE(14:1) would follow a similar pattern to SitS as it is also a dietary lipid and could simply correlate with epithelial barrier dysfunction, its lower level in the serum of CD patients suggests a different mechanism. One possible explanation is that it is linked to a cellular deficiency in plasmalogens, which is known to impact several steps of cholesterol homeostasis. A recent study showing that gut microbial species can influence host cholesterol species provides, however, another interesting potential explanation. Specifically, metagenomic analyses discovered a microbial cholesterol dehydrogenase named ismA, and that ismA+ species decreased fecal and serum cholesterol in humans. Lower CE(14:1) in the serum of CD patients may reflect changes in the gut microbiome that increase the proportion of ismA+ species.

Taken together, these five annotated classifiers, as well as many of the correlated lipids within their clusters, appear to capture multiple different biologic mechanisms, which is reasonable to assume, are associated with the etiology and/or pathology of CD.

Example 4. Circulating Lipids are Differently Associated with CD Disease Behavior and Location Subtypes To explore the relationship between circulating lipids and CD subtypes, the entire IBDGC-2 dataset, which was larger and more representative in terms of disease behavior and location than IBDGC-1, was further analyzed. As a first step, it was tested whether the inclusion of B1 impacted on the previous results that focused on the B2 and B3 phenotypes. It was found that, compared to the previous results obtained with B2/B3, four new features showed evidence of association with CD (all patients) vs controls (p-value<1E-4 (q-value<8E-4) and $|\log_2(FC)|>0.3$), likely gained by the increase in power due to increased sample size (Table 5). Table 5 lists the 37 lipid features associated with CD (all patients including B1, B2 and B3) vs control with p-value<1E-4 and |log 2(FC)|>0.3 in IBDGC-2. Feature and lipid IDs, association with CD vs control (p- and q-values) as well as effect size of change (log 2(FC)) and standard error (SE) are shown. Bold feature IDs correspond to features with p-value>1E-4 and/or |log 2(FC)|<0.3 for the analysis focused on B2/B3 in IBDGC-2.

TABLE 5

| | | CD vs control | | | |
|---|---|---|---|---|---|
| Feature ID | Lipid ID | $\log_2(FC)$ | SE | p-value | q-value |
| Neg:468.3817@12.87 | VLCDCA 28:1(OH) | −1.10 | 0.09 | 2.55E−30 | 2.04E−27 |
| Pos:468.3809@12.93 | VLCDCA 28:1(OH) | −0.81 | 0.07 | 7.54E−28 | 3.02E−25 |
| Neg:446.3394@13.11 | VLCDCA 28:4 | −0.71 | 0.08 | 5.32E−18 | 1.42E−15 |
| Pos:534.4276@14.26 | | −0.57 | 0.07 | 7.88E−14 | 1.58E−11 |
| Pos:552.4389@14.25 | | −0.60 | 0.08 | 1.49E−13 | 2.38E−11 |
| Pos:771.5425@19.10 | | 0.44 | 0.06 | 9.08E−12 | 9.08E−10 |
| Neg:725.5345@25.50 | PE(O-16:0/20:4) | −0.52 | 0.07 | 1.74E−11 | 1.55E−09 |
| Neg:494.3450@13.93 | Sitosterol sulfate | 0.59 | 0.09 | 4.11E−11 | 3.29E−09 |
| Pos:725.5367@25.70 | PE(O-16:0/20:4) | −0.49 | 0.07 | 6.52E−11 | 4.74E−09 |
| Pos:382.3253@18.09 | Cholesta-4,6-dien-3-one | 0.66 | 0.11 | 1.07E−09 | 6.57E−08 |
| Pos:308.2831@11.82 | | −0.42 | 0.07 | 8.58E−09 | 4.29E−07 |
| Pos:1215.0900@52.85 | | −0.43 | 0.07 | 9.27E−09 | 4.36E−07 |
| Pos:265.2768@11.82 | | −0.48 | 0.08 | 1.06E−08 | 4.69E−07 |
| Pos:749.5364@24.89 | | −0.33 | 0.06 | 1.37E−08 | 5.76E−07 |
| Neg:386.3151@11.79 | | −0.42 | 0.07 | 2.48E−08 | 9.47E−07 |
| Neg:642.5898@36.90 | | −0.55 | 0.10 | 3.35E−08 | 1.22E−06 |
| Neg:749.5352@24.71 | PE(O-16:0/22:6) | −0.31 | 0.06 | 7.13E−08 | 2.38E−06 |
| Pos:362.2902@11.83 | | −0.39 | 0.07 | 8.81E−08 | 2.82E−06 |
| Neg:670.6212@39.00 | | −0.45 | 0.08 | 2.02E−07 | 5.98E−06 |
| Pos:412.2979@9.95 | | 0.34 | 0.07 | 4.85E−07 | 1.37E−05 |
| Pos:684.5469@43.77 | | 0.37 | 0.07 | 5.17E−07 | 1.37E−05 |
| Pos:267.2929@13.16 | | −0.37 | 0.07 | 5.29E−07 | 1.37E−05 |
| Pos:753.5687@29.69 | PE(O-18:0/20:4) | −0.35 | 0.07 | 9.30E−07 | 2.19E−05 |
| Pos:239.2616@11.48 | | −0.35 | 0.07 | 1.06E−06 | 2.42E−05 |
| Pos:310.2988@13.17 | | −0.35 | 0.07 | 1.16E−06 | 2.51E−05 |
| Pos:613.5800@52.89 | CE(14:0) | −0.32 | 0.06 | 1.52E−06 | 3.13E−05 |
| Neg:360.2995@11.43 | | −0.36 | 0.07 | 1.73E−06 | 3.46E−05 |
| Pos:336.2748@11.48 | | −0.30 | 0.06 | 2.75E−06 | 5.23E−05 |
| Pos:296.2815@12.27 | | −0.38 | 0.08 | 3.88E−06 | 7.07E−05 |
| Pos:564.5340@11.48 | | −0.44 | 0.10 | 8.52E−06 | 1.34E−04 |
| Pos:753.5316@19.29 | PC(14:0_20:4) | −0.30 | 0.07 | 1.85E−05 | 2.36E−04 |
| Pos:611.5657@47.54 | CE(14:1) | −0.42 | 0.10 | 1.86E−05 | 2.36E−04 |
| Pos:803.5477@18.76 | PC(18:2/20:5) | −0.33 | 0.08 | 2.61E−05 | 3.12E−04 |

TABLE 5-continued

| | | CD vs control | | | |
|---|---|---|---|---|---|
| Feature ID | Lipid ID | $log_2$(FC) | SE | p-value | q-value |
| Neg:416.2750@13.07 | | 0.31 | 0.07 | 3.34E−05 | 3.58E−04 |
| Neg:254.2259@11.45 | | 0.40 | 0.10 | 3.72E−05 | 3.75E−04 |
| Neg:442.2743@13.07 | | 0.30 | 0.07 | 5.17E−05 | 4.75E−04 |
| Pos:308.2823@12.00 | | −0.30 | 0.08 | 7.02E−05 | 6.04E−04 |

Figure 5A:
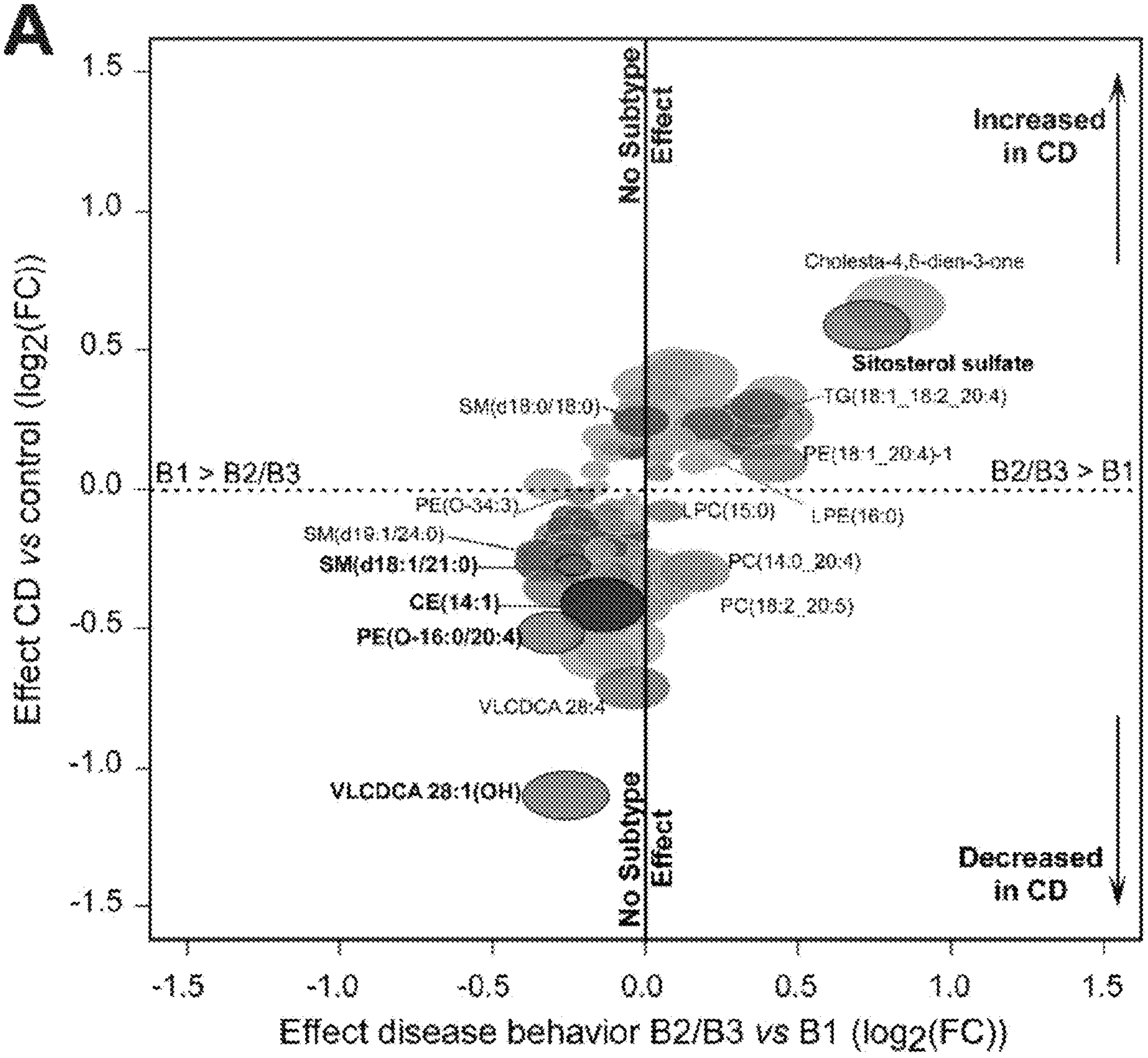
FIG. 5A-FIG. 5D show the 182 features associated with p-value<1E-4 for at least one CD subtype in IBDGC-2. Fold-change ($log_2$) in MS signal intensity values for each feature with respect to disease subtypes is shown on separate axes. Disease behavior is illustrated in FIG. 5A and FIG. 5B, while disease location is illustrated in FIG. 5C and FIG. 5D. A subtype-dependent effect would fall outside the first diagonal in FIG. 5B and FIG. 5D and/or far from the vertical x=0 axis in FIG. 5A and FIG. 5C. Ellipses correspond to 95% confidence intervals. Circled lipids with bold ID are components of the classification model.
Figure 5B:
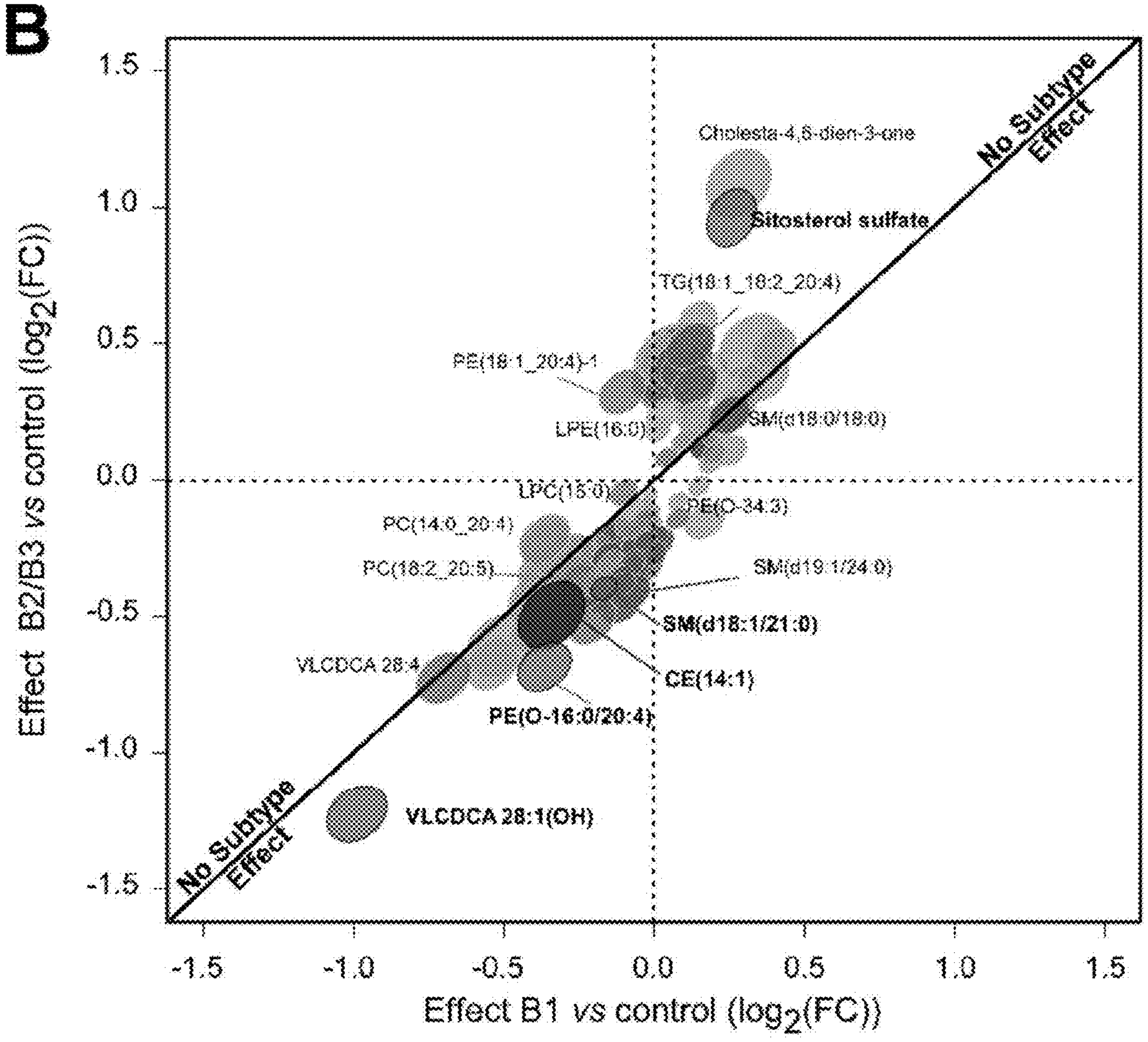
Figure 5C:
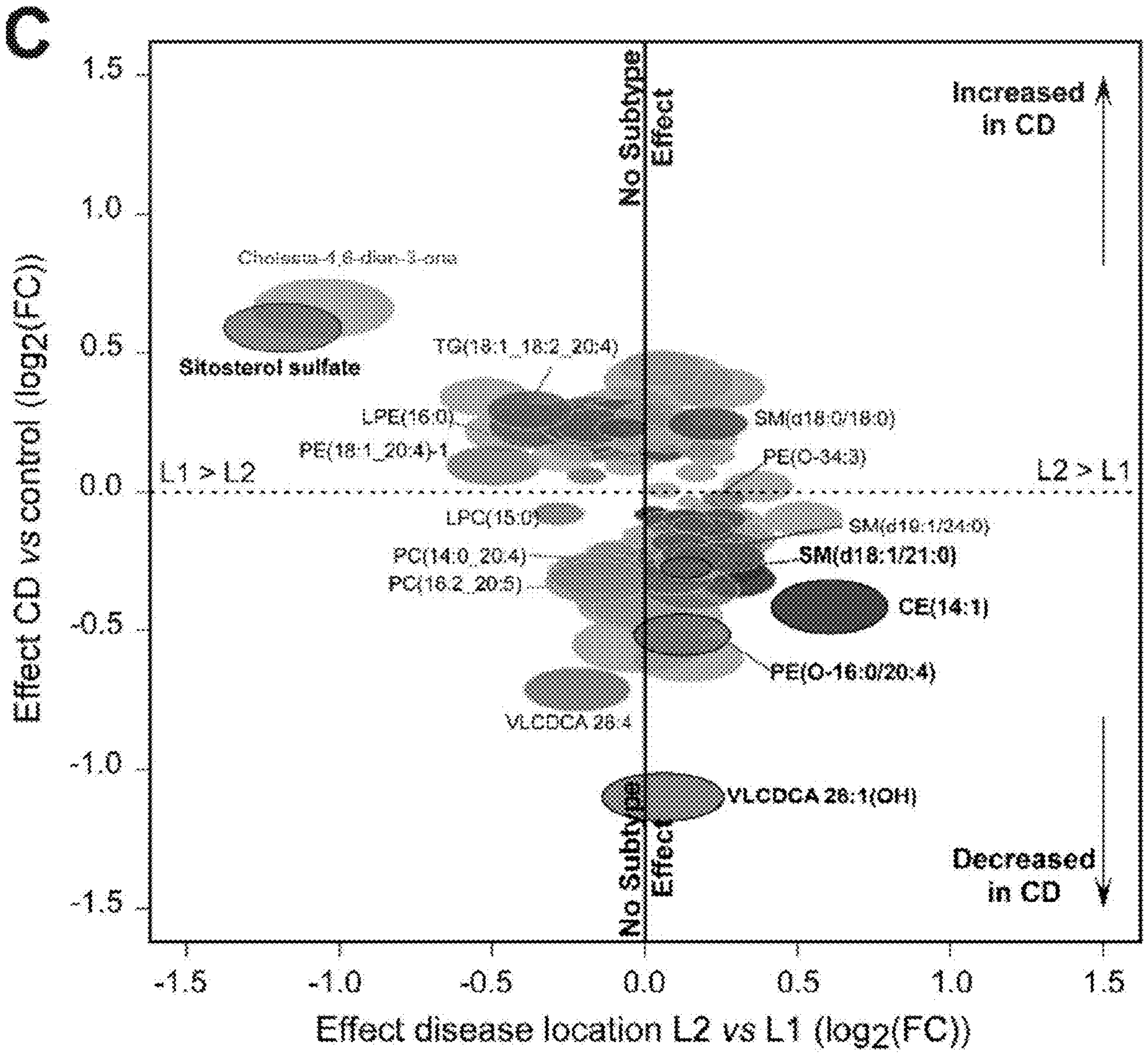
Figure 5D:
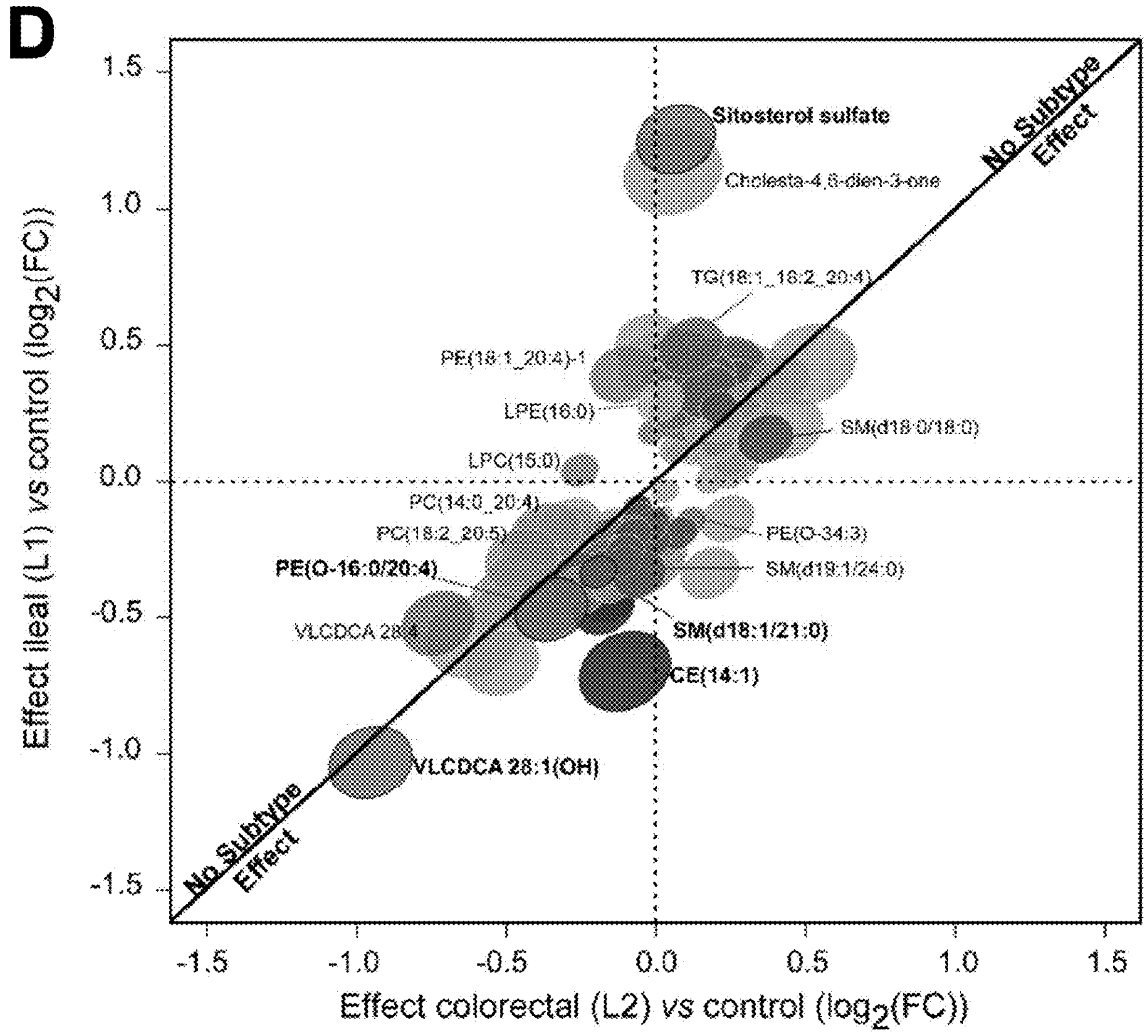

In contrast, half of the B2/B3-associated features failed to reach the significance threshold in "all CD vs controls" analysis, indeed suggesting an impact of disease subtype on the association to some lipid features. To assess this directly, we tested each feature for association to a specific disease location or behavior and found 182 associations with p-value<1E-4 for at least one subtype (behavior (138), location (94); Tables 6A-6J). Next, to better interpret the relationship between these features and disease subtypes, their effect sizes were plotted with respect to disease status on separate axes (FIG. 5). This representation highlights distinct patterns for multiple lipid features. Of note, in terms of disease behavior, the strongest effects were observed for PE(O-16:0/20:4), VLCDCA 28:1(OH), SitS and $C_{4,6}D_3O$, all being more pronounced in B2/B3 and much less so in B1 (FIG. 5A-B). In terms of disease location, the strongest effects were observed for SitS, $C_{4,6}D_3O$ and CE(14:1) in ileal disease (L1) (FIG. 5C-D). Taken together, these results suggest that circulating levels of specific lipids differentially perturbed between phenotypic subgroups of CD, with SitS and $C_{4,6}D_3O$ having the largest effect sizes. Tables 6A-6J lists the 182 lipid features associated to at least one of the CD subtypes with p-value<1E-4 in IBDGC-2. Feature and lipid IDs, association with each subtype considered (p- and q-values) as well as effect size of change (log 2(FC)) and standard error (SE) are shown.

TABLE 6A

| | | CD vs control | | | |
|---|---|---|---|---|---|
| Feature ID | Lipid ID | $log_2$(FC) | SE | p-value | q-value |
| Neg:494.3450@13.93 | Sitosterol sulfate | 0.59 | 0.09 | 4.11E−11 | 3.29E−09 |
| Neg:632.3875@20.55 | | −0.06 | 0.03 | 1.32E−02 | 2.70E−02 |
| Pos:382.3253@18.09 | Cholesta-4,6-dien-3-one | 0.66 | 0.11 | 1.07E−09 | 6.57E−08 |
| Neg:976.7275@20.56 | | −0.08 | 0.04 | 1.94E−02 | 3.35E−02 |
| Neg:588.3810@20.55 | | −0.07 | 0.03 | 8.49E−03 | 2.11E−02 |
| Pos:863.6407@30.12 | | −0.10 | 0.06 | 1.17E−01 | 1.06E−01 |
| Neg:890.7125@20.56 | | −0.11 | 0.04 | 1.26E−02 | 2.62E−02 |
| Pos:1254.0843@20.73 | | −0.10 | 0.04 | 1.21E−02 | 2.56E−02 |
| Neg:932.7214@20.56 | | −0.13 | 0.04 | 4.03E−03 | 1.33E−02 |
| Neg:1300.0741@20.57 | | −0.08 | 0.04 | 4.83E−02 | 5.80E−02 |
| Neg:1000.7305@20.57 | | −0.08 | 0.04 | 3.85E−02 | 5.06E−02 |
| Neg:999.7325@20.57 | | −0.08 | 0.04 | 4.34E−02 | 5.48E−02 |
| Neg:602.3689@20.56 | | −0.09 | 0.03 | 8.45E−03 | 2.11E−02 |
| Neg:959.7195@20.57 | | −0.05 | 0.03 | 5.29E−02 | 6.16E−02 |
| Neg:956.7237@20.57 | | −0.10 | 0.04 | 7.98E−03 | 2.02E−02 |
| Neg:888.7128@20.56 | | −0.11 | 0.04 | 8.33E−03 | 2.10E−02 |
| Pos:859.7415@20.74 | | −0.03 | 0.02 | 7.89E−02 | 8.10E−02 |
| Neg:1014.7189@20.56 | | −0.08 | 0.03 | 1.42E−02 | 2.81E−02 |
| Neg:916.7128@20.56 | | −0.11 | 0.04 | 6.82E−03 | 1.84E−02 |
| Pos:873.7556@20.73 | | −0.06 | 0.03 | 3.48E−02 | 4.74E−02 |
| Neg:574.3676@20.53 | | −0.06 | 0.03 | 2.67E−02 | 4.13E−02 |
| Pos:716.5465@17.11 | PE(O-34:3) | −0.02 | 0.03 | 4.88E−01 | 2.77E−01 |
| Neg:522.3685@20.56 | | −0.09 | 0.04 | 1.34E−02 | 2.72E−02 |
| Neg:548.3686@20.55 | | −0.10 | 0.04 | 8.88E−03 | 2.17E−02 |
| Pos:412.2979@9.95 | | 0.34 | 0.07 | 4.85E−07 | 1.37E−05 |
| Pos:674.5372@17.33 | SM(d16:1/16:0) | −0.15 | 0.03 | 2.95E−06 | 5.49E−05 |
| Neg:942.7111@20.55 | | −0.08 | 0.04 | 1.84E−02 | 3.26E−02 |
| Neg:532.3584@20.55 | | −0.17 | 0.07 | 9.72E−03 | 2.30E−02 |
| Neg:466.3396@20.56 | | −0.17 | 0.06 | 5.81E−03 | 1.65E−02 |
| Pos:481.3172@8.20 | LPC(15:0) | −0.08 | 0.04 | 5.41E−02 | 6.24E−02 |
| Neg:604.3632@20.56 | | −0.14 | 0.05 | 7.74E−03 | 1.98E−02 |
| Pos:1405.1372@20.63 | | 0.02 | 0.06 | 7.24E−01 | 3.52E−01 |
| Neg:765.5307@23.93 | PE(18:1_20:4)-1 | 0.10 | 0.07 | 1.72E−01 | 1.37E−01 |
| Pos:611.5657@47.54 | CE(14:1) | −0.42 | 0.10 | 1.86E−05 | 2.36E−04 |
| Pos:842.7249@37.94 | SM(d44:1) | −0.10 | 0.04 | 1.62E−02 | 3.04E−02 |
| Neg:874.7121@36.84 | SM(d43:1) | −0.11 | 0.04 | 5.67E−03 | 1.63E−02 |
| Neg:577.3692@20.56 | | −0.16 | 0.06 | 1.18E−02 | 2.53E−02 |
| Pos:919.7688@45.95 | | 0.22 | 0.07 | 2.56E−03 | 9.40E−03 |
| Pos:700.5335@17.33 | | −0.14 | 0.04 | 2.63E−04 | 1.77E−03 |
| Neg:541.3371@9.22 | LPC(16:0) | 0.06 | 0.03 | 4.84E−02 | 5.80E−02 |
| Pos:368.3443@12.77 | | −0.22 | 0.04 | 3.68E−08 | 1.28E−06 |
| Pos:797.6758@35.44 | GlcCer(d18:1/23:0) | −0.12 | 0.04 | 3.11E−03 | 1.09E−02 |
| Pos:784.6473@28.86 | SM(d18:1/22:1) | −0.14 | 0.03 | 5.72E−05 | 5.14E−04 |
| Neg:466.3133@12.72 | Cholesterol sulfate | −0.19 | 0.05 | 2.47E−05 | 3.00E−04 |
| Pos:699.5646@21.73 | | 0.13 | 0.04 | 2.24E−04 | 1.60E−03 |
| Pos:802.6908@35.79 | | −0.16 | 0.05 | 2.50E−03 | 9.22E−03 |

TABLE 6A-continued

| | | CD vs control | | | |
|---|---|---|---|---|---|
| Feature ID | Lipid ID | $log_2$(FC) | SE | p-value | q-value |
| Neg:843.6786@35.29 | GlcCer(d18:1/23:0) | −0.14 | 0.04 | 1.03E−03 | 4.89E−03 |
| Neg:848.6949@35.66 | | −0.18 | 0.05 | 5.18E−04 | 3.07E−03 |
| Pos:921.7813@49.56 | TG(18:1_18:2_20:4) | 0.29 | 0.07 | 2.45E−05 | 3.00E−04 |
| Neg:720.5416@17.20 | SM(d16:1/16:0) | −0.13 | 0.03 | 9.93E−05 | 8.11E−04 |
| Pos:832.7000@34.80 | | −0.12 | 0.04 | 3.18E−03 | 1.10E−02 |
| Neg:453.2858@9.43 | LPE(16:0) | 0.12 | 0.05 | 9.98E−03 | 2.34E−02 |
| Pos:826.6879@34.79 | | −0.10 | 0.04 | 5.78E−03 | 1.65E−02 |
| Neg:745.5689@21.54 | GlcCer(d18:1/16:0) | 0.15 | 0.03 | 9.22E−06 | 1.42E−04 |
| Pos:828.7092@36.97 | SM(d43:1) | −0.13 | 0.04 | 7.94E−04 | 4.07E−03 |
| Neg:764.5661@19.37 | | 0.07 | 0.03 | 2.59E−02 | 4.04E−02 |
| Neg:830.6500@28.63 | SM(d18:1/22:1) | −0.15 | 0.04 | 2.71E−05 | 3.19E−04 |
| Pos:895.7651@49.23 | TG(18:2_16:0_20:4) | 0.24 | 0.08 | 2.64E−03 | 9.58E−03 |
| Pos:688.5513@18.48 | SM(d33:1) | −0.17 | 0.04 | 5.83E−05 | 5.19E−04 |
| Pos:613.5800@52.89 | CE(14:0) | −0.32 | 0.06 | 1.52E−06 | 3.13E−05 |
| Pos:686.5357@16.62 | SM(d33:2) | −0.12 | 0.04 | 5.65E−04 | 3.28E−03 |
| Pos:368.3444@60.96 | CE(18:1) | −0.09 | 0.03 | 2.34E−03 | 8.86E−03 |
| Pos:688.5532@18.89 | SM(d17:1/16:0) | −0.12 | 0.03 | 1.77E−04 | 1.29E−03 |
| Pos:828.7092@36.62 | SM(d19:1/24:0) | −0.24 | 0.06 | 3.10E−05 | 3.54E−04 |
| Pos:700.5516@19.06 | SM(d18:2/16:0) | −0.27 | 0.06 | 1.36E−05 | 1.87E−04 |
| Pos:646.5049@14.73 | SM(d16:1/14:0) | −0.16 | 0.05 | 9.11E−04 | 4.47E−03 |
| Pos:798.6629@31.63 | SM(d18:2/23:0) | −0.23 | 0.04 | 2.06E−09 | 1.18E−07 |
| Pos:773.5574@19.33 | | 0.19 | 0.05 | 4.19E−05 | 4.04E−04 |
| Pos:936.7921@49.24 | | 0.28 | 0.08 | 6.19E−04 | 3.49E−03 |
| Neg:874.7116@36.49 | SM(d19:1/24:0) | −0.20 | 0.05 | 2.34E−04 | 1.62E−03 |
| Pos:1215.0900@52.85 | | −0.43 | 0.07 | 9.27E−09 | 4.36E−07 |
| Pos:453.2857@9.48 | LPE(16:0) | 0.11 | 0.04 | 1.09E−02 | 2.44E−02 |
| Pos:660.5202@15.93 | SM(d17:1/18:0) | −0.22 | 0.04 | 7.07E−07 | 1.77E−05 |
| Pos:799.6100@29.09 | PC(19:0_18:2) | −0.15 | 0.05 | 2.57E−03 | 9.41E−03 |
| Pos:720.5763@18.94 | SM(d18:0/16:0)(OH) | −0.17 | 0.04 | 2.98E−05 | 3.46E−04 |
| Neg:860.6963@35.57 | SM(d18:1/24:0) | −0.25 | 0.05 | 6.49E−06 | 1.06E−04 |
| Pos:826.6932@35.39 | SM(d18:1/25:1)-2 | −0.19 | 0.06 | 7.35E−04 | 3.86E−03 |
| Pos:814.6935@35.97 | SM(d18:1/24:0)-2 | −0.10 | 0.04 | 8.56E−03 | 2.11E−02 |
| Pos:800.6783@34.78 | SM(d18:1/25:1)-1 | −0.18 | 0.03 | 1.06E−07 | 3.25E−06 |
| Neg:734.5567@18.74 | SM(d17:1/16:0) | −0.13 | 0.03 | 3.51E−04 | 2.21E−03 |
| Pos:798.6620@30.86 | SM(d17:1/24:1) | −0.12 | 0.03 | 5.97E−04 | 3.40E−03 |
| Pos:618.5353@52.85 | CE(14:0) | −0.19 | 0.04 | 6.50E−06 | 1.06E−04 |
| Neg:765.5314@24.31 | PE(18:1_20:4)-2 | 0.22 | 0.06 | 2.93E−04 | 1.94E−03 |
| Pos:885.7788@51.00 | TG(56:4) | 0.20 | 0.06 | 9.56E−04 | 4.61E−03 |
| Pos:772.6469@30.80 | SM(d18:1/21:0) | −0.28 | 0.04 | 1.07E−12 | 1.43E−10 |
| Neg:844.6655@31.39 | SM(d17:1/24:1) | −0.23 | 0.04 | 2.30E−08 | 9.21E−07 |
| Pos:758.6315@28.70 | SM(d16:1/22:0) | −0.28 | 0.04 | 2.61E−10 | 1.74E−08 |
| Pos:928.7515@54.39 | TG(16:0_18:1_22:5) | 0.25 | 0.07 | 2.36E−04 | 1.62E−03 |
| Pos:732.6154@26.04 | SM(d18:0/18:0) | 0.25 | 0.06 | 3.35E−05 | 3.58E−04 |
| Pos:897.7805@53.99 | TG(16:0_18:1_20:4) | 0.20 | 0.07 | 6.51E−03 | 1.77E−02 |
| Pos:887.6154@20.25 | | 0.18 | 0.04 | 2.29E−06 | 4.47E−05 |
| Pos:684.5469@43.77 | | 0.37 | 0.07 | 5.17E−07 | 1.37E−05 |
| Neg:709.6577@39.12 | Cer(d19:1/24:0) | −0.17 | 0.06 | 4.10E−03 | 1.35E−02 |
| Pos:819.6146@27.95 | PC(O-18:0/22:6) | −0.17 | 0.06 | 4.41E−03 | 1.41E−02 |
| Pos:847.6474@31.97 | PC(O-20:0/22:6) | −0.18 | 0.06 | 3.31E−03 | 1.13E−02 |
| Neg:818.6498@30.55 | SM(d18:1/21:0) | −0.26 | 0.04 | 7.85E−12 | 8.98E−10 |
| Neg:793.5603@27.53 | PE(18:0_22:5) | 0.17 | 0.06 | 6.98E−03 | 1.87E−02 |
| Pos:927.8238@51.00 | TG(56:4) | 0.24 | 0.06 | 1.87E−04 | 1.35E−03 |
| Neg:446.3394@13.11 | VLCDCA 28:4 | −0.71 | 0.08 | 5.32E−18 | 1.42E−15 |
| Neg:858.6815@33.55 | SM(d18:2/24:0) | −0.15 | 0.04 | 1.61E−04 | 1.20E−03 |
| Pos:805.5628@20.77 | PC(38:6) | −0.22 | 0.04 | 7.68E−07 | 1.86E−05 |
| Neg:699.6293@39.12 | | −0.16 | 0.06 | 7.06E−03 | 1.87E−02 |
| Neg:873.6871@35.86 | | −0.25 | 0.06 | 4.83E−05 | 4.49E−04 |
| Pos:812.6785@33.81 | SM(d18:2/24:0) | −0.18 | 0.04 | 5.88E−06 | 1.02E−04 |
| Neg:872.6961@35.25 | SM(d18:1/25:1)-2 | −0.25 | 0.06 | 6.91E−06 | 1.11E−04 |
| Pos:607.4579@17.14 | LPC(24:0) | −0.14 | 0.04 | 4.85E−04 | 2.90E−03 |
| Neg:846.6815@34.58 | SM(d18:1/23:0) | −0.14 | 0.03 | 3.28E−05 | 3.58E−04 |
| Neg:850.6670@35.84 | | 0.01 | 0.03 | 8.13E−01 | 3.75E−01 |
| Neg:837.5865@23.92 | PC(O-16:0/22:6) | −0.18 | 0.05 | 5.87E−04 | 3.38E−03 |
| Pos:753.5316@19.29 | | −0.30 | 0.07 | 1.85E−05 | 2.36E−04 |
| Pos:753.5687@29.69 | PE(O-18:0/20:4) | −0.35 | 0.07 | 9.30E−07 | 2.19E−05 |
| Neg:710.6139@36.52 | Cer(d18:1/24:1) | 0.15 | 0.03 | 2.11E−05 | 2.64E−04 |
| Pos:892.6936@51.00 | | 0.21 | 0.06 | 3.20E−04 | 2.05E−03 |
| Neg:799.5353@19.15 | PC(14:0_20:4) | −0.30 | 0.08 | 9.38E−05 | 7.74E−04 |
| Pos:803.5477@18.76 | PC(18:2_20:5) | −0.33 | 0.08 | 2.61E−05 | 3.12E−04 |
| Pos:647.6132@36.64 | | 0.17 | 0.04 | 8.97E−05 | 7.48E−04 |
| Neg:845.6132@28.88 | PC(19:0_18:2) | −0.24 | 0.05 | 4.65E−06 | 8.27E−05 |
| Pos:633.6055@30.86 | SM(d17:1/24:1) | −0.28 | 0.06 | 1.31E−06 | 2.77E−05 |
| Pos:947.7953@51.13 | TG(18:1_18:2_22:5) | 0.25 | 0.09 | 5.69E−03 | 1.63E−02 |
| Pos:744.6146@26.54 | SM(d18:1/19:0) | −0.10 | 0.03 | 2.24E−03 | 8.65E−03 |
| Pos:537.5118@25.39 | | 0.15 | 0.04 | 7.10E−05 | 6.04E−04 |
| Pos:758.6315@28.51 | SM(d18:1/20:0) | 0.23 | 0.04 | 2.79E−09 | 1.49E−07 |

TABLE 6A-continued

| Feature ID | Lipid ID | CD vs control log$_2$(FC) | SE | p-value | q-value |
|---|---|---|---|---|---|
| Pos:730.5994@24.43 | SM(d36:1) | 0.14 | 0.03 | 1.80E−05 | 2.36E−04 |
| Pos:362.2902@11.83 | | −0.39 | 0.07 | 8.81E−08 | 2.82E−06 |
| Pos:559.5691@38.64 | | −0.28 | 0.07 | 3.80E−05 | 3.75E−04 |
| Neg:717.5297@26.55 | PE(16:0_18:1) | 0.19 | 0.08 | 1.62E−02 | 3.04E−02 |
| Neg:725.5345@25.50 | PE(O-16:0/20:4) | −0.52 | 0.07 | 1.74E−11 | 1.55E−09 |
| Neg:693.6257@36.52 | Cer(d18:1/24:1) | 0.18 | 0.04 | 6.04E−06 | 1.03E−04 |
| Pos:552.4389@14.25 | | −0.60 | 0.08 | 1.49E−13 | 2.38E−11 |
| Pos:725.5367@25.70 | PE(O-16:0/20:4) | −0.49 | 0.07 | 6.52E−11 | 4.74E−09 |
| Pos:717.5316@26.75 | | 0.20 | 0.08 | 1.07E−02 | 2.44E−02 |
| Neg:749.5352@24.71 | PE(O-16:0/22:6) | −0.31 | 0.06 | 7.13E−08 | 2.38E−06 |
| Neg:912.5647@22.69 | | 0.10 | 0.04 | 7.17E−03 | 1.88E−02 |
| Pos:728.5844@21.45 | SM(d18:2/18:0) | 0.15 | 0.04 | 3.76E−05 | 3.75E−04 |
| Neg:1152.7105@16.97 | | 0.15 | 0.04 | 3.25E−05 | 3.58E−04 |
| Pos:833.5946@25.01 | PC(18:1_22:5) | 0.24 | 0.09 | 7.61E−03 | 1.96E−02 |
| Pos:585.5850@38.89 | | −0.30 | 0.07 | 3.26E−05 | 3.58E−04 |
| Pos:949.8111@53.74 | TG(18:1_18:2_22:4) | 0.26 | 0.08 | 1.25E−03 | 5.61E−03 |
| Pos:468.3809@12.93 | VLCDCA 28:1(OH) | −0.81 | 0.07 | 7.54E−28 | 3.02E−25 |
| Neg:795.5534@25.83 | | 0.12 | 0.03 | 4.02E−05 | 3.93E−04 |
| Pos:482.3406@12.78 | | 0.12 | 0.03 | 1.18E−05 | 1.69E−04 |
| Neg:442.2743@13.07 | | 0.30 | 0.07 | 5.17E−05 | 4.75E−04 |
| Pos:507.3497@10.01 | | −0.18 | 0.04 | 1.38E−05 | 1.88E−04 |
| Pos:853.5630@19.62 | | −0.23 | 0.06 | 4.71E−05 | 4.44E−04 |
| Neg:670.6212@39.00 | | −0.45 | 0.08 | 2.02E−07 | 5.98E−06 |
| Pos:414.3497@20.82 | | 0.27 | 0.07 | 1.30E−04 | 9.92E−04 |
| Pos:368.3445@53.93 | CE(18:2) | −0.08 | 0.03 | 7.02E−03 | 1.87E−02 |
| Pos:629.6119@36.65 | | 0.18 | 0.04 | 3.52E−05 | 3.61E−04 |
| Neg:386.3151@11.79 | | −0.42 | 0.07 | 2.48E−08 | 9.47E−07 |
| Neg:456.2903@13.07 | | 0.25 | 0.06 | 8.59E−05 | 7.24E−04 |
| Pos:771.5425@19.10 | | 0.44 | 0.06 | 9.08E−12 | 9.08E−10 |
| Pos:942.6220@34.79 | | −0.18 | 0.04 | 1.64E−05 | 2.19E−04 |
| Pos:607.5886@30.05 | | −0.28 | 0.06 | 1.13E−06 | 2.51E−05 |
| Pos:777.5696@28.78 | PE(O-18:0/22:6) | −0.26 | 0.06 | 1.26E−05 | 1.76E−04 |
| Neg:360.2995@11.43 | | −0.36 | 0.07 | 1.73E−06 | 3.46E−05 |
| Neg:254.2259@11.45 | | 0.40 | 0.10 | 3.72E−05 | 3.75E−04 |
| Pos:282.2675@11.48 | | −0.28 | 0.06 | 1.10E−05 | 1.64E−04 |
| Pos:296.2815@12.27 | | −0.38 | 0.08 | 3.88E−06 | 7.07E−05 |
| Pos:534.4276@14.26 | | −0.57 | 0.07 | 7.88E−14 | 1.58E−11 |
| Neg:468.3817@12.87 | VLCDCA 28:1(OH) | −1.10 | 0.09 | 2.55E−30 | 2.04E−27 |
| Neg:823.5341@18.59 | | −0.29 | 0.07 | 5.55E−05 | 5.05E−04 |
| Pos:265.2768@11.82 | | −0.48 | 0.08 | 1.06E−08 | 4.69E−07 |
| Pos:401.3327@13.20 | | 0.16 | 0.04 | 4.42E−05 | 4.21E−04 |
| Neg:1560.1702@24.20 | | 0.20 | 0.04 | 4.99E−07 | 1.37E−05 |
| Pos:425.3507@9.33 | C18:1 carnitine | 0.27 | 0.06 | 1.16E−05 | 1.68E−04 |
| Neg:774.5880@21.27 | SM(d18:2/18:0) | 0.16 | 0.04 | 3.40E−05 | 3.58E−04 |
| Pos:495.3680@10.90 | | −0.16 | 0.04 | 2.35E−04 | 1.62E−03 |
| Pos:239.2616@11.48 | | −0.35 | 0.07 | 1.06E−06 | 2.42E−05 |
| Pos:635.6214@33.95 | Cer(d18:1/23:0) | −0.19 | 0.05 | 6.27E−05 | 5.45E−04 |
| Pos:564.5340@11.48 | | −0.44 | 0.10 | 8.52E−06 | 1.34E−04 |
| Pos:308.2823@12.00 | | −0.30 | 0.08 | 7.02E−05 | 6.04E−04 |
| Pos:401.3489@15.84 | | 0.13 | 0.03 | 6.05E−05 | 5.32E−04 |
| Neg:642.5898@36.90 | | −0.55 | 0.10 | 3.35E−08 | 1.22E−06 |
| Pos:336.2748@11.48 | | −0.30 | 0.06 | 2.75E−06 | 5.23E−05 |
| Pos:415.3510@13.21 | | 0.17 | 0.04 | 3.52E−05 | 3.61E−04 |
| Neg:416.2750@13.07 | | 0.31 | 0.07 | 3.34E−05 | 3.58E−04 |
| Pos:310.2988@13.17 | | −0.35 | 0.07 | 1.16E−06 | 2.51E−05 |
| Pos:308.2831@11.82 | | −0.42 | 0.07 | 8.58E−09 | 4.29E−07 |
| Pos:749.5364@24.89 | | −0.33 | 0.06 | 1.37E−08 | 5.76E−07 |
| Pos:267.2929@13.16 | | −0.37 | 0.07 | 5.29E−07 | 1.37E−05 |
| Pos:399.3348@8.85 | C16:0 carnitine | 0.19 | 0.04 | 1.10E−05 | 1.64E−04 |
| Pos:607.5179@28.48 | DG(16:0_18:2) | 0.22 | 0.08 | 4.93E−03 | 1.51E−02 |

TABLE 6B

| Feature ID | Lipid ID | Disease behaviors vs control B1 log$_2$(FC) | SE | p-value | q-value |
|---|---|---|---|---|---|
| Neg:494.3450@13.93 | Sitosterol sulfate | 0.26 | 0.08 | 2.03E−03 | 2.50E−02 |
| Neg:632.3875@20.55 | | −0.02 | 0.03 | 5.74E−01 | 4.73E−01 |
| Pos:382.3253@18.09 | Cholesta-4,6-dien-3-one | 0.28 | 0.11 | 1.02E−02 | 6.93E−02 |
| Neg:976.7275@20.56 | | −0.04 | 0.04 | 3.14E−01 | 3.85E−01 |
| Neg:588.3810@20.55 | | 0.00 | 0.03 | 9.99E−01 | 5.68E−01 |

TABLE 6B-continued

| Feature ID | Lipid ID | Disease behaviors vs control B1 log$_2$(FC) | SE | p-value | q-value |
|---|---|---|---|---|---|
| Pos:863.6407@30.12 | | −0.06 | 0.07 | 4.07E−01 | 4.26E−01 |
| Neg:890.7125@20.56 | | −0.06 | 0.05 | 2.20E−01 | 3.31E−01 |
| Pos:1254.0843@20.73 | | −0.04 | 0.05 | 3.64E−01 | 4.11E−01 |
| Neg:932.7214@20.56 | | −0.07 | 0.05 | 1.77E−01 | 2.98E−01 |
| Neg:1300.0741@20.57 | | −0.02 | 0.05 | 6.94E−01 | 5.03E−01 |
| Neg:1000.7305@20.57 | | −0.01 | 0.04 | 7.55E−01 | 5.12E−01 |
| Neg:999.7325@20.57 | | −0.01 | 0.05 | 8.77E−01 | 5.37E−01 |
| Neg:602.3689@20.56 | | −0.03 | 0.04 | 4.70E−01 | 4.43E−01 |
| Neg:959.7195@20.57 | | −0.03 | 0.03 | 3.43E−01 | 3.99E−01 |
| Neg:956.7237@20.57 | | −0.03 | 0.04 | 4.43E−01 | 4.38E−01 |
| Neg:888.7128@20.56 | | −0.06 | 0.05 | 2.02E−01 | 3.15E−01 |
| Pos:859.7415@20.74 | | −0.01 | 0.02 | 5.88E−01 | 4.77E−01 |
| Neg:1014.7189@20.56 | | −0.04 | 0.04 | 3.30E−01 | 3.92E−01 |
| Neg:916.7128@20.56 | | −0.04 | 0.04 | 3.75E−01 | 4.15E−01 |
| Pos:873.7556@20.73 | | −0.03 | 0.03 | 3.54E−01 | 4.05E−01 |
| Neg:574.3676@20.53 | | −0.01 | 0.03 | 7.38E−01 | 5.10E−01 |
| Pos:716.5465@17.11 | PE(O-34:3) | 0.08 | 0.04 | 3.43E−02 | 1.23E−01 |
| Neg:522.3685@20.56 | | −0.05 | 0.04 | 2.27E−01 | 3.37E−01 |
| Neg:548.3686@20.55 | | −0.05 | 0.04 | 2.66E−01 | 3.60E−01 |
| Pos:412.2979@9.95 | | 0.14 | 0.07 | 4.00E−02 | 1.35E−01 |
| Pos:674.5372@17.33 | SM(d16:1/16:0) | −0.07 | 0.04 | 6.72E−02 | 1.80E−01 |
| Neg:942.7111@20.55 | | −0.02 | 0.04 | 7.14E−01 | 5.06E−01 |
| Neg:532.3584@20.55 | | −0.08 | 0.08 | 2.97E−01 | 3.73E−01 |
| Neg:466.3396@20.56 | | −0.06 | 0.07 | 4.11E−01 | 4.28E−01 |
| Pos:481.3172@8.20 | LPC(15:0) | −0.10 | 0.05 | 2.50E−02 | 1.08E−01 |
| Neg:604.3632@20.56 | | −0.07 | 0.06 | 2.57E−01 | 3.58E−01 |
| Pos:1405.1372@20.63 | | 0.17 | 0.07 | 1.13E−02 | 7.42E−02 |
| Neg:765.5307@23.93 | PE(18:1_20:4)-1 | −0.11 | 0.08 | 1.80E−01 | 2.99E−01 |
| Pos:611.5657@47.54 | CE(14:1) | −0.34 | 0.11 | 2.20E−03 | 2.58E−02 |
| Pos:842.7249@37.94 | SM(d44:1) | 0.02 | 0.05 | 6.28E−01 | 4.90E−01 |
| Neg:874.7121@36.84 | SM(d43:1) | 0.01 | 0.04 | 8.41E−01 | 5.29E−01 |
| Neg:577.3692@20.56 | | −0.08 | 0.07 | 2.69E−01 | 3.60E−01 |
| Pos:919.7688@45.95 | | 0.07 | 0.09 | 4.11E−01 | 4.28E−01 |
| Pos:700.5335@17.33 | | −0.08 | 0.05 | 8.20E−02 | 2.00E−01 |
| Neg:541.3371@9.22 | LPC(16:0) | 0.04 | 0.04 | 2.75E−01 | 3.64E−01 |
| Pos:368.3443@12.77 | | −0.14 | 0.04 | 1.41E−03 | 1.92E−02 |
| Pos:797.6758@35.44 | GlcCer(d18:1/23:0) | −0.05 | 0.05 | 2.78E−01 | 3.64E−01 |
| Pos:784.6473@28.86 | SM(d18:1/22:1) | −0.08 | 0.04 | 4.83E−02 | 1.51E−01 |
| Neg:466.3133@12.72 | Cholesterol sulfate | −0.12 | 0.05 | 1.90E−02 | 9.39E−02 |
| Pos:699.5646@21.73 | | 0.19 | 0.04 | 4.14E−06 | 4.46E−04 |
| Pos:802.6908@35.79 | | −0.05 | 0.06 | 3.56E−01 | 4.06E−01 |
| Neg:843.6786@35.29 | GlcCer(d18:1/23:0) | −0.05 | 0.05 | 2.65E−01 | 3.60E−01 |
| Neg:848.6949@35.66 | | −0.13 | 0.06 | 3.37E−02 | 1.22E−01 |
| Pos:921.7813@49.56 | TG(18:1_18:2_20:4) | 0.12 | 0.08 | 1.45E−01 | 2.73E−01 |
| Neg:720.5416@17.20 | SM(d16:1/16:0) | −0.06 | 0.04 | 1.37E−01 | 2.64E−01 |
| Pos:832.7000@34.80 | | 0.01 | 0.05 | 8.28E−01 | 5.27E−01 |
| Neg:453.2858@9.43 | LPE(16:0) | 0.03 | 0.05 | 6.26E−01 | 4.90E−01 |
| Pos:826.6879@34.79 | | −0.02 | 0.04 | 6.32E−01 | 4.91E−01 |
| Neg:745.5689@21.54 | GlcCer(d18:1/16:0) | 0.20 | 0.04 | 5.95E−07 | 8.22E−05 |
| Pos:828.7092@36.97 | SM(d43:1) | 0.00 | 0.04 | 9.92E−01 | 5.66E−01 |
| Neg:764.5661@19.37 | | 0.15 | 0.03 | 2.75E−05 | 1.51E−03 |
| Neg:830.6500@28.63 | SM(d18:1/22:1) | −0.11 | 0.04 | 1.17E−02 | 7.47E−02 |
| Pos:895.7651@49.23 | TG(18:2_16:0_20:4) | 0.07 | 0.09 | 4.36E−01 | 4.37E−01 |
| Pos:688.5513@18.48 | SM(d33:1) | −0.07 | 0.05 | 1.56E−01 | 2.84E−01 |
| Pos:613.5800@52.89 | CE(14:0) | −0.25 | 0.08 | 1.12E−03 | 1.61E−02 |
| Pos:686.5357@16.62 | SM(d33:2) | −0.07 | 0.04 | 9.75E−02 | 2.18E−01 |
| Pos:368.3444@60.96 | CE(18:1) | −0.04 | 0.03 | 2.88E−01 | 3.71E−01 |
| Pos:688.5532@18.89 | SM(d17:1/16:0) | −0.03 | 0.04 | 4.56E−01 | 4.41E−01 |
| Pos:828.7092@36.62 | SM(d19:1/24:0) | −0.08 | 0.06 | 2.24E−01 | 3.35E−01 |
| Pos:700.5516@19.06 | SM(d18:2/16:0) | −0.11 | 0.07 | 1.19E−01 | 2.42E−01 |
| Pos:646.5049@14.73 | SM(d16:1/14:0) | −0.13 | 0.06 | 2.13E−02 | 9.84E−02 |
| Pos:798.6629@31.63 | SM(d18:2/23:0) | −0.10 | 0.04 | 1.38E−02 | 8.11E−02 |
| Pos:773.5574@19.33 | | 0.26 | 0.05 | 1.25E−06 | 1.49E−04 |
| Pos:936.7921@49.24 | | 0.14 | 0.10 | 1.64E−01 | 2.89E−01 |
| Neg:874.7116@36.49 | SM(d19:1/24:0) | −0.07 | 0.06 | 2.57E−01 | 3.58E−01 |
| Pos:1215.0900@52.85 | | −0.30 | 0.08 | 4.05E−04 | 8.42E−03 |
| Pos:453.2857@9.48 | LPE(16:0) | 0.02 | 0.05 | 7.00E−01 | 5.04E−01 |
| Pos:660.5202@15.93 | SM(d17:1/18:0) | −0.16 | 0.05 | 2.23E−03 | 2.59E−02 |
| Pos:799.6100@29.09 | PC(19:0_18:2) | −0.03 | 0.06 | 5.94E−01 | 4.79E−01 |
| Pos:720.5763@18.94 | SM(d18:0/16:0)(OH) | −0.06 | 0.05 | 1.56E−01 | 2.83E−01 |
| Neg:860.6963@35.57 | SM(d18:1/24:0) | −0.12 | 0.06 | 4.71E−02 | 1.49E−01 |
| Pos:826.6932@35.39 | SM(d18:1/25:1)-2 | −0.08 | 0.07 | 2.38E−01 | 3.45E−01 |
| Pos:814.6935@35.97 | SM(d18:1/24:0)-2 | 0.01 | 0.04 | 8.84E−01 | 5.38E−01 |
| Pos:800.6783@34.78 | SM(d18:1/25:1)-1 | −0.07 | 0.04 | 6.46E−02 | 1.77E−01 |
| Neg:734.5567@18.74 | SM(d17:1/16:0) | −0.04 | 0.04 | 3.87E−01 | 4.21E−01 |

TABLE 6B-continued

| Feature ID | Lipid ID | Disease behaviors vs control B1 log$_2$(FC) | SE | p-value | q-value |
|---|---|---|---|---|---|
| Pos:798.6620@30.86 | SM(d17:1/24:1) | −0.07 | 0.04 | 9.12E−02 | 2.11E−01 |
| Pos:618.5353@52.85 | CE(14:0) | −0.14 | 0.05 | 4.40E−03 | 3.92E−02 |
| Neg:765.5314@24.31 | PE(18:1_20:4)-2 | 0.13 | 0.07 | 6.03E−02 | 1.71E−01 |
| Pos:885.7788@51.00 | TG(56:4) | 0.07 | 0.07 | 3.21E−01 | 3.87E−01 |
| Pos:772.6469@30.80 | SM(d18:1/21:0) | −0.17 | 0.04 | 1.30E−04 | 4.24E−03 |
| Neg:844.6655@31.39 | SM(d17:1/24:1) | −0.11 | 0.04 | 1.15E−02 | 7.42E−02 |
| Pos:758.6315@28.70 | SM(d16:1/22:0) | −0.19 | 0.05 | 4.06E−04 | 8.42E−03 |
| Pos:928.7515@54.39 | TG(16:0_18:1_22:5) | 0.10 | 0.08 | 2.03E−01 | 3.15E−01 |
| Pos:732.6154@26.04 | SM(d18:0/18:0) | 0.25 | 0.07 | 2.61E−04 | 6.54E−03 |
| Pos:897.7805@53.99 | TG(16:0_18:1_20:4) | 0.05 | 0.09 | 5.43E−01 | 4.62E−01 |
| Pos:887.6154@20.25 | | 0.19 | 0.04 | 1.82E−05 | 1.31E−03 |
| Pos:684.5469@43.77 | | 0.36 | 0.09 | 3.05E−05 | 1.57E−03 |
| Neg:709.6577@39.12 | Cer(d19:1/24:0) | −0.06 | 0.07 | 3.29E−01 | 3.91E−01 |
| Pos:819.6146@27.95 | PC(O-18:0/22:6) | −0.04 | 0.07 | 5.82E−01 | 4.75E−01 |
| Pos:847.6474@31.97 | PC(O-20:0/22:6) | −0.06 | 0.07 | 3.70E−01 | 4.13E−01 |
| Neg:818.6498@30.55 | SM(d18:1/21:0) | −0.16 | 0.04 | 1.64E−04 | 4.84E−03 |
| Neg:793.5603@27.53 | PE(18:0_22:5) | 0.02 | 0.07 | 7.43E−01 | 5.11E−01 |
| Pos:927.8238@51.00 | TG(56:4) | 0.14 | 0.08 | 7.41E−02 | 1.92E−01 |
| Neg:446.3394@13.11 | VLCDCA 28:4 | −0.70 | 0.09 | 1.63E−13 | 5.84E−11 |
| Neg:858.6815@33.55 | SM(d18:2/24:0) | −0.06 | 0.04 | 1.81E−01 | 3.00E−01 |
| Pos:805.5628@20.77 | PC(38:6) | −0.19 | 0.05 | 3.16E−04 | 7.11E−03 |
| Neg:699.6293@39.12 | | −0.05 | 0.07 | 4.64E−01 | 4.41E−01 |
| Neg:873.6871@35.86 | | −0.16 | 0.07 | 3.04E−02 | 1.18E−01 |
| Pos:812.6785@33.81 | SM(d18:2/24:0) | −0.07 | 0.04 | 9.89E−02 | 2.19E−01 |
| Neg:872.6961@35.25 | SM(d18:1/25:1)-2 | −0.10 | 0.06 | 9.57E−02 | 2.16E−01 |
| Pos:607.4579@17.14 | LPC(24:0) | −0.07 | 0.05 | 1.10E−01 | 2.34E−01 |
| Neg:846.6815@34.58 | SM(d18:1/23:0) | −0.05 | 0.04 | 1.84E−01 | 3.02E−01 |
| Neg:850.6670@35.84 | | 0.08 | 0.03 | 1.14E−02 | 7.42E−02 |
| Neg:837.5865@23.92 | PC(O-16:0/22:6) | −0.10 | 0.06 | 1.22E−01 | 2.45E−01 |
| Pos:753.5316@19.29 | | −0.36 | 0.08 | 9.96E−06 | 7.67E−04 |
| Pos:753.5687@29.69 | PE(O-18:0/20:4) | −0.21 | 0.08 | 9.82E−03 | 6.81E−02 |
| Neg:710.6139@36.52 | Cer(d18:1/24:1) | 0.11 | 0.04 | 3.96E−03 | 3.75E−02 |
| Pos:892.6936@51.00 | | 0.14 | 0.07 | 4.87E−02 | 1.51E−01 |
| Neg:799.5353@19.15 | PC(14:0_20:4) | −0.36 | 0.08 | 2.38E−05 | 1.42E−03 |
| Pos:803.5477@18.76 | PC(18:2_20:5) | −0.28 | 0.09 | 1.80E−03 | 2.34E−02 |
| Pos:647.6132@36.64 | | 0.14 | 0.05 | 6.99E−03 | 5.40E−02 |
| Neg:845.6132@28.88 | PC(19:0_18:2) | −0.15 | 0.06 | 1.35E−02 | 8.00E−02 |
| Pos:633.6055@30.86 | SM(d17:1/24:1) | −0.17 | 0.06 | 9.76E−03 | 6.81E−02 |
| Pos:947.7953@51.13 | TG(18:1_18:2_22:5) | 0.07 | 0.11 | 5.27E−01 | 4.58E−01 |
| Pos:744.6146@26.54 | SM(d18:1/19:0) | −0.03 | 0.04 | 3.97E−01 | 4.25E−01 |
| Pos:537.5118@25.39 | | 0.19 | 0.04 | 2.02E−05 | 1.36E−03 |
| Pos:758.6315@28.51 | SM(d18:1/20:0) | 0.22 | 0.04 | 6.10E−07 | 8.22E−05 |
| Pos:730.5994@24.43 | SM(d36:1) | 0.16 | 0.04 | 4.49E−05 | 2.20E−03 |
| Pos:362.2902@11.83 | | −0.34 | 0.08 | 7.52E−05 | 3.12E−03 |
| Pos:559.5691@38.64 | | −0.28 | 0.08 | 3.13E−04 | 7.11E−03 |
| Neg:717.5297@26.55 | PE(16:0_18:1) | 0.01 | 0.09 | 8.99E−01 | 5.41E−01 |
| Neg:725.5345@25.50 | PE(O-16:0/20:4) | −0.36 | 0.09 | 5.84E−05 | 2.62E−03 |
| Neg:693.6257@36.52 | Cer(d18:1/24:1) | 0.13 | 0.05 | 4.02E−03 | 3.77E−02 |
| Pos:552.4389@14.25 | | −0.54 | 0.09 | 3.12E−09 | 6.73E−07 |
| Pos:725.5367@25.70 | PE(O-16:0/20:4) | −0.34 | 0.09 | 1.25E−04 | 4.20E−03 |
| Pos:717.5316@26.75 | | 0.03 | 0.09 | 7.57E−01 | 5.13E−01 |
| Neg:749.5352@24.71 | PE(O-16:0/22:6) | −0.23 | 0.07 | 5.97E−04 | 1.05E−02 |
| Neg:912.5647@22.69 | | 0.02 | 0.04 | 7.04E−01 | 5.04E−01 |
| Pos:728.5844@21.45 | SM(d18:2/18:0) | 0.16 | 0.04 | 1.16E−04 | 4.09E−03 |
| Neg:1152.7105@16.97 | | 0.16 | 0.04 | 1.04E−04 | 4.02E−03 |
| Pos:833.5946@25.01 | PC(18:1_22:5) | 0.05 | 0.11 | 6.31E−01 | 4.91E−01 |
| Pos:585.5850@38.89 | | −0.30 | 0.08 | 3.87E−04 | 8.35E−03 |
| Pos:949.8111@53.74 | TG(18:1_18:2_22:4) | 0.10 | 0.10 | 3.12E−01 | 3.83E−01 |
| Pos:468.3809@12.93 | VLCDCA 28:1(OH) | −0.77 | 0.08 | 1.22E−19 | 6.59E−17 |
| Neg:795.5534@25.83 | | 0.11 | 0.03 | 2.10E−03 | 2.54E−02 |
| Pos:482.3406@12.78 | | 0.09 | 0.03 | 4.14E−03 | 3.78E−02 |
| Neg:442.2743@13.07 | | 0.28 | 0.09 | 1.01E−03 | 1.56E−02 |
| Pos:507.3497@10.01 | | −0.13 | 0.05 | 5.07E−03 | 4.25E−02 |
| Pos:853.5630@19.62 | | −0.14 | 0.06 | 2.67E−02 | 1.10E−01 |
| Neg:670.6212@39.00 | | −0.37 | 0.10 | 3.16E−04 | 7.11E−03 |
| Pos:414.3497@20.82 | | 0.16 | 0.08 | 5.09E−02 | 1.54E−01 |
| Pos:368.3445@53.93 | CE(18:2) | −0.02 | 0.03 | 5.84E−01 | 4.76E−01 |
| Pos:629.6119@36.65 | | 0.12 | 0.05 | 1.39E−02 | 8.15E−02 |
| Neg:386.3151@11.79 | | −0.40 | 0.09 | 6.14E−06 | 5.52E−04 |
| Neg:456.2903@13.07 | | 0.23 | 0.07 | 1.80E−03 | 2.34E−02 |
| Pos:771.5425@19.10 | | 0.40 | 0.07 | 9.64E−08 | 1.73E−05 |
| Pos:942.6220@34.79 | | −0.12 | 0.05 | 9.15E−03 | 6.55E−02 |
| Pos:607.5886@30.05 | | −0.19 | 0.07 | 3.50E−03 | 3.49E−02 |
| Pos:777.5696@28.78 | PE(O-18:0/22:6) | −0.14 | 0.06 | 2.34E−02 | 1.05E−01 |
| Neg:360.2995@11.43 | | −0.36 | 0.09 | 6.49E−05 | 2.80E−03 |

TABLE 6B-continued

| Feature ID | Lipid ID | Disease behaviors vs control B1 | | | |
|---|---|---|---|---|---|
| | | $log_2$(FC) | SE | p-value | q-value |
| Neg:254.2259@11.45 | | 0.33 | 0.11 | 3.71E−03 | 3.61E−02 |
| Pos:282.2675@11.48 | | −0.29 | 0.07 | 1.71E−04 | 4.84E−03 |
| Pos:296.2815@12.27 | | −0.32 | 0.09 | 8.38E−04 | 1.37E−02 |
| Pos:534.4276@14.26 | | −0.53 | 0.08 | 1.34E−09 | 3.60E−07 |
| Neg:468.3817@12.87 | VLCDCA 28:1(OH) | −0.99 | 0.10 | 4.61E−20 | 4.96E−17 |
| Neg:823.5341@18.59 | | −0.28 | 0.08 | 5.64E−04 | 1.01E−02 |
| Pos:265.2768@11.82 | | −0.44 | 0.10 | 6.80E−06 | 5.63E−04 |
| Pos:401.3327@13.20 | | 0.17 | 0.05 | 4.92E−04 | 9.81E−03 |
| Neg:1560.1702@24.20 | | 0.18 | 0.05 | 1.18E−04 | 4.09E−03 |
| Pos:425.3507@9.33 | C18:1 carnitine | 0.27 | 0.07 | 1.03E−04 | 4.02E−03 |
| Neg:774.5880@21.27 | SM(d18:2/18:0) | 0.16 | 0.04 | 2.41E−04 | 6.33E−03 |
| Pos:495.3680@10.90 | | −0.10 | 0.05 | 3.72E−02 | 1.29E−01 |
| Pos:239.2616@11.48 | | −0.37 | 0.09 | 2.21E−05 | 1.40E−03 |
| Pos:635.6214@33.95 | Cer(d18:1/23:0) | −0.11 | 0.05 | 3.24E−02 | 1.22E−01 |
| Pos:564.5340@11.48 | | −0.41 | 0.12 | 5.54E−04 | 1.01E−02 |
| Pos:308.2823@12.00 | | −0.28 | 0.09 | 1.77E−03 | 2.34E−02 |
| Pos:401.3489@15.84 | | 0.11 | 0.04 | 4.79E−03 | 4.16E−02 |
| Neg:642.5898@36.90 | | −0.51 | 0.12 | 2.81E−05 | 1.51E−03 |
| Pos:336.2748@11.48 | | −0.28 | 0.07 | 1.68E−04 | 4.84E−03 |
| Pos:415.3510@13.21 | | 0.17 | 0.05 | 5.12E−04 | 9.85E−03 |
| Neg:416.2750@13.07 | | 0.29 | 0.08 | 6.05E−04 | 1.05E−02 |
| Pos:310.2988@13.17 | | −0.28 | 0.08 | 1.09E−03 | 1.59E−02 |
| Pos:308.2831@11.82 | | −0.40 | 0.08 | 4.92E−06 | 4.82E−04 |
| Pos:749.5364@24.89 | | −0.24 | 0.06 | 2.49E−04 | 6.39E−03 |
| Pos:267.2929@13.16 | | −0.29 | 0.08 | 5.35E−04 | 1.01E−02 |
| Pos:399.3348@8.85 | C16:0 carnitine | 0.21 | 0.05 | 5.66E−05 | 2.62E−03 |
| Pos:607.5179@28.48 | DG(16:0_18:2) | 0.02 | 0.09 | 8.04E−01 | 5.23E−01 |

TABLE 6C

| Feature ID | Lipid ID | Disease behaviors vs control B2/B3 | | | |
|---|---|---|---|---|---|
| | | $log_2$(FC) | SE | p-value | q-value |
| Neg:494.3450@13.93 | Sitosterol sulfate | 0.96 | 0.11 | 1.79E−17 | 2.76E−15 |
| Neg:632.3875@20.55 | | −0.12 | 0.03 | 3.44E−04 | 1.24E−03 |
| Pos:382.3253@18.09 | Cholesta-4,6-dien-3-one | 1.09 | 0.13 | 6.87E−16 | 6.14E−14 |
| Neg:976.7275@20.56 | | −0.13 | 0.04 | 2.12E−03 | 4.22E−03 |
| Neg:588.3810@20.55 | | −0.16 | 0.03 | 5.59E−06 | 4.67E−05 |
| Pos:863.6407@30.12 | | −0.14 | 0.08 | 6.42E−02 | 4.66E−02 |
| Neg:890.7125@20.56 | | −0.16 | 0.05 | 2.43E−03 | 4.54E−03 |
| Pos:1254.0843@20.73 | | −0.17 | 0.05 | 9.29E−04 | 2.51E−03 |
| Neg:932.7214@20.56 | | −0.19 | 0.05 | 2.99E−04 | 1.12E−03 |
| Neg:1300.0741@20.57 | | −0.15 | 0.05 | 2.03E−03 | 4.12E−03 |
| Neg:1000.7305@20.57 | | −0.15 | 0.05 | 8.73E−04 | 2.41E−03 |
| Neg:999.7325@20.57 | | −0.17 | 0.05 | 7.00E−04 | 2.07E−03 |
| Neg:602.3689@20.56 | | −0.15 | 0.04 | 8.32E−05 | 4.34E−04 |
| Neg:959.7195@20.57 | | −0.08 | 0.03 | 1.44E−02 | 1.60E−02 |
| Neg:956.7237@20.57 | | −0.18 | 0.05 | 9.66E−05 | 4.81E−04 |
| Neg:888.7128@20.56 | | −0.17 | 0.05 | 1.19E−03 | 2.96E−03 |
| Pos:859.7415@20.74 | | −0.06 | 0.02 | 1.99E−02 | 2.04E−02 |
| Neg:1014.7189@20.56 | | −0.13 | 0.04 | 8.78E−04 | 2.41E−03 |
| Neg:916.7128@20.56 | | −0.18 | 0.05 | 1.17E−04 | 5.50E−04 |
| Pos:873.7556@20.73 | | −0.10 | 0.04 | 1.25E−02 | 1.45E−02 |
| Neg:574.3676@20.53 | | −0.11 | 0.03 | 3.64E−04 | 1.28E−03 |
| Pos:716.5465@17.11 | PE(O-34:3) | −0.14 | 0.04 | 6.55E−04 | 1.98E−03 |
| Neg:522.3685@20.56 | | −0.14 | 0.05 | 2.93E−03 | 5.17E−03 |
| Neg:548.3686@20.55 | | −0.15 | 0.05 | 7.44E−04 | 2.14E−03 |
| Pos:412.2979@9.95 | | 0.57 | 0.08 | 2.95E−11 | 1.14E−09 |
| Pos:674.5372@17.33 | SM(d16:1/16:0) | −0.24 | 0.04 | 5.17E−10 | 1.88E−08 |
| Neg:942.7111@20.55 | | −0.17 | 0.04 | 1.38E−04 | 6.25E−04 |
| Neg:532.3584@20.55 | | −0.28 | 0.08 | 6.27E−04 | 1.91E−03 |
| Neg:466.3396@20.56 | | −0.29 | 0.07 | 8.87E−05 | 4.53E−04 |
| Pos:481.3172@8.20 | LPC(15:0) | −0.04 | 0.05 | 3.72E−01 | 1.59E−01 |
| Neg:604.3632@20.56 | | −0.22 | 0.06 | 5.08E−04 | 1.63E−03 |
| Pos:1405.1372@20.63 | | −0.15 | 0.07 | 2.91E−02 | 2.67E−02 |
| Neg:765.5307@23.93 | PE(18:1_20:4)-1 | 0.32 | 0.08 | 8.67E−05 | 4.46E−04 |
| Pos:611.5657@47.54 | CE(14:1) | −0.50 | 0.12 | 6.97E−05 | 3.85E−04 |
| Pos:842.7249@37.94 | SM(d44:1) | −0.23 | 0.05 | 5.19E−06 | 4.39E−05 |
| Neg:874.7121@36.84 | SM(d43:1) | −0.23 | 0.04 | 1.98E−07 | 2.78E−06 |
| Neg:577.3692@20.56 | | −0.25 | 0.08 | 1.34E−03 | 3.20E−03 |

TABLE 6C-continued

| Feature ID | Lipid ID | Disease behaviors vs control B2/B3 log$_2$(FC) | SE | p-value | q-value |
|---|---|---|---|---|---|
| Pos:919.7688@45.95 | | 0.38 | 0.09 | 1.81E−05 | 1.23E−04 |
| Pos:700.5335@17.33 | | −0.20 | 0.05 | 1.08E−05 | 8.24E−05 |
| Neg:541.3371@9.22 | LPC(16:0) | 0.08 | 0.04 | 2.06E−02 | 2.08E−02 |
| Pos:368.3443@12.77 | | −0.31 | 0.05 | 6.23E−10 | 2.03E−08 |
| Pos:797.6758@35.44 | GlcCer(d18:1/23:0) | −0.19 | 0.05 | 6.03E−05 | 3.48E−04 |
| Pos:784.6473@28.86 | SM(d18:1/22:1) | −0.20 | 0.04 | 2.10E−06 | 2.20E−05 |
| Neg:466.3133@12.72 | Cholesterol sulfate | −0.28 | 0.05 | 6.88E−07 | 7.72E−06 |
| Pos:699.5646@21.73 | | 0.07 | 0.04 | 1.13E−01 | 6.96E−02 |
| Pos:802.6908@35.79 | | −0.27 | 0.06 | 1.52E−05 | 1.12E−04 |
| Neg:843.6786@35.29 | GlcCer(d18:1/23:0) | −0.23 | 0.05 | 5.19E−06 | 4.39E−05 |
| Neg:848.6949@35.66 | | −0.24 | 0.06 | 1.07E−04 | 5.20E−04 |
| Pos:921.7813@49.56 | TG(18:1_18:2_20:4) | 0.49 | 0.08 | 1.27E−08 | 2.38E−07 |
| Neg:720.5416@17.20 | SM(d16:1/16:0) | −0.21 | 0.04 | 3.29E−08 | 5.65E−07 |
| Pos:832.7000@34.80 | | −0.27 | 0.05 | 6.60E−08 | 1.07E−06 |
| Neg:453.2858@9.43 | LPE(16:0) | 0.24 | 0.06 | 8.37E−05 | 4.34E−04 |
| Pos:826.6879@34.79 | | −0.19 | 0.04 | 1.54E−05 | 1.12E−04 |
| Neg:745.5689@21.54 | GlcCer(d18:1/16:0) | 0.10 | 0.04 | 1.92E−02 | 1.98E−02 |
| Pos:828.7092@36.97 | SM(d43:1) | −0.27 | 0.05 | 5.29E−09 | 1.17E−07 |
| Neg:764.5661@19.37 | | −0.02 | 0.04 | 5.79E−01 | 2.20E−01 |
| Neg:830.6500@28.63 | SM(d18:1/22:1) | −0.20 | 0.04 | 2.74E−06 | 2.74E−05 |
| Pos:895.7651@49.23 | TG(18:2_16:0_20:4) | 0.42 | 0.10 | 2.53E−05 | 1.65E−04 |
| Pos:688.5513@18.48 | SM(d33:1) | −0.29 | 0.05 | 3.06E−08 | 5.40E−07 |
| Pos:613.5800@52.89 | CE(14:0) | −0.39 | 0.08 | 4.01E−06 | 3.87E−05 |
| Pos:686.5357@16.62 | SM(d33:2) | −0.18 | 0.04 | 3.15E−05 | 2.01E−04 |
| Pos:368.3444@60.96 | CE(18:1) | −0.15 | 0.04 | 9.89E−05 | 4.89E−04 |
| Pos:688.5532@18.89 | SM(d17:1/16:0) | −0.23 | 0.04 | 6.58E−09 | 1.40E−07 |
| Pos:828.7092@36.62 | SM(d19:1/24:0) | −0.41 | 0.07 | 2.43E−09 | 6.24E−08 |
| Pos:700.5516@19.06 | SM(d18:2/16:0) | −0.45 | 0.08 | 7.83E−09 | 1.56E−07 |
| Pos:646.5049@14.73 | SM(d16:1/14:0) | −0.20 | 0.06 | 1.31E−03 | 3.14E−03 |
| Pos:798.6629@31.63 | SM(d18:2/23:0) | −0.38 | 0.04 | 6.96E−16 | 6.14E−14 |
| Pos:773.5574@19.33 | | 0.11 | 0.05 | 4.74E−02 | 3.79E−02 |
| Pos:936.7921@49.24 | | 0.44 | 0.10 | 2.55E−05 | 1.65E−04 |
| Neg:874.7116@36.49 | SM(d19:1/24:0) | −0.35 | 0.06 | 1.50E−07 | 2.21E−06 |
| Pos:1215.0900@52.85 | | −0.57 | 0.09 | 1.32E−09 | 3.71E−08 |
| Pos:453.2857@9.48 | LPE(16:0) | 0.21 | 0.05 | 7.38E−05 | 3.96E−04 |
| Pos:660.5202@15.93 | SM(d17:1/18:0) | −0.28 | 0.05 | 7.62E−08 | 1.18E−06 |
| Pos:799.6100@29.09 | PC(19:0_18:2) | −0.28 | 0.06 | 2.75E−06 | 2.74E−05 |
| Pos:720.5763@18.94 | SM(d18:0/16:0)(OH) | −0.28 | 0.05 | 7.01E−09 | 1.44E−07 |
| Neg:860.6963@35.57 | SM(d18:1/24:0) | −0.39 | 0.06 | 4.07E−09 | 9.68E−08 |
| Pos:826.6932@35.39 | SM(d18:1/25:1)-2 | −0.32 | 0.07 | 4.46E−06 | 4.05E−05 |
| Pos:814.6935@35.97 | SM(d18:1/24:0)-2 | −0.21 | 0.05 | 4.36E−06 | 4.02E−05 |
| Pos:800.6783@34.78 | SM(d18:1/25:1)-1 | −0.32 | 0.04 | 1.71E−13 | 1.17E−11 |
| Neg:734.5567@18.74 | SM(d17:1/16:0) | −0.23 | 0.04 | 3.40E−08 | 5.67E−07 |
| Pos:798.6620@30.86 | SM(d17:1/24:1) | −0.18 | 0.04 | 3.51E−05 | 2.19E−04 |
| Pos:618.5353@52.85 | CE(14:0) | −0.25 | 0.05 | 4.10E−06 | 3.89E−05 |
| Neg:765.5314@24.31 | PE(18:1_20:4)-2 | 0.32 | 0.08 | 3.93E−05 | 2.40E−04 |
| Pos:885.7788@51.00 | TG(56:4) | 0.34 | 0.07 | 4.56E−06 | 4.08E−05 |
| Pos:772.6469@30.80 | SM(d18:1/21:0) | −0.40 | 0.04 | 5.12E−18 | 1.05E−15 |
| Neg:844.6655@31.39 | SM(d17:1/24:1) | −0.36 | 0.05 | 2.86E−13 | 1.60E−11 |
| Pos:758.6315@28.70 | SM(d16:1/22:0) | −0.38 | 0.05 | 6.83E−13 | 3.25E−11 |
| Pos:928.7515@54.39 | TG(16:0_18:1_22:5) | 0.41 | 0.08 | 6.52E−07 | 7.46E−06 |
| Pos:732.6154@26.04 | SM(d18:0/18:0) | 0.24 | 0.07 | 6.04E−04 | 1.85E−03 |
| Pos:897.7805@53.99 | TG(16:0_18:1_20:4) | 0.37 | 0.09 | 6.75E−05 | 3.81E−04 |
| Pos:887.6154@20.25 | | 0.17 | 0.05 | 3.85E−04 | 1.32E−03 |
| Pos:684.5469@43.77 | | 0.38 | 0.09 | 2.84E−05 | 1.83E−04 |
| Neg:709.6577@39.12 | Cer(d19:1/24:0) | −0.28 | 0.07 | 7.94E−05 | 4.23E−04 |
| Pos:819.6146@27.95 | PC(O-18:0/22:6) | −0.32 | 0.07 | 1.79E−05 | 1.23E−04 |
| Pos:847.6474@31.97 | PC(O-20:0/22:6) | −0.32 | 0.08 | 4.73E−05 | 2.79E−04 |
| Neg:818.6498@30.55 | SM(d18:1/21:0) | −0.38 | 0.04 | 6.03E−17 | 7.44E−15 |
| Neg:793.5603@27.53 | PE(18:0_22:5) | 0.34 | 0.08 | 3.22E−05 | 2.03E−04 |
| Pos:927.8238@51.00 | TG(56:4) | 0.35 | 0.08 | 6.40E−06 | 5.20E−05 |
| Neg:446.3394@13.11 | VLCDCA 28:4 | −0.73 | 0.09 | 1.38E−13 | 1.06E−11 |
| Neg:858.6815@33.55 | SM(d18:2/24:0) | −0.25 | 0.05 | 3.46E−07 | 4.27E−06 |
| Pos:805.5628@20.77 | PC(38:6) | −0.26 | 0.06 | 8.96E−06 | 7.00E−05 |
| Neg:699.6293@39.12 | | −0.29 | 0.07 | 9.51E−05 | 4.77E−04 |
| Neg:873.6871@35.86 | | −0.37 | 0.07 | 1.20E−06 | 1.33E−05 |
| Pos:812.6785@33.81 | SM(d18:2/24:0) | −0.31 | 0.05 | 1.75E−09 | 4.70E−08 |
| Neg:872.6961@35.25 | SM(d18:1/25:1)-2 | −0.42 | 0.07 | 7.98E−10 | 2.46E−08 |
| Pos:607.4579@17.14 | LPC(24:0) | −0.22 | 0.05 | 1.64E−05 | 1.14E−04 |
| Neg:846.6815@34.58 | SM(d18:1/23:0) | −0.24 | 0.04 | 3.50E−09 | 8.65E−08 |
| Neg:850.6670@35.84 | | −0.08 | 0.03 | 2.28E−02 | 2.23E−02 |
| Neg:837.5865@23.92 | PC(O-16:0/22:6) | −0.28 | 0.06 | 1.62E−05 | 1.14E−04 |
| Pos:753.5316@19.29 | | −0.24 | 0.09 | 6.98E−03 | 9.43E−03 |
| Pos:753.5687@29.69 | PE(O-18:0/20:4) | −0.52 | 0.09 | 1.17E−08 | 2.26E−07 |
| Neg:710.6139@36.52 | Cer(d18:1/24:1) | 0.18 | 0.04 | 3.59E−05 | 2.22E−04 |

TABLE 6C-continued

| Feature ID | Lipid ID | Disease behaviors vs control B2/B3 | | | |
|---|---|---|---|---|---|
| | | $log_2(FC)$ | SE | p-value | q-value |
| Pos:892.6936@51.00 | | 0.29 | 0.07 | 8.14E−05 | 4.30E−04 |
| Neg:799.5353@19.15 | PC(14:0_20:4) | −0.22 | 0.09 | 2.05E−02 | 2.08E−02 |
| Pos:803.5477@18.76 | PC(18:2_20:5) | −0.37 | 0.09 | 6.98E−05 | 3.85E−04 |
| Pos:647.6132@36.64 | | 0.21 | 0.06 | 1.77E−04 | 7.64E−04 |
| Neg:845.6132@28.88 | PC(19:0_18:2) | −0.34 | 0.06 | 6.87E−08 | 1.09E−06 |
| Pos:633.6055@30.86 | SM(d17:1/24:1) | −0.41 | 0.07 | 2.49E−08 | 4.52E−07 |
| Pos:947.7953@51.13 | TG(18:1_18:2_22:5) | 0.45 | 0.11 | 5.67E−05 | 3.30E−04 |
| Pos:744.6146@26.54 | SM(d18:1/19:0) | −0.18 | 0.04 | 6.76E−06 | 5.42E−05 |
| Pos:537.5118@25.39 | | 0.11 | 0.05 | 1.90E−02 | 1.97E−02 |
| Pos:758.6315@28.51 | SM(d18:1/20:0) | 0.24 | 0.05 | 2.34E−07 | 3.21E−06 |
| Pos:730.5994@24.43 | SM(d36:1) | 0.12 | 0.04 | 2.96E−03 | 5.18E−03 |
| Pos:362.2902@11.83 | | −0.45 | 0.09 | 3.53E−07 | 4.27E−06 |
| Pos:559.5691@38.64 | | −0.28 | 0.08 | 7.71E−04 | 2.16E−03 |
| Neg:717.5297@26.55 | PE(16:0_18:1) | 0.38 | 0.09 | 7.06E−05 | 3.86E−04 |
| Neg:725.5345@25.50 | PE(O-16:0/20:4) | −0.69 | 0.09 | 2.13E−13 | 1.32E−11 |
| Neg:693.6257@36.52 | Cer(d18:1/24:1) | 0.24 | 0.05 | 3.36E−06 | 3.29E−05 |
| Pos:552.4389@14.25 | | −0.68 | 0.09 | 3.98E−12 | 1.76E−10 |
| Pos:725.5367@25.70 | PE(O-16:0/20:4) | −0.65 | 0.09 | 6.85E−13 | 3.25E−11 |
| Pos:717.5316@26.75 | | 0.39 | 0.09 | 4.74E−05 | 2.79E−04 |
| Neg:749.5352@24.71 | PE(O-16:0/22:6) | −0.41 | 0.07 | 4.60E−09 | 1.05E−07 |
| Neg:912.5647@22.69 | | 0.19 | 0.04 | 1.60E−05 | 1.14E−04 |
| Pos:728.5844@21.45 | SM(d18:2/18:0) | 0.13 | 0.04 | 3.59E−03 | 5.89E−03 |
| Neg:1152.7105@16.97 | | 0.13 | 0.04 | 3.26E−03 | 5.57E−03 |
| Pos:833.5946@25.01 | PC(18:1_22:5) | 0.47 | 0.11 | 1.99E−05 | 1.33E−04 |
| Pos:585.5850@38.89 | | −0.30 | 0.09 | 7.06E−04 | 2.07E−03 |
| Pos:949.8111@53.74 | TG(18:1_18:2_22:4) | 0.44 | 0.10 | 1.60E−05 | 1.14E−04 |
| Pos:468.3809@12.93 | VLCDCA 28:1(OH) | −0.86 | 0.08 | 1.11E−21 | 3.42E−19 |
| Neg:795.5534@25.83 | | 0.13 | 0.04 | 3.09E−04 | 1.16E−03 |
| Pos:482.3406@12.78 | | 0.14 | 0.03 | 1.09E−05 | 8.24E−05 |
| Neg:442.2743@13.07 | | 0.32 | 0.09 | 3.85E−04 | 1.32E−03 |
| Pos:507.3497@10.01 | | −0.22 | 0.05 | 1.09E−05 | 8.24E−05 |
| Pos:853.5630@19.62 | | −0.32 | 0.07 | 2.38E−06 | 2.45E−05 |
| Neg:670.6212@39.00 | | −0.53 | 0.10 | 3.93E−07 | 4.67E−06 |
| Pos:414.3497@20.82 | | 0.39 | 0.09 | 7.80E−06 | 6.18E−05 |
| Pos:368.3445@53.93 | CE(18:2) | −0.15 | 0.04 | 7.22E−05 | 3.91E−04 |
| Pos:629.6119@36.65 | | 0.24 | 0.05 | 1.38E−05 | 1.03E−04 |
| Neg:386.3151@11.79 | | −0.44 | 0.09 | 1.23E−06 | 1.33E−05 |
| Neg:456.2903@13.07 | | 0.27 | 0.08 | 3.72E−04 | 1.30E−03 |
| Pos:771.5425@19.10 | | 0.48 | 0.08 | 5.49E−10 | 1.88E−08 |
| Pos:942.6220@34.79 | | −0.25 | 0.05 | 1.60E−06 | 1.71E−05 |
| Pos:607.5886@30.05 | | −0.39 | 0.07 | 1.25E−07 | 1.89E−06 |
| Pos:777.5696@28.78 | PE(O-18:0/22:6) | −0.38 | 0.07 | 2.57E−07 | 3.38E−06 |
| Neg:360.2995@11.43 | | −0.37 | 0.09 | 4.37E−05 | 2.62E−04 |
| Neg:254.2259@11.45 | | 0.49 | 0.12 | 4.27E−05 | 2.58E−04 |
| Pos:282.2675@11.48 | | −0.27 | 0.07 | 3.25E−04 | 1.19E−03 |
| Pos:296.2815@12.27 | | −0.44 | 0.10 | 5.96E−06 | 4.91E−05 |
| Pos:534.4276@14.26 | | −0.61 | 0.09 | 2.23E−11 | 9.16E−10 |
| Neg:468.3817@12.87 | VLCDCA 28:1(OH) | −1.23 | 0.10 | 7.69E−27 | 4.75E−24 |
| Neg:823.5341@18.59 | | −0.30 | 0.09 | 1.06E−03 | 2.70E−03 |
| Pos:265.2768@11.82 | | −0.53 | 0.10 | 1.95E−07 | 2.78E−06 |
| Pos:401.3327@13.20 | | 0.16 | 0.05 | 1.30E−03 | 3.13E−03 |
| Neg:1560.1702@24.20 | | 0.23 | 0.05 | 4.86E−06 | 4.23E−05 |
| Pos:425.3507@9.33 | C18:1 carnitine | 0.26 | 0.08 | 7.52E−04 | 2.14E−03 |
| Neg:774.5880@21.27 | SM(d18:2/18:0) | 0.15 | 0.05 | 1.49E−03 | 3.36E−03 |
| Pos:495.3680@10.90 | | −0.22 | 0.05 | 6.78E−05 | 3.81E−04 |
| Pos:239.2616@11.48 | | −0.33 | 0.08 | 6.37E−05 | 3.64E−04 |
| Pos:635.6214@33.95 | Cer(d18:1/23:0) | −0.28 | 0.06 | 4.69E−06 | 4.14E−05 |
| Pos:564.5340@11.48 | | −0.47 | 0.12 | 9.46E−05 | 4.77E−04 |
| Pos:308.2823@12.00 | | −0.33 | 0.09 | 3.21E−04 | 1.19E−03 |
| Pos:401.3489@15.84 | | 0.15 | 0.04 | 1.13E−04 | 5.46E−04 |
| Neg:642.5898@36.90 | | −0.60 | 0.12 | 3.30E−07 | 4.24E−06 |
| Pos:336.2748@11.48 | | −0.32 | 0.07 | 2.33E−05 | 1.55E−04 |
| Pos:415.3510@13.21 | | 0.17 | 0.05 | 1.06E−03 | 2.70E−03 |
| Neg:416.2750@13.07 | | 0.33 | 0.09 | 3.30E−04 | 1.20E−03 |
| Pos:310.2988@13.17 | | −0.44 | 0.09 | 6.21E−07 | 7.24E−06 |
| Pos:308.2831@11.82 | | −0.46 | 0.09 | 2.40E−07 | 3.23E−06 |
| Pos:749.5364@24.89 | | −0.43 | 0.07 | 1.13E−09 | 3.31E−08 |
| Pos:267.2929@13.16 | | −0.45 | 0.09 | 3.44E−07 | 4.27E−06 |
| Pos:399.3348@8.85 | C16:0 carnitine | 0.18 | 0.05 | 1.07E−03 | 2.70E−03 |
| Pos:607.5179@28.48 | DG(16:0_18:2) | 0.44 | 0.09 | 4.19E−06 | 3.92E−05 |

TABLE 6D

| | | Disease behavior B2/B3 vs B1 | | | |
|---|---|---|---|---|---|
| Feature ID | Lipid ID | $log_2$(FC) | SE | p-value | q-value |
| Neg:494.3450@13.93 | Sitosterol sulfate | 0.72 | 0.14 | 6.23E−07 | 6.16E−04 |
| Neg:632.3875@20.55 | | −0.10 | 0.03 | 3.42E−03 | 3.72E−02 |
| Pos:382.3253@18.09 | Cholesta-4,6-dien-3-one | 0.82 | 0.16 | 1.15E−06 | 6.16E−04 |
| Neg:976.7275@20.56 | | −0.09 | 0.06 | 1.01E−01 | 1.78E−01 |
| Neg:588.3810@20.55 | | −0.16 | 0.04 | 8.27E−05 | 5.02E−03 |
| Pos:863.6407@30.12 | | −0.08 | 0.10 | 3.91E−01 | 3.49E−01 |
| Neg:890.7125@20.56 | | −0.10 | 0.07 | 1.22E−01 | 1.96E−01 |
| Pos:1254.0843@20.73 | | −0.12 | 0.06 | 3.15E−02 | 1.01E−01 |
| Neg:932.7214@20.56 | | −0.13 | 0.07 | 6.04E−02 | 1.36E−01 |
| Neg:1300.0741@20.57 | | −0.12 | 0.06 | 3.71E−02 | 1.09E−01 |
| Neg:1000.7305@20.57 | | −0.14 | 0.06 | 1.64E−02 | 8.26E−02 |
| Neg:999.7325@20.57 | | −0.16 | 0.06 | 9.38E−03 | 6.13E−02 |
| Neg:602.3689@20.56 | | −0.13 | 0.05 | 1.32E−02 | 7.49E−02 |
| Neg:959.7195@20.57 | | −0.06 | 0.04 | 2.17E−01 | 2.53E−01 |
| Neg:956.7237@20.57 | | −0.15 | 0.06 | 1.39E−02 | 7.55E−02 |
| Neg:888.7128@20.56 | | −0.11 | 0.06 | 9.54E−02 | 1.71E−01 |
| Pos:859.7415@20.74 | | −0.05 | 0.03 | 9.60E−02 | 1.72E−01 |
| Neg:1014.7189@20.56 | | −0.09 | 0.05 | 6.73E−02 | 1.43E−01 |
| Neg:916.7128@20.56 | | −0.14 | 0.06 | 2.05E−02 | 8.66E−02 |
| Pos:873.7556@20.73 | | −0.06 | 0.04 | 1.24E−01 | 1.98E−01 |
| Neg:574.3676@20.53 | | −0.10 | 0.04 | 7.92E−03 | 5.46E−02 |
| Pos:716.5465@17.11 | PE(O-34:3) | −0.21 | 0.05 | 2.95E−05 | 3.51E−03 |
| Neg:522.3685@20.56 | | −0.09 | 0.06 | 1.17E−01 | 1.92E−01 |
| Neg:548.3686@20.55 | | −0.11 | 0.06 | 5.59E−02 | 1.32E−01 |
| Pos:412.2979@9.95 | | 0.43 | 0.10 | 5.51E−05 | 4.22E−03 |
| Pos:674.5372@17.33 | SM(d16:1/16:0) | −0.17 | 0.05 | 2.41E−04 | 8.63E−03 |
| Neg:942.7111@20.55 | | −0.15 | 0.06 | 7.69E−03 | 5.46E−02 |
| Neg:532.3584@20.55 | | −0.20 | 0.10 | 5.37E−02 | 1.28E−01 |
| Neg:466.3396@20.56 | | −0.23 | 0.09 | 1.03E−02 | 6.44E−02 |
| Pos:481.3172@8.20 | LPC(15:0) | 0.07 | 0.06 | 2.98E−01 | 3.02E−01 |
| Neg:604.3632@20.56 | | −0.15 | 0.08 | 6.03E−02 | 1.36E−01 |
| Pos:1405.1372@20.63 | | −0.32 | 0.08 | 9.25E−05 | 5.21E−03 |
| Neg:765.5307@23.93 | PE(18:1_20:4)-1 | 0.42 | 0.11 | 1.62E−04 | 7.39E−03 |
| Pos:611.5657@47.54 | CE(14:1) | −0.14 | 0.14 | 3.12E−01 | 3.10E−01 |
| Pos:842.7249@37.94 | SM(d44:1) | −0.25 | 0.05 | 6.54E−06 | 1.14E−03 |
| Neg:874.7121@36.84 | SM(d43:1) | −0.25 | 0.06 | 2.64E−05 | 3.51E−03 |
| Neg:577.3692@20.56 | | −0.17 | 0.09 | 7.76E−02 | 1.53E−01 |
| Pos:919.7688@45.95 | | 0.31 | 0.10 | 2.22E−03 | 3.13E−02 |
| Pos:700.5335@17.33 | | −0.12 | 0.05 | 2.15E−02 | 8.66E−02 |
| Neg:541.3371@9.22 | LPC(16:0) | 0.05 | 0.05 | 3.25E−01 | 3.17E−01 |
| Pos:368.3443@12.77 | | −0.16 | 0.06 | 8.08E−03 | 5.49E−02 |
| Pos:797.6758@35.44 | GlcCer(d18:1/23:0) | −0.14 | 0.06 | 2.29E−02 | 8.87E−02 |
| Pos:784.6473@28.86 | SM(d18:1/22:1) | −0.12 | 0.05 | 1.32E−02 | 7.49E−02 |
| Neg:466.3133@12.72 | Cholesterol sulfate | −0.14 | 0.07 | 4.80E−02 | 1.21E−01 |
| Pos:699.5646@21.73 | | −0.12 | 0.05 | 3.03E−02 | 9.94E−02 |
| Pos:802.6908@35.79 | | −0.21 | 0.08 | 7.85E−03 | 5.46E−02 |
| Neg:843.6786@35.29 | GlcCer(d18:1/23:0) | −0.18 | 0.06 | 5.09E−03 | 4.53E−02 |
| Neg:848.6949@35.66 | | −0.12 | 0.08 | 1.52E−01 | 2.18E−01 |
| Pos:921.7813@49.56 | TG(18:1_18:2_20:4) | 0.37 | 0.10 | 1.79E−04 | 7.67E−03 |
| Neg:720.5416@17.20 | SM(d16:1/16:0) | −0.15 | 0.05 | 3.63E−03 | 3.85E−02 |
| Pos:832.7000@34.80 | | −0.28 | 0.06 | 7.43E−06 | 1.14E−03 |
| Neg:453.2858@9.43 | LPE(16:0) | 0.21 | 0.07 | 4.87E−03 | 4.52E−02 |
| Pos:826.6879@34.79 | | −0.17 | 0.05 | 2.61E−03 | 3.36E−02 |
| Neg:745.5689@21.54 | GlcCer(d18:1/16:0) | −0.10 | 0.05 | 4.48E−02 | 1.19E−01 |
| Pos:828.7092@36.97 | SM(d43:1) | −0.27 | 0.06 | 2.91E−06 | 6.57E−04 |
| Neg:764.5661@19.37 | | −0.17 | 0.05 | 6.12E−04 | 1.68E−02 |
| Neg:830.6500@28.63 | SM(d18:1/22:1) | −0.09 | 0.05 | 8.60E−02 | 1.61E−01 |
| Pos:895.7651@49.23 | TG(18:2_16:0_20:4) | 0.34 | 0.10 | 1.28E−03 | 2.36E−02 |
| Pos:688.5513@18.48 | SM(d33:1) | −0.21 | 0.06 | 1.01E−03 | 2.20E−02 |
| Pos:613.5800@52.89 | CE(14:0) | −0.14 | 0.09 | 1.45E−01 | 2.13E−01 |
| Pos:686.5357@16.62 | SM(d33:2) | −0.12 | 0.05 | 2.45E−02 | 9.09E−02 |
| Pos:368.3444@60.96 | CE(18:1) | −0.11 | 0.04 | 4.86E−03 | 4.52E−02 |
| Pos:688.5532@18.89 | SM(d17:1/16:0) | −0.20 | 0.05 | 4.11E−05 | 4.20E−03 |
| Pos:828.7092@36.62 | SM(d19:1/24:0) | −0.34 | 0.08 | 8.43E−05 | 5.02E−03 |
| Pos:700.5516@19.06 | SM(d18:2/16:0) | −0.34 | 0.09 | 1.16E−04 | 5.92E−03 |
| Pos:646.5049@14.73 | SM(d16:1/14:0) | −0.06 | 0.07 | 4.18E−01 | 3.63E−01 |
| Pos:798.6629@31.63 | SM(d18:2/23:0) | −0.28 | 0.06 | 3.07E−06 | 6.57E−04 |
| Pos:773.5574@19.33 | | −0.14 | 0.07 | 5.21E−02 | 1.26E−01 |
| Pos:936.7921@49.24 | | 0.30 | 0.11 | 5.14E−03 | 4.53E−02 |
| Neg:874.7116@36.49 | SM(d19:1/24:0) | −0.28 | 0.08 | 8.59E−04 | 2.04E−02 |
| Pos:1215.0900@52.85 | | −0.26 | 0.11 | 1.72E−02 | 8.37E−02 |
| Pos:453.2857@9.48 | LPE(16:0) | 0.19 | 0.06 | 2.87E−03 | 3.49E−02 |
| Pos:660.5202@15.93 | SM(d17:1/18:0) | −0.12 | 0.07 | 6.80E−02 | 1.44E−01 |
| Pos:799.6100@29.09 | PC(19:0_18:2) | −0.25 | 0.07 | 2.42E−04 | 8.63E−03 |
| Pos:720.5763@18.94 | SM(d18:0/16:0)(OH) | −0.21 | 0.06 | 3.67E−04 | 1.19E−02 |

TABLE 6D-continued

| Feature ID | Lipid ID | Disease behavior B2/B3 vs B1 log$_2$(FC) | SE | p-value | q-value |
|---|---|---|---|---|---|
| Neg:860.6963@35.57 | SM(d18:1/24:0) | −0.27 | 0.08 | 1.64E−03 | 2.78E−02 |
| Pos:826.6932@35.39 | SM(d18:1/25:1)-2 | −0.24 | 0.08 | 3.80E−03 | 3.96E−02 |
| Pos:814.6935@35.97 | SM(d18:1/24:0)-2 | −0.22 | 0.05 | 4.31E−05 | 4.20E−03 |
| Pos:800.6783@34.78 | SM(d18:1/25:1)-1 | −0.25 | 0.05 | 2.15E−06 | 6.57E−04 |
| Neg:734.5567@18.74 | SM(d17:1/16:0) | −0.19 | 0.05 | 4.12E−04 | 1.30E−02 |
| Pos:798.6620@30.86 | SM(d17:1/24:1) | −0.11 | 0.05 | 3.62E−02 | 1.08E−01 |
| Pos:618.5353@52.85 | CE(14:0) | −0.10 | 0.06 | 1.07E−01 | 1.83E−01 |
| Neg:765.5314@24.31 | PE(18:1_20:4)-2 | 0.17 | 0.09 | 4.52E−02 | 1.19E−01 |
| Pos:885.7788@51.00 | TG(56:4) | 0.26 | 0.08 | 2.34E−03 | 3.21E−02 |
| Pos:772.6469@30.80 | SM(d18:1/21:0) | −0.24 | 0.06 | 5.40E−05 | 4.22E−03 |
| Neg:844.6655@31.39 | SM(d17:1/24:1) | −0.26 | 0.06 | 6.10E−05 | 4.36E−03 |
| Pos:758.6315@28.70 | SM(d16:1/22:0) | −0.20 | 0.06 | 1.40E−03 | 2.50E−02 |
| Pos:928.7515@54.39 | TG(16:0_18:1_22:5) | 0.31 | 0.09 | 1.39E−03 | 2.50E−02 |
| Pos:732.6154@26.04 | SM(d18:0/18:0) | −0.01 | 0.09 | 8.80E−01 | 5.33E−01 |
| Pos:897.7805@53.99 | TG(16:0_18:1_20:4) | 0.31 | 0.10 | 1.90E−03 | 2.83E−02 |
| Pos:887.6154@20.25 | | −0.03 | 0.05 | 6.24E−01 | 4.50E−01 |
| Pos:684.5469@43.77 | | 0.00 | 0.11 | 9.66E−01 | 5.57E−01 |
| Neg:709.6577@39.12 | Cer(d19:1/24:0) | −0.22 | 0.09 | 1.52E−02 | 7.97E−02 |
| Pos:819.6146@27.95 | PC(O-18:0/22:6) | −0.28 | 0.09 | 1.77E−03 | 2.79E−02 |
| Pos:847.6474@31.97 | PC(O-20:0/22:6) | −0.25 | 0.09 | 6.58E−03 | 5.07E−02 |
| Neg:818.6498@30.55 | SM(d18:1/21:0) | −0.22 | 0.06 | 2.27E−04 | 8.63E−03 |
| Neg:793.5603@27.53 | PE(18:0_22:5) | 0.31 | 0.10 | 1.88E−03 | 2.83E−02 |
| Pos:927.8238@51.00 | TG(56:4) | 0.21 | 0.09 | 2.33E−02 | 8.93E−02 |
| Neg:446.3394@13.11 | VLCDCA 28:4 | −0.04 | 0.12 | 7.28E−01 | 4.89E−01 |
| Neg:858.6815@33.55 | SM(d18:2/24:0) | −0.20 | 0.06 | 9.77E−04 | 2.18E−02 |
| Pos:805.5628@20.77 | PC(38:6) | −0.07 | 0.06 | 2.90E−01 | 2.98E−01 |
| Neg:699.6293@39.12 | | −0.24 | 0.09 | 9.58E−03 | 6.18E−02 |
| Neg:873.6871@35.86 | | −0.20 | 0.09 | 2.95E−02 | 9.90E−02 |
| Pos:812.6785@33.81 | SM(d18:2/24:0) | −0.24 | 0.06 | 8.07E−05 | 5.02E−03 |
| Neg:872.6961@35.25 | SM(d18:1/25:1)-2 | −0.31 | 0.08 | 3.25E−04 | 1.12E−02 |
| Pos:607.4579@17.14 | LPC(24:0) | −0.14 | 0.06 | 1.98E−02 | 8.64E−02 |
| Neg:846.6815@34.58 | SM(d18:1/23:0) | −0.20 | 0.05 | 1.16E−04 | 5.92E−03 |
| Neg:850.6670@35.84 | | −0.16 | 0.04 | 5.47E−05 | 4.22E−03 |
| Neg:837.5865@23.92 | PC(O-16:0/22:6) | −0.18 | 0.08 | 2.27E−02 | 8.84E−02 |
| Pos:753.5316@19.29 | | 0.13 | 0.11 | 2.31E−01 | 2.62E−01 |
| Pos:753.5687@29.69 | PE(O-18:0/20:4) | −0.29 | 0.11 | 6.71E−03 | 5.07E−02 |
| Neg:710.6139@36.52 | Cer(d18:1/24:1) | 0.07 | 0.05 | 1.74E−01 | 2.30E−01 |
| Pos:892.6936@51.00 | | 0.15 | 0.08 | 6.16E−02 | 1.37E−01 |
| Neg:799.5353@19.15 | PC(14:0_20:4) | 0.16 | 0.12 | 1.70E−01 | 2.28E−01 |
| Pos:803.5477@18.76 | PC(18:2_20:5) | −0.09 | 0.12 | 4.35E−01 | 3.71E−01 |
| Pos:647.6132@36.64 | | 0.07 | 0.06 | 2.42E−01 | 2.69E−01 |
| Neg:845.6132@28.88 | PC(19:0_18:2) | −0.19 | 0.08 | 1.44E−02 | 7.73E−02 |
| Pos:633.6055@30.86 | SM(d17:1/24:1) | −0.26 | 0.09 | 3.14E−03 | 3.61E−02 |
| Pos:947.7953@51.13 | TG(18:1_18:2_22:5) | 0.39 | 0.13 | 2.85E−03 | 3.49E−02 |
| Pos:744.6146@26.54 | SM(d18:1/19:0) | −0.15 | 0.05 | 2.59E−03 | 3.36E−02 |
| Pos:537.5118@25.39 | | −0.07 | 0.06 | 2.14E−01 | 2.51E−01 |
| Pos:758.6315@28.51 | SM(d18:1/20:0) | 0.02 | 0.06 | 7.90E−01 | 5.10E−01 |
| Pos:730.5994@24.43 | SM(d36:1) | −0.04 | 0.05 | 3.71E−01 | 3.39E−01 |
| Pos:362.2902@11.83 | | −0.10 | 0.11 | 3.51E−01 | 3.30E−01 |
| Pos:559.5691@38.64 | | 0.00 | 0.11 | 9.75E−01 | 5.58E−01 |
| Neg:717.5297@26.55 | PE(16:0_18:1) | 0.37 | 0.12 | 1.90E−03 | 2.83E−02 |
| Neg:725.5345@25.50 | PE(O-16:0/20:4) | −0.31 | 0.11 | 5.12E−03 | 4.53E−02 |
| Neg:693.6257@36.52 | Cer(d18:1/24:1) | 0.10 | 0.06 | 7.85E−02 | 1.53E−01 |
| Pos:552.4389@14.25 | | −0.15 | 0.13 | 2.39E−01 | 2.67E−01 |
| Pos:725.5367@25.70 | PE(O-16:0/20:4) | −0.30 | 0.11 | 5.04E−03 | 4.53E−02 |
| Pos:717.5316@26.75 | | 0.37 | 0.12 | 2.39E−03 | 3.24E−02 |
| Neg:749.5352@24.71 | PE(O-16:0/22:6) | −0.18 | 0.09 | 5.35E−02 | 1.28E−01 |
| Neg:912.5647@22.69 | | 0.16 | 0.05 | 3.32E−03 | 3.71E−02 |
| Pos:728.5844@21.45 | SM(d18:2/18:0) | −0.04 | 0.05 | 4.58E−01 | 3.82E−01 |
| Neg:1152.7105@16.97 | | −0.03 | 0.05 | 5.66E−01 | 4.27E−01 |
| Pos:833.5946@25.01 | PC(18:1_22:5) | 0.42 | 0.14 | 2.51E−03 | 3.36E−02 |
| Pos:585.5850@38.89 | | −0.01 | 0.11 | 9.23E−01 | 5.45E−01 |
| Pos:949.8111@53.74 | TG(18:1_18:2_22:4) | 0.35 | 0.11 | 1.25E−03 | 2.35E−02 |
| Pos:468.3809@12.93 | VLCDCA 28:1(OH) | −0.10 | 0.11 | 3.29E−01 | 3.17E−01 |
| Neg:795.5534@25.83 | | 0.03 | 0.04 | 4.63E−01 | 3.84E−01 |
| Pos:482.3406@12.78 | | 0.05 | 0.04 | 1.55E−01 | 2.18E−01 |
| Neg:442.2743@13.07 | | 0.03 | 0.11 | 8.22E−01 | 5.21E−01 |
| Pos:507.3497@10.01 | | −0.08 | 0.06 | 1.73E−01 | 2.29E−01 |
| Pos:853.5630@19.62 | | −0.18 | 0.09 | 3.51E−02 | 1.08E−01 |
| Neg:670.6212@39.00 | | −0.15 | 0.13 | 2.41E−01 | 2.68E−01 |
| Pos:414.3497@20.82 | | 0.22 | 0.10 | 2.78E−02 | 9.66E−02 |
| Pos:368.3445@53.93 | CE(18:2) | −0.13 | 0.04 | 1.86E−03 | 2.83E−02 |
| Pos:629.6119@36.65 | | 0.11 | 0.06 | 6.06E−02 | 1.36E−01 |
| Neg:386.3151@11.79 | | −0.03 | 0.11 | 8.08E−01 | 5.15E−01 |
| Neg:456.2903@13.07 | | 0.03 | 0.10 | 7.39E−01 | 4.93E−01 |

TABLE 6D-continued

| | | Disease behavior B2/B3 vs B1 | | | |
|---|---|---|---|---|---|
| Feature ID | Lipid ID | $log_2$(FC) | SE | p-value | q-value |
| Pos:771.5425@19.10 | | 0.09 | 0.10 | 3.63E−01 | 3.37E−01 |
| Pos:942.6220@34.79 | | −0.13 | 0.07 | 4.59E−02 | 1.19E−01 |
| Pos:607.5886@30.05 | | −0.20 | 0.09 | 2.16E−02 | 8.66E−02 |
| Pos:777.5696@28.78 | PE(O-18:0/22:6) | −0.23 | 0.09 | 1.34E−02 | 7.54E−02 |
| Neg:360.2995@11.43 | | 0.00 | 0.12 | 9.79E−01 | 5.59E−01 |
| Neg:254.2259@11.45 | | 0.15 | 0.15 | 3.00E−01 | 3.03E−01 |
| Pos:282.2675@11.48 | | 0.02 | 0.10 | 8.51E−01 | 5.27E−01 |
| Pos:296.2815@12.27 | | −0.10 | 0.13 | 4.19E−01 | 3.63E−01 |
| Pos:534.4276@14.26 | | −0.09 | 0.12 | 4.40E−01 | 3.74E−01 |
| Neg:468.3817@12.87 | VLCDCA 28:1(OH) | −0.26 | 0.14 | 6.76E−02 | 1.43E−01 |
| Neg:823.5341@18.59 | | −0.01 | 0.11 | 9.62E−01 | 5.55E−01 |
| Pos:265.2768@11.82 | | −0.08 | 0.13 | 5.25E−01 | 4.12E−01 |
| Pos:401.3327@13.20 | | 0.00 | 0.06 | 9.96E−01 | 5.64E−01 |
| Neg:1560.1702@24.20 | | 0.05 | 0.06 | 4.13E−01 | 3.60E−01 |
| Pos:425.3507@9.33 | C18:1 carnitine | −0.02 | 0.09 | 8.32E−01 | 5.22E−01 |
| Neg:774.5880@21.27 | SM(d18:2/18:0) | −0.02 | 0.06 | 7.87E−01 | 5.10E−01 |
| Pos:495.3680@10.90 | | −0.12 | 0.06 | 4.55E−02 | 1.19E−01 |
| Pos:239.2616@11.48 | | 0.04 | 0.11 | 6.94E−01 | 4.74E−01 |
| Pos:635.6214@33.95 | Cer(d18:1/23:0) | −0.17 | 0.07 | 1.50E−02 | 7.87E−02 |
| Pos:564.5340@11.48 | | −0.06 | 0.15 | 6.86E−01 | 4.72E−01 |
| Pos:308.2823@12.00 | | −0.04 | 0.12 | 7.27E−01 | 4.88E−01 |
| Pos:401.3489@15.84 | | 0.05 | 0.05 | 3.42E−01 | 3.24E−01 |
| Neg:642.5898@36.90 | | −0.09 | 0.15 | 5.64E−01 | 4.27E−01 |
| Pos:336.2748@11.48 | | −0.03 | 0.10 | 7.67E−01 | 5.01E−01 |
| Pos:415.3510@13.21 | | 0.00 | 0.06 | 9.97E−01 | 5.64E−01 |
| Neg:416.2750@13.07 | | 0.02 | 0.11 | 8.43E−01 | 5.24E−01 |
| Pos:310.2988@13.17 | | −0.15 | 0.11 | 1.72E−01 | 2.29E−01 |
| Pos:308.2831@11.82 | | −0.05 | 0.11 | 6.50E−01 | 4.58E−01 |
| Pos:749.5364@24.89 | | −0.18 | 0.09 | 4.25E−02 | 1.18E−01 |
| Pos:267.2929@13.16 | | −0.14 | 0.11 | 2.10E−01 | 2.50E−01 |
| Pos:399.3348@8.85 | C16:0 carnitine | −0.04 | 0.07 | 5.80E−01 | 4.33E−01 |
| Pos:607.5179@28.48 | DG(16:0_18:2) | 0.42 | 0.11 | 1.37E−04 | 6.65E−03 |

TABLE 6E

| | | Disease locations vs control L1 | | | |
|---|---|---|---|---|---|
| Feature ID | Lipid ID | $log_2$(FC) | SE | p-value | q-value |
| Neg:494.3450@13.93 | Sitosterol sulfate | 1.26 | 0.13 | 3.44E−21 | 3.26E−18 |
| Neg:632.3875@20.55 | | −0.17 | 0.04 | 1.11E−05 | 2.76E−04 |
| Pos:382.3253@18.09 | Cholesta-4,6-dien-3-one | 1.14 | 0.16 | 2.57E−12 | 6.09E−10 |
| Neg:976.7275@20.56 | | −0.25 | 0.05 | 2.94E−06 | 1.40E−04 |
| Neg:588.3810@20.55 | | −0.20 | 0.04 | 4.56E−06 | 1.70E−04 |
| Pos:863.6407@30.12 | | −0.34 | 0.09 | 3.56E−04 | 3.45E−03 |
| Neg:890.7125@20.56 | | −0.29 | 0.06 | 5.37E−06 | 1.70E−04 |
| Pos:1254.0843@20.73 | | −0.30 | 0.06 | 1.93E−06 | 1.08E−04 |
| Neg:932.7214@20.56 | | −0.32 | 0.06 | 1.05E−06 | 6.61E−05 |
| Neg:1300.0741@20.57 | | −0.26 | 0.06 | 1.18E−05 | 2.79E−04 |
| Neg:1000.7305@20.57 | | −0.25 | 0.06 | 1.13E−05 | 2.76E−04 |
| Neg:999.7325@20.57 | | −0.26 | 0.06 | 2.39E−05 | 4.69E−04 |
| Neg:602.3689@20.56 | | −0.22 | 0.05 | 6.81E−06 | 2.02E−04 |
| Neg:959.7195@20.57 | | −0.17 | 0.04 | 3.75E−05 | 6.73E−04 |
| Neg:956.7237@20.57 | | −0.27 | 0.06 | 2.51E−06 | 1.25E−04 |
| Neg:888.7128@20.56 | | −0.29 | 0.06 | 5.14E−06 | 1.70E−04 |
| Pos:859.7415@20.74 | | −0.12 | 0.03 | 7.14E−05 | 1.11E−03 |
| Neg:1014.7189@20.56 | | −0.22 | 0.05 | 6.18E−06 | 1.89E−04 |
| Neg:916.7128@20.56 | | −0.27 | 0.06 | 4.91E−06 | 1.70E−04 |
| Pos:873.7556@20.73 | | −0.18 | 0.04 | 5.65E−05 | 9.09E−04 |
| Neg:574.3676@20.53 | | −0.16 | 0.04 | 4.43E−05 | 7.78E−04 |
| Pos:716.5465@17.11 | PE(O-34:3) | −0.14 | 0.05 | 4.87E−03 | 2.08E−02 |
| Neg:522.3685@20.56 | | −0.23 | 0.06 | 5.60E−05 | 9.09E−04 |
| Neg:548.3686@20.55 | | −0.24 | 0.05 | 1.55E−05 | 3.41E−04 |
| Pos:412.2979@9.95 | | 0.51 | 0.10 | 4.65E−07 | 3.40E−05 |
| Pos:674.5372@17.33 | SM(d16:1/16:0) | −0.27 | 0.05 | 5.78E−08 | 6.86E−06 |
| Neg:942.7111@20.55 | | −0.23 | 0.05 | 2.28E−05 | 4.69E−04 |
| Neg:532.3584@20.55 | | −0.42 | 0.10 | 2.08E−05 | 4.40E−04 |
| Neg:466.3396@20.56 | | −0.40 | 0.09 | 9.30E−06 | 2.52E−04 |
| Pos:481.3172@8.20 | LPC(15:0) | 0.04 | 0.06 | 4.88E−01 | 3.45E−01 |
| Neg:604.3632@20.56 | | −0.32 | 0.08 | 2.42E−05 | 4.69E−04 |
| Pos:1405.1372@20.63 | | −0.14 | 0.09 | 1.12E−01 | 1.41E−01 |

TABLE 6E-continued

| | | Disease locations vs control L1 | | | |
|---|---|---|---|---|---|
| Feature ID | Lipid ID | $log_2(FC)$ | SE | p-value | q-value |
| Neg:765.5307@23.93 | PE(18:1_20:4)-1 | 0.39 | 0.11 | 2.57E−04 | 2.71E−03 |
| Pos:611.5657@47.54 | CE(14:1) | −0.70 | 0.15 | 2.38E−06 | 1.25E−04 |
| Pos:842.7249@37.94 | SM(d44:1) | −0.19 | 0.06 | 1.82E−03 | 1.10E−02 |
| Neg:874.7121@36.84 | SM(d43:1) | −0.23 | 0.06 | 8.92E−05 | 1.25E−03 |
| Neg:577.3692@20.56 | | −0.37 | 0.09 | 6.61E−05 | 1.05E−03 |
| Pos:919.7688@45.95 | | 0.44 | 0.11 | 9.11E−05 | 1.25E−03 |
| Pos:700.5335@17.33 | | −0.27 | 0.06 | 3.66E−06 | 1.58E−04 |
| Neg:541.3371@9.22 | LPC(16:0) | 0.18 | 0.05 | 9.89E−05 | 1.32E−03 |
| Pos:368.3443@12.77 | | −0.39 | 0.06 | 2.09E−10 | 3.97E−08 |
| Pos:797.6758@35.44 | GlcCer(d18:1/23:0) | −0.22 | 0.06 | 2.34E−04 | 2.55E−03 |
| Pos:784.6473@28.86 | SM(d18:1/22:1) | −0.23 | 0.05 | 9.82E−06 | 2.52E−04 |
| Neg:466.3133@12.72 | Cholesterol sulfate | −0.36 | 0.07 | 4.51E−07 | 3.40E−05 |
| Pos:699.5646@21.73 | | 0.03 | 0.05 | 5.86E−01 | 3.81E−01 |
| Pos:802.6908@35.79 | | −0.30 | 0.08 | 1.62E−04 | 1.97E−03 |
| Neg:843.6786@35.29 | GlcCer(d18:1/23:0) | −0.23 | 0.06 | 4.54E−04 | 4.07E−03 |
| Neg:848.6949@35.66 | | −0.33 | 0.08 | 3.50E−05 | 6.51E−04 |
| Pos:921.7813@49.56 | TG(18:1_18:2_20:4) | 0.49 | 0.11 | 4.45E−06 | 1.70E−04 |
| Neg:720.5416@17.20 | SM(d16:1/16:0) | −0.22 | 0.05 | 1.38E−05 | 3.19E−04 |
| Pos:832.7000@34.80 | | −0.22 | 0.06 | 4.07E−04 | 3.82E−03 |
| Neg:453.2858@9.43 | LPE(16:0) | 0.29 | 0.07 | 7.67E−05 | 1.12E−03 |
| Pos:826.6879@34.79 | | −0.23 | 0.06 | 5.44E−05 | 9.06E−04 |
| Neg:745.5689@21.54 | GlcCer(d18:1/16:0) | 0.07 | 0.05 | 2.02E−01 | 2.05E−01 |
| Pos:828.7092@36.97 | SM(d43:1) | −0.22 | 0.06 | 1.45E−04 | 1.83E−03 |
| Neg:764.5661@19.37 | | 0.01 | 0.05 | 8.95E−01 | 4.73E−01 |
| Neg:830.6500@28.63 | SM(d18:1/22:1) | −0.24 | 0.05 | 8.50E−06 | 2.44E−04 |
| Pos:895.7651@49.23 | TG(18:2_16:0_20:4) | 0.43 | 0.12 | 3.28E−04 | 3.31E−03 |
| Pos:688.5513@18.48 | SM(d33:1) | −0.26 | 0.07 | 7.65E−05 | 1.12E−03 |
| Pos:613.5800@52.89 | CE(14:0) | −0.47 | 0.10 | 3.58E−06 | 1.58E−04 |
| Pos:686.5357@16.62 | SM(d33:2) | −0.19 | 0.05 | 3.68E−04 | 3.53E−03 |
| Pos:368.3444@60.96 | CE(18:1) | −0.13 | 0.04 | 2.53E−03 | 1.38E−02 |
| Pos:688.5532@18.89 | SM(d17:1/16:0) | −0.18 | 0.05 | 3.74E−04 | 3.55E−03 |
| Pos:828.7092@36.62 | SM(d19:1/24:0) | −0.34 | 0.09 | 8.37E−05 | 1.19E−03 |
| Pos:700.5516@19.06 | SM(d18:2/16:0) | −0.42 | 0.09 | 8.98E−06 | 2.51E−04 |
| Pos:646.5049@14.73 | SM(d16:1/14:0) | −0.31 | 0.08 | 5.28E−05 | 8.95E−04 |
| Pos:798.6629@31.63 | SM(d18:2/23:0) | −0.30 | 0.06 | 7.61E−07 | 5.16E−05 |
| Pos:773.5574@19.33 | | 0.07 | 0.07 | 3.01E−01 | 2.60E−01 |
| Pos:936.7921@49.24 | | 0.44 | 0.13 | 5.02E−04 | 4.27E−03 |
| Neg:874.7116@36.49 | SM(d19:1/24:0) | −0.29 | 0.08 | 5.87E−04 | 4.72E−03 |
| Pos:1215.0900@52.85 | | −0.60 | 0.11 | 1.52E−07 | 1.44E−05 |
| Pos:453.2857@9.48 | LPE(16:0) | 0.22 | 0.06 | 6.95E−04 | 5.45E−03 |
| Pos:660.5202@15.93 | SM(d17:1/18:0) | −0.31 | 0.07 | 3.82E−06 | 1.58E−04 |
| Pos:799.6100@29.09 | PC(19:0_18:2) | −0.24 | 0.07 | 9.93E−04 | 7.19E−03 |
| Pos:720.5763@18.94 | SM(d18:0/16:0)(OH) | −0.23 | 0.06 | 2.13E−04 | 2.35E−03 |
| Neg:860.6963@35.57 | SM(d18:1/24:0) | −0.34 | 0.08 | 7.60E−05 | 1.12E−03 |
| Pos:826.6932@35.39 | SM(d18:1/25:1)-2 | −0.30 | 0.09 | 6.36E−04 | 5.03E−03 |
| Pos:814.6935@35.97 | SM(d18:1/24:0)-2 | −0.16 | 0.06 | 6.06E−03 | 2.36E−02 |
| Pos:800.6783@34.78 | SM(d18:1/25:1)-1 | −0.24 | 0.05 | 5.25E−06 | 1.70E−04 |
| Neg:734.5567@18.74 | SM(d17:1/16:0) | −0.16 | 0.05 | 2.83E−03 | 1.50E−02 |
| Pos:798.6620@30.86 | SM(d17:1/24:1) | −0.19 | 0.05 | 4.78E−04 | 4.20E−03 |
| Pos:618.5353@52.85 | CE(14:0) | −0.26 | 0.07 | 1.13E−04 | 1.48E−03 |
| Neg:765.5314@24.31 | PE(18:1_20:4)-2 | 0.28 | 0.09 | 2.87E−03 | 1.50E−02 |
| Pos:885.7788@51.00 | TG(56:4) | 0.26 | 0.09 | 4.49E−03 | 1.97E−02 |
| Pos:772.6469@30.80 | SM(d18:1/21:0) | −0.33 | 0.06 | 1.61E−08 | 2.54E−06 |
| Neg:844.6655@31.39 | SM(d17:1/24:1) | −0.26 | 0.06 | 3.17E−05 | 6.01E−04 |
| Pos:758.6315@28.70 | SM(d16:1/22:0) | −0.32 | 0.07 | 1.77E−06 | 1.05E−04 |
| Pos:928.7515@54.39 | TG(16:0_18:1_22:5) | 0.37 | 0.10 | 2.48E−04 | 2.65E−03 |
| Pos:732.6154@26.04 | SM(d18:0/18:0) | 0.16 | 0.09 | 7.91E−02 | 1.13E−01 |
| Pos:897.7805@53.99 | TG(16:0_18:1_20:4) | 0.33 | 0.11 | 3.12E−03 | 1.58E−02 |
| Pos:887.6154@20.25 | | 0.14 | 0.06 | 1.60E−02 | 4.42E−02 |
| Pos:684.5469@43.77 | | 0.20 | 0.11 | 7.69E−02 | 1.11E−01 |
| Neg:709.6577@39.12 | Cer(d19:1/24:0) | −0.25 | 0.09 | 5.01E−03 | 2.09E−02 |
| Pos:819.6146@27.95 | PC(O-18:0/22:6) | −0.29 | 0.09 | 1.48E−03 | 9.42E−03 |
| Pos:847.6474@31.97 | PC(O-20:0/22:6) | −0.34 | 0.10 | 4.94E−04 | 4.27E−03 |
| Neg:818.6498@30.55 | SM(d18:1/21:0) | −0.31 | 0.06 | 1.02E−07 | 1.07E−05 |
| Neg:793.5603@27.53 | PE(18:0_22:5) | 0.30 | 0.10 | 2.25E−03 | 1.25E−02 |
| Pos:927.8238@51.00 | TG(56:4) | 0.33 | 0.10 | 8.06E−04 | 6.03E−03 |
| Neg:446.3394@13.11 | VLCDCA 28:4 | −0.52 | 0.12 | 1.48E−05 | 3.34E−04 |
| Neg:858.6815@33.55 | SM(d18:2/24:0) | −0.17 | 0.06 | 4.81E−03 | 2.08E−02 |
| Pos:805.5628@20.77 | PC(38:6) | −0.16 | 0.07 | 1.81E−02 | 4.78E−02 |
| Neg:699.6293@39.12 | | −0.23 | 0.09 | 1.28E−02 | 3.92E−02 |
| Neg:873.6871@35.86 | | −0.40 | 0.09 | 1.80E−05 | 3.89E−04 |
| Pos:812.6785@33.81 | SM(d18:2/24:0) | −0.19 | 0.06 | 1.69E−03 | 1.04E−02 |
| Neg:872.6961@35.25 | SM(d18:1/25:1)-2 | −0.30 | 0.09 | 4.10E−04 | 3.82E−03 |
| Pos:607.4579@17.14 | LPC(24:0) | −0.18 | 0.06 | 3.53E−03 | 1.74E−02 |
| Neg:846.6815@34.58 | SM(d18:1/23:0) | −0.17 | 0.05 | 1.03E−03 | 7.21E−03 |

TABLE 6E-continued

| Feature ID | Lipid ID | Disease locations vs control L1 log$_2$(FC) | SE | p-value | q-value |
|---|---|---|---|---|---|
| Neg:850.6670@35.84 | | −0.03 | 0.04 | 4.46E−01 | 3.30E−01 |
| Neg:837.5865@23.92 | PC(O-16:0/22:6) | −0.26 | 0.08 | 1.38E−03 | 9.00E−03 |
| Pos:753.5316@19.29 | | −0.23 | 0.11 | 3.72E−02 | 7.32E−02 |
| Pos:753.5687@29.69 | PE(O-18:0/20:4) | −0.32 | 0.11 | 3.42E−03 | 1.70E−02 |
| Neg:710.6139@36.52 | Cer(d18:1/24:1) | 0.09 | 0.05 | 7.94E−02 | 1.13E−01 |
| Pos:892.6936@51.00 | | 0.26 | 0.09 | 4.08E−03 | 1.88E−02 |
| Neg:799.5353@19.15 | PC(14:0_20:4) | −0.19 | 0.12 | 9.82E−02 | 1.31E−01 |
| Pos:803.5477@18.76 | PC(18:2_20:5) | −0.29 | 0.12 | 1.49E−02 | 4.19E−02 |
| Pos:647.6132@36.64 | | 0.11 | 0.07 | 9.92E−02 | 1.32E−01 |
| Neg:845.6132@28.88 | PC(19:0_18:2) | −0.31 | 0.08 | 7.36E−05 | 1.12E−03 |
| Pos:633.6055@30.86 | SM(d17:1/24:1) | −0.34 | 0.09 | 1.51E−04 | 1.89E−03 |
| Pos:947.7953@51.13 | TG(18:1_18:2_22:5) | 0.39 | 0.14 | 5.81E−03 | 2.28E−02 |
| Pos:744.6146@26.54 | SM(d18:1/19:0) | −0.13 | 0.05 | 1.45E−02 | 4.13E−02 |
| Pos:537.5118@25.39 | | 0.13 | 0.06 | 2.38E−02 | 5.68E−02 |
| Pos:758.6315@28.51 | SM(d18:1/20:0) | 0.27 | 0.06 | 4.88E−06 | 1.70E−04 |
| Pos:730.5994@24.43 | SM(d36:1) | 0.14 | 0.05 | 5.78E−03 | 2.28E−02 |
| Pos:362.2902@11.83 | | −0.46 | 0.11 | 3.66E−05 | 6.68E−04 |
| Pos:559.5691@38.64 | | −0.17 | 0.11 | 1.13E−01 | 1.42E−01 |
| Neg:717.5297@26.55 | PE(16:0_18:1) | 0.27 | 0.12 | 2.72E−02 | 6.17E−02 |
| Neg:725.5345@25.50 | PE(O-16:0/20:4) | −0.47 | 0.11 | 4.92E−05 | 8.50E−04 |
| Neg:693.6257@36.52 | Cer(d18:1/24:1) | 0.14 | 0.06 | 2.48E−02 | 5.79E−02 |
| Pos:552.4389@14.25 | | −0.67 | 0.12 | 5.57E−08 | 6.86E−06 |
| Pos:725.5367@25.70 | PE(O-16:0/20:4) | −0.45 | 0.11 | 7.79E−05 | 1.12E−03 |
| Pos:717.5316@26.75 | | 0.27 | 0.12 | 2.43E−02 | 5.74E−02 |
| Neg:749.5352@24.71 | PE(O-16:0/22:6) | −0.35 | 0.09 | 9.42E−05 | 1.28E−03 |
| Neg:912.5647@22.69 | | 0.12 | 0.05 | 2.77E−02 | 6.24E−02 |
| Pos:728.5844@21.45 | SM(d18:2/18:0) | 0.15 | 0.05 | 5.04E−03 | 2.09E−02 |
| Neg:1152.7105@16.97 | | 0.14 | 0.05 | 1.12E−02 | 3.57E−02 |
| Pos:833.5946@25.01 | PC(18:1_22:5) | 0.37 | 0.14 | 8.27E−03 | 2.92E−02 |
| Pos:585.5850@38.89 | | −0.23 | 0.11 | 3.73E−02 | 7.33E−02 |
| Pos:949.8111@53.74 | TG(18:1_18:2_22:4) | 0.32 | 0.12 | 9.03E−03 | 3.11E−02 |
| Pos:468.3809@12.93 | VLCDCA 28:1(OH) | −0.81 | 0.10 | 5.70E−14 | 2.59E−11 |
| Neg:795.5534@25.83 | | 0.11 | 0.04 | 9.17E−03 | 3.13E−02 |
| Pos:482.3406@12.78 | | 0.14 | 0.04 | 5.66E−04 | 4.63E−03 |
| Neg:442.2743@13.07 | | 0.38 | 0.11 | 8.89E−04 | 6.54E−03 |
| Pos:507.3497@10.01 | | −0.17 | 0.06 | 5.65E−03 | 2.26E−02 |
| Pos:853.5630@19.62 | | −0.22 | 0.09 | 1.10E−02 | 3.53E−02 |
| Neg:670.6212@39.00 | | −0.45 | 0.13 | 7.44E−04 | 5.70E−03 |
| Pos:414.3497@20.82 | | 0.23 | 0.11 | 3.05E−02 | 6.65E−02 |
| Pos:368.3445@53.93 | CE(18:2) | −0.09 | 0.04 | 4.11E−02 | 7.65E−02 |
| Pos:629.6119@36.65 | | 0.15 | 0.07 | 2.38E−02 | 5.68E−02 |
| Neg:386.3151@11.79 | | −0.43 | 0.11 | 1.83E−04 | 2.12E−03 |
| Neg:456.2903@13.07 | | 0.31 | 0.10 | 1.58E−03 | 9.92E−03 |
| Pos:771.5425@19.10 | | 0.37 | 0.10 | 1.69E−04 | 1.99E−03 |
| Pos:942.6220@34.79 | | −0.13 | 0.06 | 4.78E−02 | 8.31E−02 |
| Pos:607.5886@30.05 | | −0.33 | 0.09 | 2.36E−04 | 2.55E−03 |
| Pos:777.5696@28.78 | PE(O-18:0/22:6) | −0.22 | 0.09 | 1.29E−02 | 3.93E−02 |
| Neg:360.2995@11.43 | | −0.38 | 0.12 | 1.02E−03 | 7.20E−03 |
| Neg:254.2259@11.45 | | 0.43 | 0.15 | 3.76E−03 | 1.80E−02 |
| Pos:282.2675@11.48 | | −0.32 | 0.10 | 8.96E−04 | 6.54E−03 |
| Pos:296.2815@12.27 | | −0.39 | 0.13 | 2.16E−03 | 1.22E−02 |
| Pos:534.4276@14.26 | | −0.60 | 0.11 | 1.80E−07 | 1.55E−05 |
| Neg:468.3817@12.87 | VLCDCA 28:1(OH) | −1.03 | 0.13 | 8.19E−14 | 2.59E−11 |
| Neg:823.5341@18.59 | | −0.32 | 0.11 | 3.74E−03 | 1.80E−02 |
| Pos:265.2768@11.82 | | −0.57 | 0.13 | 9.57E−06 | 2.52E−04 |
| Pos:401.3327@13.20 | | 0.17 | 0.06 | 6.99E−03 | 2.60E−02 |
| Neg:1560.1702@24.20 | | 0.22 | 0.06 | 3.51E−04 | 3.43E−03 |
| Pos:425.3507@9.33 | C18:1 carnitine | 0.27 | 0.09 | 3.76E−03 | 1.80E−02 |
| Neg:774.5880@21.27 | SM(d18:2/18:0) | 0.18 | 0.06 | 2.21E−03 | 1.24E−02 |
| Pos:495.3680@10.90 | | −0.16 | 0.07 | 1.57E−02 | 4.36E−02 |
| Pos:239.2616@11.48 | | −0.41 | 0.11 | 2.02E−04 | 2.31E−03 |
| Pos:635.6214@33.95 | Cer(d18:1/23:0) | −0.22 | 0.07 | 2.36E−03 | 1.30E−02 |
| Pos:564.5340@11.48 | | −0.48 | 0.15 | 1.88E−03 | 1.12E−02 |
| Pos:308.2823@12.00 | | −0.41 | 0.12 | 5.05E−04 | 4.27E−03 |
| Pos:401.3489@15.84 | | 0.11 | 0.05 | 2.31E−02 | 5.61E−02 |
| Neg:642.5898@36.90 | | −0.57 | 0.15 | 2.12E−04 | 2.35E−03 |
| Pos:336.2748@11.48 | | −0.31 | 0.10 | 1.91E−03 | 1.13E−02 |
| Pos:415.3510@13.21 | | 0.17 | 0.06 | 6.25E−03 | 2.42E−02 |
| Neg:416.2750@13.07 | | 0.36 | 0.11 | 1.57E−03 | 9.92E−03 |
| Pos:310.2988@13.17 | | −0.37 | 0.11 | 1.01E−03 | 7.20E−03 |
| Pos:308.2831@11.82 | | −0.48 | 0.11 | 2.36E−05 | 4.69E−04 |
| Pos:749.5364@24.89 | | −0.30 | 0.09 | 7.06E−04 | 5.45E−03 |
| Pos:267.2929@13.16 | | −0.40 | 0.11 | 4.77E−04 | 4.20E−03 |

TABLE 6E-continued

| Feature ID | Lipid ID | Disease locations vs control L1 log$_2$(FC) | SE | p-value | q-value |
|---|---|---|---|---|---|
| Pos:399.3348@8.85 | C16:0 carnitine | 0.21 | 0.07 | 1.69E−03 | 1.04E−02 |
| Pos:607.5179@28.48 | DG(16:0_18:2) | 0.22 | 0.12 | 7.04E−02 | 1.06E−01 |

TABLE 6F

| Feature ID | Lipid ID | Disease locations vs control L3 log$_2$(FC) | SE | p-value | q-value |
|---|---|---|---|---|---|
| Neg:494.3450@13.93 | Sitosterol sulfate | 0.47 | 0.10 | 2.74E−06 | 1.22E−04 |
| Neg:632.3875@20.55 | | −0.06 | 0.03 | 6.63E−02 | 1.14E−01 |
| Pos:382.3253@18.09 | Cholesta-4,6-dien-3-one | 0.68 | 0.12 | 9.48E−08 | 6.32E−06 |
| Neg:976.7275@20.56 | | −0.07 | 0.04 | 7.61E−02 | 1.22E−01 |
| Neg:588.3810@20.55 | | −0.06 | 0.03 | 7.42E−02 | 1.20E−01 |
| Pos:863.6407@30.12 | | −0.10 | 0.07 | 1.97E−01 | 2.06E−01 |
| Neg:890.7125@20.56 | | −0.10 | 0.05 | 4.15E−02 | 8.55E−02 |
| Pos:1254.0843@20.73 | | −0.06 | 0.05 | 2.25E−01 | 2.25E−01 |
| Neg:932.7214@20.56 | | −0.12 | 0.05 | 2.20E−02 | 6.54E−02 |
| Neg:1300.0741@20.57 | | −0.06 | 0.05 | 2.12E−01 | 2.16E−01 |
| Neg:1000.7305@20.57 | | −0.06 | 0.04 | 1.73E−01 | 1.89E−01 |
| Neg:999.7325@20.57 | | −0.07 | 0.05 | 1.64E−01 | 1.83E−01 |
| Neg:602.3689@20.56 | | −0.08 | 0.04 | 3.99E−02 | 8.40E−02 |
| Neg:959.7195@20.57 | | −0.05 | 0.03 | 1.47E−01 | 1.74E−01 |
| Neg:956.7237@20.57 | | −0.09 | 0.04 | 5.23E−02 | 9.90E−02 |
| Neg:888.7128@20.56 | | −0.11 | 0.05 | 3.21E−02 | 7.62E−02 |
| Pos:859.7415@20.74 | | −0.02 | 0.02 | 4.60E−01 | 3.36E−01 |
| Neg:1014.7189@20.56 | | −0.07 | 0.04 | 6.47E−02 | 1.13E−01 |
| Neg:916.7128@20.56 | | −0.10 | 0.05 | 2.98E−02 | 7.41E−02 |
| Pos:873.7556@20.73 | | −0.05 | 0.04 | 1.44E−01 | 1.72E−01 |
| Neg:574.3676@20.53 | | −0.05 | 0.03 | 1.22E−01 | 1.55E−01 |
| Pos:716.5465@17.11 | PE(O-34:3) | −0.03 | 0.04 | 5.23E−01 | 3.60E−01 |
| Neg:522.3685@20.56 | | −0.10 | 0.04 | 2.56E−02 | 7.09E−02 |
| Neg:548.3686@20.55 | | −0.10 | 0.04 | 2.81E−02 | 7.23E−02 |
| Pos:412.2979@9.95 | | 0.42 | 0.08 | 2.44E−07 | 1.43E−05 |
| Pos:674.5372@17.33 | SM(d16:1/16:0) | −0.15 | 0.04 | 1.88E−04 | 3.37E−03 |
| Neg:942.7111@20.55 | | −0.08 | 0.04 | 7.04E−02 | 1.17E−01 |
| Neg:532.3584@20.55 | | −0.16 | 0.08 | 3.63E−02 | 8.03E−02 |
| Neg:466.3396@20.56 | | −0.15 | 0.07 | 3.89E−02 | 8.31E−02 |
| Pos:481.3172@8.20 | LPC(15:0) | −0.05 | 0.05 | 2.82E−01 | 2.58E−01 |
| Neg:604.3632@20.56 | | −0.13 | 0.06 | 2.91E−02 | 7.35E−02 |
| Pos:1405.1372@20.63 | | 0.00 | 0.07 | 9.49E−01 | 4.81E−01 |
| Neg:765.5307@23.93 | PE(18:1_20:4)-1 | 0.03 | 0.08 | 7.10E−01 | 4.18E−01 |
| Pos:611.5657@47.54 | CE(14:1) | −0.43 | 0.12 | 2.46E−04 | 3.90E−03 |
| Pos:842.7249@37.94 | SM(d44:1) | −0.13 | 0.05 | 9.49E−03 | 4.57E−02 |
| Neg:874.7121@36.84 | SM(d43:1) | −0.11 | 0.05 | 2.20E−02 | 6.54E−02 |
| Neg:577.3692@20.56 | | −0.15 | 0.07 | 3.38E−02 | 7.74E−02 |
| Pos:919.7688@45.95 | | 0.21 | 0.09 | 1.71E−02 | 5.69E−02 |
| Pos:700.5335@17.33 | | −0.12 | 0.05 | 7.91E−03 | 4.17E−02 |
| Neg:541.3371@9.22 | LPC(16:0) | 0.03 | 0.04 | 4.30E−01 | 3.23E−01 |
| Pos:368.3443@12.77 | | −0.16 | 0.05 | 5.69E−04 | 6.85E−03 |
| Pos:797.6758@35.44 | GlcCer(d18:1/23:0) | −0.13 | 0.05 | 8.18E−03 | 4.22E−02 |
| Pos:784.6473@28.86 | SM(d18:1/22:1) | −0.14 | 0.04 | 8.40E−04 | 9.35E−03 |
| Neg:466.3133@12.72 | Cholesterol sulfate | −0.16 | 0.06 | 3.59E−03 | 2.52E−02 |
| Pos:699.5646@21.73 | | 0.13 | 0.04 | 2.15E−03 | 1.69E−02 |
| Pos:802.6908@35.79 | | −0.16 | 0.06 | 9.32E−03 | 4.51E−02 |
| Neg:843.6786@35.29 | GlcCer(d18:1/23:0) | −0.17 | 0.05 | 1.08E−03 | 1.14E−02 |
| Neg:848.6949@35.66 | | −0.18 | 0.06 | 4.46E−03 | 2.94E−02 |
| Pos:921.7813@49.56 | TG(18:1_18:2_20:4) | 0.27 | 0.08 | 1.45E−03 | 1.43E−02 |
| Neg:720.5416@17.20 | SM(d16:1/16:0) | −0.13 | 0.04 | 1.05E−03 | 1.14E−02 |
| Pos:832.7000@34.80 | | −0.13 | 0.05 | 8.59E−03 | 4.34E−02 |
| Neg:453.2858@9.43 | LPE(16:0) | 0.08 | 0.06 | 1.51E−01 | 1.77E−01 |
| Pos:826.6879@34.79 | | −0.07 | 0.04 | 1.14E−01 | 1.50E−01 |
| Neg:745.5689@21.54 | GlcCer(d18:1/16:0) | 0.15 | 0.04 | 2.97E−04 | 4.40E−03 |
| Pos:828.7092@36.97 | SM(d43:1) | −0.13 | 0.05 | 4.87E−03 | 3.09E−02 |
| Neg:764.5661@19.37 | | 0.05 | 0.04 | 1.79E−01 | 1.94E−01 |
| Neg:830.6500@28.63 | SM(d18:1/22:1) | −0.14 | 0.04 | 8.16E−04 | 9.18E−03 |
| Pos:895.7651@49.23 | TG(18:2_16:0_20:4) | 0.20 | 0.10 | 3.56E−02 | 7.90E−02 |
| Pos:688.5513@18.48 | SM(d33:1) | −0.19 | 0.05 | 2.17E−04 | 3.62E−03 |
| Pos:613.5800@52.89 | CE(14:0) | −0.31 | 0.08 | 9.21E−05 | 2.10E−03 |
| Pos:686.5357@16.62 | SM(d33:2) | −0.14 | 0.04 | 1.17E−03 | 1.21E−02 |
| Pos:368.3444@60.96 | CE(18:1) | −0.10 | 0.04 | 3.88E−03 | 2.65E−02 |

TABLE 6F-continued

| Feature ID | Lipid ID | Disease locations vs control L3 log$_2$(FC) | SE | p-value | q-value |
|---|---|---|---|---|---|
| Pos:688.5532@18.89 | SM(d17:1/16:0) | −0.14 | 0.04 | 3.38E−04 | 4.78E−03 |
| Pos:828.7092@36.62 | SM(d19:1/24:0) | −0.26 | 0.07 | 1.42E−04 | 2.79E−03 |
| Pos:700.5516@19.06 | SM(d18:2/16:0) | −0.24 | 0.07 | 1.78E−03 | 1.58E−02 |
| Pos:646.5049@14.73 | SM(d16:1/14:0) | −0.12 | 0.06 | 3.76E−02 | 8.15E−02 |
| Pos:798.6629@31.63 | SM(d18:2/23:0) | −0.26 | 0.05 | 5.06E−08 | 3.94E−06 |
| Pos:773.5574@19.33 | | 0.21 | 0.06 | 1.27E−04 | 2.68E−03 |
| Pos:936.7921@49.24 | | 0.26 | 0.10 | 1.03E−02 | 4.68E−02 |
| Neg:874.7116@36.49 | SM(d19:1/24:0) | −0.23 | 0.07 | 4.74E−04 | 6.23E−03 |
| Pos:1215.0900@52.85 | | −0.40 | 0.09 | 9.32E−06 | 3.35E−04 |
| Pos:453.2857@9.48 | LPE(16:0) | 0.08 | 0.05 | 1.11E−01 | 1.49E−01 |
| Pos:660.5202@15.93 | SM(d17:1/18:0) | −0.21 | 0.05 | 6.89E−05 | 1.84E−03 |
| Pos:799.6100@29.09 | PC(19:0_18:2) | −0.13 | 0.06 | 2.83E−02 | 7.24E−02 |
| Pos:720.5763@18.94 | SM(d18:0/16:0)(OH) | −0.18 | 0.05 | 2.23E−04 | 3.66E−03 |
| Neg:860.6963@35.57 | SM(d18:1/24:0) | −0.27 | 0.07 | 7.08E−05 | 1.84E−03 |
| Pos:826.6932@35.39 | SM(d18:1/25:1)-2 | −0.18 | 0.07 | 9.73E−03 | 4.61E−02 |
| Pos:814.6935@35.97 | SM(d18:1/24:0)-2 | −0.10 | 0.04 | 2.26E−02 | 6.62E−02 |
| Pos:800.6783@34.78 | SM(d18:1/25:1)-1 | −0.19 | 0.04 | 8.12E−06 | 3.03E−04 |
| Neg:734.5567@18.74 | SM(d17:1/16:0) | −0.16 | 0.04 | 2.93E−04 | 4.40E−03 |
| Pos:798.6620@30.86 | SM(d17:1/24:1) | −0.11 | 0.04 | 9.70E−03 | 4.61E−02 |
| Pos:618.5353@52.85 | CE(14:0) | −0.20 | 0.05 | 1.43E−04 | 2.79E−03 |
| Neg:765.5314@24.31 | PE(18:1_20:4)-2 | 0.26 | 0.07 | 5.72E−04 | 6.85E−03 |
| Pos:885.7788@51.00 | TG(56:4) | 0.23 | 0.07 | 2.01E−03 | 1.66E−02 |
| Pos:772.6469@30.80 | SM(d18:1/21:0) | −0.28 | 0.05 | 1.50E−09 | 1.55E−07 |
| Neg:844.6655@31.39 | SM(d17:1/24:1) | −0.27 | 0.05 | 7.27E−08 | 5.23E−06 |
| Pos:758.6315@28.70 | SM(d16:1/22:0) | −0.30 | 0.05 | 1.30E−08 | 1.10E−06 |
| Pos:928.7515@54.39 | TG(16:0_18:1_22:5) | 0.21 | 0.08 | 1.00E−02 | 4.64E−02 |
| Pos:732.6154@26.04 | SM(d18:0/18:0) | 0.23 | 0.07 | 1.56E−03 | 1.50E−02 |
| Pos:897.7805@53.99 | TG(16:0_18:1_20:4) | 0.16 | 0.09 | 7.41E−02 | 1.20E−01 |
| Pos:887.6154@20.25 | | 0.17 | 0.05 | 2.15E−04 | 3.62E−03 |
| Pos:684.5469@43.77 | | 0.42 | 0.09 | 2.72E−06 | 1.22E−04 |
| Neg:709.6577@39.12 | Cer(d19:1/24:0) | −0.18 | 0.07 | 1.05E−02 | 4.69E−02 |
| Pos:819.6146@27.95 | PC(O-18:0/22:6) | −0.13 | 0.07 | 6.85E−02 | 1.15E−01 |
| Pos:847.6474@31.97 | PC(O-20:0/22:6) | −0.12 | 0.08 | 1.23E−01 | 1.56E−01 |
| Neg:818.6498@30.55 | SM(d18:1/21:0) | −0.28 | 0.05 | 4.49E−09 | 4.19E−07 |
| Neg:793.5603@27.53 | PE(18:0_22:5) | 0.12 | 0.08 | 1.09E−01 | 1.47E−01 |
| Pos:927.8238@51.00 | TG(56:4) | 0.22 | 0.08 | 3.98E−03 | 2.69E−02 |
| Neg:446.3394@13.11 | VLCDCA 28:4 | −0.79 | 0.09 | 9.01E−16 | 2.80E−13 |
| Neg:858.6815@33.55 | SM(d18:2/24:0) | −0.18 | 0.05 | 1.83E−04 | 3.37E−03 |
| Pos:805.5628@20.77 | PC(38:6) | −0.23 | 0.05 | 3.90E−05 | 1.22E−03 |
| Neg:699.6293@39.12 | | −0.18 | 0.07 | 1.33E−02 | 5.34E−02 |
| Neg:873.6871@35.86 | | −0.19 | 0.07 | 8.60E−03 | 4.34E−02 |
| Pos:812.6785@33.81 | SM(d18:2/24:0) | −0.22 | 0.05 | 5.60E−06 | 2.27E−04 |
| Neg:872.6961@35.25 | SM(d18:1/25:1)-2 | −0.27 | 0.07 | 8.48E−05 | 2.04E−03 |
| Pos:607.4579@17.14 | LPC(24:0) | −0.14 | 0.05 | 3.75E−03 | 2.60E−02 |
| Neg:846.6815@34.58 | SM(d18:1/23:0) | −0.15 | 0.04 | 2.58E−04 | 4.02E−03 |
| Neg:850.6670@35.84 | | 0.02 | 0.03 | 6.08E−01 | 3.91E−01 |
| Neg:837.5865@23.92 | PC(O-16:0/22:6) | −0.16 | 0.07 | 1.63E−02 | 5.66E−02 |
| Pos:753.5316@19.29 | | −0.30 | 0.09 | 5.35E−04 | 6.85E−03 |
| Pos:753.5687@29.69 | PE(O-18:0/20:4) | −0.45 | 0.09 | 2.45E−07 | 1.43E−05 |
| Neg:710.6139@36.52 | Cer(d18:1/24:1) | 0.16 | 0.04 | 9.82E−05 | 2.18E−03 |
| Pos:892.6936@51.00 | | 0.21 | 0.07 | 2.66E−03 | 1.96E−02 |
| Neg:799.5353@19.15 | PC(14:0_20:4) | −0.32 | 0.09 | 5.63E−04 | 6.85E−03 |
| Pos:803.5477@18.76 | PC(18:2_20:5) | −0.29 | 0.09 | 2.00E−03 | 1.66E−02 |
| Pos:647.6132@36.64 | | 0.19 | 0.05 | 4.53E−04 | 6.05E−03 |
| Neg:845.6132@28.88 | PC(19:0_18:2) | −0.20 | 0.06 | 1.25E−03 | 1.27E−02 |
| Pos:633.6055@30.86 | SM(d17:1/24:1) | −0.28 | 0.07 | 8.54E−05 | 2.04E−03 |
| Pos:947.7953@51.13 | TG(18:1_18:2_22:5) | 0.20 | 0.11 | 7.64E−02 | 1.22E−01 |
| Pos:744.6146@26.54 | SM(d18:1/19:0) | −0.11 | 0.04 | 6.10E−03 | 3.70E−02 |
| Pos:537.5118@25.39 | | 0.13 | 0.05 | 4.80E−03 | 3.07E−02 |
| Pos:758.6315@28.51 | SM(d18:1/20:0) | 0.22 | 0.05 | 3.09E−06 | 1.31E−04 |
| Pos:730.5994@24.43 | SM(d36:1) | 0.11 | 0.04 | 5.85E−03 | 3.62E−02 |
| Pos:362.2902@11.83 | | −0.37 | 0.09 | 2.60E−05 | 8.38E−04 |
| Pos:559.5691@38.64 | | −0.34 | 0.08 | 5.27E−05 | 1.54E−03 |
| Neg:717.5297@26.55 | PE(16:0_18:1) | 0.18 | 0.10 | 6.44E−02 | 1.13E−01 |
| Neg:725.5345@25.50 | PE(O-16:0/20:4) | −0.61 | 0.09 | 5.86E−11 | 1.37E−08 |
| Neg:693.6257@36.52 | Cer(d18:1/24:1) | 0.19 | 0.05 | 1.14E−04 | 2.47E−03 |
| Pos:552.4389@14.25 | | −0.60 | 0.10 | 8.67E−10 | 1.16E−07 |
| Pos:725.5367@25.70 | PE(O-16:0/20:4) | −0.58 | 0.09 | 2.33E−10 | 4.36E−08 |
| Pos:717.5316@26.75 | | 0.19 | 0.10 | 4.63E−02 | 9.12E−02 |
| Neg:749.5352@24.71 | PE(O-16:0/22:6) | −0.32 | 0.07 | 8.07E−06 | 3.03E−04 |
| Neg:912.5647@22.69 | | 0.09 | 0.04 | 3.72E−02 | 8.12E−02 |
| Pos:728.5844@21.45 | SM(d18:2/18:0) | 0.11 | 0.04 | 1.15E−02 | 4.87E−02 |
| Neg:1152.7105@16.97 | | 0.13 | 0.04 | 1.94E−03 | 1.66E−02 |
| Pos:833.5946@25.01 | PC(18:1_22:5) | 0.19 | 0.11 | 8.69E−02 | 1.31E−01 |
| Pos:585.5850@38.89 | | −0.33 | 0.09 | 2.07E−04 | 3.62E−03 |

TABLE 6F-continued

| | | Disease locations vs control L3 | | | |
|---|---|---|---|---|---|
| Feature ID | Lipid ID | $log_2$(FC) | SE | p-value | q-value |
| Pos:949.8111@53.74 | TG(18:1_18:2_22:4) | 0.24 | 0.10 | 1.53E−02 | 5.55E−02 |
| Pos:468.3809@12.93 | VLCDCA 28:1(OH) | −0.83 | 0.08 | 1.42E−21 | 6.62E−19 |
| Neg:795.5534@25.83 | | 0.14 | 0.03 | 6.43E−05 | 1.82E−03 |
| Pos:482.3406@12.78 | | 0.10 | 0.03 | 1.68E−03 | 1.54E−02 |
| Neg:442.2743@13.07 | | 0.24 | 0.09 | 8.02E−03 | 4.18E−02 |
| Pos:507.3497@10.01 | | −0.19 | 0.05 | 8.89E−05 | 2.08E−03 |
| Pos:853.5630@19.62 | | −0.21 | 0.07 | 1.98E−03 | 1.66E−02 |
| Neg:670.6212@39.00 | | −0.50 | 0.10 | 2.73E−06 | 1.22E−04 |
| Pos:414.3497@20.82 | | 0.33 | 0.08 | 1.44E−04 | 2.79E−03 |
| Pos:368.3445@53.93 | CE(18:2) | −0.08 | 0.04 | 3.28E−02 | 7.66E−02 |
| Pos:629.6119@36.65 | | 0.18 | 0.05 | 4.49E−04 | 6.05E−03 |
| Neg:386.3151@11.79 | | −0.37 | 0.09 | 4.23E−05 | 1.27E−03 |
| Neg:456.2903@13.07 | | 0.20 | 0.08 | 9.29E−03 | 4.51E−02 |
| Pos:771.5425@19.10 | | 0.49 | 0.08 | 6.32E−10 | 9.83E−08 |
| Pos:942.6220@34.79 | | −0.26 | 0.05 | 6.78E−07 | 3.52E−05 |
| Pos:607.5886@30.05 | | −0.27 | 0.07 | 1.79E−04 | 3.37E−03 |
| Pos:777.5696@28.78 | PE(O-18:0/22:6) | −0.31 | 0.07 | 1.27E−05 | 4.40E−04 |
| Neg:360.2995@11.43 | | −0.31 | 0.09 | 7.70E−04 | 8.88E−03 |
| Neg:254.2259@11.45 | | 0.32 | 0.12 | 6.76E−03 | 3.90E−02 |
| Pos:282.2675@11.48 | | −0.21 | 0.08 | 7.98E−03 | 4.18E−02 |
| Pos:296.2815@12.27 | | −0.34 | 0.10 | 6.62E−04 | 7.83E−03 |
| Pos:534.4276@14.26 | | −0.55 | 0.09 | 1.47E−09 | 1.55E−07 |
| Neg:468.3817@12.87 | VLCDCA 28:1(OH) | −1.19 | 0.11 | 1.25E−25 | 1.17E−22 |
| Neg:823.5341@18.59 | | −0.24 | 0.09 | 6.98E−03 | 3.93E−02 |
| Pos:265.2768@11.82 | | −0.40 | 0.10 | 7.85E−05 | 1.98E−03 |
| Pos:401.3327@13.20 | | 0.17 | 0.05 | 5.23E−04 | 6.78E−03 |
| Neg:1560.1702@24.20 | | 0.19 | 0.05 | 1.29E−04 | 2.68E−03 |
| Pos:425.3507@9.33 | C18:1 carnitine | 0.24 | 0.07 | 1.08E−03 | 1.14E−02 |
| Neg:774.5880@21.27 | SM(d18:2/18:0) | 0.12 | 0.05 | 8.53E−03 | 4.34E−02 |
| Pos:495.3680@10.90 | | −0.16 | 0.05 | 2.11E−03 | 1.68E−02 |
| Pos:239.2616@11.48 | | −0.27 | 0.09 | 2.02E−03 | 1.66E−02 |
| Pos:635.6214@33.95 | Cer(d18:1/23:0) | −0.17 | 0.06 | 3.76E−03 | 2.60E−02 |
| Pos:564.5340@11.48 | | −0.39 | 0.12 | 1.40E−03 | 1.39E−02 |
| Pos:308.2823@12.00 | | −0.21 | 0.09 | 2.62E−02 | 7.09E−02 |
| Pos:401.3489@15.84 | | 0.15 | 0.04 | 2.46E−04 | 3.90E−03 |
| Neg:642.5898@36.90 | | −0.52 | 0.12 | 2.33E−05 | 7.79E−04 |
| Pos:336.2748@11.48 | | −0.29 | 0.08 | 3.01E−04 | 4.40E−03 |
| Pos:415.3510@13.21 | | 0.16 | 0.05 | 1.40E−03 | 1.39E−02 |
| Neg:416.2750@13.07 | | 0.25 | 0.09 | 6.15E−03 | 3.70E−02 |
| Pos:310.2988@13.17 | | −0.33 | 0.09 | 2.11E−04 | 3.62E−03 |
| Pos:308.2831@11.82 | | −0.36 | 0.09 | 7.06E−05 | 1.84E−03 |
| Pos:749.5364@24.89 | | −0.36 | 0.07 | 4.00E−07 | 2.20E−05 |
| Pos:267.2929@13.16 | | −0.34 | 0.09 | 1.85E−04 | 3.37E−03 |
| Pos:399.3348@8.85 | C16:0 carnitine | 0.17 | 0.05 | 1.66E−03 | 1.53E−02 |
| Pos:607.5179@28.48 | DG(16:0_18:2) | 0.21 | 0.09 | 2.72E−02 | 7.14E−02 |

TABLE 6G

| | | Disease locations vs control L2 | | | |
|---|---|---|---|---|---|
| Feature ID | Lipid ID | $log_2$(FC) | SE | p-value | q-value |
| Neg:494.3450@13.93 | Sitosterol sulfate | 0.07 | 0.13 | 6.08E−01 | 5.95E−01 |
| Neg:632.3875@20.55 | | 0.05 | 0.04 | 2.66E−01 | 4.55E−01 |
| Pos:382.3253@18.09 | Cholesta-4,6-dien-3-one | 0.06 | 0.16 | 7.30E−01 | 6.31E−01 |
| Neg:976.7275@20.56 | | 0.07 | 0.06 | 2.31E−01 | 4.24E−01 |
| Neg:588.3810@20.55 | | 0.03 | 0.04 | 4.52E−01 | 5.39E−01 |
| Pos:863.6407@30.12 | | 0.18 | 0.10 | 6.57E−02 | 2.55E−01 |
| Neg:890.7125@20.56 | | 0.06 | 0.07 | 3.47E−01 | 4.96E−01 |
| Pos:1254.0843@20.73 | | 0.01 | 0.06 | 8.72E−01 | 6.62E−01 |
| Neg:932.7214@20.56 | | 0.05 | 0.07 | 4.95E−01 | 5.54E−01 |
| Neg:1300.0741@20.57 | | 0.06 | 0.06 | 3.06E−01 | 4.72E−01 |
| Neg:1000.7305@20.57 | | 0.06 | 0.06 | 2.75E−01 | 4.59E−01 |
| Neg:999.7325@20.57 | | 0.07 | 0.06 | 2.76E−01 | 4.59E−01 |
| Neg:602.3689@20.56 | | 0.04 | 0.05 | 4.00E−01 | 5.19E−01 |
| Neg:959.7195@20.57 | | 0.06 | 0.04 | 1.99E−01 | 4.03E−01 |
| Neg:956.7237@20.57 | | 0.04 | 0.06 | 4.84E−01 | 5.51E−01 |
| Neg:888.7128@20.56 | | 0.05 | 0.06 | 4.65E−01 | 5.42E−01 |
| Pos:859.7415@20.74 | | 0.02 | 0.03 | 4.25E−01 | 5.29E−01 |
| Neg:1014.7189@20.56 | | 0.04 | 0.05 | 4.12E−01 | 5.24E−01 |
| Neg:916.7128@20.56 | | 0.04 | 0.06 | 4.61E−01 | 5.41E−01 |

TABLE 6G-continued

| | | Disease locations vs control L2 | | | |
|---|---|---|---|---|---|
| Feature ID | Lipid ID | $log_2$(FC) | SE | p-value | q-value |
| Pos:873.7556@20.73 | | 0.03 | 0.05 | 4.60E−01 | 5.41E−01 |
| Neg:574.3676@20.53 | | 0.04 | 0.04 | 3.96E−01 | 5.19E−01 |
| Pos:716.5465@17.11 | PE(O-34:3) | 0.12 | 0.05 | 3.01E−02 | 1.64E−01 |
| Neg:522.3685@20.56 | | 0.06 | 0.06 | 3.52E−01 | 4.97E−01 |
| Neg:548.3686@20.55 | | 0.04 | 0.06 | 4.49E−01 | 5.39E−01 |
| Pos:412.2979@9.95 | | −0.03 | 0.10 | 7.64E−01 | 6.39E−01 |
| Pos:674.5372@17.33 | SM(d16:1/16:0) | −0.04 | 0.05 | 4.03E−01 | 5.19E−01 |
| Neg:942.7111@20.55 | | 0.05 | 0.06 | 4.00E−01 | 5.19E−01 |
| Neg:532.3584@20.55 | | 0.05 | 0.10 | 6.17E−01 | 5.98E−01 |
| Neg:466.3396@20.56 | | 0.03 | 0.09 | 7.78E−01 | 6.42E−01 |
| Pos:481.3172@8.20 | LPC(15:0) | −0.25 | 0.06 | 6.71E−05 | 6.77E−03 |
| Neg:604.3632@20.56 | | 0.03 | 0.08 | 6.62E−01 | 6.14E−01 |
| Pos:1405.1372@20.63 | | 0.24 | 0.09 | 7.90E−03 | 7.55E−02 |
| Neg:765.5307@23.93 | PE(18:1_20:4)-1 | −0.11 | 0.11 | 3.31E−01 | 4.84E−01 |
| Pos:611.5657@47.54 | CE(14:1) | −0.10 | 0.15 | 4.97E−01 | 5.54E−01 |
| Pos:842.7249@37.94 | SM(d44:1) | 0.08 | 0.06 | 2.23E−01 | 4.24E−01 |
| Neg:874.7121@36.84 | SM(d43:1) | 0.04 | 0.06 | 5.27E−01 | 5.66E−01 |
| Neg:577.3692@20.56 | | 0.04 | 0.10 | 6.55E−01 | 6.14E−01 |
| Pos:919.7688@45.95 | | −0.01 | 0.12 | 9.33E−01 | 6.73E−01 |
| Pos:700.5335@17.33 | | −0.04 | 0.06 | 5.23E−01 | 5.65E−01 |
| Neg:541.3371@9.22 | LPC(16:0) | −0.01 | 0.05 | 8.32E−01 | 6.56E−01 |
| Pos:368.3443@12.77 | | −0.15 | 0.06 | 1.77E−02 | 1.17E−01 |
| Pos:797.6758@35.44 | GlcCer(d18:1/23:0) | 0.02 | 0.06 | 6.91E−01 | 6.20E−01 |
| Pos:784.6473@28.86 | SM(d18:1/22:1) | −0.03 | 0.05 | 5.43E−01 | 5.72E−01 |
| Neg:466.3133@12.72 | Cholesterol sulfate | −0.08 | 0.07 | 2.55E−01 | 4.46E−01 |
| Pos:699.5646@21.73 | | 0.25 | 0.06 | 2.05E−05 | 3.56E−03 |
| Pos:802.6908@35.79 | | 0.01 | 0.08 | 8.63E−01 | 6.59E−01 |
| Neg:843.6786@35.29 | GlcCer(d18:1/23:0) | 0.03 | 0.07 | 7.08E−01 | 6.23E−01 |
| Neg:848.6949@35.66 | | −0.02 | 0.08 | 8.19E−01 | 6.51E−01 |
| Pos:921.7813@49.56 | TG(18:1_18:2_20:4) | 0.12 | 0.11 | 2.97E−01 | 4.70E−01 |
| Neg:720.5416@17.20 | SM(d16:1/16:0) | −0.03 | 0.05 | 5.64E−01 | 5.79E−01 |
| Pos:832.7000@34.80 | | 0.02 | 0.07 | 7.35E−01 | 6.31E−01 |
| Neg:453.2858@9.43 | LPE(16:0) | 0.01 | 0.08 | 8.56E−01 | 6.59E−01 |
| Pos:826.6879@34.79 | | −0.03 | 0.06 | 6.40E−01 | 6.07E−01 |
| Neg:745.5689@21.54 | GlcCer(d18:1/16:0) | 0.25 | 0.05 | 5.26E−06 | 1.40E−03 |
| Pos:828.7092@36.97 | SM(d43:1) | −0.01 | 0.06 | 8.54E−01 | 6.58E−01 |
| Neg:764.5661@19.37 | | 0.18 | 0.05 | 3.33E−04 | 1.56E−02 |
| Neg:830.6500@28.63 | SM(d18:1/22:1) | −0.06 | 0.06 | 3.23E−01 | 4.80E−01 |
| Pos:895.7651@49.23 | TG(18:2_16:0_20:4) | 0.07 | 0.13 | 5.68E−01 | 5.80E−01 |
| Pos:688.5513@18.48 | SM(d33:1) | −0.04 | 0.07 | 5.39E−01 | 5.71E−01 |
| Pos:613.5800@52.89 | CE(14:0) | −0.17 | 0.10 | 9.44E−02 | 2.93E−01 |
| Pos:686.5357@16.62 | SM(d33:2) | −0.02 | 0.06 | 6.89E−01 | 6.20E−01 |
| Pos:368.3444@60.96 | CE(18:1) | −0.01 | 0.05 | 8.83E−01 | 6.63E−01 |
| Pos:688.5532@18.89 | SM(d17:1/16:0) | −0.02 | 0.05 | 7.31E−01 | 6.31E−01 |
| Pos:828.7092@36.62 | SM(d19:1/24:0) | −0.06 | 0.09 | 5.40E−01 | 5.71E−01 |
| Pos:700.5516@19.06 | SM(d18:2/16:0) | −0.16 | 0.10 | 1.05E−01 | 3.04E−01 |
| Pos:646.5049@14.73 | SM(d16:1/14:0) | −0.10 | 0.08 | 1.97E−01 | 4.03E−01 |
| Pos:798.6629@31.63 | SM(d18:2/23:0) | −0.11 | 0.06 | 7.79E−02 | 2.72E−01 |
| Pos:773.5574@19.33 | | 0.27 | 0.07 | 1.89E−04 | 1.16E−02 |
| Pos:936.7921@49.24 | | 0.14 | 0.13 | 2.94E−01 | 4.70E−01 |
| Neg:874.7116@36.49 | SM(d19:1/24:0) | −0.03 | 0.09 | 7.21E−01 | 6.29E−01 |
| Pos:1215.0900@52.85 | | −0.30 | 0.12 | 1.03E−02 | 9.02E−02 |
| Pos:453.2857@9.48 | LPE(16:0) | 0.03 | 0.07 | 6.47E−01 | 6.11E−01 |
| Pos:660.5202@15.93 | SM(d17:1/18:0) | −0.13 | 0.07 | 5.50E−02 | 2.29E−01 |
| Pos:799.6100@29.09 | PC(19:0_18:2) | −0.06 | 0.07 | 4.18E−01 | 5.25E−01 |
| Pos:720.5763@18.94 | SM(d18:0/16:0)(OH) | −0.07 | 0.06 | 3.04E−01 | 4.71E−01 |
| Neg:860.6963@35.57 | SM(d18:1/24:0) | −0.11 | 0.09 | 2.19E−01 | 4.23E−01 |
| Pos:826.6932@35.39 | SM(d18:1/25:1)-2 | −0.09 | 0.09 | 3.12E−01 | 4.73E−01 |
| Pos:814.6935@35.97 | SM(d18:1/24:0)-2 | −0.01 | 0.06 | 8.25E−01 | 6.54E−01 |
| Pos:800.6783@34.78 | SM(d18:1/25:1)-1 | −0.11 | 0.06 | 5.29E−02 | 2.25E−01 |
| Neg:734.5567@18.74 | SM(d17:1/16:0) | −0.02 | 0.06 | 6.63E−01 | 6.14E−01 |
| Pos:798.6620@30.86 | SM(d17:1/24:1) | −0.06 | 0.06 | 2.63E−01 | 4.53E−01 |
| Pos:618.5353@52.85 | CE(14:0) | −0.11 | 0.07 | 9.87E−02 | 2.97E−01 |
| Neg:765.5314@24.31 | PE(18:1_20:4)-2 | 0.07 | 0.10 | 4.49E−01 | 5.39E−01 |
| Pos:885.7788@51.00 | TG(56:4) | 0.07 | 0.10 | 4.57E−01 | 5.40E−01 |
| Pos:772.6469@30.80 | SM(d18:1/21:0) | −0.19 | 0.06 | 1.54E−03 | 3.58E−02 |
| Neg:844.6655@31.39 | SM(d17:1/24:1) | −0.10 | 0.06 | 1.11E−01 | 3.10E−01 |
| Pos:758.6315@28.70 | SM(d16:1/22:0) | −0.17 | 0.07 | 1.13E−02 | 9.39E−02 |
| Pos:928.7515@54.39 | TG(16:0_18:1_22:5) | 0.16 | 0.11 | 1.28E−01 | 3.29E−01 |
| Pos:732.6154@26.04 | SM(d18:0/18:0) | 0.37 | 0.09 | 1.06E−04 | 9.02E−03 |
| Pos:897.7805@53.99 | TG(16:0_18:1_20:4) | 0.11 | 0.12 | 3.29E−01 | 4.83E−01 |
| Pos:887.6154@20.25 | | 0.26 | 0.06 | 1.53E−05 | 3.34E−03 |
| Pos:684.5469@43.77 | | 0.44 | 0.12 | 1.89E−04 | 1.16E−02 |
| Neg:709.6577@39.12 | Cer(d19:1/24:0) | −0.05 | 0.09 | 6.20E−01 | 6.00E−01 |
| Pos:819.6146@27.95 | PC(O-18:0/22:6) | −0.10 | 0.10 | 2.95E−01 | 4.70E−01 |

TABLE 6G-continued

| | | Disease locations vs control L2 | | | |
|---|---|---|---|---|---|
| Feature ID | Lipid ID | $log_2$(FC) | SE | p-value | q-value |
| Pos:847.6474@31.97 | PC(O-20:0/22:6) | −0.14 | 0.10 | 1.56E−01 | 3.52E−01 |
| Neg:818.6498@30.55 | SM(d18:1/21:0) | −0.18 | 0.06 | 2.44E−03 | 4.66E−02 |
| Neg:793.5603@27.53 | PE(18:0_22:5) | 0.11 | 0.10 | 2.68E−01 | 4.55E−01 |
| Pos:927.8238@51.00 | TG(56:4) | 0.17 | 0.10 | 9.06E−02 | 2.90E−01 |
| Neg:446.3394@13.11 | VLCDCA 28:4 | −0.73 | 0.12 | 1.13E−08 | 4.94E−06 |
| Neg:858.6815@33.55 | SM(d18:2/24:0) | −0.05 | 0.06 | 4.30E−01 | 5.31E−01 |
| Pos:805.5628@20.77 | PC(38:6) | −0.28 | 0.07 | 1.24E−04 | 9.56E−03 |
| Neg:699.6293@39.12 | | −0.05 | 0.10 | 6.17E−01 | 5.98E−01 |
| Neg:873.6871@35.86 | | −0.25 | 0.10 | 1.04E−02 | 9.06E−02 |
| Pos:812.6785@33.81 | SM(d18:2/24:0) | −0.08 | 0.06 | 2.35E−01 | 4.28E−01 |
| Neg:872.6961@35.25 | SM(d18:1/25:1)-2 | −0.15 | 0.09 | 1.01E−01 | 2.98E−01 |
| Pos:607.4579@17.14 | LPC(24:0) | −0.08 | 0.07 | 2.02E−01 | 4.05E−01 |
| Neg:846.6815@34.58 | SM(d18:1/23:0) | −0.08 | 0.05 | 1.49E−01 | 3.46E−01 |
| Neg:850.6670@35.84 | | 0.03 | 0.04 | 4.62E−01 | 5.41E−01 |
| Neg:837.5865@23.92 | PC(O-16:0/22:6) | −0.15 | 0.09 | 9.07E−02 | 2.90E−01 |
| Pos:753.5316@19.29 | | −0.40 | 0.11 | 5.26E−04 | 2.30E−02 |
| Pos:753.5687@29.69 | PE(O-18:0/20:4) | −0.16 | 0.11 | 1.54E−01 | 3.52E−01 |
| Neg:710.6139@36.52 | Cer(d18:1/24:1) | 0.16 | 0.05 | 2.59E−03 | 4.66E−02 |
| Pos:892.6936@51.00 | | 0.15 | 0.09 | 1.06E−01 | 3.04E−01 |
| Neg:799.5353@19.15 | PC(14:0_20:4) | −0.37 | 0.12 | 2.67E−03 | 4.72E−02 |
| Pos:803.5477@18.76 | PC(18:2_20:5) | −0.45 | 0.12 | 3.33E−04 | 1.56E−02 |
| Pos:647.6132@36.64 | | 0.20 | 0.07 | 5.02E−03 | 6.64E−02 |
| Neg:845.6132@28.88 | PC(19:0_18:2) | −0.22 | 0.08 | 7.60E−03 | 7.50E−02 |
| Pos:633.6055@30.86 | SM(d17:1/24:1) | −0.22 | 0.09 | 1.68E−02 | 1.15E−01 |
| Pos:947.7953@51.13 | TG(18:1_18:2_22:5) | 0.22 | 0.15 | 1.31E−01 | 3.35E−01 |
| Pos:744.6146@26.54 | SM(d18:1/19:0) | −0.06 | 0.05 | 2.96E−01 | 4.70E−01 |
| Pos:537.5118@25.39 | | 0.21 | 0.06 | 6.41E−04 | 2.47E−02 |
| Pos:758.6315@28.51 | SM(d18:1/20:0) | 0.21 | 0.06 | 8.01E−04 | 2.87E−02 |
| Pos:730.5994@24.43 | SM(d36:1) | 0.21 | 0.05 | 1.10E−04 | 9.02E−03 |
| Pos:362.2902@11.83 | | −0.34 | 0.12 | 3.16E−03 | 5.12E−02 |
| Pos:559.5691@38.64 | | −0.28 | 0.11 | 1.02E−02 | 9.00E−02 |
| Neg:717.5297@26.55 | PE(16:0_18:1) | 0.12 | 0.13 | 3.54E−01 | 4.99E−01 |
| Neg:725.5345@25.50 | PE(O-16:0/20:4) | −0.35 | 0.12 | 3.99E−03 | 5.87E−02 |
| Neg:693.6257@36.52 | Cer(d18:1/24:1) | 0.21 | 0.06 | 1.20E−03 | 3.40E−02 |
| Pos:552.4389@14.25 | | −0.52 | 0.13 | 4.99E−05 | 6.48E−03 |
| Pos:725.5367@25.70 | PE(O-16:0/20:4) | −0.33 | 0.12 | 5.13E−03 | 6.65E−02 |
| Pos:717.5316@26.75 | | 0.13 | 0.13 | 3.14E−01 | 4.74E−01 |
| Neg:749.5352@24.71 | PE(O-16:0/22:6) | −0.26 | 0.09 | 5.72E−03 | 6.97E−02 |
| Neg:912.5647@22.69 | | 0.07 | 0.06 | 2.25E−01 | 4.24E−01 |
| Pos:728.5844@21.45 | SM(d18:2/18:0) | 0.21 | 0.06 | 2.04E−04 | 1.16E−02 |
| Neg:1152.7105@16.97 | | 0.19 | 0.06 | 9.71E−04 | 3.10E−02 |
| Pos:833.5946@25.01 | PC(18:1_22:5) | 0.24 | 0.15 | 1.01E−01 | 2.98E−01 |
| Pos:585.5850@38.89 | | −0.31 | 0.12 | 7.62E−03 | 7.50E−02 |
| Pos:949.8111@53.74 | TG(18:1_18:2_22:4) | 0.24 | 0.13 | 6.18E−02 | 2.47E−01 |
| Pos:468.3809@12.93 | VLCDCA 28:1(OH) | −0.72 | 0.11 | 1.02E−10 | 6.71E−08 |
| Neg:795.5534@25.83 | | 0.08 | 0.05 | 7.81E−02 | 2.72E−01 |
| Pos:482.3406@12.78 | | 0.12 | 0.04 | 4.31E−03 | 6.17E−02 |
| Neg:442.2743@13.07 | | 0.33 | 0.12 | 6.39E−03 | 7.21E−02 |
| Pos:507.3497@10.01 | | −0.13 | 0.06 | 3.78E−02 | 1.89E−01 |
| Pos:853.5630@19.62 | | −0.27 | 0.09 | 2.57E−03 | 4.66E−02 |
| Neg:670.6212@39.00 | | −0.37 | 0.14 | 7.32E−03 | 7.50E−02 |
| Pos:414.3497@20.82 | | 0.18 | 0.11 | 1.09E−01 | 3.08E−01 |
| Pos:368.3445@53.93 | CE(18:2) | −0.06 | 0.05 | 1.88E−01 | 3.92E−01 |
| Pos:629.6119@36.65 | | 0.19 | 0.07 | 6.28E−03 | 7.21E−02 |
| Neg:386.3151@11.79 | | −0.50 | 0.12 | 2.78E−05 | 4.04E−03 |
| Neg:456.2903@13.07 | | 0.27 | 0.10 | 7.84E−03 | 7.55E−02 |
| Pos:771.5425@19.10 | | 0.41 | 0.10 | 5.88E−05 | 6.48E−03 |
| Pos:942.6220@34.79 | | −0.08 | 0.07 | 2.23E−01 | 4.24E−01 |
| Pos:607.5886@30.05 | | −0.28 | 0.09 | 2.43E−03 | 4.66E−02 |
| Pos:777.5696@28.78 | PE(O-18:0/22:6) | −0.17 | 0.09 | 7.66E−02 | 2.72E−01 |
| Neg:360.2995@11.43 | | −0.45 | 0.12 | 2.01E−04 | 1.16E−02 |
| Neg:254.2259@11.45 | | 0.51 | 0.15 | 9.09E−04 | 3.05E−02 |
| Pos:282.2675@11.48 | | −0.38 | 0.10 | 2.01E−04 | 1.16E−02 |
| Pos:296.2815@12.27 | | −0.45 | 0.13 | 6.37E−04 | 2.47E−02 |
| Pos:534.4276@14.26 | | −0.54 | 0.12 | 5.33E−06 | 1.40E−03 |
| Neg:468.3817@12.87 | VLCDCA 28:1(OH) | −0.95 | 0.14 | 3.09E−11 | 4.05E−08 |
| Neg:823.5341@18.59 | | −0.38 | 0.11 | 1.17E−03 | 3.40E−02 |
| Pos:265.2768@11.82 | | −0.54 | 0.13 | 5.93E−05 | 6.48E−03 |
| Pos:401.3327@13.20 | | 0.15 | 0.06 | 2.04E−02 | 1.29E−01 |
| Neg:1560.1702@24.20 | | 0.20 | 0.06 | 1.52E−03 | 3.58E−02 |
| Pos:425.3507@9.33 | C18:1 carnitine | 0.30 | 0.10 | 1.96E−03 | 4.29E−02 |
| Neg:774.5880@21.27 | SM(d18:2/18:0) | 0.20 | 0.06 | 8.51E−04 | 2.93E−02 |
| Pos:495.3680@10.90 | | −0.14 | 0.07 | 4.37E−02 | 2.01E−01 |
| Pos:239.2616@11.48 | | −0.45 | 0.11 | 9.73E−05 | 9.02E−03 |
| Pos:635.6214@33.95 | Cer(d18:1/23:0) | −0.21 | 0.08 | 7.41E−03 | 7.50E−02 |

TABLE 6G-continued

| | | Disease locations vs control L2 | | | |
|---|---|---|---|---|---|
| Feature ID | Lipid ID | $log_2$(FC) | SE | p-value | q-value |
| Pos:564.5340@11.48 | | −0.52 | 0.16 | 1.20E−03 | 3.40E−02 |
| Pos:308.2823@12.00 | | −0.39 | 0.12 | 1.32E−03 | 3.54E−02 |
| Pos:401.3489@15.84 | | 0.13 | 0.05 | 1.48E−02 | 1.08E−01 |
| Neg:642.5898@36.90 | | −0.61 | 0.16 | 1.53E−04 | 1.12E−02 |
| Pos:336.2748@11.48 | | −0.33 | 0.10 | 1.37E−03 | 3.58E−02 |
| Pos:415.3510@13.21 | | 0.18 | 0.06 | 4.50E−03 | 6.27E−02 |
| Neg:416.2750@13.07 | | 0.36 | 0.12 | 2.47E−03 | 4.66E−02 |
| Pos:310.2988@13.17 | | −0.38 | 0.12 | 1.00E−03 | 3.12E−02 |
| Pos:308.2831@11.82 | | −0.50 | 0.12 | 2.17E−05 | 3.56E−03 |
| Pos:749.5364@24.89 | | −0.29 | 0.09 | 1.79E−03 | 4.05E−02 |
| Pos:267.2929@13.16 | | −0.41 | 0.12 | 5.76E−04 | 2.36E−02 |
| Pos:399.3348@8.85 | C16:0 carnitine | 0.22 | 0.07 | 2.24E−03 | 4.66E−02 |
| Pos:607.5179@28.48 | DG(16:0_18:2) | 0.22 | 0.13 | 7.78E−02 | 2.72E−01 |

TABLE 6H

| | | Disease location L2 vs L1 | | | |
|---|---|---|---|---|---|
| Feature ID | Lipid ID | $log_2$(FC) | SE | p-value | q-value |
| Neg:494.3450@13.93 | Sitosterol sulfate | −1.19 | 0.19 | 3.49E−09 | 4.83E−06 |
| Neg:632.3875@20.55 | | 0.22 | 0.05 | 4.51E−06 | 3.12E−03 |
| Pos:382.3253@18.09 | Cholesta-4,6-dien-3-one | −1.05 | 0.23 | 8.79E−06 | 4.06E−03 |
| Neg:976.7275@20.56 | | 0.32 | 0.08 | 4.89E−05 | 1.42E−02 |
| Neg:588.3810@20.55 | | 0.23 | 0.06 | 6.75E−05 | 1.42E−02 |
| Pos:863.6407@30.12 | | 0.52 | 0.13 | 8.07E−05 | 1.42E−02 |
| Neg:890.7125@20.56 | | 0.36 | 0.09 | 1.12E−04 | 1.42E−02 |
| Pos:1254.0843@20.73 | | 0.31 | 0.08 | 1.14E−04 | 1.42E−02 |
| Neg:932.7214@20.56 | | 0.36 | 0.09 | 1.15E−04 | 1.42E−02 |
| Neg:1300.0741@20.57 | | 0.32 | 0.08 | 1.20E−04 | 1.42E−02 |
| Neg:1000.7305@20.57 | | 0.31 | 0.08 | 1.23E−04 | 1.42E−02 |
| Neg:999.7325@20.57 | | 0.32 | 0.08 | 1.85E−04 | 1.70E−02 |
| Neg:602.3689@20.56 | | 0.26 | 0.07 | 1.93E−04 | 1.70E−02 |
| Neg:959.7195@20.57 | | 0.23 | 0.06 | 2.03E−04 | 1.70E−02 |
| Neg:956.7237@20.57 | | 0.31 | 0.08 | 2.04E−04 | 1.70E−02 |
| Neg:888.7128@20.56 | | 0.33 | 0.09 | 2.09E−04 | 1.70E−02 |
| Pos:859.7415@20.74 | | 0.14 | 0.04 | 2.66E−04 | 1.76E−02 |
| Neg:1014.7189@20.56 | | 0.26 | 0.07 | 2.69E−04 | 1.76E−02 |
| Neg:916.7128@20.56 | | 0.31 | 0.08 | 2.79E−04 | 1.76E−02 |
| Pos:873.7556@20.73 | | 0.21 | 0.06 | 2.94E−04 | 1.76E−02 |
| Neg:574.3676@20.53 | | 0.20 | 0.05 | 3.06E−04 | 1.76E−02 |
| Pos:716.5465@17.11 | PE(O-34:3) | 0.26 | 0.07 | 3.17E−04 | 1.76E−02 |
| Neg:522.3685@20.56 | | 0.28 | 0.08 | 3.48E−04 | 1.77E−02 |
| Neg:548.3686@20.55 | | 0.28 | 0.08 | 3.58E−04 | 1.77E−02 |
| Pos:412.2979@9.95 | | −0.52 | 0.15 | 4.33E−04 | 2.06E−02 |
| Pos:674.5372@17.33 | SM(d16:1/16:0) | 0.23 | 0.06 | 4.65E−04 | 2.13E−02 |
| Neg:942.7111@20.55 | | 0.27 | 0.08 | 4.78E−04 | 2.13E−02 |
| Neg:532.3584@20.55 | | 0.47 | 0.14 | 8.92E−04 | 3.34E−02 |
| Neg:466.3396@20.56 | | 0.42 | 0.13 | 9.18E−04 | 3.34E−02 |
| Pos:481.3172@8.20 | LPC(15:0) | −0.29 | 0.09 | 1.06E−03 | 3.68E−02 |
| Neg:604.3632@20.56 | | 0.35 | 0.11 | 1.22E−03 | 3.77E−02 |
| Pos:1405.1372@20.63 | | 0.37 | 0.11 | 1.36E−03 | 4.00E−02 |
| Neg:765.5307@23.93 | PE(18:1_20:4)-1 | −0.50 | 0.16 | 1.63E−03 | 4.26E−02 |
| Pos:611.5657@47.54 | CE(14:1) | 0.60 | 0.19 | 1.66E−03 | 4.26E−02 |
| Pos:842.7249@37.94 | SM(d44:1) | 0.25 | 0.08 | 1.69E−03 | 4.26E−02 |
| Neg:874.7121@36.84 | SM(d43:1) | 0.26 | 0.08 | 1.83E−03 | 4.32E−02 |
| Neg:577.3692@20.56 | | 0.41 | 0.13 | 1.84E−03 | 4.32E−02 |
| Pos:919.7688@45.95 | | −0.45 | 0.14 | 1.95E−03 | 4.49E−02 |
| Pos:700.5335@17.33 | | 0.23 | 0.07 | 2.21E−03 | 5.02E−02 |
| Neg:541.3371@9.22 | LPC(16:0) | −0.19 | 0.06 | 2.70E−03 | 5.93E−02 |
| Pos:368.3443@12.77 | | 0.25 | 0.08 | 3.02E−03 | 6.42E−02 |
| Pos:797.6758@35.44 | GlcCer(d18:1/23:0) | 0.25 | 0.08 | 3.42E−03 | 6.75E−02 |
| Pos:784.6473@28.86 | SM(d18:1/22:1) | 0.20 | 0.07 | 3.74E−03 | 6.92E−02 |
| Neg:466.3133@12.72 | Cholesterol sulfate | 0.29 | 0.10 | 4.06E−03 | 7.29E−02 |
| Pos:699.5646@21.73 | | 0.22 | 0.08 | 5.51E−03 | 9.29E−02 |
| Pos:802.6908@35.79 | | 0.31 | 0.11 | 5.78E−03 | 9.35E−02 |
| Neg:843.6786@35.29 | GlcCer(d18:1/23:0) | 0.25 | 0.09 | 6.54E−03 | 1.03E−01 |
| Neg:848.6949@35.66 | | 0.31 | 0.11 | 7.25E−03 | 1.04E−01 |
| Pos:921.7813@49.56 | TG(18:1_18:2_20:4) | −0.38 | 0.14 | 7.45E−03 | 1.06E−01 |
| Neg:720.5416@17.20 | SM(d16:1/16:0) | 0.19 | 0.07 | 7.65E−03 | 1.08E−01 |
| Pos:832.7000@34.80 | | 0.24 | 0.09 | 7.97E−03 | 1.09E−01 |

TABLE 6H-continued

| Feature ID | Lipid ID | Disease location L2 vs L1 log$_2$(FC) | SE | p-value | q-value |
|---|---|---|---|---|---|
| Neg:453.2858@9.43 | LPE(16:0) | −0.28 | 0.10 | 8.62E−03 | 1.10E−01 |
| Pos:826.6879@34.79 | | 0.20 | 0.08 | 9.46E−03 | 1.15E−01 |
| Neg:745.5689@21.54 | GlcCer(d18:1/16:0) | 0.18 | 0.07 | 1.09E−02 | 1.21E−01 |
| Pos:828.7092@36.97 | SM(d43:1) | 0.20 | 0.08 | 1.34E−02 | 1.35E−01 |
| Neg:764.5661@19.37 | | 0.17 | 0.07 | 1.40E−02 | 1.40E−01 |
| Neg:830.6500@28.63 | SM(d18:1/22:1) | 0.18 | 0.07 | 1.48E−02 | 1.41E−01 |
| Pos:895.7651@49.23 | TG(18:2_16:0_20:4) | −0.36 | 0.15 | 1.58E−02 | 1.43E−01 |
| Pos:688.5513@18.48 | SM(d33:1) | 0.22 | 0.09 | 1.71E−02 | 1.48E−01 |
| Pos:613.5800@52.89 | CE(14:0) | 0.30 | 0.13 | 2.04E−02 | 1.63E−01 |
| Pos:686.5357@16.62 | SM(d33:2) | 0.17 | 0.07 | 2.28E−02 | 1.75E−01 |
| Pos:368.3444@60.96 | CE(18:1) | 0.12 | 0.05 | 2.31E−02 | 1.75E−01 |
| Pos:688.5532@18.89 | SM(d17:1/16:0) | 0.15 | 0.07 | 2.37E−02 | 1.77E−01 |
| Pos:828.7092@36.62 | SM(d19:1/24:0) | 0.27 | 0.12 | 3.01E−02 | 2.01E−01 |
| Pos:700.5516@19.06 | SM(d18:2/16:0) | 0.27 | 0.13 | 3.29E−02 | 2.09E−01 |
| Pos:646.5049@14.73 | SM(d16:1/14:0) | 0.21 | 0.10 | 3.80E−02 | 2.29E−01 |
| Pos:798.6629@31.63 | SM(d18:2/23:0) | 0.18 | 0.09 | 3.92E−02 | 2.33E−01 |
| Pos:773.5574@19.33 | | 0.20 | 0.10 | 4.07E−02 | 2.36E−01 |
| Pos:936.7921@49.24 | | −0.31 | 0.15 | 4.25E−02 | 2.42E−01 |
| Neg:874.7116@36.49 | SM(d19:1/24:0) | 0.24 | 0.12 | 4.27E−02 | 2.42E−01 |
| Pos:1215.0900@52.85 | | 0.31 | 0.15 | 4.53E−02 | 2.54E−01 |
| Pos:453.2857@9.48 | LPE(16:0) | −0.18 | 0.09 | 4.61E−02 | 2.57E−01 |
| Pos:660.5202@15.93 | SM(d17:1/18:0) | 0.18 | 0.09 | 5.04E−02 | 2.61E−01 |
| Pos:799.6100@29.09 | PC(19:0_18:2) | 0.18 | 0.09 | 5.35E−02 | 2.69E−01 |
| Pos:720.5763@18.94 | SM(d18:0/16:0)(OH) | 0.16 | 0.08 | 5.54E−02 | 2.77E−01 |
| Neg:860.6963@35.57 | SM(d18:1/24:0) | 0.21 | 0.12 | 8.01E−02 | 3.16E−01 |
| Pos:826.6932@35.39 | SM(d18:1/25:1)-2 | 0.20 | 0.12 | 8.05E−02 | 3.16E−01 |
| Pos:814.6935@35.97 | SM(d18:1/24:0)-2 | 0.13 | 0.08 | 8.33E−02 | 3.21E−01 |
| Pos:800.6783@34.78 | SM(d18:1/25:1)-1 | 0.13 | 0.07 | 8.74E−02 | 3.25E−01 |
| Neg:734.5567@18.74 | SM(d17:1/16:0) | 0.13 | 0.08 | 8.84E−02 | 3.26E−01 |
| Pos:798.6620@30.86 | SM(d17:1/24:1) | 0.12 | 0.07 | 9.95E−02 | 3.42E−01 |
| Pos:618.5353@52.85 | CE(14:0) | 0.14 | 0.09 | 1.02E−01 | 3.44E−01 |
| Neg:765.5314@24.31 | PE(18:1_20:4)-2 | −0.20 | 0.12 | 1.06E−01 | 3.51E−01 |
| Pos:885.7788@51.00 | TG(56:4) | −0.19 | 0.12 | 1.10E−01 | 3.55E−01 |
| Pos:772.6469@30.80 | SM(d18:1/21:0) | 0.13 | 0.08 | 1.11E−01 | 3.56E−01 |
| Neg:844.6655@31.39 | SM(d17:1/24:1) | 0.14 | 0.09 | 1.14E−01 | 3.60E−01 |
| Pos:758.6315@28.70 | SM(d16:1/22:0) | 0.14 | 0.09 | 1.14E−01 | 3.60E−01 |
| Pos:928.7515@54.39 | TG(16:0_18:1_22:5) | −0.21 | 0.13 | 1.15E−01 | 3.61E−01 |
| Pos:732.6154@26.04 | SM(d18:0/18:0) | 0.20 | 0.13 | 1.21E−01 | 3.70E−01 |
| Pos:897.7805@53.99 | TG(16:0_18:1_20:4) | −0.21 | 0.14 | 1.26E−01 | 3.74E−01 |
| Pos:887.6154@20.25 | | 0.12 | 0.08 | 1.31E−01 | 3.82E−01 |
| Pos:684.5469@43.77 | | 0.24 | 0.16 | 1.34E−01 | 3.82E−01 |
| Neg:709.6577@39.12 | Cer(d19:1/24:0) | 0.19 | 0.13 | 1.37E−01 | 3.82E−01 |
| Pos:819.6146@27.95 | PC(O-18:0/22:6) | 0.19 | 0.13 | 1.40E−01 | 3.82E−01 |
| Pos:847.6474@31.97 | PC(O-20:0/22:6) | 0.19 | 0.13 | 1.43E−01 | 3.82E−01 |
| Neg:818.6498@30.55 | SM(d18:1/21:0) | 0.12 | 0.09 | 1.58E−01 | 3.97E−01 |
| Neg:793.5603@27.53 | PE(18:0_22:5) | −0.19 | 0.14 | 1.81E−01 | 4.15E−01 |
| Pos:927.8238@51.00 | TG(56:4) | −0.16 | 0.13 | 2.02E−01 | 4.29E−01 |
| Neg:446.3394@13.11 | VLCDCA 28:4 | −0.22 | 0.17 | 2.02E−01 | 4.29E−01 |
| Neg:858.6815@33.55 | SM(d18:2/24:0) | 0.11 | 0.08 | 2.02E−01 | 4.29E−01 |
| Pos:805.5628@20.77 | PC(38:6) | −0.11 | 0.09 | 2.08E−01 | 4.30E−01 |
| Neg:699.6293@39.12 | | 0.16 | 0.13 | 2.09E−01 | 4.30E−01 |
| Neg:873.6871@35.86 | | 0.16 | 0.13 | 2.13E−01 | 4.35E−01 |
| Pos:812.6785@33.81 | SM(d18:2/24:0) | 0.11 | 0.09 | 2.18E−01 | 4.38E−01 |
| Neg:872.6961@35.25 | SM(d18:1/25:1)-2 | 0.15 | 0.12 | 2.24E−01 | 4.45E−01 |
| Pos:607.4579@17.14 | LPC(24:0) | 0.10 | 0.08 | 2.43E−01 | 4.58E−01 |
| Neg:846.6815@34.58 | SM(d18:1/23:0) | 0.08 | 0.07 | 2.57E−01 | 4.60E−01 |
| Neg:850.6670@35.84 | | 0.06 | 0.06 | 2.91E−01 | 4.81E−01 |
| Neg:837.5865@23.92 | PC(O-16:0/22:6) | 0.12 | 0.11 | 3.06E−01 | 4.90E−01 |
| Pos:753.5316@19.29 | | −0.15 | 0.15 | 3.07E−01 | 4.90E−01 |
| Pos:753.5687@29.69 | PE(O-18:0/20:4) | 0.16 | 0.15 | 3.09E−01 | 4.91E−01 |
| Neg:710.6139@36.52 | Cer(d18:1/24:1) | 0.07 | 0.07 | 3.25E−01 | 5.04E−01 |
| Pos:892.6936@51.00 | | −0.11 | 0.11 | 3.27E−01 | 5.05E−01 |
| Neg:799.5353@19.15 | PC(14:0_20:4) | −0.16 | 0.16 | 3.34E−01 | 5.09E−01 |
| Pos:803.5477@18.76 | PC(18:2_20:5) | −0.16 | 0.17 | 3.36E−01 | 5.09E−01 |
| Pos:647.6132@36.64 | | 0.08 | 0.09 | 3.47E−01 | 5.17E−01 |
| Neg:845.6132@28.88 | PC(19:0_18:2) | 0.10 | 0.11 | 3.48E−01 | 5.17E−01 |
| Pos:633.6055@30.86 | SM(d17:1/24:1) | 0.11 | 0.12 | 3.64E−01 | 5.26E−01 |
| Pos:947.7953@51.13 | TG(18:1_18:2_22:5) | −0.17 | 0.19 | 3.67E−01 | 5.27E−01 |
| Pos:744.6146@26.54 | SM(d18:1/19:0) | 0.06 | 0.07 | 3.77E−01 | 5.29E−01 |
| Pos:537.5118@25.39 | | 0.07 | 0.08 | 3.78E−01 | 5.30E−01 |
| Pos:758.6315@28.51 | SM(d18:1/20:0) | −0.07 | 0.09 | 3.90E−01 | 5.32E−01 |
| Pos:730.5994@24.43 | SM(d36:1) | 0.06 | 0.07 | 4.08E−01 | 5.43E−01 |
| Pos:362.2902@11.83 | | 0.13 | 0.15 | 4.10E−01 | 5.44E−01 |
| Pos:559.5691@38.64 | | −0.12 | 0.15 | 4.23E−01 | 5.49E−01 |
| Neg:717.5297@26.55 | PE(16:0_18:1) | −0.13 | 0.17 | 4.39E−01 | 5.57E−01 |

TABLE 6H-continued

| Feature ID | Lipid ID | Disease location L2 vs L1 log$_2$(FC) | SE | p-value | q-value |
|---|---|---|---|---|---|
| Neg:725.5345@25.50 | PE(O-16:0/20:4) | 0.12 | 0.16 | 4.39E−01 | 5.57E−01 |
| Neg:693.6257@36.52 | Cer(d18:1/24:1) | 0.06 | 0.08 | 4.40E−01 | 5.57E−01 |
| Pos:552.4389@14.25 | | 0.14 | 0.18 | 4.42E−01 | 5.58E−01 |
| Pos:725.5367@25.70 | PE(O-16:0/20:4) | 0.11 | 0.15 | 4.53E−01 | 5.65E−01 |
| Pos:717.5316@26.75 | | −0.13 | 0.17 | 4.55E−01 | 5.66E−01 |
| Neg:749.5352@24.71 | PE(O-16:0/22:6) | 0.09 | 0.13 | 4.81E−01 | 5.86E−01 |
| Neg:912.5647@22.69 | | −0.05 | 0.08 | 4.82E−01 | 5.86E−01 |
| Pos:728.5844@21.45 | SM(d18:2/18:0) | 0.05 | 0.07 | 5.11E−01 | 5.99E−01 |
| Neg:1152.7105@16.97 | | 0.05 | 0.07 | 5.26E−01 | 6.07E−01 |
| Pos:833.5946@25.01 | PC(18:1_22:5) | −0.12 | 0.19 | 5.51E−01 | 6.19E−01 |
| Pos:585.5850@38.89 | | −0.09 | 0.16 | 5.81E−01 | 6.32E−01 |
| Pos:949.8111@53.74 | TG(18:1_18:2_22:4) | −0.08 | 0.15 | 5.86E−01 | 6.35E−01 |
| Pos:468.3809@12.93 | VLCDCA 28:1(OH) | 0.08 | 0.15 | 5.96E−01 | 6.39E−01 |
| Neg:795.5534@25.83 | | −0.03 | 0.06 | 6.26E−01 | 6.49E−01 |
| Pos:482.3406@12.78 | | −0.02 | 0.05 | 6.46E−01 | 6.55E−01 |
| Neg:442.2743@13.07 | | −0.07 | 0.16 | 6.59E−01 | 6.57E−01 |
| Pos:507.3497@10.01 | | 0.04 | 0.08 | 6.60E−01 | 6.57E−01 |
| Pos:853.5630@19.62 | | −0.05 | 0.12 | 6.60E−01 | 6.57E−01 |
| Neg:670.6212@39.00 | | 0.08 | 0.18 | 6.62E−01 | 6.58E−01 |
| Pos:414.3497@20.82 | | −0.06 | 0.14 | 6.72E−01 | 6.61E−01 |
| Pos:368.3445@53.93 | CE(18:2) | 0.02 | 0.06 | 6.79E−01 | 6.62E−01 |
| Pos:629.6119@36.65 | | 0.03 | 0.09 | 6.93E−01 | 6.65E−01 |
| Neg:386.3151@11.79 | | −0.06 | 0.16 | 6.96E−01 | 6.65E−01 |
| Neg:456.2903@13.07 | | −0.05 | 0.14 | 6.99E−01 | 6.65E−01 |
| Pos:771.5425@19.10 | | 0.05 | 0.14 | 7.00E−01 | 6.65E−01 |
| Pos:942.6220@34.79 | | 0.04 | 0.09 | 7.05E−01 | 6.65E−01 |
| Pos:607.5886@30.05 | | 0.05 | 0.12 | 7.11E−01 | 6.68E−01 |
| Pos:777.5696@28.78 | PE(O-18:0/22:6) | 0.05 | 0.13 | 7.12E−01 | 6.68E−01 |
| Neg:360.2995@11.43 | | −0.06 | 0.16 | 7.18E−01 | 6.70E−01 |
| Neg:254.2259@11.45 | | 0.07 | 0.21 | 7.28E−01 | 6.71E−01 |
| Pos:282.2675@11.48 | | −0.05 | 0.14 | 7.34E−01 | 6.72E−01 |
| Pos:296.2815@12.27 | | −0.06 | 0.18 | 7.39E−01 | 6.72E−01 |
| Pos:534.4276@14.26 | | 0.05 | 0.16 | 7.50E−01 | 6.72E−01 |
| Neg:468.3817@12.87 | VLCDCA 28:1(OH) | 0.06 | 0.20 | 7.70E−01 | 6.75E−01 |
| Neg:823.5341@18.59 | | −0.04 | 0.15 | 7.88E−01 | 6.80E−01 |
| Pos:265.2768@11.82 | | 0.04 | 0.18 | 8.12E−01 | 6.87E−01 |
| Pos:401.3327@13.20 | | −0.02 | 0.08 | 8.18E−01 | 6.87E−01 |
| Neg:1560.1702@24.20 | | −0.02 | 0.09 | 8.46E−01 | 6.97E−01 |
| Pos:425.3507@9.33 | C18:1 carnitine | 0.02 | 0.12 | 8.54E−01 | 6.99E−01 |
| Neg:774.5880@21.27 | SM(d18:2/18:0) | 0.01 | 0.08 | 8.54E−01 | 6.99E−01 |
| Pos:495.3680@10.90 | | 0.02 | 0.09 | 8.57E−01 | 7.00E−01 |
| Pos:239.2616@11.48 | | −0.03 | 0.16 | 8.64E−01 | 7.02E−01 |
| Pos:635.6214@33.95 | Cer(d18:1/23:0) | 0.02 | 0.10 | 8.66E−01 | 7.02E−01 |
| Pos:564.5340@11.48 | | −0.03 | 0.21 | 8.69E−01 | 7.02E−01 |
| Pos:308.2823@12.00 | | 0.02 | 0.17 | 8.82E−01 | 7.07E−01 |
| Pos:401.3489@15.84 | | 0.01 | 0.07 | 8.86E−01 | 7.07E−01 |
| Neg:642.5898@36.90 | | −0.03 | 0.21 | 8.92E−01 | 7.08E−01 |
| Pos:336.2748@11.48 | | −0.02 | 0.14 | 8.99E−01 | 7.09E−01 |
| Pos:415.3510@13.21 | | 0.01 | 0.08 | 9.04E−01 | 7.09E−01 |
| Neg:416.2750@13.07 | | −0.01 | 0.16 | 9.28E−01 | 7.15E−01 |
| Pos:310.2988@13.17 | | −0.01 | 0.16 | 9.30E−01 | 7.15E−01 |
| Pos:308.2831@11.82 | | −0.01 | 0.16 | 9.33E−01 | 7.16E−01 |
| Pos:749.5364@24.89 | | 0.01 | 0.13 | 9.38E−01 | 7.17E−01 |
| Pos:267.2929@13.16 | | −0.01 | 0.16 | 9.60E−01 | 7.24E−01 |
| Pos:399.3348@8.85 | C16:0 carnitine | 0.00 | 0.09 | 9.63E−01 | 7.24E−01 |
| Pos:607.5179@28.48 | DG(16:0_18:2) | 0.01 | 0.16 | 9.72E−01 | 7.25E−01 |

TABLE 6I

| Feature ID | Lipid ID | Disease behavior and location: conditional on each other Disease behavior log$_2$(FC) | SE | p-value | q-value |
|---|---|---|---|---|---|
| Neg:494.3450@13.93 | Sitosterol sulfate | 0.49 | 0.14 | 7.58E−04 | 4.19E−02 |
| Neg:632.3875@20.55 | | −0.05 | 0.03 | 1.33E−01 | 2.38E−01 |
| Pos:382.3253@18.09 | Cholesta-4,6-dien-3-one | 0.63 | 0.17 | 2.64E−04 | 2.16E−02 |
| Neg:976.7275@20.56 | | −0.02 | 0.06 | 7.89E−01 | 5.09E−01 |
| Neg:588.3810@20.55 | | −0.12 | 0.04 | 5.25E−03 | 8.24E−02 |
| Pos:863.6407@30.12 | | 0.05 | 0.10 | 5.81E−01 | 4.47E−01 |
| Neg:890.7125@20.56 | | −0.02 | 0.07 | 8.11E−01 | 5.16E−01 |

TABLE 6I-continued

| Feature ID | Lipid ID | Disease behavior and location: conditional on each other Disease behavior | | | |
|---|---|---|---|---|---|
| | | log2(FC) | SE | p-value | q-value |
| Pos:1254.0843@20.73 | | −0.05 | 0.06 | 3.69E−01 | 3.69E−01 |
| Neg:932.7214@20.56 | | −0.04 | 0.07 | 5.47E−01 | 4.37E−01 |
| Neg:1300.0741@20.57 | | −0.05 | 0.06 | 4.06E−01 | 3.83E−01 |
| Neg:1000.7305@20.57 | | −0.07 | 0.06 | 2.39E−01 | 3.05E−01 |
| Neg:999.7325@20.57 | | −0.09 | 0.06 | 1.54E−01 | 2.52E−01 |
| Neg:602.3689@20.56 | | −0.07 | 0.05 | 1.93E−01 | 2.76E−01 |
| Neg:959.7195@20.57 | | 0.00 | 0.05 | 9.59E−01 | 5.51E−01 |
| Neg:956.7237@20.57 | | −0.08 | 0.06 | 1.99E−01 | 2.78E−01 |
| Neg:888.7128@20.56 | | −0.03 | 0.07 | 6.71E−01 | 4.74E−01 |
| Pos:859.7415@20.74 | | −0.01 | 0.03 | 6.57E−01 | 4.71E−01 |
| Neg:1014.7189@20.56 | | −0.03 | 0.05 | 5.32E−01 | 4.33E−01 |
| Neg:916.7128@20.56 | | −0.07 | 0.06 | 2.47E−01 | 3.09E−01 |
| Pos:873.7556@20.73 | | −0.01 | 0.04 | 7.54E−01 | 4.98E−01 |
| Neg:574.3676@20.53 | | −0.06 | 0.04 | 1.25E−01 | 2.33E−01 |
| Pos:716.5465@17.11 | PE(O-34:3) | −0.17 | 0.05 | 1.51E−03 | 6.52E−02 |
| Neg:522.3685@20.56 | | −0.02 | 0.06 | 7.17E−01 | 4.87E−01 |
| Neg:548.3686@20.55 | | −0.04 | 0.06 | 4.59E−01 | 4.09E−01 |
| Pos:412.2979@9.95 | | 0.34 | 0.11 | 2.33E−03 | 7.10E−02 |
| Pos:674.5372@17.33 | SM(d16:1/16:0) | −0.13 | 0.05 | 7.73E−03 | 8.95E−02 |
| Neg:942.7111@20.55 | | −0.09 | 0.06 | 1.13E−01 | 2.22E−01 |
| Neg:532.3584@20.55 | | −0.09 | 0.11 | 3.97E−01 | 3.80E−01 |
| Neg:466.3396@20.56 | | −0.15 | 0.10 | 1.25E−01 | 2.33E−01 |
| Pos:481.3172@8.20 | LPC(15:0) | −0.01 | 0.07 | 9.21E−01 | 5.43E−01 |
| Neg:604.3632@20.56 | | −0.07 | 0.08 | 4.10E−01 | 3.85E−01 |
| Pos:1405.1372@20.63 | | −0.26 | 0.08 | 2.56E−03 | 7.10E−02 |
| Neg:765.5307@23.93 | PE(18:1_20:4)-1 | 0.34 | 0.12 | 3.89E−03 | 8.04E−02 |
| Pos:611.5657@47.54 | CE(14:1) | 0.01 | 0.14 | 9.32E−01 | 5.46E−01 |
| Pos:842.7249@37.94 | SM(d44:1) | −0.22 | 0.06 | 2.38E−04 | 2.11E−02 |
| Neg:874.7121@36.84 | SM(d43:1) | −0.21 | 0.06 | 7.87E−04 | 4.19E−02 |
| Neg:577.3692@20.56 | | −0.07 | 0.10 | 4.58E−01 | 4.09E−01 |
| Pos:919.7688@45.95 | | 0.23 | 0.11 | 3.22E−02 | 1.51E−01 |
| Pos:700.5335@17.33 | | −0.08 | 0.06 | 1.81E−01 | 2.67E−01 |
| Neg:541.3371@9.22 | LPC(16:0) | 0.00 | 0.05 | 9.52E−01 | 5.49E−01 |
| Pos:368.3443@12.77 | | −0.11 | 0.06 | 8.06E−02 | 1.93E−01 |
| Pos:797.6758@35.44 | GlcCer(d18:1/23:0) | −0.09 | 0.06 | 1.74E−01 | 2.63E−01 |
| Pos:784.6473@28.86 | SM(d18:1/22:1) | −0.08 | 0.05 | 1.13E−01 | 2.22E−01 |
| Neg:466.3133@12.72 | Cholesterol sulfate | −0.08 | 0.07 | 2.90E−01 | 3.32E−01 |
| Pos:699.5646@21.73 | | −0.08 | 0.06 | 1.95E−01 | 2.76E−01 |
| Pos:802.6908@35.79 | | −0.16 | 0.08 | 6.74E−02 | 1.83E−01 |
| Neg:843.6786@35.29 | GlcCer(d18:1/23:0) | −0.14 | 0.07 | 4.59E−02 | 1.59E−01 |
| Neg:848.6949@35.66 | | −0.05 | 0.09 | 5.90E−01 | 4.49E−01 |
| Pos:921.7813@49.56 | TG(18:1_18:2_20:4) | 0.32 | 0.10 | 2.53E−03 | 7.10E−02 |
| Neg:720.5416@17.20 | SM(d16:1/16:0) | −0.12 | 0.05 | 3.32E−02 | 1.52E−01 |
| Pos:832.7000@34.80 | | −0.25 | 0.07 | 1.40E−04 | 2.11E−02 |
| Neg:453.2858@9.43 | LPE(16:0) | 0.16 | 0.08 | 4.10E−02 | 1.55E−01 |
| Pos:826.6879@34.79 | | −0.13 | 0.06 | 2.37E−02 | 1.34E−01 |
| Neg:745.5689@21.54 | GlcCer(d18:1/16:0) | −0.06 | 0.05 | 2.28E−01 | 2.96E−01 |
| Pos:828.7092@36.97 | SM(d43:1) | −0.25 | 0.06 | 4.58E−05 | 1.22E−02 |
| Neg:764.5661@19.37 | | −0.14 | 0.05 | 5.90E−03 | 8.66E−02 |
| Neg:830.6500@28.63 | SM(d18:1/22:1) | −0.05 | 0.06 | 3.50E−01 | 3.60E−01 |
| Pos:895.7651@49.23 | TG(18:2_16:0_20:4) | 0.29 | 0.11 | 1.08E−02 | 1.02E−01 |
| Pos:688.5513@18.48 | SM(d33:1) | −0.18 | 0.07 | 8.49E−03 | 9.53E−02 |
| Pos:613.5800@52.89 | CE(14:0) | −0.07 | 0.10 | 4.85E−01 | 4.17E−01 |
| Pos:686.5357@16.62 | SM(d33:2) | −0.09 | 0.05 | 1.19E−01 | 2.27E−01 |
| Pos:368.3444@60.96 | CE(18:1) | −0.09 | 0.04 | 3.02E−02 | 1.48E−01 |
| Pos:688.5532@18.89 | SM(d17:1/16:0) | −0.18 | 0.05 | 4.03E−04 | 3.06E−02 |
| Pos:828.7092@36.62 | SM(d19:1/24:0) | −0.31 | 0.09 | 6.97E−04 | 4.19E−02 |
| Pos:700.5516@19.06 | SM(d18:2/16:0) | −0.31 | 0.09 | 8.98E−04 | 4.55E−02 |
| Pos:646.5049@14.73 | SM(d16:1/14:0) | −0.01 | 0.08 | 9.26E−01 | 5.45E−01 |
| Pos:798.6629@31.63 | SM(d18:2/23:0) | −0.27 | 0.06 | 2.58E−05 | 1.22E−02 |
| Pos:773.5574@19.33 | | −0.10 | 0.07 | 1.88E−01 | 2.73E−01 |
| Pos:936.7921@49.24 | | 0.26 | 0.11 | 2.54E−02 | 1.37E−01 |
| Neg:874.7116@36.49 | SM(d19:1/24:0) | −0.25 | 0.09 | 5.04E−03 | 8.24E−02 |
| Pos:1215.0900@52.85 | | −0.21 | 0.12 | 7.16E−02 | 1.84E−01 |
| Pos:453.2857@9.48 | LPE(16:0) | 0.17 | 0.07 | 1.46E−02 | 1.15E−01 |
| Pos:660.5202@15.93 | SM(d17:1/18:0) | −0.09 | 0.07 | 2.21E−01 | 2.93E−01 |
| Pos:799.6100@29.09 | PC(19:0_18:2) | −0.23 | 0.07 | 1.39E−03 | 6.42E−02 |
| Pos:720.5763@18.94 | SM(d18:0/16:0)(OH) | −0.20 | 0.06 | 2.01E−03 | 7.10E−02 |
| Neg:860.6963@35.57 | SM(d18:1/24:0) | −0.25 | 0.09 | 6.80E−03 | 8.72E−02 |
| Pos:826.6932@35.39 | SM(d18:1/25:1)-2 | −0.21 | 0.09 | 1.48E−02 | 1.15E−01 |
| Pos:814.6935@35.97 | SM(d18:1/24:0)-2 | −0.21 | 0.06 | 2.05E−04 | 2.11E−02 |
| Pos:800.6783@34.78 | SM(d18:1/25:1)-1 | −0.25 | 0.05 | 1.03E−05 | 1.10E−02 |
| Neg:734.5567@18.74 | SM(d17:1/16:0) | −0.18 | 0.06 | 1.74E−03 | 6.88E−02 |
| Pos:798.6620@30.86 | SM(d17:1/24:1) | −0.09 | 0.06 | 1.05E−01 | 2.13E−01 |

TABLE 6I-continued

| Feature ID | Lipid ID | Disease behavior and location: conditional on each other Disease behavior log$_2$(FC) | SE | p-value | q-value |
|---|---|---|---|---|---|
| Pos:618.5353@52.85 | CE(14:0) | −0.07 | 0.07 | 2.65E−01 | 3.17E−01 |
| Neg:765.5314@24.31 | PE(18:1_20:4)-2 | 0.14 | 0.09 | 1.25E−01 | 2.33E−01 |
| Pos:885.7788@51.00 | TG(56:4) | 0.24 | 0.09 | 8.04E−03 | 9.21E−02 |
| Pos:772.6469@30.80 | SM(d18:1/21:0) | −0.23 | 0.06 | 2.10E−04 | 2.11E−02 |
| Neg:844.6655@31.39 | SM(d17:1/24:1) | −0.25 | 0.07 | 2.33E−04 | 2.11E−02 |
| Pos:758.6315@28.70 | SM(d16:1/22:0) | −0.19 | 0.07 | 4.85E−03 | 8.24E−02 |
| Pos:928.7515@54.39 | TG(16:0_18:1_22:5) | 0.29 | 0.10 | 4.79E−03 | 8.24E−02 |
| Pos:732.6154@26.04 | SM(d18:0/18:0) | 0.04 | 0.10 | 6.75E−01 | 4.75E−01 |
| Pos:897.7805@53.99 | TG(16:0_18:1_20:4) | 0.29 | 0.10 | 6.14E−03 | 8.72E−02 |
| Pos:887.6154@20.25 | | 0.00 | 0.06 | 9.68E−01 | 5.53E−01 |
| Pos:684.5469@43.77 | | 0.07 | 0.12 | 5.45E−01 | 4.36E−01 |
| Neg:709.6577@39.12 | Cer(d19:1/24:0) | −0.19 | 0.09 | 4.21E−02 | 1.56E−01 |
| Pos:819.6146@27.95 | PC(O-18:0/22:6) | −0.26 | 0.09 | 5.42E−03 | 8.31E−02 |
| Pos:847.6474@31.97 | PC(O-20:0/22:6) | −0.23 | 0.10 | 1.87E−02 | 1.25E−01 |
| Neg:818.6498@30.55 | SM(d18:1/21:0) | −0.22 | 0.06 | 6.75E−04 | 4.19E−02 |
| Neg:793.5603@27.53 | PE(18:0_22:5) | 0.30 | 0.10 | 4.92E−03 | 8.24E−02 |
| Pos:927.8238@51.00 | TG(56:4) | 0.19 | 0.10 | 5.22E−02 | 1.65E−01 |
| Neg:446.3394@13.11 | VLCDCA 28:4 | −0.11 | 0.13 | 3.95E−01 | 3.79E−01 |
| Neg:858.6815@33.55 | SM(d18:2/24:0) | −0.19 | 0.06 | 2.40E−03 | 7.10E−02 |
| Pos:805.5628@20.77 | PC(38:6) | −0.11 | 0.07 | 1.08E−01 | 2.18E−01 |
| Neg:699.6293@39.12 | | −0.22 | 0.10 | 2.19E−02 | 1.30E−01 |
| Neg:873.6871@35.86 | | −0.18 | 0.10 | 6.34E−02 | 1.79E−01 |
| Pos:812.6785@33.81 | SM(d18:2/24:0) | −0.24 | 0.06 | 1.86E−04 | 2.11E−02 |
| Neg:872.6961@35.25 | SM(d18:1/25:1)-2 | −0.31 | 0.09 | 7.40E−04 | 4.19E−02 |
| Pos:607.4579@17.14 | LPC(24:0) | −0.13 | 0.06 | 4.06E−02 | 1.55E−01 |
| Neg:846.6815@34.58 | SM(d18:1/23:0) | −0.20 | 0.05 | 2.32E−04 | 2.11E−02 |
| Neg:850.6670@35.84 | | −0.16 | 0.04 | 9.57E−05 | 2.04E−02 |
| Neg:837.5865@23.92 | PC(O-16:0/22:6) | −0.18 | 0.09 | 4.08E−02 | 1.55E−01 |
| Pos:753.5316@19.29 | | 0.10 | 0.11 | 3.71E−01 | 3.69E−01 |
| Pos:753.5687@29.69 | PE(O-18:0/20:4) | −0.29 | 0.11 | 1.22E−02 | 1.06E−01 |
| Neg:710.6139@36.52 | Cer(d18:1/24:1) | 0.10 | 0.05 | 6.82E−02 | 1.84E−01 |
| Pos:892.6936@51.00 | | 0.14 | 0.08 | 1.04E−01 | 2.12E−01 |
| Neg:799.5353@19.15 | PC(14:0_20:4) | 0.14 | 0.12 | 2.70E−01 | 3.20E−01 |
| Pos:803.5477@18.76 | PC(18:2_20:5) | −0.15 | 0.13 | 2.32E−01 | 3.00E−01 |
| Pos:647.6132@36.64 | | 0.11 | 0.07 | 1.09E−01 | 2.18E−01 |
| Neg:845.6132@28.88 | PC(19:0_18:2) | −0.18 | 0.08 | 2.41E−02 | 1.35E−01 |
| Pos:633.6055@30.86 | SM(d17:1/24:1) | −0.26 | 0.09 | 5.01E−03 | 8.24E−02 |
| Pos:947.7953@51.13 | TG(18:1_18:2_22:5) | 0.40 | 0.14 | 4.51E−03 | 8.24E−02 |
| Pos:744.6146@26.54 | SM(d18:1/19:0) | −0.16 | 0.05 | 4.00E−03 | 8.04E−02 |
| Pos:537.5118@25.39 | | −0.06 | 0.06 | 3.19E−01 | 3.49E−01 |
| Pos:758.6315@28.51 | SM(d18:1/20:0) | 0.00 | 0.06 | 9.71E−01 | 5.54E−01 |
| Pos:730.5994@24.43 | SM(d36:1) | −0.03 | 0.05 | 5.19E−01 | 4.29E−01 |
| Pos:362.2902@11.83 | | −0.08 | 0.12 | 4.93E−01 | 4.20E−01 |
| Pos:559.5691@38.64 | | −0.04 | 0.12 | 7.40E−01 | 4.95E−01 |
| Neg:717.5297@26.55 | PE(16:0_18:1) | 0.39 | 0.13 | 2.55E−03 | 7.10E−02 |
| Neg:725.5345@25.50 | PE(O-16:0/20:4) | −0.32 | 0.12 | 7.11E−03 | 8.72E−02 |
| Neg:693.6257@36.52 | Cer(d18:1/24:1) | 0.14 | 0.06 | 2.99E−02 | 1.48E−01 |
| Pos:552.4389@14.25 | | −0.13 | 0.14 | 3.33E−01 | 3.53E−01 |
| Pos:725.5367@25.70 | PE(O-16:0/20:4) | −0.31 | 0.11 | 6.81E−03 | 8.72E−02 |
| Pos:717.5316@26.75 | | 0.38 | 0.13 | 3.13E−03 | 7.57E−02 |
| Neg:749.5352@24.71 | PE(O-16:0/22:6) | −0.18 | 0.10 | 7.30E−02 | 1.84E−01 |
| Neg:912.5647@22.69 | | 0.17 | 0.06 | 4.19E−03 | 8.06E−02 |
| Pos:728.5844@21.45 | SM(d18:2/18:0) | −0.03 | 0.06 | 5.85E−01 | 4.47E−01 |
| Neg:1152.7105@16.97 | | −0.02 | 0.06 | 7.08E−01 | 4.84E−01 |
| Pos:833.5946@25.01 | PC(18:1_22:5) | 0.44 | 0.15 | 2.73E−03 | 7.10E−02 |
| Pos:585.5850@38.89 | | −0.04 | 0.12 | 7.57E−01 | 4.98E−01 |
| Pos:949.8111@53.74 | TG(18:1_18:2_22:4) | 0.37 | 0.11 | 1.22E−03 | 5.93E−02 |
| Pos:468.3809@12.93 | VLCDCA 28:1(OH) | −0.10 | 0.11 | 4.00E−01 | 3.80E−01 |
| Neg:795.5534@25.83 | | 0.03 | 0.04 | 5.48E−01 | 4.37E−01 |
| Pos:482.3406@12.78 | | 0.05 | 0.04 | 1.79E−01 | 2.66E−01 |
| Neg:442.2743@13.07 | | 0.01 | 0.12 | 9.40E−01 | 5.47E−01 |
| Pos:507.3497@10.01 | | −0.08 | 0.06 | 1.98E−01 | 2.77E−01 |
| Pos:853.5630@19.62 | | −0.22 | 0.09 | 1.58E−02 | 1.18E−01 |
| Neg:670.6212@39.00 | | −0.15 | 0.13 | 2.77E−01 | 3.24E−01 |
| Pos:414.3497@20.82 | | 0.24 | 0.11 | 2.89E−02 | 1.47E−01 |
| Pos:368.3445@53.93 | CE(18:2) | −0.14 | 0.04 | 1.58E−03 | 6.52E−02 |
| Pos:629.6119@36.65 | | 0.14 | 0.06 | 3.15E−02 | 1.51E−01 |
| Neg:386.3151@11.79 | | −0.05 | 0.12 | 6.86E−01 | 4.77E−01 |
| Neg:456.2903@13.07 | | 0.02 | 0.10 | 8.34E−01 | 5.21E−01 |
| Pos:771.5425@19.10 | | 0.12 | 0.11 | 2.66E−01 | 3.18E−01 |
| Pos:942.6220@34.79 | | −0.14 | 0.07 | 4.71E−02 | 1.59E−01 |
| Pos:607.5886@30.05 | | −0.21 | 0.09 | 2.10E−02 | 1.29E−01 |
| Pos:777.5696@28.78 | PE(O-18:0/22:6) | −0.25 | 0.10 | 1.26E−02 | 1.08E−01 |
| Neg:360.2995@11.43 | | −0.02 | 0.13 | 8.70E−01 | 5.31E−01 |

TABLE 6I-continued

| Feature ID | Lipid ID | Disease behavior and location: conditional on each other Disease behavior | | | |
|---|---|---|---|---|---|
| | | log2(FC) | SE | p-value | q-value |
| Neg:254.2259@11.45 | | 0.20 | 0.16 | 2.17E−01 | 2.91E−01 |
| Pos:282.2675@11.48 | | 0.01 | 0.10 | 9.42E−01 | 5.47E−01 |
| Pos:296.2815@12.27 | | −0.13 | 0.14 | 3.24E−01 | 3.49E−01 |
| Pos:534.4276@14.26 | | −0.09 | 0.12 | 4.82E−01 | 4.17E−01 |
| Neg:468.3817@12.87 | VLCDCA 28:1(OH) | −0.28 | 0.15 | 6.62E−02 | 1.83E−01 |
| Neg:823.5341@18.59 | | −0.02 | 0.12 | 8.80E−01 | 5.31E−01 |
| Pos:265.2768@11.82 | | −0.08 | 0.14 | 5.57E−01 | 4.38E−01 |
| Pos:401.3327@13.20 | | 0.00 | 0.06 | 9.36E−01 | 5.47E−01 |
| Neg:1560.1702@24.20 | | 0.05 | 0.07 | 4.24E−01 | 3.92E−01 |
| Pos:425.3507@9.33 | C18:1 carnitine | −0.01 | 0.09 | 8.76E−01 | 5.31E−01 |
| Neg:774.5880@21.27 | SM(d18:2/18:0) | −0.01 | 0.06 | 8.27E−01 | 5.19E−01 |
| Pos:495.3680@10.90 | | −0.14 | 0.07 | 3.91E−02 | 1.55E−01 |
| Pos:239.2616@11.48 | | 0.04 | 0.12 | 7.23E−01 | 4.88E−01 |
| Pos:635.6214@33.95 | Cer(d18:1/23:0) | −0.19 | 0.08 | 1.14E−02 | 1.04E−01 |
| Pos:564.5340@11.48 | | −0.08 | 0.16 | 6.23E−01 | 4.57E−01 |
| Pos:308.2823@12.00 | | −0.04 | 0.13 | 7.51E−01 | 4.97E−01 |
| Pos:401.3489@15.84 | | 0.06 | 0.05 | 2.86E−01 | 3.30E−01 |
| Neg:642.5898@36.90 | | −0.11 | 0.16 | 5.06E−01 | 4.26E−01 |
| Pos:336.2748@11.48 | | −0.04 | 0.11 | 7.17E−01 | 4.87E−01 |
| Pos:415.3510@13.21 | | 0.00 | 0.06 | 9.67E−01 | 5.52E−01 |
| Neg:416.2750@13.07 | | 0.02 | 0.12 | 8.60E−01 | 5.27E−01 |
| Pos:310.2988@13.17 | | −0.18 | 0.12 | 1.37E−01 | 2.40E−01 |
| Pos:308.2831@11.82 | | −0.06 | 0.12 | 6.07E−01 | 4.53E−01 |
| Pos:749.5364@24.89 | | −0.21 | 0.10 | 3.30E−02 | 1.52E−01 |
| Pos:267.2929@13.16 | | −0.17 | 0.12 | 1.76E−01 | 2.64E−01 |
| Pos:399.3348@8.85 | C16:0 carnitine | −0.04 | 0.07 | 5.44E−01 | 4.36E−01 |
| Pos:607.5179@28.48 | DG(16:0_18:2) | 0.48 | 0.11 | 4.37E−05 | 1.22E−02 |

TABLE 6J

| Feature ID | Lipid ID | Disease behavior and location: conditional on each other Disease location | | | |
|---|---|---|---|---|---|
| | | log2(FC) | SE | p-value | q-value |
| Neg:494.3450@13.93 | Sitosterol sulfate | −0.95 | 0.20 | 3.85E−06 | 6.44E−03 |
| Neg:632.3875@20.55 | | 0.19 | 0.05 | 1.29E−04 | 7.20E−02 |
| Pos:382.3253@18.09 | Cholesta-4,6-dien-3-one | −0.74 | 0.24 | 2.13E−03 | 1.13E−01 |
| Neg:976.7275@20.56 | | 0.31 | 0.08 | 2.03E−04 | 7.36E−02 |
| Neg:588.3810@20.55 | | 0.17 | 0.06 | 4.25E−03 | 1.62E−01 |
| Pos:863.6407@30.12 | | 0.54 | 0.14 | 1.05E−04 | 7.20E−02 |
| Neg:890.7125@20.56 | | 0.35 | 0.10 | 4.03E−04 | 9.64E−02 |
| Pos:1254.0843@20.73 | | 0.28 | 0.08 | 8.99E−04 | 1.03E−01 |
| Neg:932.7214@20.56 | | 0.34 | 0.10 | 6.44E−04 | 1.03E−01 |
| Neg:1300.0741@20.57 | | 0.29 | 0.09 | 8.67E−04 | 1.03E−01 |
| Neg:1000.7305@20.57 | | 0.28 | 0.09 | 1.31E−03 | 1.03E−01 |
| Neg:999.7325@20.57 | | 0.28 | 0.09 | 2.39E−03 | 1.14E−01 |
| Neg:602.3689@20.56 | | 0.23 | 0.07 | 2.16E−03 | 1.13E−01 |
| Neg:959.7195@20.57 | | 0.23 | 0.07 | 4.74E−04 | 9.91E−02 |
| Neg:956.7237@20.57 | | 0.27 | 0.09 | 2.22E−03 | 1.13E−01 |
| Neg:888.7128@20.56 | | 0.32 | 0.09 | 8.65E−04 | 1.03E−01 |
| Pos:859.7415@20.74 | | 0.14 | 0.04 | 1.09E−03 | 1.03E−01 |
| Neg:1014.7189@20.56 | | 0.24 | 0.07 | 1.36E−03 | 1.03E−01 |
| Neg:916.7128@20.56 | | 0.27 | 0.09 | 2.51E−03 | 1.17E−01 |
| Pos:873.7556@20.73 | | 0.20 | 0.06 | 1.02E−03 | 1.03E−01 |
| Neg:574.3676@20.53 | | 0.17 | 0.06 | 3.96E−03 | 1.62E−01 |
| Pos:716.5465@17.11 | PE(O-34:3) | 0.18 | 0.07 | 1.79E−02 | 3.22E−01 |
| Neg:522.3685@20.56 | | 0.27 | 0.08 | 1.25E−03 | 1.03E−01 |
| Neg:548.3686@20.55 | | 0.26 | 0.08 | 1.96E−03 | 1.13E−01 |
| Pos:412.2979@9.95 | | −0.36 | 0.15 | 2.00E−02 | 3.32E−01 |
| Pos:674.5372@17.33 | SM(d16:1/16:0) | 0.17 | 0.07 | 1.54E−02 | 2.97E−01 |
| Neg:942.7111@20.55 | | 0.23 | 0.08 | 5.91E−03 | 1.85E−01 |
| Neg:532.3584@20.55 | | 0.43 | 0.15 | 4.68E−03 | 1.64E−01 |
| Neg:466.3396@20.56 | | 0.35 | 0.13 | 9.39E−03 | 2.23E−01 |
| Pos:481.3172@8.20 | LPC(15:0) | −0.29 | 0.09 | 1.96E−03 | 1.13E−01 |
| Neg:604.3632@20.56 | | 0.32 | 0.11 | 5.93E−03 | 1.85E−01 |
| Pos:1405.1372@20.63 | | 0.24 | 0.12 | 4.29E−02 | 4.28E−01 |
| Neg:765.5307@23.93 | PE(18:1_20:4)-1 | −0.33 | 0.16 | 4.41E−02 | 4.31E−01 |
| Pos:611.5657@47.54 | CE(14:1) | 0.61 | 0.20 | 2.96E−03 | 1.27E−01 |
| Pos:842.7249@37.94 | SM(d44:1) | 0.14 | 0.08 | 7.87E−02 | 5.46E−01 |

TABLE 6J-continued

| Feature ID | Lipid ID | Disease behavior and location: conditional on each other Disease location log$_2$(FC) | SE | p-value | q-value |
|---|---|---|---|---|---|
| Neg:874.7121@36.84 | SM(d43:1) | 0.16 | 0.08 | 6.66E−02 | 5.27E−01 |
| Neg:577.3692@20.56 | | 0.37 | 0.14 | 7.68E−03 | 2.04E−01 |
| Pos:919.7688@45.95 | | −0.33 | 0.15 | 2.80E−02 | 3.77E−01 |
| Pos:700.5335@17.33 | | 0.19 | 0.08 | 1.56E−02 | 2.97E−01 |
| Neg:541.3371@9.22 | LPC(16:0) | −0.19 | 0.07 | 4.70E−03 | 1.64E−01 |
| Pos:368.3443@12.77 | | 0.19 | 0.09 | 2.81E−02 | 3.77E−01 |
| Pos:797.6758@35.44 | GlcCer(d18:1/23:0) | 0.20 | 0.09 | 2.23E−02 | 3.51E−01 |
| Pos:784.6473@28.86 | SM(d18:1/22:1) | 0.16 | 0.07 | 2.89E−02 | 3.81E−01 |
| Neg:466.3133@12.72 | Cholesterol sulfate | 0.25 | 0.11 | 1.96E−02 | 3.32E−01 |
| Pos:699.5646@21.73 | | 0.18 | 0.08 | 3.06E−02 | 3.97E−01 |
| Pos:802.6908@35.79 | | 0.24 | 0.12 | 4.85E−02 | 4.46E−01 |
| Neg:843.6786@35.29 | GlcCer(d18:1/23:0) | 0.18 | 0.09 | 6.01E−02 | 5.00E−01 |
| Neg:848.6949@35.66 | | 0.29 | 0.12 | 1.99E−02 | 3.32E−01 |
| Pos:921.7813@49.56 | TG(18:1_18:2_20:4) | −0.22 | 0.15 | 1.31E−01 | 6.32E−01 |
| Neg:720.5416@17.20 | SM(d16:1/16:0) | 0.14 | 0.08 | 7.40E−02 | 5.46E−01 |
| Pos:832.7000@34.80 | | 0.11 | 0.09 | 2.17E−01 | 7.09E−01 |
| Neg:453.2858@9.43 | LPE(16:0) | −0.20 | 0.11 | 7.58E−02 | 5.46E−01 |
| Pos:826.6879@34.79 | | 0.14 | 0.08 | 9.41E−02 | 5.82E−01 |
| Neg:745.5689@21.54 | GlcCer(d18:1/16:0) | 0.15 | 0.08 | 4.83E−02 | 4.46E−01 |
| Pos:828.7092@36.97 | SM(d43:1) | 0.08 | 0.08 | 3.31E−01 | 7.87E−01 |
| Neg:764.5661@19.37 | | 0.10 | 0.07 | 1.67E−01 | 6.59E−01 |
| Neg:830.6500@28.63 | SM(d18:1/22:1) | 0.16 | 0.08 | 4.96E−02 | 4.49E−01 |
| Pos:895.7651@49.23 | TG(18:2_16:0_20:4) | −0.22 | 0.16 | 1.60E−01 | 6.48E−01 |
| Pos:688.5513@18.48 | SM(d33:1) | 0.13 | 0.10 | 1.77E−01 | 6.61E−01 |
| Pos:613.5800@52.89 | CE(14:0) | 0.27 | 0.14 | 5.35E−02 | 4.69E−01 |
| Pos:686.5357@16.62 | SM(d33:2) | 0.12 | 0.08 | 1.09E−01 | 6.05E−01 |
| Pos:368.3444@60.96 | CE(18:1) | 0.08 | 0.06 | 1.63E−01 | 6.53E−01 |
| Pos:688.5532@18.89 | SM(d17:1/16:0) | 0.07 | 0.07 | 3.49E−01 | 7.99E−01 |
| Pos:828.7092@36.62 | SM(d19:1/24:0) | 0.11 | 0.13 | 3.72E−01 | 8.09E−01 |
| Pos:700.5516@19.06 | SM(d18:2/16:0) | 0.12 | 0.13 | 3.78E−01 | 8.10E−01 |
| Pos:646.5049@14.73 | SM(d16:1/14:0) | 0.21 | 0.11 | 5.65E−02 | 4.79E−01 |
| Pos:798.6629@31.63 | SM(d18:2/23:0) | 0.05 | 0.09 | 6.04E−01 | 8.38E−01 |
| Pos:773.5574@19.33 | | 0.15 | 0.10 | 1.43E−01 | 6.41E−01 |
| Pos:936.7921@49.24 | | −0.18 | 0.16 | 2.54E−01 | 7.31E−01 |
| Neg:874.7116@36.49 | SM(d19:1/24:0) | 0.12 | 0.12 | 3.43E−01 | 7.96E−01 |
| Pos:1215.0900@52.85 | | 0.21 | 0.16 | 2.08E−01 | 7.06E−01 |
| Pos:453.2857@9.48 | LPE(16:0) | −0.10 | 0.10 | 2.99E−01 | 7.68E−01 |
| Pos:660.5202@15.93 | SM(d17:1/18:0) | 0.14 | 0.10 | 1.58E−01 | 6.48E−01 |
| Pos:799.6100@29.09 | PC(19:0_18:2) | 0.07 | 0.10 | 4.68E−01 | 8.26E−01 |
| Pos:720.5763@18.94 | SM(d18:0/16:0)(OH) | 0.07 | 0.09 | 4.55E−01 | 8.26E−01 |
| Neg:860.6963@35.57 | SM(d18:1/24:0) | 0.09 | 0.13 | 4.75E−01 | 8.26E−01 |
| Pos:826.6932@35.39 | SM(d18:1/25:1)-2 | 0.10 | 0.12 | 4.22E−01 | 8.18E−01 |
| Pos:814.6935@35.97 | SM(d18:1/24:0)-2 | 0.03 | 0.08 | 7.20E−01 | 8.46E−01 |
| Pos:800.6783@34.78 | SM(d18:1/25:1)-1 | 0.01 | 0.08 | 9.20E−01 | 8.72E−01 |
| Neg:734.5567@18.74 | SM(d17:1/16:0) | 0.04 | 0.08 | 5.98E−01 | 8.38E−01 |
| Pos:798.6620@30.86 | SM(d17:1/24:1) | 0.08 | 0.08 | 3.25E−01 | 7.85E−01 |
| Pos:618.5353@52.85 | CE(14:0) | 0.11 | 0.09 | 2.52E−01 | 7.30E−01 |
| Neg:765.5314@24.31 | PE(18:1_20:4)-2 | −0.13 | 0.13 | 3.25E−01 | 7.85E−01 |
| Pos:885.7788@51.00 | TG(56:4) | −0.07 | 0.13 | 5.57E−01 | 8.37E−01 |
| Pos:772.6469@30.80 | SM(d18:1/21:0) | 0.02 | 0.09 | 8.21E−01 | 8.63E−01 |
| Neg:844.6655@31.39 | SM(d17:1/24:1) | 0.02 | 0.09 | 8.23E−01 | 8.63E−01 |
| Pos:758.6315@28.70 | SM(d16:1/22:0) | 0.05 | 0.09 | 6.08E−01 | 8.38E−01 |
| Pos:928.7515@54.39 | TG(16:0_18:1_22:5) | −0.07 | 0.14 | 6.11E−01 | 8.38E−01 |
| Pos:732.6154@26.04 | SM(d18:0/18:0) | 0.23 | 0.14 | 1.10E−01 | 6.05E−01 |
| Pos:897.7805@53.99 | TG(16:0_18:1_20:4) | −0.07 | 0.15 | 6.21E−01 | 8.38E−01 |
| Pos:887.6154@20.25 | | 0.12 | 0.08 | 1.54E−01 | 6.48E−01 |
| Pos:684.5469@43.77 | | 0.27 | 0.17 | 1.07E−01 | 6.05E−01 |
| Neg:709.6577@39.12 | Cer(d19:1/24:0) | 0.09 | 0.13 | 4.88E−01 | 8.31E−01 |
| Pos:819.6146@27.95 | PC(O-18:0/22:6) | 0.06 | 0.13 | 6.69E−01 | 8.43E−01 |
| Pos:847.6474@31.97 | PC(O-20:0/22:6) | 0.08 | 0.14 | 5.73E−01 | 8.37E−01 |
| Neg:818.6498@30.55 | SM(d18:1/21:0) | 0.01 | 0.09 | 8.77E−01 | 8.71E−01 |
| Neg:793.5603@27.53 | PE(18:0_22:5) | −0.04 | 0.15 | 7.76E−01 | 8.51E−01 |
| Pos:927.8238@51.00 | TG(56:4) | −0.07 | 0.13 | 6.01E−01 | 8.38E−01 |
| Neg:446.3394@13.11 | VLCDCA 28:4 | −0.28 | 0.19 | 1.36E−01 | 6.34E−01 |
| Neg:858.6815@33.55 | SM(d18:2/24:0) | 0.01 | 0.09 | 8.84E−01 | 8.72E−01 |
| Pos:805.5628@20.77 | PC(38:6) | −0.16 | 0.09 | 8.10E−02 | 5.46E−01 |
| Neg:699.6293@39.12 | | 0.05 | 0.14 | 7.01E−01 | 8.45E−01 |
| Neg:873.6871@35.86 | | 0.07 | 0.14 | 6.02E−01 | 8.38E−01 |
| Pos:812.6785@33.81 | SM(d18:2/24:0) | −0.01 | 0.09 | 8.91E−01 | 8.72E−01 |
| Neg:872.6961@35.25 | SM(d18:1/25:1)-2 | 0.00 | 0.13 | 9.77E−01 | 8.81E−01 |
| Pos:607.4579@17.14 | LPC(24:0) | 0.03 | 0.09 | 7.02E−01 | 8.45E−01 |
| Neg:846.6815@34.58 | SM(d18:1/23:0) | −0.02 | 0.08 | 8.30E−01 | 8.65E−01 |
| Neg:850.6670@35.84 | | −0.02 | 0.06 | 7.14E−01 | 8.46E−01 |
| Neg:837.5865@23.92 | PC(O-16:0/22:6) | 0.03 | 0.12 | 8.05E−01 | 8.61E−01 |

TABLE 6J-continued

| | | Disease behavior and location: conditional on each other Disease location | | | |
|---|---|---|---|---|---|
| Feature ID | Lipid ID | $log_2(FC)$ | SE | p-value | q-value |
| Pos:753.5316@19.29 | | −0.10 | 0.16 | 5.20E−01 | 8.37E−01 |
| Pos:753.5687@29.69 | PE(O-18:0/20:4) | 0.01 | 0.16 | 9.35E−01 | 8.74E−01 |
| Neg:710.6139@36.52 | Cer(d18:1/24:1) | 0.12 | 0.07 | 1.18E−01 | 6.14E−01 |
| Pos:892.6936@51.00 | | −0.04 | 0.12 | 7.25E−01 | 8.46E−01 |
| Neg:799.5353@19.15 | PC(14:0_20:4) | −0.09 | 0.17 | 6.03E−01 | 8.38E−01 |
| Pos:803.5477@18.76 | PC(18:2_20:5) | −0.23 | 0.18 | 1.87E−01 | 6.86E−01 |
| Pos:647.6132@36.64 | | 0.14 | 0.09 | 1.48E−01 | 6.45E−01 |
| Neg:845.6132@28.88 | PC(19:0_18:2) | 0.01 | 0.11 | 9.25E−01 | 8.73E−01 |
| Pos:633.6055@30.86 | SM(d17:1/24:1) | −0.02 | 0.13 | 8.99E−01 | 8.72E−01 |
| Pos:947.7953@51.13 | TG(18:1_18:2_22:5) | 0.03 | 0.19 | 8.86E−01 | 8.72E−01 |
| Pos:744.6146@26.54 | SM(d18:1/19:0) | −0.01 | 0.08 | 8.61E−01 | 8.68E−01 |
| Pos:537.5118@25.39 | | 0.04 | 0.09 | 6.33E−01 | 8.38E−01 |
| Pos:758.6315@28.51 | SM(d18:1/20:0) | −0.07 | 0.09 | 4.14E−01 | 8.16E−01 |
| Pos:730.5994@24.43 | SM(d36:1) | 0.04 | 0.07 | 5.84E−01 | 8.37E−01 |
| Pos:362.2902@11.83 | | 0.09 | 0.17 | 5.96E−01 | 8.38E−01 |
| Pos:559.5691@38.64 | | −0.14 | 0.16 | 3.87E−01 | 8.16E−01 |
| Neg:717.5297@26.55 | PE(16:0_18:1) | 0.06 | 0.18 | 7.43E−01 | 8.47E−01 |
| Neg:725.5345@25.50 | PE(O-16:0/20:4) | −0.04 | 0.16 | 8.30E−01 | 8.65E−01 |
| Neg:693.6257@36.52 | Cer(d18:1/24:1) | 0.13 | 0.09 | 1.36E−01 | 6.34E−01 |
| Pos:552.4389@14.25 | | 0.07 | 0.19 | 7.03E−01 | 8.45E−01 |
| Pos:725.5367@25.70 | PE(O-16:0/20:4) | −0.04 | 0.16 | 8.09E−01 | 8.62E−01 |
| Pos:717.5316@26.75 | | 0.06 | 0.18 | 7.40E−01 | 8.47E−01 |
| Neg:749.5352@24.71 | PE(O-16:0/22:6) | 0.00 | 0.14 | 9.73E−01 | 8.81E−01 |
| Neg:912.5647@22.69 | | 0.03 | 0.08 | 7.32E−01 | 8.47E−01 |
| Pos:728.5844@21.45 | SM(d18:2/18:0) | 0.03 | 0.08 | 6.72E−01 | 8.43E−01 |
| Neg:1152.7105@16.97 | | 0.04 | 0.08 | 6.45E−01 | 8.40E−01 |
| Pos:833.5946@25.01 | PC(18:1_22:5) | 0.10 | 0.20 | 6.23E−01 | 8.38E−01 |
| Pos:585.5850@38.89 | | −0.10 | 0.17 | 5.32E−01 | 8.37E−01 |
| Pos:949.8111@53.74 | TG(18:1_18:2_22:4) | 0.10 | 0.16 | 5.32E−01 | 8.37E−01 |
| Pos:468.3809@12.93 | VLCDCA 28:1(OH) | 0.03 | 0.16 | 8.41E−01 | 8.68E−01 |
| Neg:795.5534@25.83 | | −0.01 | 0.06 | 8.06E−01 | 8.61E−01 |
| Pos:482.3406@12.78 | | 0.00 | 0.06 | 9.67E−01 | 8.81E−01 |
| Neg:442.2743@13.07 | | −0.07 | 0.17 | 6.99E−01 | 8.45E−01 |
| Pos:507.3497@10.01 | | 0.00 | 0.09 | 9.69E−01 | 8.81E−01 |
| Pos:853.5630@19.62 | | −0.16 | 0.13 | 2.05E−01 | 7.06E−01 |
| Neg:670.6212@39.00 | | 0.01 | 0.19 | 9.78E−01 | 8.81E−01 |
| Pos:414.3497@20.82 | | 0.06 | 0.15 | 7.12E−01 | 8.46E−01 |
| Pos:368.3445@53.93 | CE(18:2) | −0.05 | 0.06 | 4.69E−01 | 8.26E−01 |
| Pos:629.6119@36.65 | | 0.10 | 0.09 | 2.59E−01 | 7.37E−01 |
| Neg:386.3151@11.79 | | −0.09 | 0.17 | 6.12E−01 | 8.38E−01 |
| Neg:456.2903@13.07 | | −0.04 | 0.15 | 7.74E−01 | 8.51E−01 |
| Pos:771.5425@19.10 | | 0.11 | 0.15 | 4.53E−01 | 8.26E−01 |
| Pos:942.6220@34.79 | | −0.03 | 0.10 | 7.33E−01 | 8.47E−01 |
| Pos:607.5886@30.05 | | −0.06 | 0.13 | 6.43E−01 | 8.40E−01 |
| Pos:777.5696@28.78 | PE(O-18:0/22:6) | −0.07 | 0.14 | 5.95E−01 | 8.38E−01 |
| Neg:360.2995@11.43 | | −0.07 | 0.18 | 6.93E−01 | 8.44E−01 |
| Neg:254.2259@11.45 | | 0.17 | 0.22 | 4.48E−01 | 8.26E−01 |
| Pos:282.2675@11.48 | | −0.04 | 0.14 | 7.71E−01 | 8.51E−01 |
| Pos:296.2815@12.27 | | −0.13 | 0.19 | 5.11E−01 | 8.37E−01 |
| Pos:534.4276@14.26 | | 0.01 | 0.18 | 9.58E−01 | 8.78E−01 |
| Neg:468.3817@12.87 | VLCDCA 28:1(OH) | −0.08 | 0.21 | 7.11E−01 | 8.46E−01 |
| Neg:823.5341@18.59 | | −0.05 | 0.16 | 7.61E−01 | 8.49E−01 |
| Pos:265.2768@11.82 | | 0.00 | 0.19 | 9.87E−01 | 8.83E−01 |
| Pos:401.3327@13.20 | | −0.02 | 0.09 | 8.07E−01 | 8.62E−01 |
| Neg:1560.1702@24.20 | | 0.01 | 0.09 | 9.21E−01 | 8.72E−01 |
| Pos:425.3507@9.33 | C18:1 carnitine | 0.02 | 0.13 | 9.07E−01 | 8.72E−01 |
| Neg:774.5880@21.27 | SM(d18:2/18:0) | 0.01 | 0.08 | 9.24E−01 | 8.73E−01 |
| Pos:495.3680@10.90 | | −0.05 | 0.09 | 5.78E−01 | 8.37E−01 |
| Pos:239.2616@11.48 | | −0.01 | 0.17 | 9.71E−01 | 8.81E−01 |
| Pos:635.6214@33.95 | Cer(d18:1/23:0) | −0.08 | 0.11 | 4.64E−01 | 8.26E−01 |
| Pos:564.5340@11.48 | | −0.07 | 0.22 | 7.44E−01 | 8.47E−01 |
| Pos:308.2823@12.00 | | 0.00 | 0.18 | 9.78E−01 | 8.81E−01 |
| Pos:401.3489@15.84 | | 0.04 | 0.07 | 6.11E−01 | 8.38E−01 |
| Neg:642.5898@36.90 | | −0.08 | 0.23 | 7.19E−01 | 8.46E−01 |
| Pos:336.2748@11.48 | | −0.04 | 0.15 | 8.06E−01 | 8.61E−01 |
| Pos:415.3510@13.21 | | 0.01 | 0.08 | 8.98E−01 | 8.72E−01 |
| Neg:416.2750@13.07 | | 0.00 | 0.17 | 9.82E−01 | 8.82E−01 |
| Pos:310.2988@13.17 | | −0.10 | 0.17 | 5.45E−01 | 8.37E−01 |
| Pos:308.2831@11.82 | | −0.04 | 0.17 | 7.96E−01 | 8.59E−01 |
| Pos:749.5364@24.89 | | −0.09 | 0.14 | 4.98E−01 | 8.33E−01 |
| Pos:267.2929@13.16 | | −0.09 | 0.17 | 6.02E−01 | 8.38E−01 |
| Pos:399.3348@8.85 | C16:0 carnitine | −0.03 | 0.10 | 7.98E−01 | 8.60E−01 |
| Pos:607.5179@28.48 | DG(16:0_18:2) | 0.24 | 0.16 | 1.35E−01 | 6.34E−01 |

Figure 6A:
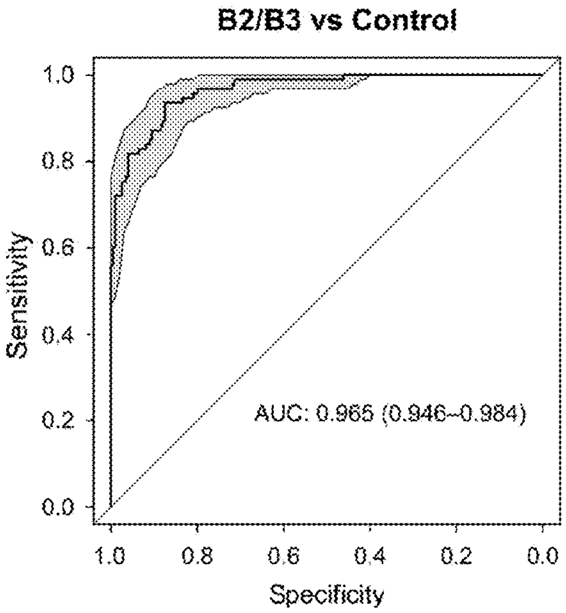
FIG. 6A and FIG. 6B are ROC curves that show the performance of the classification model to discriminate case vs control phenotypes. Performance was tested in the IBDGC-2 dataset consisting of all B2/B3 and control samples (FIG. 6A) or in the entire IBDGC-2 dataset (including all CD patients) (FIG. 6B). X- and y-axes show the specificity and sensitivity of the model, respectively. The 95% confidence interval is shown in grey and performances are expressed as AUC. Estimations of out-of-samples performance are reported in FIG. 8 and FIG. 9.
Figure 6B:
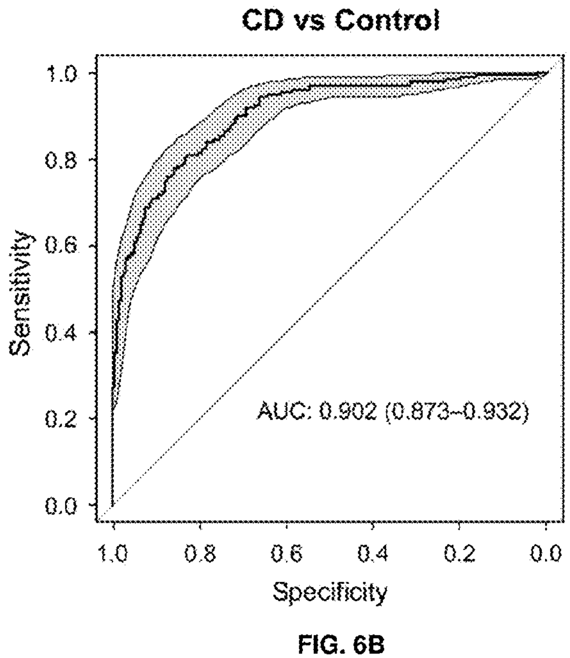
Figure 6C:
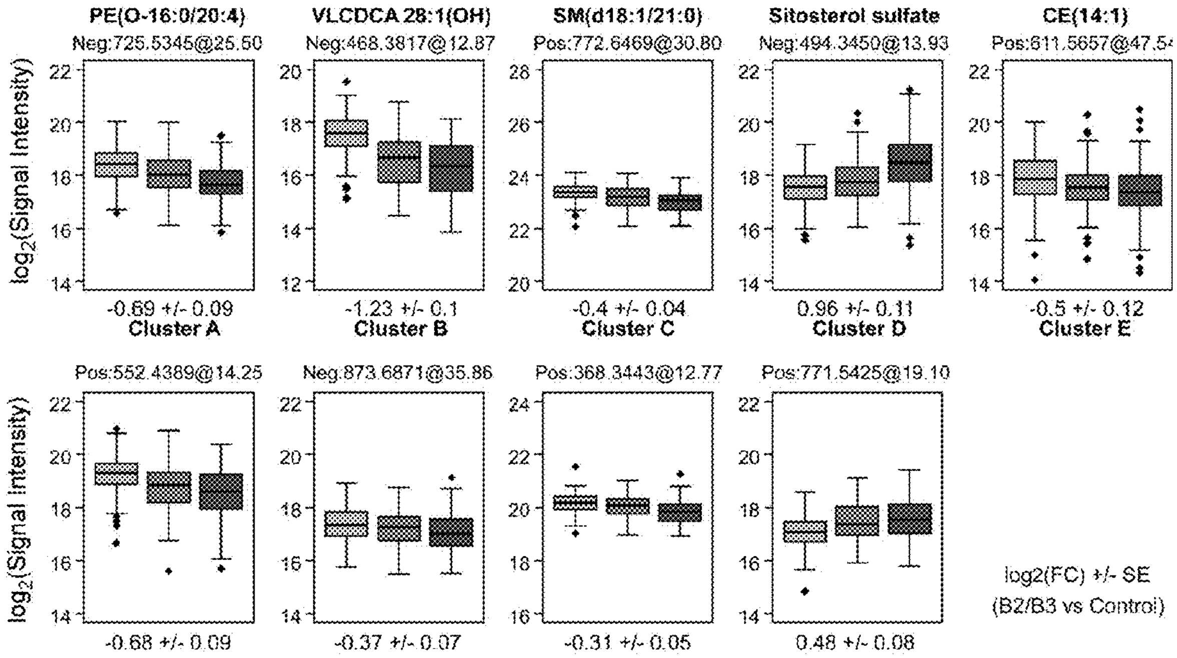
FIG. 6C shows boxplots representing MS signal intensity values ($log_2$) with quartiles for the nine classifiers, within control subjects (left box), B1 (center box) and B2/B3 patients (right box) in IBDGC-2.
Figure 7A:
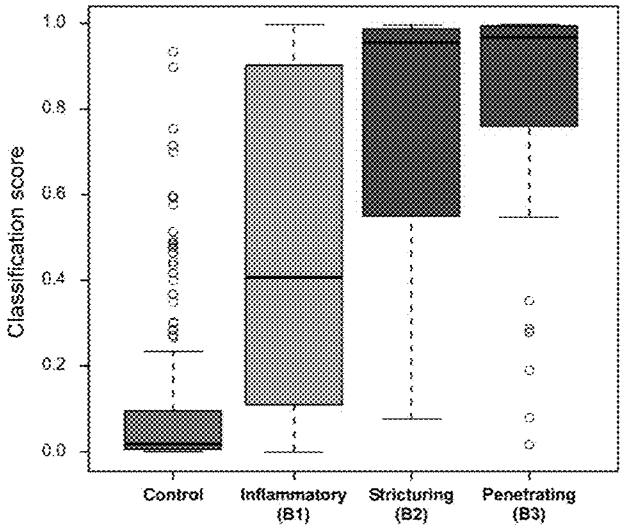
FIG. 7A and FIG. 7B are boxplots representing the distribution of score from the classification model (FIG. 6) for discriminating case vs control in the different subtypes of disease locations (FIG. 7A) and behaviors (FIG. 7B). Circles are outliers.
Figure 7B:
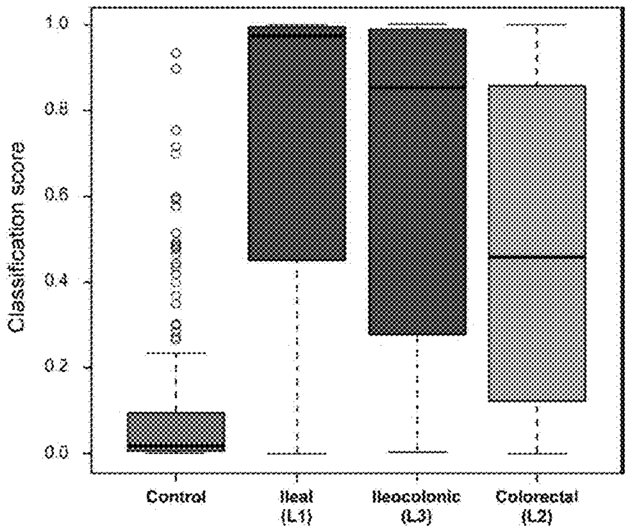

Example 5. Models Using Nine or Fewer Lipid Features are Strong Disease Classifiers Given the relatively strong effect sizes for many of the features, we decided to assess their ability in building a disease classifier. Specifically, we built a model using the B2/B3-associated features with p-value<0.05 and $|\log_2(FC)|>0.3$ obtained in IBDGC-2, trained and tested with all of the B2/B3 and control samples in the IBDGC-2 dataset. The purpose of this model was to use a minimal number of features while reaching maximal classification performance. The ROC curve for this model showed a very high performance with an AUC of 0.97 (FIG. 6A). Moreover, this model also performed very well (AUC of 0.90) when tested against the entire IBDGC-2 dataset that also included B1 (FIG. 6B). Discrimination from controls was however better for (i) ileal presentations (L1 and L3) than for colorectal-only (L2), and (ii) stricturing or penetrating (B2/B3) than for inflammatory (B1) (FIG. 7). It is important to note that, despite the large number of B2/B3-associated features (FIG. 2), the model was made from only nine lipid features (FIG. 6) that were representative of six different correlation clusters and 2 individual features of the lipid network (classifiers are shown in bold in FIG. 3), including the five annotated classifiers PE(O-16:0/20:4), VLCDCA) 28:1(OH), SM(d18:1/21:0), SitS and CE(14:1).

Figure 8A:
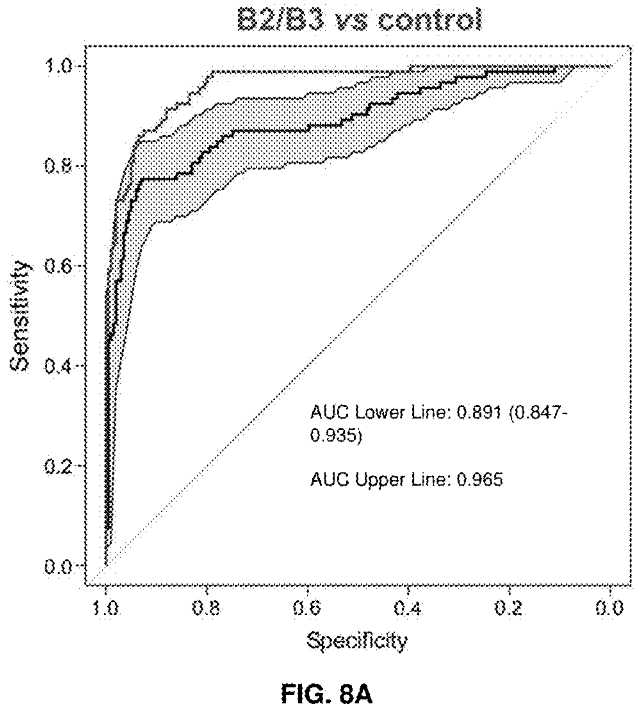
FIG. 8A and FIG. 8B are ROC curves that present the five-fold cross validation for the classification model built with 9 classifiers (FIG. 6), for discriminating B2/B3 CD vs control (FIG. 8A) or CD vs control (FIG. 8B), in IBDGC-2. X- and y-axes correspond to the specificity and sensitivity of the model, respectively. The panels show one representative iteration of the ROC curves (bold black line) resulting from the five-fold cross validation, with 95% CI (grey area) as an estimate of out-of-sample performance. The top line corresponds to the ROC curve when the model is built and tested using the same samples, namely all B2/B3 and controls (FIG. 8A) or all CD patients and controls (FIG. 8B). The classification performances are expressed as AUC. The resulting ΔAUC are of 0.085 (FIG. 8A) and 0.074 (FIG. 8B), implying low over-estimation of the classification performance due to over-fitting in our setting.
Figure 8B:
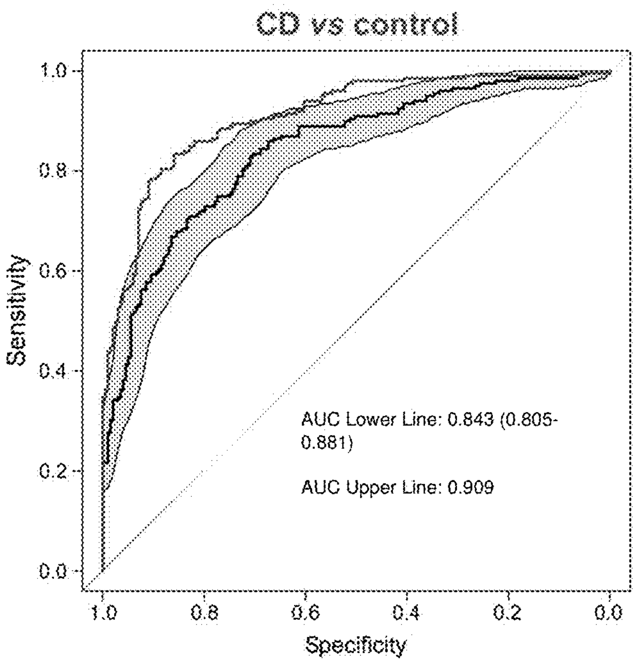
Figure 9B:
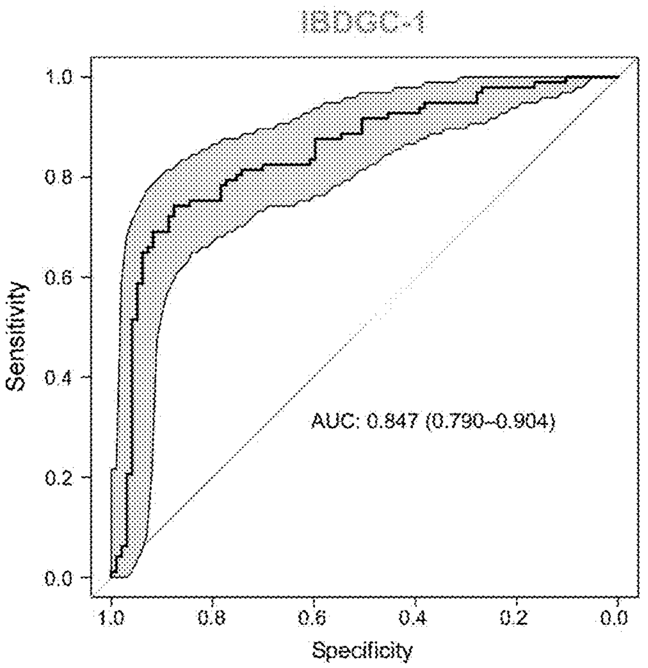

Since performance is always overestimated by using the same samples for training and validation, we addressed this by using two different approaches. We first performed cross-validations using distinct subparts of the IBDGC-2 dataset for training and validation. In doing so, the ROC curves yielded an average AUC>0.84, implying low over-estimation due to over-fitting in our setting (FIG. 8). To further test the robustness of this approach, we built an alternate model in IBDGC-2 using only a subset of the B2/B3-associated lipids with p-value<1E-4 and $|\log_2(FC)|>0.3$, that were also detected in IBDGC-1 (listed in Tables 4A and 4B). Built in this way, this alternate model shared four out of its five components with the primary model (Table 7), and it was possible to test it independently in IBDGC-1. This confirmed the very good classification performance of the model with an AUC of 0.85 even with this more restricted set of lipid features (FIG. 9B). Table 7 lists the five components of the alternate classification model. Feature and lipid IDs, association with B2/B3 vs control (p- and q-values) as well as effect size ($\log_2(FC)$) and standard error (SE) from IBDGC-2 are shown. This alternate version shares VLCDCA 28:1(OH), PE(O-16:0/20:4), SM(d18:1/21:0) and SitS with the classification model described in FIG. 6.

TABLE 7

| | | B2/B3 vs control | | | |
|---|---|---|---|---|---|
| Feature ID | Lipid ID | p-value | q-value | $\log_2$(FC) | SE |
| Neg:468.3817@12.87 | VLCDCA 28:1(OH) | 7.69E−27 | 4.50E−24 | −1.23 | 0.10 |
| Neg:725.5345@25.50 | PE(O-16:0/20:4) | 2.13E−13 | 1.30E−11 | −0.69 | 0.09 |
| Pos:772.6469@30.80 | SM(d18:1/21:0) | 5.12E−18 | 1.00E−15 | −0.40 | 0.04 |
| Neg:494.3450@13.93 | Sitosterol sulfate | 1.79E−17 | 2.60E−15 | 0.96 | 0.11 |
| Pos:921.7813@49.56 | TG(18:1 18:2 20:4) | 1.27E−08 | 2.30E−07 | 0.49 | 0.08 |

Example 6. A Study Identifies Circulating Lipids Modulated by Vedolizumab Treatment With the assumption that quantitative changes in serum lipids from patients with CD are at least in part a result of pathogenic mechanisms, the relationships between circulating lipids and response to therapy was examined. To do so, we analyzed an independent cohort of 92 IBD patients that were treated with Vedolizumab, with serum samples taken just prior to initiation of therapy (baseline) and at first assessment visit (week 14), using the same MS instrument than the IBDGC-1 samples. The demographic and clinical information for these subjects is presented in Table 8. Table 8 presents the demographic and clinical phenotypes of the IBD subjects retained into the final dataset. CD and UC were independently analyzed in the VEDO-CD and VEDO-UC subsets of the dataset, respectively.

TABLE 8

| | VEDO | | | |
|---|---|---|---|---|
| | CD | | UC | |
| | Total (n = 42) | Active (w0) (n = 32) | Total (n = 50) | Active (w0) (n = 43) |
| Age at recruitment | | | | |
| Median | 20 | 20 | 25 | 27 |
| Quartiles: Q1-Q3 | 16-26 | 15.5-25.3 | 22-39 | 20.5-40.5 |
| BMI | | | | |

TABLE 8-continued

| | VEDO | | | |
|---|---|---|---|---|
| | CD | | UC | |
| | Total (n = 42) | Active (w0) (n = 32) | Total (n = 50) | Active (w0) (n = 43) |
| Median | 24.8 | 24.8 | 24.2 | 24.3 |
| Quartiles: Q1-Q3 | 21.8-27.3 | 21.8-28.0 | 21.8-27.6 | 22.2-27.6 |
| Female gender [n (%)] | 20 (47.6) | 18 (56.3) | 21 (42) | 15 (34.9) |
| Montreal Classification | | | | |
| Disease behaviors (B) | | | | |
| Inflammatory (B1) [n (%)] | 17 (40.5) | 14 (43.7) | — | — |
| Stricturing (B2) [n (%)] | 7 (16.7) | 4 (12.5) | — | — |
| Penetrating (B3) [n (%)] | 14 (33.3) | 11 (34.4) | — | — |
| Missing [n (%)] | 4 (9.5) | 3 (9.4) | — | — |
| Disease locations (L) | | | — | — |
| Ileal (L1) [n (%)] | 4 (9.5) | 3 (9.4) | — | — |
| Colorectal (L2) [n (%)] | 7 (16.7) | 6 (18.8) | — | — |
| Ileocolonic (L3) [n (%)] | 25 (59.5) | 18 (56.2) | — | — |
| Missing [n (%)] | 6 (14.3) | 5 (15.6) | — | — |
| Disease extent (E) | | | | |
| E1 [n (%)] | — | — | 3 (6) | 2 (4.7) |
| E2 [n (%)] | — | — | 13 (26) | 13 (30.2) |
| E3 [n (%)] | — | — | 30 (60) | 24 (55.8) |
| Missing [n (%)] | — | — | 4 (8) | 4 (9.3) |
| Samples at weeks 0 and 14 | | 19 | | 24 |
| Response and/or remission | | | | |
| Yes | | 7 | | 13 |
| No | 12 | | | 11 |

Figure 10B:
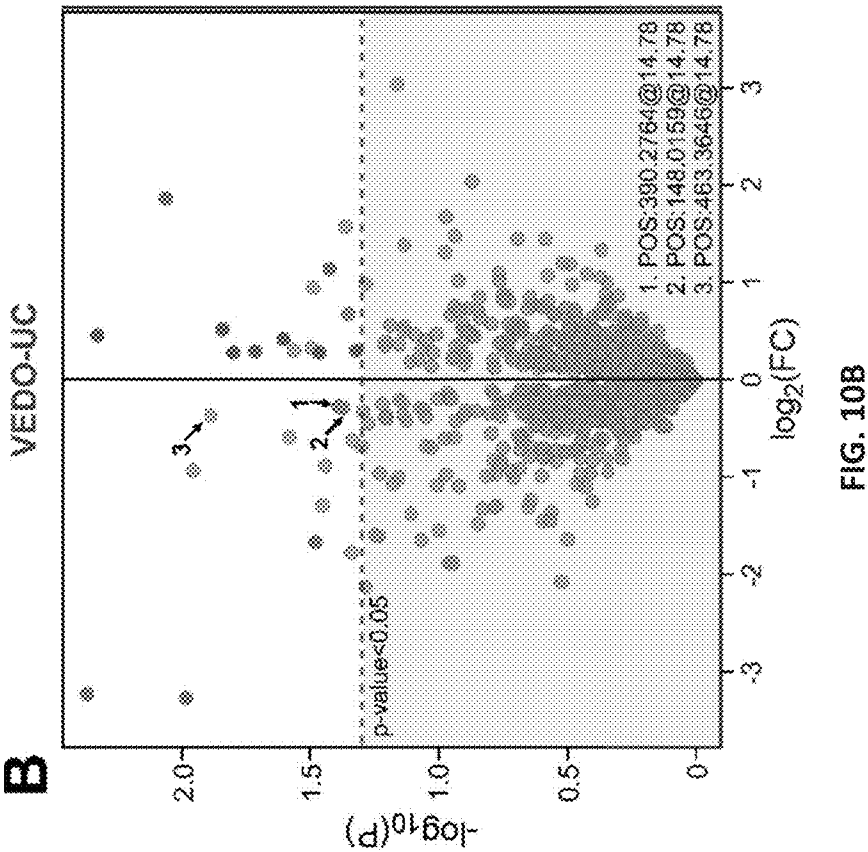
FIG. 10A and FIG. 10B are volcano plots showing all 1111 features detected in the serum samples of CD and UC patients from the VEDO-CD (FIG. 10A) and VEDO-UC (FIG. 10B) datasets. They illustrate the association between variation in lipid levels, occurring from baseline to week 14, with vedolizumab response status. X-axes show fold-change ($log_2$) of variation in MS signal intensity values for each feature for response vs non-response. Y-axes show association p-values ($-log_{10}$). Arrows point at three features with similar effects in CD and UC patients.
Figure 10A:
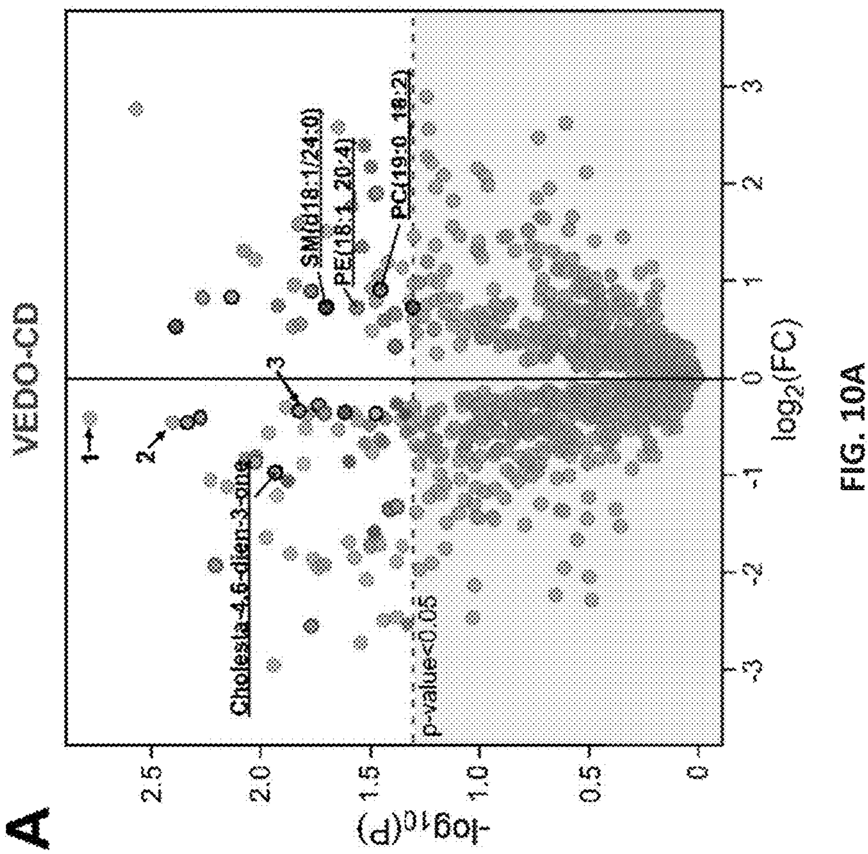

These MS data were processed as described above, with 1111 lipid features retained in the final dataset. Statistical analyses were focused on serum samples from CD (VEDO-CD subset) and UC patients (VEDO-UC subset) with active disease at baseline, for whom therapeutic response data at week 14 was available (i.e. clinical response and/or remission) and with serum samples collected at both timepoints (i.e. weeks 0 and 14). The results suggest that Vedolizumab treatment alters the level of circulating lipid features from baseline to week 14 in CD and UC patients. Specifically, 101 and 27 features had variation associated with Vedolizumab response vs non-response with p-value<0.05 in CD and UC (FIGS. 10A and 10B), respectively, of which 42 and 14 were annotated by MS/MS to 35 and 13 structurally unique lipid molecular species (Tables 9 and 10). Of note, only three features affected by therapy had similar effects in CD and UC patients.

Table 9 lists 101 lipid features with variation occurring from baseline to week 14 associated with Vedolizumab response status at p-value<0.05 in CD patients of the VEDO dataset (VEDO-CD). Feature and lipid IDs, association (p- and q-values) as well as effect size of change (log 2(FC)) and standard error (SE) are shown. Bold features have variation also associated with Vedolizumab response vs non-response in UC patients. Bold lipids were associated with B2/B3 vs control p-value<1E-4 and |log 2(FC)|>0.3 in IBDGC-2.

Table 10 lists 27 lipid features with changes (w0-w14) associated with Vedolizumab response vs non-response with p-value<0.05 in UC patients of the VEDO dataset (VEDO-UC). Feature and lipid IDs, association (p- and q-values) as well as effect size (log 2(FC)) and standard error (SE) are shown. Bold features have changes also associated with Vedolizumab response vs non-response in CD patients.

TABLE 9

| VEDO-CD | | | | | |
|---|---|---|---|---|---|
| | | Resp vs non-resp | | | |
| Feature ID | Lipid ID | $log_2$(FC) | SE | p-value | q-value |
| Pos: 390.2764@14.78 | | −0.42 | 0.11 | 1.66E−03 | 3.38E−01 |
| Pos: 941.8382@56.27 | | 2.77 | 0.78 | 2.68E−03 | 3.38E−01 |
| Pos: 148.0159@14.78 | | −0.46 | 0.14 | 3.94E−03 | 3.38E−01 |
| Pos: 770.6272@28.47 | SM(d18:2/21:0) | 0.53 | 0.16 | 4.08E−03 | 3.38E−01 |
| Pos: 436.4376@15.94 | | −0.46 | 0.14 | 4.60E−03 | 3.38E−01 |
| Pos: 489.3801@14.78 | | −0.41 | 0.13 | 5.30E−03 | 3.38E−01 |
| Pos: 807.5771@24.29 | PC(16:0_22:5) | 0.83 | 0.26 | 5.40E−03 | 3.38E−01 |
| Neg: 956.9768@27.73 | | −1.05 | 0.33 | 5.89E−03 | 3.38E−01 |
| Pos: 589.5780@41.39 | | −1.93 | 0.61 | 6.24E−03 | 3.38E−01 |
| Pos: 517.3156@8.00 | | −1.12 | 0.36 | 7.09E−03 | 3.38E−01 |
| Pos: 771.5760@25.74 | PC(17:0_18:2) | 0.83 | 0.27 | 7.40E−03 | 3.38E−01 |
| Pos: 1628.1322@24.27 | PC(16:0_18:2) | 1.31 | 0.44 | 8.40E−03 | 3.38E−01 |

TABLE 9-continued

| | | | | | |
|---|---|---|---|---|---|
| Pos: 569.3466@10.11 | LPC(22:5) | −0.83 | 0.28 | 8.55E−03 | 3.38E−01 |
| Pos: 806.5633@22.22 | | 1.22 | 0.41 | 9.44E−03 | 3.38E−01 |
| Pos: 649.6352@36.40 | Cer(d18:1/24:0) | −0.86 | 0.29 | 9.49E−03 | 3.38E−01 |
| Pos: 635.6194@35.19 | Cer(d18:1/23:0) | −0.82 | 0.28 | 9.53E−03 | 3.38E−01 |
| Pos: 591.3520@9.04 | | −1.64 | 0.57 | 1.06E−02 | 3.38E−01 |
| Pos: 477.3438@14.78 | | −0.56 | 0.20 | 1.09E−02 | 3.38E−01 |
| Pos: 1323.1806@65.36 | | −2.96 | 1.04 | 1.15E−02 | 3.38E−01 |
| Pos: 382.3224@19.12 | **Cholesta-4,6-dien-3-one** | −0.97 | 0.34 | 1.17E−02 | 3.38E−01 |
| Pos: 647.6195@33.38 | Cer(d18:1/24:1) | −1.21 | 0.43 | 1.19E−02 | 3.38E−01 |
| Pos: 791.5804@24.13 | PC(O-18:1/20:5) | 0.74 | 0.26 | 1.20E−02 | 3.38E−01 |
| Pos: 646.5645@64.81 | | −0.30 | 0.11 | 1.31E−02 | 3.38E−01 |
| Pos: 565.5413@25.44 | SM(d18:1/18:0) | −1.06 | 0.38 | 1.33E−02 | 3.38E−01 |
| Pos: 325.3699@9.03 | | −1.80 | 0.65 | 1.36E−02 | 3.38E−01 |
| Pos: 743.5447@22.42 | PC(15:0_18:2) | 0.53 | 0.19 | 1.41E−02 | 3.38E−01 |
| Pos: 1537.6033@24.27 | PC(16:0_18:2) | 0.95 | 0.35 | 1.43E−02 | 3.38E−01 |
| Pos: 807.5769@24.48 | PC(18:1_20:4) | 1.58 | 0.58 | 1.49E−02 | 3.38E−01 |
| Pos: 463.3646@14.78 | | −0.34 | 0.12 | 1.50E−02 | 3.38E−01 |
| Pos: 769.5597@23.08 | PC(17:1_18:2) | 0.55 | 0.20 | 1.51E−02 | 3.38E−01 |
| Pos: 621.6039@33.24 | Cer(d18:1/22:0) | −0.88 | 0.33 | 1.57E−02 | 3.38E−01 |
| Neg: 569.3673@11.51 | | −0.52 | 0.19 | 1.60E−02 | 3.38E−01 |
| Pos: 1272.9192@14.58 | | −0.38 | 0.14 | 1.64E−02 | 3.38E−01 |
| Pos: 601.5775@40.16 | | −2.55 | 0.96 | 1.70E−02 | 3.38E−01 |
| Pos: 743.5812@26.45 | PC(O-16:0/18:2) | 0.89 | 0.33 | 1.70E−02 | 3.38E−01 |
| Pos: 684.5542@18.59 | | −1.87 | 0.70 | 1.74E−02 | 3.38E−01 |
| Neg: 873.5678@27.39 | | −0.32 | 0.12 | 1.77E−02 | 3.38E−01 |
| Pos: 537.4657@29.83 | | −1.96 | 0.74 | 1.82E−02 | 3.38E−01 |
| Pos: 1271.1487@64.80 | | −0.28 | 0.11 | 1.84E−02 | 3.38E−01 |
| Pos: 519.4999@35.27 | | −1.92 | 0.74 | 1.93E−02 | 3.38E−01 |
| Pos: 547.5311@37.81 | | −1.92 | 0.74 | 1.95E−02 | 3.38E−01 |
| Pos: 430.1700@16.13 | | −0.36 | 0.14 | 1.95E−02 | 3.38E−01 |
| Pos: 814.6905@36.62 | **SM(d18:1/24:0)** | 0.73 | 0.28 | 1.99E−02 | 3.38E−01 |
| Pos: 947.7916@52.25 | | 1.51 | 0.58 | 2.00E−02 | 3.38E−01 |
| Pos: 367.4165@13.82 | | −0.53 | 0.21 | 2.25E−02 | 3.38E−01 |
| Pos: 875.7919@52.61 | | 2.58 | 1.02 | 2.25E−02 | 3.38E−01 |
| Neg: 776.6022@25.74 | SM(d18:1/18:0) | −0.36 | 0.14 | 2.42E−02 | 3.38E−01 |
| Pos: 631.6248@46.48 | | −1.69 | 0.68 | 2.51E−02 | 3.38E−01 |
| Pos: 263.2607@21.77 | SM(d18:1/16:0) | −0.86 | 0.35 | 2.53E−02 | 3.38E−01 |
| Pos: 917.7449@45.16 | TG(56:9) | 1.76 | 0.72 | 2.58E−02 | 3.38E−01 |
| Pos: 629.6093@42.78 | | −1.85 | 0.76 | 2.68E−02 | 3.38E−01 |
| Pos: 1096.8147@14.92 | | −0.37 | 0.15 | 2.68E−02 | 3.38E−01 |
| Pos: 765.5291@25.21 | **PE(18:1_20:4)** | 0.72 | 0.30 | 2.74E−02 | 3.38E−01 |
| Neg: 569.3674@11.32 | | −0.44 | 0.18 | 2.76E−02 | 3.38E−01 |
| Pos: 282.2550@9.66 | | −2.72 | 1.13 | 2.85E−02 | 3.38E−01 |
| Pos: 869.7460@49.57 | TG(52:5) | 1.35 | 0.56 | 2.89E−02 | 3.38E−01 |
| Pos: 893.7454@46.27 | TG(54:7) | 2.39 | 1.00 | 2.96E−02 | 3.38E−01 |
| Pos: 545.3476@9.91 | LPC(20:3) | −0.67 | 0.28 | 2.98E−02 | 3.38E−01 |
| Pos: 312.2655@9.95 | | −2.07 | 0.87 | 3.03E−02 | 3.38E−01 |
| Pos: 571.3624@10.65 | LPC(22:4) | −0.48 | 0.21 | 3.15E−02 | 3.38E−01 |
| Pos: 575.5622@40.09 | | −1.72 | 0.73 | 3.15E−02 | 3.38E−01 |
| Pos: 712.5849@21.83 | | −1.71 | 0.73 | 3.16E−02 | 3.38E−01 |
| Pos: 883.7605@51.43 | TG(53:5) | 2.17 | 0.92 | 3.18E−02 | 3.38E−01 |
| Neg: 410.2421@10.05 | | −1.74 | 0.74 | 3.18E−02 | 3.38E−01 |
| Pos: 733.5600@25.92 | PC(16:0_16:0) | 0.93 | 0.40 | 3.21E−02 | 3.38E−01 |
| Pos: 2388.6414@23.86 | | 0.48 | 0.21 | 3.22E−02 | 3.38E−01 |
| Pos: 467.2999@11.13 | | −0.77 | 0.33 | 3.22E−02 | 3.38E−01 |
| Pos: 770.6272@28.47 | | −1.58 | 0.68 | 3.28E−02 | 3.38E−01 |
| Pos: 890.7314@57.37 | | 1.89 | 0.81 | 3.28E−02 | 3.38E−01 |
| Pos: 603.5935@42.79 | | −1.63 | 0.70 | 3.33E−02 | 3.38E−01 |
| Pos: 799.6069@30.23 | **PC(19:0_18:2)** | 0.79 | 0.34 | 3.35E−02 | 3.38E−01 |
| Pos: 521.5880@23.30 | | −0.37 | 0.16 | 3.35E−02 | 3.38E−01 |
| Pos: 1003.8536@54.38 | | 1.90 | 0.82 | 3.37E−02 | 3.38E−01 |
| Pos: 1515.1224@24.27 | PC(16:0_18:2) | 1.05 | 0.45 | 3.45E−02 | 3.38E−01 |
| Pos: 627.5936@40.47 | | −1.72 | 0.74 | 3.48E−02 | 3.38E−01 |
| Pos: 547.3623@10.97 | LPC(20:2) | −0.63 | 0.27 | 3.48E−02 | 3.38E−01 |
| Pos: 797.5910@26.85 | PC(19:1_18:2) | 0.91 | 0.39 | 3.51E−02 | 3.38E−01 |
| Pos: 521.3480@10.44 | LPC(18:1) | −0.66 | 0.29 | 3.62E−02 | 3.38E−01 |
| Pos: 369.3594@11.45 | | −2.49 | 1.09 | 3.62E−02 | 3.38E−01 |
| Pos: 769.5966@26.99 | PC(O-18:1/18:2) | 0.59 | 0.26 | 3.65E−02 | 3.38E−01 |
| Neg: 509.3466@11.87 | LPC(17:1) | −0.42 | 0.18 | 3.70E−02 | 3.38E−01 |
| Pos: 925.8074@48.88 | | 1.19 | 0.53 | 3.78E−02 | 3.38E−01 |
| Pos: 617.6090@44.50 | | −1.35 | 0.60 | 3.86E−02 | 3.38E−01 |
| Pos: 3068.1849@24.27 | | 0.67 | 0.30 | 4.05E−02 | 3.38E−01 |
| Pos: 733.5610@26.42 | PC(16:0_16:0) | 0.32 | 0.15 | 4.10E−02 | 3.38E−01 |
| Pos: 2310.6278@24.27 | PC(16:0_18:2) | 0.65 | 0.29 | 4.11E−02 | 3.38E−01 |
| Pos: 341.3282@9.65 | | −2.46 | 1.11 | 4.15E−02 | 3.38E−01 |
| Pos: 491.4684@30.61 | | −1.89 | 0.85 | 4.16E−02 | 3.38E−01 |
| Neg: 688.5497@21.79 | SM(d18:1/16:0) | −0.27 | 0.12 | 4.16E−02 | 3.38E−01 |
| Pos: 593.5728@37.39 | | −1.32 | 0.60 | 4.17E−02 | 3.38E−01 |
| Pos: 895.7613@49.94 | | 2.81 | 1.28 | 4.26E−02 | 3.38E−01 |

TABLE 9-continued

| | | | | | |
|---|---|---|---|---|---|
| Neg: 569.3679@11.87 | | −0.43 | 0.20 | 4.36E−02 | 3.38E−01 |
| Pos: 843.7302@48.51 | | 1.13 | 0.52 | 4.43E−02 | 3.38E−01 |
| Pos: 545.5150@35.91 | | −1.73 | 0.80 | 4.45E−02 | 3.38E−01 |
| Neg: 750.5863@23.32 | SM(d18:0/16:0) | −0.38 | 0.17 | 4.56E−02 | 3.38E−01 |
| Pos: 800.5433@18.73 | | −0.31 | 0.15 | 4.59E−02 | 3.38E−01 |
| Neg: 567.3521@10.53 | LPC(18:1) | −0.56 | 0.26 | 4.61E−02 | 3.38E−01 |
| Pos: 877.8075@58.49 | TG(52:1) | −2.54 | 1.18 | 4.69E−02 | 3.38E−01 |
| Pos: 570.3750@8.23 | | 0.79 | 0.37 | 4.77E−02 | 3.38E−01 |
| Neg: 507.3307@10.53 | | −0.51 | 0.24 | 4.98E−02 | 3.38E−01 |
| Pos: 765.5649@23.61 | PC(O-16:0/20:5) | 0.72 | 0.34 | 4.98E−02 | 3.38E−01 |

IBDGC-2

| | B2/B3 vs control | | | |
|---|---|---|---|---|
| Feature ID | log2(FC) | SE | p-value | q-value |
| Pos: 390.2779@13.85 | 0.10 | 0.06 | 7.20E−02 | 4.83E−02 |
| Pos: 148.0164@13.85 | 0.12 | 0.05 | 2.29E−02 | 2.13E−02 |
| Pos: 770.6287@27.41 | −0.13 | 0.04 | 2.47E−03 | 4.39E−03 |
| Pos: 436.4381@15.00 | 0.16 | 0.07 | 2.41E−02 | 2.21E−02 |
| Pos: 489.3823@13.85 | 0.09 | 0.07 | 2.07E−01 | 1.02E−01 |
| Pos: 807.5781@23.21 | 0.14 | 0.06 | 2.83E−02 | 2.50E−02 |
| Pos: 589.5800@40.22 | −0.43 | 0.12 | 2.75E−04 | 9.95E−04 |
| Pos: 517.3171@7.44 | 0.00 | 0.08 | 9.62E−01 | 3.04E−01 |
| Pos: 771.5789@24.65 | −0.15 | 0.06 | 1.44E−02 | 1.53E−02 |
| Pos: 569.3486@9.41 | 0.12 | 0.08 | 1.13E−01 | 6.65E−02 |
| Pos: 806.5657@21.16 | −0.03 | 0.11 | 8.18E−01 | 2.71E−01 |
| Pos: 649.6383@35.36 | −0.16 | 0.06 | 1.07E−02 | 1.24E−02 |
| Pos: 635.6214@33.95 | −0.28 | 0.06 | 4.69E−06 | 3.95E−05 |
| Pos: 1323.1861@61.15 | −0.06 | 0.04 | 1.61E−01 | 8.56E−02 |
| Pos: 382.3253@18.09 | 1.09 | 0.13 | 6.87E−16 | 5.90E−14 |
| Pos: 647.6221@32.07 | −0.01 | 0.07 | 9.04E−01 | 2.90E−01 |
| Pos: 791.5838@23.05 | −0.17 | 0.10 | 7.36E−02 | 4.89E−02 |
| Pos: 646.5646@60.68 | 0.02 | 0.04 | 6.29E−01 | 2.24E−01 |
| Pos: 565.5440@24.17 | 0.06 | 0.07 | 3.37E−01 | 1.42E−01 |
| Pos: 325.3707@8.35 | −0.01 | 0.07 | 9.09E−01 | 2.91E−01 |
| Pos: 743.5474@21.38 | −0.04 | 0.06 | 4.38E−01 | 1.71E−01 |
| Pos: 1537.6065@23.21 | −0.01 | 0.09 | 9.00E−01 | 2.89E−01 |
| Pos: 463.3661@13.85 | 0.13 | 0.06 | 2.16E−02 | 2.04E−02 |
| Pos: 769.5626@22.02 | 0.00 | 0.05 | 9.91E−01 | 3.09E−01 |
| Pos: 621.6062@31.91 | −0.08 | 0.05 | 1.04E−01 | 6.24E−02 |
| Neg: 569.3690@10.65 | −0.07 | 0.05 | 1.54E−01 | 8.29E−02 |
| Pos: 601.5794@39.10 | −0.25 | 0.12 | 2.99E−02 | 2.58E−02 |
| Pos: 743.5841@25.36 | −0.22 | 0.06 | 5.79E−04 | 1.72E−03 |
| Neg: 873.5688@25.83 | 0.08 | 0.04 | 3.22E−02 | 2.73E−02 |
| Pos: 1271.1542@60.70 | −0.08 | 0.04 | 4.84E−02 | 3.67E−02 |
| Pos: 519.5020@34.02 | −0.06 | 0.12 | 6.22E−01 | 2.21E−01 |
| Pos: 547.5331@36.81 | 0.09 | 0.11 | 4.30E−01 | 1.69E−01 |
| Neg: 860.6963@35.57 | −0.39 | 0.06 | 4.07E−09 | 9.20E−08 |
| Pos: 367.4172@12.94 | 0.06 | 0.05 | 2.17E−01 | 1.05E−01 |
| Neg: 776.6038@24.23 | 0.10 | 0.04 | 2.42E−02 | 2.22E−02 |
| Pos: 631.6280@44.77 | −0.18 | 0.10 | 6.81E−02 | 4.65E−02 |
| Pos: 629.6121@41.48 | −0.01 | 0.12 | 9.34E−01 | 2.97E−01 |
| Neg: 765.5314@24.31 | 0.32 | 0.08 | 3.93E−05 | 2.30E−04 |
| Neg: 569.3690@10.65 | −0.07 | 0.05 | 1.54E−01 | 8.29E−02 |
| Pos: 869.7542@47.32 | 0.19 | 0.11 | 9.36E−02 | 5.80E−02 |
| Pos: 545.3481@9.23 | 0.07 | 0.06 | 2.18E−01 | 1.05E−01 |
| Pos: 571.3642@9.94 | 0.10 | 0.06 | 8.79E−02 | 5.53E−02 |
| Pos: 575.5644@39.04 | −0.17 | 0.11 | 1.33E−01 | 7.43E−02 |
| Pos: 712.5880@20.77 | 0.04 | 0.12 | 7.27E−01 | 2.48E−01 |
| Neg: 410.2441@9.25 | −0.03 | 0.12 | 7.72E−01 | 2.59E−01 |
| Pos: 467.3018@10.41 | 0.06 | 0.06 | 2.74E−01 | 1.24E−01 |
| Pos: 890.7359@53.45 | 0.27 | 0.10 | 8.86E−03 | 1.07E−02 |
| Pos: 603.5966@41.48 | −0.14 | 0.10 | 1.74E−01 | 9.03E−02 |
| Neg: 845.6132@28.88 | −0.34 | 0.06 | 6.87E−08 | 1.00E−06 |
| Pos: 521.5896@22.05 | 0.08 | 0.04 | 4.97E−02 | 3.74E−02 |
| Pos: 1515.1267@23.21 | −0.04 | 0.09 | 6.44E−01 | 2.27E−01 |
| Pos: 627.5962@39.39 | −0.08 | 0.12 | 4.89E−01 | 1.84E−01 |
| Pos: 547.3641@10.25 | −0.01 | 0.06 | 8.11E−01 | 2.70E−01 |
| Pos: 797.5941@25.76 | −0.02 | 0.05 | 6.96E−01 | 2.41E−01 |
| Pos: 521.3483@9.74 | 0.02 | 0.05 | 6.37E−01 | 2.25E−01 |
| Pos: 769.6001@25.90 | −0.08 | 0.06 | 1.91E−01 | 9.61E−02 |
| Neg: 509.3480@11.00 | −0.09 | 0.07 | 1.92E−01 | 9.61E−02 |
| Pos: 617.6122@43.01 | −0.30 | 0.10 | 4.34E−03 | 6.35E−03 |
| Pos: 733.5628@25.34 | 0.09 | 0.04 | 1.93E−02 | 1.89E−02 |
| Pos: 491.4696@29.29 | −0.30 | 0.13 | 2.16E−02 | 2.04E−02 |
| Neg: 688.5506@20.40 | 0.00 | 0.03 | 9.81E−01 | 3.08E−01 |
| Pos: 843.7357@46.42 | 0.19 | 0.12 | 9.88E−02 | 6.04E−02 |
| Pos: 545.5168@34.77 | 0.05 | 0.13 | 7.22E−01 | 2.47E−01 |

TABLE 9-continued

| | | | | |
|---|---|---|---|---|
| Neg: 750.5876@21.88 | −0.05 | 0.04 | 2.64E−01 | 1.20E−01 |
| Pos: 800.5461@17.57 | 0.01 | 0.03 | 8.45E−01 | 2.77E−01 |
| Neg: 567.3539@9.50 | 0.07 | 0.06 | 2.71E−01 | 1.23E−01 |
| Neg: 507.3322@9.49 | 0.05 | 0.06 | 3.93E−01 | 1.58E−01 |
| Pos: 765.5676@22.52 | −0.37 | 0.10 | 2.26E−04 | 9.07E−04 |

TABLE 10

| | Feature characteristics | | | resp vs non-resp | | | |
|---|---|---|---|---|---|---|---|
| Feature ID | m/z | RT | Lipid ID | $log_2$(FC) | SE | p-value | q-value |
| Pos: 847.7624@59.62 | 848.7702 | 59.62 | TG(50:2) | −3.23 | 1.01 | 4.31E−03 | 1.00 |
| Pos: 852.6873@33.99 | 853.6951 | 33.99 | SM(d18:1/24:1) | 0.45 | 0.14 | 4.71E−03 | 1.00 |
| Pos: 953.8392@53.87 | 954.847 | 53.87 | TG(58:5) | 1.86 | 0.64 | 8.66E−03 | 1.00 |
| Pos: 851.7918@58.04 | 852.7996 | 58.04 | TG(50:0) | −3.27 | 1.16 | 1.04E−02 | 1.00 |
| Pos: 576.5094@22.60 | 577.5172 | 22.6 | | −0.94 | 0.34 | 1.11E−02 | 1.00 |
| **Pos: 463.3646@14.78** | 464.3724 | 14.78 | | −0.37 | 0.14 | 1.30E−02 | 1.00 |
| Neg: 872.6952@35.56 | 871.6874 | 35.56 | SM(d19:1/24:1) | 0.51 | 0.19 | 1.46E−02 | 1.00 |
| Neg: 856.6648@31.03 | 855.657 | 31.03 | SM(d18:2/24:1) | 0.28 | 0.11 | 1.60E−02 | 1.00 |
| Neg: 858.6807@34.33 | 857.6729 | 34.33 | SM(d18:1/24:1) | 0.29 | 0.12 | 1.94E−02 | 1.00 |
| Pos: 828.7062@37.86 | 829.714 | 37.86 | SM(d19:1/24:0) | 0.42 | 0.17 | 2.50E−02 | 1.00 |
| Pos: 837.6230@30.60 | 838.6308 | 30.6 | | −0.59 | 0.25 | 2.64E−02 | 1.00 |
| Pos: 826.6878@35.78 | 827.6956 | 35.78 | | 0.30 | 0.13 | 2.74E−02 | 1.00 |
| Neg: 844.6641@32.27 | 843.6563 | 32.27 | | 0.32 | 0.14 | 3.22E−02 | 1.00 |
| Pos: 545.3310@8.59 | 546.3388 | 8.59 | | 0.95 | 0.41 | 3.25E−02 | 1.00 |
| Pos: 833.7451@55.85 | 834.7529 | 55.85 | TG(49:2) | −1.67 | 0.73 | 3.32E−02 | 1.00 |
| Pos: 828.7064@37.52 | 829.7142 | 37.52 | SM(d18:1/25:0) | 0.28 | 0.12 | 3.42E−02 | 1.00 |
| Pos: 867.7296@46.79 | 868.7374 | 46.79 | | −1.30 | 0.58 | 3.53E−02 | 1.00 |
| Pos: 493.3152@8.40 | 494.323 | 8.4 | | −0.89 | 0.40 | 3.61E−02 | 1.00 |
| Pos: 919.7611@49.60 | 920.7689 | 49.6 | TG(56:8) | 1.14 | 0.51 | 3.77E−02 | 1.00 |
| **Pos: 390.2764@14.78** | 391.2842 | 14.78 | | −0.27 | 0.13 | 4.09E−02 | 1.00 |
| Pos: 761.5914@30.44 | 762.5992 | 30.44 | PC(18:0_16:0) | −0.29 | 0.13 | 4.14E−02 | 1.00 |
| **Pos: 148.0159@14.78** | 149.0237 | 14.78 | | −0.29 | 0.13 | 4.25E−02 | 1.00 |
| Pos: 122.1093@56.99 | 123.1171 | 56.99 | | 1.57 | 0.73 | 4.34E−02 | 1.00 |
| Neg: 791.5442@27.92 | 790.5364 | 27.92 | PE(18:0_22:6) | 0.67 | 0.32 | 4.44E−02 | 1.00 |
| Pos: 414.3484@24.75 | 415.3562 | 24.75 | | −1.78 | 0.84 | 4.58E−02 | 1.00 |
| Pos: 368.3437@51.52 | 369.3515 | 51.52 | | −0.62 | 0.29 | 4.62E−02 | 1.00 |
| Neg: 830.6486@30.24 | 829.6408 | 30.24 | SM(d18:1/22:1) | 0.30 | 0.14 | 4.77E−02 | 1.00 |

Figure 10C:
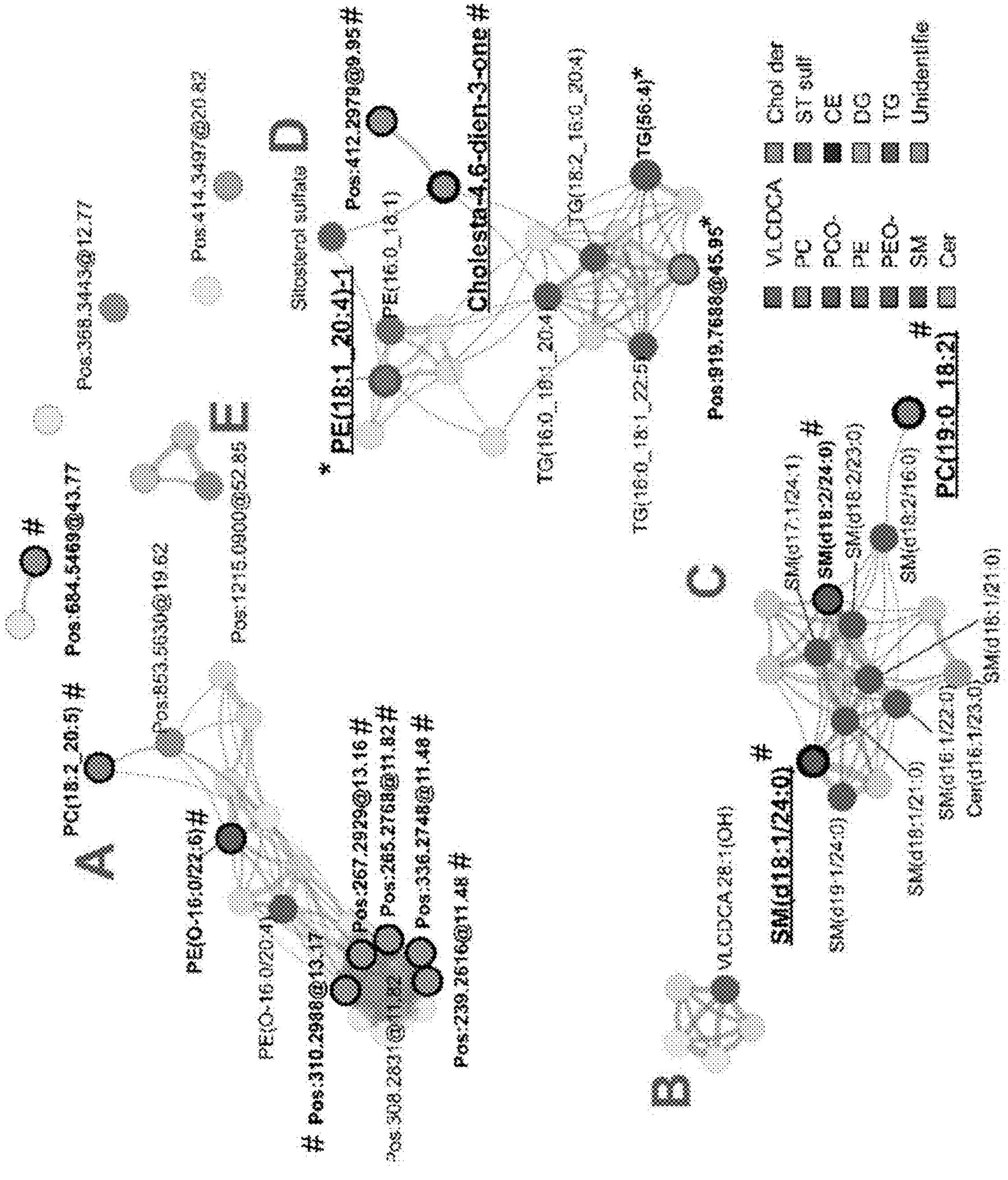
FIG. 10C shows CD-associated features reaching our thresholds in IBDGC-2 that were also detected in VEDO (Tables 11A-11D) and are represented on the correlation network (FIG. 3). Bolded and underlined IDs correspond to features associated with response to therapy at p-value<0.2 and p-value<0.05, respectively. Contrary to features marked with an asterisk, those marked with "#" tended to be normalized during response to therapy.

When comparing these 35 lipids associated with Vedolizumab response (p-value<0.05) in CD patients with the list of metabolites significantly associated (p-value<10E-4, FC>0.3) with B2/B3 in IBDGC-2, four were in common (FIG. 10C and Tables 11A-11 D). Tables 11A-11 D lists 35 lipid features detected in VEDO and associated with B2/B3 with p-value<1E-4 and |log 2(FC)|>0.3 in IBDGC-2. Feature and lipid IDs, association of variation with therapeutic response (i.e. responders vs non-responders (p- and q-values) or variation within responders or non-responders, as well as effect size (log 2(FC)) and standard error (SE) are shown. Results from IBDGC-2 have also been added for comparison

TABLE 11A

| Feature ID | | | IBDGC-2: B2/B3 vs control | | | | |
|---|---|---|---|---|---|---|---|
| IBDGC-2 | VEDO | Lipid ID | Cluster | $log_2$(FC) | SE | p-value | q-value |
| Neg: 468.3817@12.87 | Neg: 468.3817@13.89 | VLCDCA 28:1(OH) | B | −1.23 | 0.10 | 7.69E−27 | 4.53E−24 |
| Neg: 725.5345@25.50 | Neg: 725.5345@26.2 | PE(O-16:0/20:4) | A | −0.69 | 0.09 | 2.13E−13 | 1.26E−11 |
| Pos: 1215.0900@52.85 | Pos: 1215.0852@55.72 | | E | −0.57 | 0.09 | 1.32E−09 | 3.54E−08 |
| Pos: 265.2768@11.82 | Pos: 265.2763@12.63 | | A | −0.53 | 0.10 | 1.95E−07 | 2.65E−06 |
| Pos: 308.2831@11.82 | Pos: 308.2821@12.63 | | A | −0.46 | 0.09 | 2.40E−07 | 3.08E−06 |
| Pos: 700.5516@19.06 | Neg: 746.5548@18.88 | SM(d18:2/16:0) | C | −0.45 | 0.08 | 7.83E−09 | 1.49E−07 |
| Pos: 267.2929@13.16 | Pos: 267.2922@14.04 | | A | −0.45 | 0.09 | 3.44E−07 | 4.07E−06 |
| Pos: 310.2988@13.17 | Pos: 310.2978@14.04 | | A | −0.44 | 0.09 | 6.21E−07 | 6.90E−06 |
| Pos: 828.7092@36.62 | Pos: 828.7062@37.86 | SM(d19:1/24:0) | C | −0.41 | 0.07 | 2.43E−09 | 5.95E−08 |
| Neg: 749.5352@24.71 | Neg: 749.5352@24.71 | PE(O-16:0/22:6) | A | −0.41 | 0.07 | 4.60E−09 | 1.00E−07 |

TABLE 11A-continued

| Feature ID | | | IBDGC-2: B2/B3 vs control | | | | |
|---|---|---|---|---|---|---|---|
| IBDGC-2 | VEDO | Lipid ID | Cluster | $log_2$(FC) | SE | p-value | q-value |
| Pos: 772.6469@30.80 | Pos: 772.6438@31.89 | SM(d18:1/21:0) | C | −0.40 | 0.04 | 5.12E−18 | 1.01E−15 |
| Neg: 860.6963@35.57 | Pos: 814.6905@36.62 | **SM(d18:1/24:0)** | C | −0.39 | 0.06 | 4.07E−09 | 9.23E−08 |
| Pos: 798.6629@31.63 | Pos: 798.6596@32.74 | SM(d18:2/23:0) | C | −0.38 | 0.04 | 6.96E−16 | 5.85E−14 |
| Pos: 758.6315@28.70 | Pos: 758.6286@29.77 | SM(d16:1/22:0) | C | −0.38 | 0.05 | 6.83E−13 | 3.10E−11 |
| Neg: 818.6498@30.55 | Neg: 818.6487@32.19 | SM(d18:1/21:0) | C | −0.38 | 0.04 | 6.03E−17 | 7.10E−15 |
| Pos: 803.5477@18.76 | Pos: 803.5442@19.77 | PC(18:2_20:5) | A | −0.37 | 0.09 | 6.98E−05 | 3.67E−04 |
| Neg: 844.6655@31.39 | Neg: 844.6643@33.06 | SM(d17:1/24:1) | C | −0.36 | 0.05 | 2.86E−13 | 1.53E−11 |
| Neg: 845.6132@28.88 | Pos: 799.6069@30.23 | **PC(19:0_18:2)** | C | −0.34 | 0.06 | 6.87E−08 | 1.04E−06 |
| Pos: 239.2616@11.48 | Pos: 239.2610@12.27 | | A | −0.33 | 0.08 | 6.37E−05 | 3.47E−04 |
| Pos: 853.5630@19.62 | Pos: 853.5599@20.66 | | A | −0.32 | 0.07 | 2.38E−06 | 2.34E−05 |
| Pos: 336.2748@11.48 | Pos: 336.2732@12.27 | | A | −0.32 | 0.07 | 2.33E−05 | 1.48E−04 |
| Pos: 812.6785@33.81 | Pos: 812.6758@34.89 | SM(d18:2/24:0) | C | −0.31 | 0.05 | 1.75E−09 | 4.49E−08 |
| Pos: 368.3443@12.77 | Pos: 368.3432@13.51 | | | −0.31 | 0.05 | 6.23E−10 | 1.93E−08 |
| Neg: 765.5314@24.31 | Pos: 765.5291@25.21 | **PE(18:1_20:4)-1** | D | 0.32 | 0.08 | 3.93E−05 | 2.29E−04 |
| Pos: 927.8238@51.00 | Pos: 927.8237@53.87 | TG(56:4) | D | 0.35 | 0.08 | 6.40E−06 | 4.96E−05 |
| Pos: 897.7805@53.99 | Pos: 897.7775@57.31 | TG(16:0_18:1_20:4) | D | 0.37 | 0.09 | 6.75E−05 | 3.63E−04 |
| Pos: 684.5469@43.77 | Pos: 684.5437@45.31 | | | 0.38 | 0.09 | 2.84E−05 | 1.75E−04 |
| Neg: 717.5297@26.55 | Pos: 717.5285@27.85 | PE(16:0_18:1) | D | 0.38 | 0.09 | 7.06E−05 | 3.68E−04 |
| Pos: 919.7688@45.95 | Pos: 919.7609@48.46 | | D | 0.38 | 0.09 | 1.81E−05 | 1.17E−04 |
| Pos: 414.3497@20.82 | Pos: 414.3482@21.92 | | | 0.39 | 0.09 | 7.80E−06 | 5.89E−05 |
| Pos: 928.7515@54.39 | Pos: 928.7474@57.90 | TG(16:0_18:1_22:5) | D | 0.41 | 0.08 | 6.52E−07 | 7.11E−06 |
| Pos: 895.7651@49.23 | Pos: 895.7609@52.46 | TG(18:2_16:0_20:4) | D | 0.42 | 0.10 | 2.53E−05 | 1.58E−04 |
| Pos: 412.2979@9.95 | Pos: 412.2975@10.73 | | D | 0.57 | 0.08 | 2.95E−11 | 1.09E−09 |
| Neg: 494.3450@13.93 | Neg: 494.3417@14.83 | Sitosterol sulfate | D | 0.96 | 0.11 | 1.79E−17 | 2.63E−15 |
| Pos: 382.3253@18.09 | Pos: 382.3224@19.12 | **Cholesta-4,6-dien-3-one** | D | 1.09 | 0.13 | 6.87E−16 | 5.85E−14 |

TABLE 11B

| Feature ID | | | VEDO CD: Therapeutic Response | | | |
|---|---|---|---|---|---|---|
| IBDGC-2 | VEDO | Lipid ID | $log_2$(FC) | SE | p-value | q-value |
| Neg: 468.3817@12.87 | Neg: 468.3817@13.89 | VLCDCA 28:1(OH) | 0.32 | 0.53 | 0.556 | 0.326 |
| Neg: 725.5345@25.50 | Neg: 725.5345@26.2 | PE(O-16:0/20:4) | 0.22 | 0.38 | 0.569 | 0.326 |
| Pos: 1215.0900@52.85 | Pos: 1215.0852@55.72 | | 0.70 | 0.59 | 0.251 | 0.212 |
| Pos: 265.2768@11.82 | Pos: 265.2763@12.63 | | 0.63 | 0.39 | 0.124 | 0.133 |
| Pos: 308.2831@11.82 | Pos: 308.2821@12.63 | | 0.30 | 0.39 | 0.457 | 0.294 |
| Pos: 700.5516@19.06 | Neg: 746.5548@18.88 | SM(d18:2/16:0) | −0.04 | 0.18 | 0.819 | 0.397 |
| Pos: 267.2929@13.16 | Pos: 267.2922@14.04 | | 0.54 | 0.29 | 0.076 | 0.119 |
| Pos: 310.2988@13.17 | Pos: 310.2978@14.04 | | 0.55 | 0.30 | 0.088 | 0.119 |
| Pos: 828.7092@36.62 | Pos: 828.7062@37.86 | SM(d19:1/24:0) | −0.10 | 0.29 | 0.733 | 0.379 |
| Neg: 749.5352@24.71 | Neg: 749.5352@24.71 | PE(O-16:0/22:6) | 0.41 | 0.24 | 0.103 | 0.119 |
| Pos: 772.6469@30.80 | Pos: 772.6438@31.89 | SM(d18:1/21:0) | 0.21 | 0.18 | 0.263 | 0.212 |
| Neg: 860.6963@35.57 | Pos: 814.6905@36.62 | **SM(d18:1/24:0)** | 0.73 | 0.28 | 0.020 | 0.117 |
| Pos: 798.6629@31.63 | Pos: 798.6596@32.74 | SM(d18:2/23:0) | 0.11 | 0.22 | 0.627 | 0.346 |
| Pos: 758.6315@28.70 | Pos: 758.6286@29.77 | SM(d16:1/22:0) | −0.48 | 0.63 | 0.465 | 0.294 |
| Neg: 818.6498@30.55 | Neg: 818.6487@32.19 | SM(d18:1/21:0) | 0.00 | 0.15 | 0.975 | 0.446 |
| Pos: 803.5477@18.76 | Pos: 803.5442@19.77 | PC(18:2_20:5) | 0.98 | 0.50 | 0.065 | 0.117 |
| Neg: 844.6655@31.39 | Neg: 844.6643@33.06 | SM(d17:1/24:1) | 0.22 | 0.16 | 0.201 | 0.189 |
| Neg: 845.6132@28.88 | Pos: 799.6069@30.23 | **PC(19:0_18:2)** | 0.79 | 0.34 | 0.033 | 0.117 |
| Pos: 239.2616@11.48 | Pos: 239.2610@12.27 | | 0.47 | 0.32 | 0.164 | 0.164 |
| Pos: 853.5630@19.62 | Pos: 853.5599@20.66 | | −0.08 | 0.32 | 0.794 | 0.397 |
| Pos: 336.2748@11.48 | Pos: 336.2732@12.27 | | 0.61 | 0.35 | 0.104 | 0.119 |
| Pos: 812.6785@33.81 | Pos: 812.6758@34.89 | SM(d18:2/24:0) | 0.49 | 0.25 | 0.062 | 0.117 |
| Pos: 368.3443@12.77 | Pos: 368.3432@13.51 | | 0.24 | 0.21 | 0.265 | 0.212 |
| Neg: 765.5314@24.31 | Pos: 765.5291@25.21 | **PE(18:1_20:4)-1** | 0.72 | 0.30 | 0.027 | 0.117 |
| Pos: 927.8238@51.00 | Pos: 927.8237@53.87 | TG(56:4) | 2.89 | 1.41 | 0.058 | 0.117 |
| Pos: 897.7805@53.99 | Pos: 897.7775@57.31 | TG(16:0_18:1_20:4) | 1.45 | 1.89 | 0.454 | 0.294 |
| Pos: 684.5469@43.77 | Pos: 684.5437@45.31 | | −0.41 | 0.24 | 0.104 | 0.119 |
| Neg: 717.5297@26.55 | Pos: 717.5285@27.85 | PE(16:0_18:1) | 0.26 | 0.36 | 0.478 | 0.294 |
| Pos: 919.7688@45.95 | Pos: 919.7609@48.46 | | 1.37 | 0.68 | 0.063 | 0.117 |
| Pos: 414.3497@20.82 | Pos: 414.3482@21.92 | | −0.41 | 0.42 | 0.346 | 0.264 |
| Pos: 928.7515@54.39 | Pos: 928.7474@57.90 | TG(16:0_18:1_22:5) | 0.53 | 0.68 | 0.447 | 0.294 |
| Pos: 895.7651@49.23 | Pos: 895.7609@52.46 | TG(18:2_16:0_20:4) | −0.38 | 0.92 | 0.681 | 0.363 |
| Pos: 412.2979@9.95 | Pos: 412.2975@10.73 | | −1.00 | 0.50 | 0.066 | 0.117 |
| Neg: 494.3450@13.93 | Neg: 494.3417@14.83 | Sitosterol sulfate | −0.02 | 0.18 | 0.903 | 0.425 |
| Pos: 382.3253@18.09 | Pos: 382.3224@19.12 | **Cholesta-4,6-dien-3-one** | −0.97 | 0.34 | 0.012 | 0.117 |

TABLE 11C

| Feature ID | | VEDO CD: Responders | | | |
|---|---|---|---|---|---|
| IBDGC-2 | VEDO | $log_2$(FC) | SE | p-value | q-value |
| Neg:468.3817@12.87 | Neg:468.3817@13.89 | 0.14 | 0.36 | 0.712 | 0.543 |
| Neg:725.5345@25.50 | Neg:725.5345@26.2 | 0.25 | 0.26 | 0.345 | 0.490 |
| Pos:1215.0900@52.85 | Pos:1215.0852@55.72 | 0.68 | 0.42 | 0.121 | 0.428 |
| Pos:265.2768@11.82 | Pos:265.2763@12.63 | 0.12 | 0.29 | 0.673 | 0.543 |
| Pos:308.2831@11.82 | Pos:308.2821@12.63 | −0.04 | 0.29 | 0.894 | 0.621 |
| Pos:700.5516@19.06 | Neg:746.5548@18.88 | 0.05 | 0.13 | 0.731 | 0.543 |
| Pos:267.2929@13.16 | Pos:267.2922@14.04 | 0.11 | 0.21 | 0.605 | 0.543 |
| Pos:310.2988@13.17 | Pos:310.2978@14.04 | 0.11 | 0.22 | 0.644 | 0.543 |
| Pos:828.7092@36.62 | Pos:828.7062@37.86 | 0.11 | 0.20 | 0.593 | 0.543 |
| Neg:749.5352@24.71 | Neg:749.5352@24.71 | 0.32 | 0.17 | 0.080 | 0.428 |
| Pos:772.6469@30.80 | Pos:772.6438@31.89 | 0.33 | 0.13 | 0.022 | 0.309 |
| Neg:860.6963@35.57 | Pos:814.6905@36.62 | 0.37 | 0.23 | 0.130 | 0.428 |
| Pos:798.6629@31.63 | Pos:798.6596@32.74 | 0.15 | 0.16 | 0.357 | 0.490 |
| Pos:758.6315@28.70 | Pos:758.6286@29.77 | 0.06 | 0.45 | 0.892 | 0.621 |
| Neg:818.6498@30.55 | Neg:818.6487@32.19 | 0.11 | 0.10 | 0.310 | 0.490 |
| Pos:803.5477@18.76 | Pos:803.5442@19.77 | 0.24 | 0.36 | 0.516 | 0.543 |
| Neg:844.6655@31.39 | Neg:844.6643@33.06 | 0.27 | 0.11 | 0.027 | 0.309 |
| Neg:845.6132@28.88 | Pos:799.6069@30.23 | 0.50 | 0.25 | 0.065 | 0.428 |
| Pos:239.2616@11.48 | Pos:239.2610@12.27 | 0.11 | 0.24 | 0.650 | 0.543 |
| Pos:853.5630@19.62 | Pos:853.5599@20.66 | −0.12 | 0.22 | 0.593 | 0.543 |
| Pos:336.2748@11.48 | Pos:336.2732@12.27 | 0.25 | 0.28 | 0.392 | 0.495 |
| Pos:812.6785@33.81 | Pos:812.6758@34.89 | 0.15 | 0.18 | 0.408 | 0.495 |
| Pos:368.3443@12.77 | Pos:368.3432@13.51 | 0.20 | 0.15 | 0.191 | 0.490 |
| Neg:765.5314@24.31 | Pos:765.5291@25.21 | 0.23 | 0.22 | 0.318 | 0.490 |
| Pos:927.8238@51.00 | Pos:927.8237@53.87 | 1.33 | 0.99 | 0.194 | 0.490 |
| Pos:897.7805@53.99 | Pos:897.7775@57.31 | 1.23 | 1.31 | 0.362 | 0.490 |
| Pos:684.5469@43.77 | Pos:684.5437@45.31 | −0.19 | 0.17 | 0.286 | 0.490 |
| Neg:717.5297@26.55 | Pos:717.5285@27.85 | −0.12 | 0.26 | 0.658 | 0.543 |
| Pos:919.7688@45.95 | Pos:919.7609@48.46 | 0.37 | 0.50 | 0.461 | 0.530 |
| Pos:414.3497@20.82 | Pos:414.3482@21.92 | −0.28 | 0.30 | 0.362 | 0.490 |
| Pos:928.7515@54.39 | Pos:928.7474@57.90 | 0.04 | 0.47 | 0.938 | 0.621 |
| Pos:895.7651@49.23 | Pos:895.7609@52.46 | 0.23 | 0.65 | 0.723 | 0.543 |
| Pos:412.2979@9.95 | Pos:412.2975@10.73 | −0.57 | 0.35 | 0.127 | 0.428 |
| Neg:494.3450@13.93 | Neg:494.3417@14.83 | 0.01 | 0.13 | 0.944 | 0.621 |
| Pos:382.3253@18.09 | Pos:382.3224@19.12 | −0.33 | 0.26 | 0.233 | 0.490 |

TABLE 11D

| Feature ID | | VEDO CD: Non-Responders | | | |
|---|---|---|---|---|---|
| IBDGC-2 | VEDO | $log_2$(FC) | SE | p-value | q-value |
| Neg:468.3817@12.87 | Neg:468.3817@13.89 | −0.25 | 0.28 | 0.382 | 0.588 |
| Neg:725.5345@25.50 | Neg:725.5345@26.2 | −0.02 | 0.20 | 0.934 | 0.758 |
| Pos:1215.0900@52.85 | Pos:1215.0852@55.72 | 0.27 | 0.32 | 0.405 | 0.589 |
| Pos:265.2768@11.82 | Pos:265.2763@12.63 | −0.20 | 0.22 | 0.383 | 0.588 |
| Pos:308.2831@11.82 | Pos:308.2821@12.63 | −0.07 | 0.22 | 0.761 | 0.758 |
| Pos:700.5516@19.06 | Neg:746.5548@18.88 | −0.07 | 0.10 | 0.528 | 0.659 |
| Pos:267.2929@13.16 | Pos:267.2922@14.04 | −0.22 | 0.16 | 0.196 | 0.493 |
| Pos:310.2988@13.17 | Pos:310.2978@14.04 | −0.23 | 0.17 | 0.190 | 0.493 |
| Pos:828.7092@36.62 | Pos:828.7062@37.86 | 0.12 | 0.16 | 0.470 | 0.618 |
| Neg:749.5352@24.71 | Neg:749.5352@24.71 | 0.03 | 0.13 | 0.804 | 0.758 |
| Pos:772.6469@30.80 | Pos:772.6438@31.89 | 0.20 | 0.10 | 0.063 | 0.493 |
| Neg:860.6963@35.57 | Pos:814.6905@36.62 | −0.03 | 0.18 | 0.880 | 0.758 |
| Pos:798.6629@31.63 | Pos:798.6596@32.74 | 0.14 | 0.12 | 0.255 | 0.541 |
| Pos:758.6315@28.70 | Pos:758.6286@29.77 | 0.20 | 0.35 | 0.564 | 0.659 |
| Neg:818.6498@30.55 | Neg:818.6487@32.19 | 0.14 | 0.08 | 0.082 | 0.493 |
| Pos:803.5477@18.76 | Pos:803.5442@19.77 | −0.45 | 0.27 | 0.119 | 0.493 |
| Neg:844.6655@31.39 | Neg:844.6643@33.06 | 0.10 | 0.09 | 0.277 | 0.546 |
| Neg:845.6132@28.88 | Pos:799.6069@30.23 | −0.04 | 0.19 | 0.848 | 0.758 |
| Pos:239.2616@11.48 | Pos:239.2610@12.27 | −0.10 | 0.18 | 0.606 | 0.659 |
| Pos:853.5630@19.62 | Pos:853.5599@20.66 | 0.01 | 0.17 | 0.953 | 0.758 |
| Pos:336.2748@11.48 | Pos:336.2732@12.27 | 0.01 | 0.21 | 0.961 | 0.758 |
| Pos:812.6785@33.81 | Pos:812.6758@34.89 | −0.17 | 0.14 | 0.229 | 0.527 |
| Pos:368.3443@12.77 | Pos:368.3432@13.51 | 0.06 | 0.11 | 0.620 | 0.659 |
| Neg:765.5314@24.31 | Pos:765.5291@25.21 | −0.28 | 0.17 | 0.118 | 0.493 |
| Pos:927.8238@51.00 | Pos:927.8237@53.87 | −1.09 | 0.75 | 0.167 | 0.493 |
| Pos:897.7805@53.99 | Pos:897.7775@57.31 | 0.24 | 1.00 | 0.809 | 0.758 |
| Pos:684.5469@43.77 | Pos:684.5437@45.31 | 0.12 | 0.13 | 0.367 | 0.588 |
| Neg:717.5297@26.55 | Pos:717.5285@27.85 | −0.16 | 0.20 | 0.441 | 0.609 |

TABLE 11D-continued

| Feature ID | | VEDO CD: Non-Responders | | | |
|---|---|---|---|---|---|
| IBDGC-2 | VEDO | $log_2$(FC) | SE | p-value | q-value |
| Pos:919.7688@45.95 | Pos:919.7609@48.46 | −0.57 | 0.38 | 0.153 | 0.493 |
| Pos:414.3497@20.82 | Pos:414.3482@21.92 | −0.04 | 0.23 | 0.857 | 0.758 |
| Pos:928.7515@54.39 | Pos:928.7474@57.90 | −0.54 | 0.36 | 0.149 | 0.493 |
| Pos:895.7651@49.23 | Pos:895.7609@52.46 | 0.25 | 0.49 | 0.615 | 0.659 |
| Pos:412.2979@9.95 | Pos:412.2975@10.73 | 0.26 | 0.27 | 0.345 | 0.588 |
| Neg:494.3450@13.93 | Neg:494.3417@14.83 | 0.16 | 0.10 | 0.138 | 0.493 |
| Pos:382.3253@18.09 | Pos:382.3224@19.12 | 0.33 | 0.20 | 0.121 | 0.493 |

Figure 10D:
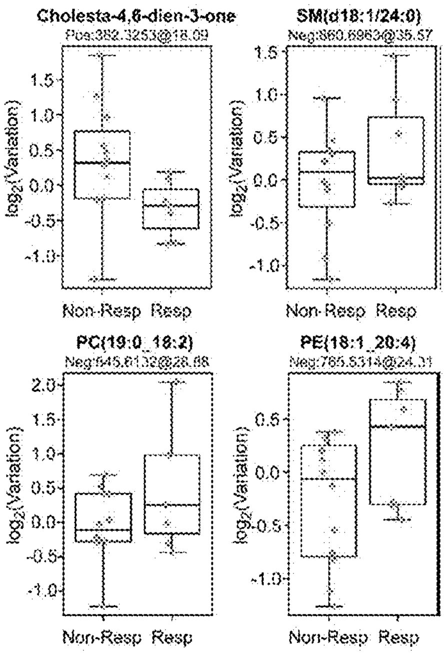
FIG. 10D shows boxplots representing the variation (intensity ratio) occurring from baseline to week 14 ($log_2$) in Vedolizumab responders (Resp) and non-responders (Non-Resp), for the four 62/63-associated lipids from IBDGC-2 that were also associated with response to therapy at p-value<0.05 (underlined IDs in FIG. 10A and FIG. 10C).

Specifically, $C_{4,6}D_3O$ (Cluster D), which had a greater than two-fold higher concentration in patients with CD than in controls, decreased significantly between weeks 0 and 14 in patients who responded to treatment and increased slightly in non-responders (FIG. 10D). Conversely, SM(d18:1/24:0) and PC(19:0_18:2) (Cluster C) were lower in patients with CD vs controls, increased significantly in responders and decreased slightly in non-responders (FIG. 10D). PE(18:1_20:4), however, which was more modestly elevated in CD patients than controls in IBDGC-2 tended to increase in the serum of responders (FIG. 10D). When relaxing the threshold in the IBDGC-2 cohort to p-value<0.05 (no FC threshold), we found an additional 16 lipid features in common (FIG. 10A: features circled in bold black or red), corresponding to 9 unique lipids, many of which showed a trend consistent with normalization (FIG. 10; features circled in black). It is important to note that the changes in lipid levels that were associated with response to treatment with vedolizumab were found to be independent of changes in the levels of the inflammatory markers C-reactive protein (CRP) and erythrocyte sedimentation rate (ESR) (p-value>0.05), which were not associated to vedolizumab response in either CD or UC patients in this study (p-value>0.2).

In summary, serum samples taken just before initiation of treatment with vedolizumab as well as samples taken at first assessment visit ~16 weeks later were analyzed. Given vedolizumab selectively inhibits leukocyte extravasation into the gut, it is expected to induce mucosal healing while intestinal tissue injury occurs in areas where activated lymphocytes produce inflammatory mediators. In responders, levels of three metabolites significantly associated with CD, namely SM(d18:1/24:0), PC(19:0_18:2) and $C_{4,6}D_3O$ tended to normalize, and were independent of the known clinical markers ESR and CRP. As mentioned earlier, these three lipid metabolites are part of Clusters C and D, suggesting that these variations reflect a return to a more normal epithelial barrier function.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

All publications, patents, and patent applications are herein incorporated by reference in their entirety to the same extent as if each individual publication, patent, or patent application was specifically and individually indicated to be incorporated by reference in its entirety.

Other embodiments are in the claims.

The invention claimed is:

1. A method for generating quantitative data for a subject consisting of determining a level of a set of biomarkers in a blood sample from the subject, wherein the set of biomarkers comprises 1) a phosphatidylethanolamine ether, 2) a sphingomyelin, 3) a cholesterol ester, 4) a very long-chain dicarboxylic acid (VLCDCA), and 5) sitosterol sulfate, and wherein the subject is suffering from an inflammatory bowel disease or is suspected of suffering from an inflammatory bowel disease.

2. The method of claim 1, wherein the phosphatidylethanolamine ether is PE(O-16:0/20:4), PE(O-18:0/20:4), PE(O-16:0/22:6), or PE(O-18:0/22:6), wherein the sphingomyelin is SM(d18:1/21:0), SM(d17:1/24:1), SM(d18:2/16:0), SM(d18:2/23:0), SM(d18:2/24:0), SM(d17:1/24:1), SM(d18:1/25:1)-2, SM(d18:1/25:1)-1, SM(d18:1/24:0), SM(d19:1/24:0), SM(d18:1/21:0), or SM(d16:1/22:0), wherein the cholesterol ester is CE(14:1) or CE(14:0), and/or wherein the VLCDCA is 28:1(OH) or 28:4.

3. The method of claim 1, wherein the determination of the level of the biomarker comprises performing an in vitro assay.

4. The method of claim 3, wherein the in vitro assay comprises spectrometry.

5. The method of claim 4, wherein the spectrometry is mass spectrometry (MS) or liquid chromatography-mass spectrometry (LC-MS).

6. The method of claim 1, wherein the blood sample is serum or plasma.

7. The method of claim 1, wherein the inflammatory bowel disease is Crohn's disease, Ulcerative Colitis, or indeterminate colitis.

8. The method of claim 1, wherein the subject is assigned a treatment regimen comprising the administration of a biologic drug.

9. The method of claim 8, wherein the biologic drug is a molecularly targeted therapy, the biologic drug an antibody, the biologic drug binds $\alpha 4\beta 7$ integrin, or the biologic drug is vedolizumab.

10. The method of claim 1, wherein the subject is a human.

11. The method of claim 1, wherein a treatment regimen is assigned to the subject.

12. The method of claim 1, wherein the phosphatidylethanolamine ether is PE(O-16:0/20:4), the sphingomyelin is SM(d18:1/21:0), the cholesterol ester is CE(14:1), and the VLCDCA is 28:1 (OH).

13. The method of claim 1, wherein the set of biomarkers further comprises a phosphatidylcholine ether, a phospholipid, cholesta-4,6-dien-3-one, a triglyceride, a diglyceride, or a ceramide.

14. The method of claim 13, wherein the phosphatidylcholine ether is PC(O-20:0/22:6) or PC(O-18:0/22:6), wherein the phospholipid is PC(18:1_22:5), PC(18:2_20:5), PC(19:0_18:2), PE(18:1_20:4)-1, PE(18:1_20:4)-2, PE(16:0_18:1), or PE(18:0_22:5), wherein the ceramide is Cer (d16:1/23:0), wherein the triglyceride is TG(16:0_18:1_20:4), TG(18:1_18:2_22:5), TG(16:0_18:1_22:5), TG(18:1_18:2_20:4), TG(56:4), TG(18:1_18:2_22:4), or TG(18:2_16_0_20:4), and/or wherein the diglyceride is DG(16:0_18:2).

* * * * *